US012006348B2

(12) United States Patent
Seidel, III et al.

(10) Patent No.: US 12,006,348 B2
(45) Date of Patent: Jun. 11, 2024

(54) T-CELL MODULATORY MULTIMERIC POLYPEPTIDE WITH CONJUGATION SITES AND METHODS OF USE THEREOF

(71) Applicant: Cue Biopharma, Inc., Cambridge, MA (US)

(72) Inventors: Ronald D. Seidel, III, Cambridge, MA (US); Rodolfo J. Chaparro, Cambridge, MA (US); John F. Ross, Cambridge, MA (US); Chee Meng Low, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 601 days.

(21) Appl. No.: 16/812,125

(22) Filed: Mar. 6, 2020

(65) Prior Publication Data

US 2020/0369745 A1  Nov. 26, 2020

Related U.S. Application Data

(63) Continuation of application No. PCT/US2018/049803, filed on Sep. 6, 2018.

(60) Provisional application No. 62/615,402, filed on Jan. 9, 2018, provisional application No. 62/609,082, filed on Dec. 21, 2017, provisional application No. 62/555,559, filed on Sep. 7, 2017.

(51) Int. Cl.
  *C07K 14/74* (2006.01)
  *A61K 38/00* (2006.01)
  *A61K 47/62* (2017.01)
  *C07K 14/005* (2006.01)
  *C12N 7/00* (2006.01)
  *C12N 9/16* (2006.01)

(52) U.S. Cl.
  CPC ........ *C07K 14/70539* (2013.01); *A61K 47/62* (2017.08); *C07K 14/005* (2013.01); *C12N 7/00* (2013.01); *C12N 9/16* (2013.01); *C12Y 301/06* (2013.01); *A61K 38/00* (2013.01); *C07K 2319/02* (2013.01); *C07K 2319/30* (2013.01); *C07K 2319/40* (2013.01); *C12N 2710/16122* (2013.01); *C12N 2710/16133* (2013.01); *C12N 2730/10122* (2013.01); *C12N 2730/10133* (2013.01)

(58) Field of Classification Search
  CPC ............ C07K 14/70539; C07K 14/005; C07K 2319/02; C07K 2319/30; C07K 2319/00; A61K 47/62; A61K 2039/605; C12N 2710/16122; C12N 2710/16133; C12N 2730/10122; C12N 7/00; C12N 9/16; C12N 2730/10133; A61P 37/02; C12Y 301/06
  See application file for complete search history.

(56) References Cited

U.S. PATENT DOCUMENTS

| | | |
|---|---|---|
| 8,992,937 B2 | 3/2015 | Hansen et al. |
| 9,494,588 B2 | 11/2016 | Springer et al. |
| 9,701,749 B2 | 7/2017 | Shibayama et al. |
| 10,048,271 B2 | 8/2018 | Almo et al. |
| 10,472,412 B2 | 11/2019 | Dimitrov et al. |
| 10,927,158 B2 | 2/2021 | Seidel, III et al. |
| 10,927,161 B2 | 2/2021 | Seidel, III et al. |
| 11,104,712 B2 | 8/2021 | Seidel, III et al. |
| 11,117,945 B2 | 9/2021 | Seidel, III et al. |
| 11,226,339 B2 | 1/2022 | Almo et al. |
| 11,339,201 B2 | 5/2022 | Garrett-Thomson et al. |
| 11,370,821 B2 | 6/2022 | Seidel, III et al. |
| 11,377,478 B2 | 7/2022 | Seidel, III et al. |
| 11,401,314 B2 | 8/2022 | Seidel, III et al. |
| 11,479,595 B2 | 10/2022 | Seidel, III et al. |
| 11,505,588 B2 | 11/2022 | Seidel, III et al. |
| 11,505,591 B2 | 11/2022 | Seidel, III et al. |
| 11,530,248 B2 | 12/2022 | Seidel, III et al. |
| 2004/0091492 A1 | 5/2004 | Ribaudo et al. |
| 2008/0219947 A1 | 9/2008 | Linette et al. |
| 2009/0117153 A1 | 5/2009 | Hansen et al. |
| 2009/0232822 A1 | 9/2009 | Joseloff et al. |
| 2011/0159023 A1 | 6/2011 | Langermann |

(Continued)

FOREIGN PATENT DOCUMENTS

| | | |
|---|---|---|
| JP | 2007/513992 A | 5/2007 |
| JP | 2017/519491 A | 7/2017 |

(Continued)

OTHER PUBLICATIONS

Ebert et al. Cancer Res 2009; 69(3):1046-54. (Year: 2009).*
Riemer et al. Journal of Biological Chemistry, 2010, 285: 29608-29622. (Year: 2010).*
Kafi K, Betting DJ, Yamada RE, Bacica M, Steward KK, Timmerman JM. Maleimide conjugation markedly enhances the immunogenicity of both human and murine idiotype-KLH vaccines. Mol Immunol. Jan. 2009;46(3):448-56. (Year: 2009).*

(Continued)

*Primary Examiner* — Nicole Kinsey White
*Assistant Examiner* — Ruixue Wang
(74) *Attorney, Agent, or Firm* — Hoffmann & Baron, LLP

(57) ABSTRACT

The present disclosure provides T-cell modulatory multimeric polypeptides ("T-Cell-MMPs") comprising an immunomodulatory polypeptide ("MOD") that may be selected to exhibit reduced binding affinity to a cognate co-immunomodulatory polypeptide ("Co-MOD") and a location for covalently attaching a molecule that can serve as an epitope, such as an epitope peptide. Once the epitope molecule is attached the resulting T-Cell-MMP-epitope conjugates are useful for modulating the activity of a T-cell by delivering immunomodulatory peptides, such as IL-2 or IL-2 variants that exhibit reduced binding affinity for IL-2R, to the T-cells in an epitope selective/specific manner, and accordingly, for modulating an immune response in an individual.

8 Claims, 19 Drawing Sheets

Specification includes a Sequence Listing.

(56) References Cited

U.S. PATENT DOCUMENTS

| | | |
|---|---|---|
| 2011/0318380 A1 | 12/2011 | Brix et al. |
| 2013/0236957 A1 | 9/2013 | Singh et al. |
| 2014/0105966 A1 | 4/2014 | Bancel et al. |
| 2015/0050303 A1 | 4/2015 | Anderson et al. |
| 2016/0229911 A1 | 8/2016 | Rabuka et al. |
| 2016/0347847 A1 | 12/2016 | Van Dijk et al. |
| 2016/0361402 A1 | 12/2016 | Pease |
| 2017/0058015 A1* | 3/2017 | Seidel, III ............... A61P 31/12 |
| 2017/0174745 A1 | 6/2017 | Dixit et al. |
| 2017/0334951 A1 | 11/2017 | O'Reilly et al. |
| 2018/0086832 A1 | 3/2018 | Vogelstein et al. |
| 2018/0282392 A1 | 10/2018 | Seidel, III et al. |
| 2019/0046648 A1 | 2/2019 | Seidel, III et al. |
| 2019/0062400 A1 | 2/2019 | Seidel, III et al. |
| 2019/0307868 A1 | 10/2019 | Rooney |
| 2019/0352363 A1 | 11/2019 | Seidel, III et al. |
| 2020/0010528 A1 | 1/2020 | Seidel, III et al. |
| 2020/0062819 A1 | 2/2020 | Dalmas et al. |
| 2020/0140519 A1 | 5/2020 | Seidel, III et al. |
| 2020/0148744 A1 | 5/2020 | Seidel, III et al. |
| 2020/0172595 A1 | 6/2020 | Seidel, III et al. |
| 2020/0207824 A1 | 7/2020 | Seidel, III et al. |
| 2020/0291355 A1 | 9/2020 | Chen et al. |
| 2020/0317747 A1 | 10/2020 | Seidel, III et al. |
| 2020/0369745 A1 | 11/2020 | Seidel, III et al. |
| 2020/0377569 A1 | 12/2020 | Seidel, III et al. |
| 2020/0407416 A1 | 12/2020 | Seidel, III et al. |
| 2021/0047384 A1 | 2/2021 | Seidel, III et al. |
| 2021/0238254 A1 | 8/2021 | Seidel, III et al. |
| 2021/0284712 A1 | 9/2021 | Seidel, III et al. |
| 2021/0393693 A1 | 12/2021 | Seidel, III et al. |
| 2022/0008467 A1 | 1/2022 | Seidel, III et al. |
| 2022/0017596 A1 | 1/2022 | Cemerski et al. |
| 2022/0017597 A1 | 1/2022 | Seidel, III et al. |
| 2022/0064247 A1 | 3/2022 | Seidel, III et al. |
| 2022/0079985 A1 | 3/2022 | Seidel, III et al. |
| 2022/0089680 A1 | 3/2022 | Seidel, III et al. |
| 2022/0089681 A1 | 3/2022 | Seidel, III et al. |
| 2022/0105162 A1 | 4/2022 | Seide, III et al. |
| 2022/0106378 A1 | 4/2022 | Seidel, III et al. |
| 2022/0112252 A1 | 4/2022 | Seidel, III et al. |
| 2022/0119483 A1 | 4/2022 | Seidel, III et al. |
| 2022/0143063 A1 | 5/2022 | Seidel, III et al. |
| 2022/0356224 A1 | 11/2022 | Seidel, III et al. |
| 2022/0389079 A1 | 12/2022 | Seidel, III et al. |
| 2023/0000914 A1 | 1/2023 | Suri |
| 2023/0052675 A1 | 2/2023 | Seidel, III et al. |
| 2023/0055644 A1 | 2/2023 | Suri |
| 2023/0109980 A1 | 4/2023 | Seidel, III et al. |
| 2023/0117521 A1 | 4/2023 | Seidel, III et al. |
| 2023/0139456 A1 | 5/2023 | Cemerski et al. |

FOREIGN PATENT DOCUMENTS

| | | |
|---|---|---|
| WO | WO 2005/058349 A2 | 6/2005 |
| WO | WO 2005/081716 A2 | 9/2005 |
| WO | WO 2010/037395 A2 | 4/2010 |
| WO | WO 2012/037551 A2 | 3/2012 |
| WO | WO 2012/145384 A1 | 10/2012 |
| WO | WO 2014/093118 A1 | 6/2014 |
| WO | WO 2015/112541 A2 | 7/2015 |
| WO | WO 2015/195531 A2 | 12/2015 |
| WO | WO 2017/068425 A1 | 4/2017 |
| WO | WO 2017/151818 A2 | 9/2017 |
| WO | WO 2017/151940 A2 | 9/2017 |
| WO | WO 2017/201131 A1 | 11/2017 |
| WO | WO 2017/201210 A1 | 11/2017 |
| WO | WO 2018/0086832 | 3/2018 |
| WO | WO 2018/119114 A1 | 6/2018 |
| WO | WO 2018/129474 A1 | 7/2018 |
| WO | WO 2018/170168 A1 | 9/2018 |
| WO | WO 2018/170475 A1 | 9/2018 |
| WO | WO 2019/051091 A1 | 3/2019 |
| WO | WO 2019/051094 A1 | 3/2019 |
| WO | WO 2019/051126 A1 | 3/2019 |
| WO | WO 2019/051127 A9 | 3/2019 |
| WO | WO 2019/139896 A1 | 7/2019 |
| WO | WO 2019/195310 A1 | 10/2019 |
| WO | WO 2020/132297 A1 | 3/2020 |
| WO | WO 2020/132135 A1 | 6/2020 |
| WO | WO 2020/132136 A1 | 6/2020 |
| WO | WO 2020/132138 A1 | 6/2020 |
| WO | WO 2020/132365 A2 | 6/2020 |
| WO | WO 2020/132366 A2 | 6/2020 |
| WO | WO 2020/132368 A1 | 6/2020 |
| WO | WO 2020/180501 A1 | 9/2020 |
| WO | WO 2020/181062 A1 | 9/2020 |
| WO | WO 2020/282272 A2 | 9/2020 |
| WO | WO 2020/243315 A1 | 12/2020 |
| WO | WO 2020/257191 A1 | 12/2020 |
| WO | WO 2021/055594 A1 | 3/2021 |
| WO | WO 2021/067404 A2 | 4/2021 |
| WO | WO 2021/081232 A1 | 4/2021 |
| WO | WO 2021/081239 A1 | 4/2021 |
| WO | WO 2021/195108 A1 | 9/2021 |
| WO | WO 2021/195411 A1 | 9/2021 |
| WO | WO 2021/231376 A2 | 11/2021 |
| WO | WO 2021/242935 A1 | 12/2021 |
| WO | WO 2022/015880 A2 | 1/2022 |
| WO | WO 2022/056014 A1 | 3/2022 |
| WO | WO 2022/056015 A1 | 3/2022 |
| WO | WO 2022/099156 A2 | 5/2022 |
| WO | WO 2022/099157 A1 | 5/2022 |
| WO | WO 2022/119958 A1 | 6/2022 |
| WO | WO 2022/197970 A2 | 9/2022 |
| WO | WO 2022/197971 A1 | 9/2022 |
| WO | WO 2022/226054 A2 | 10/2022 |
| WO | WO 2022/226069 A1 | 10/2022 |
| WO | WO 2022/226073 A1 | 10/2022 |
| WO | WO 2023/081718 A1 | 5/2023 |

OTHER PUBLICATIONS

Clo et al. Characterization of the Viral O-Glycopeptidome: a Novel Tool of Relevance for Vaccine Design and Serodiagnosis. Journal of Virology, 2012, 86: 6268-6278. (Year: 2012).*

Abbas et al., Cellular and Molecular Immunology, Ninth Edition, pp. 134-136.

Adaptimmune Corp., Spear-heading TCR, (Transforming T Cell Therapy), 2019, pp. 1-30.

Akimzhanov et al., T-Cell Receptor Complex is Essential for Fas Signal Transduction, Aug. 24, 2010, vol. 107, No. 34, pp. 15105-15110.

Allard et al., On the Mechanism of Anti-CD39 Immune CheckPoint Therapy, Journal for Immunother Therapy of Cancer, (2019), vol. 8, pp. 1-11, Doi:10.1136/jitc-2019-000186.

Attia et al., The Molecular and Functional Characteristics of HLA-G and the Interaction with Its Receptors: Where to Intervene for Cancer Immunotherapy, International Journal of Molecular Sciences, 202, vol. 21, No. 8678, pp. 1-18.

Bennett et al., Program Death-1 Engagement Upon TCR Activation Has Distinct Effects on Costimulation and Cytokine-Driven Proliferation: Attenuation of ICOS, IL-4, and IL-21, But Note CD28, IL-7, and IL-15 Responses, The Journal of Immunology, Feb. 15, 2021, pp. 711-718.

Bhan, MAGEA4 Induces Growth in Normal oral keratinocytes by Inhibiting Growth Arrest and Apoptosis, Oncology Reports, 2012, vol. 28, pp. 1498-1502.

BIO-Rad, NK Cells Mini Review, Immunology, pp. 1-7.

Bolli, MD, et al., Tissue Microarray Evaluation of Melanoma Antigen E (MADE) Tumor-Associated Antigen Expression, (Potential Indications for Specific Immunotherapy and Prognostic Relevance in Squamous Cell Lung Carcinoma, MAGE Expression: Tissue Microarray Study, 2002, vol. 236, No. 6, pp. 785-793.

Borras et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.

Caballero et al., Frequent MAGE Mutations in Human Melanoma, PLos One, Sep. 2010, vol. 5, Issue 9, pp. 1-7.

(56) References Cited

OTHER PUBLICATIONS

Catalfamo et al., Human CD8+ T Cells Store RANTES in a Unique Secretory Compartment and Release It Rapidly after TcR Stimulation, Immunity, 2004, vol. 20, pp. 219-230.
Chen et al, Improving the CH1-CK Heterodimerization and pharmacokinetics of 4Dm2m, a Novel Potent CD4-Antibody Fusion Protein Against HIV-1, MABS2016, vol. 8, No. 4, 761-774.
Chen et al., Recent Development of Genetic Code Expansion for Posttranslational Modification Studies, Molecules 2018, 23, 1662; doi:10.3390.
Clements et al., Crystal Structure of HLA-G: A Nonclassical MHC Class I Molecule Expressed at the Fetal-Maternal Interface, PNAS, Mar. 1, 2005, vol. 102, No. 9, pp. 3360-3365.
Cresswell et al, Intracellular Surveillance: Controlling the Assembly of MHC I-Peptide Complexes, Traffic, (2000) vol. 1., pp. 301-305.
Deng, The Emerging Epigenetic Role of CD8+T Cells in Autoimmune Diseases: A Systematic Review, Frontiers in Immunology, Apr. 2019, vol. 10, Article 856, pp. 1-15.
Extended European Search Opinion, European Application No. 18 853 566.0 (published under EP 3679064); 4 pages (May 4, 2021).
GeneCards, Human Gene Database, HLA-E Gene, HLA-E Protein_ HLA-E Antibody, Weizmann Institute of Science, pp. 1-24.
Hagiwara et al., Consequences of Point Mutations in Melanoma-Associated Antigen 4 (MAGE-A4) Protein: Insights from Structural and Biophysical Studies, Scientific Reports, 6:25182, DOI: 10.1038/srep25182, (2016), pp. 1-12.
Hammer et al., SARS-COV-2 Nsp 13 Encodes for an HLA-E-Stabilizing Peptide that Abrogates Inhibition of NKG2A-Expressing NK Cells, Cell Reports 38, 110503, (2022), pp.
Han et al., Dietary Gluten Triggers Concomitant Activation of CD4+ and CD8+ αβ T Cells and γδ T Cells in Celiac Disease, PNAS, Aug. 6, 2013, vol. 110, No. 32, pp. 13073-13078.
Harjanto et al., Clustering HLA Class I Superfamilies Using Structural Interaction Patterns, PLOS One, Jan. 2014, vol. 9, Issue 1, pp. 1-9.
Hausler et al., Anti-CD39 and anti-CD73 Antibodies A1 and 7G2 Improve Targeted Therapy in Ovarian Cancer by Blocking Adenosine-Dependent Immune Evasion, Am. J. Transl. Res.(2014), vol. 6, No. 2, pp. 129-139.
Heald-Sargent et al., Ready, Set, Fuse! The Coronavirus Spike Protein and Acquisition of Fusion Competence, Viruses, (2012) vol. 4, pp. 557-580.
Hebeisen et al., "Identification of Rare High-Avidity, Tumor-Reactive CD8+ T Cells by Monomeric TCR-Ligand Off-Rates Measurements on Living Cells," Cancer Research 75 (10), 1-9 (published online Mar. 25, 2015).
Hein et al., Peptide-independent stabilization of MHC class I molecules breaches cellular quality control; Journal of Cell Science 127, 2885-2897 (2014), dol: 10.1242/Jcs.145334.
Hezareh et al., Effector Function Activities of a Panel of Mutuants of a Broadly Neutralizing Antibody Against Human Immunodeficiency Virus Type 1, Journal of Virology, Dec. 2001, vol. 75, No. 24, pp. 12161-12168.
Hilton et al., Polymorphic HLA-C Receptors Balance the Functional Characteristics of KIR Haplotypes, J Immunol., Oct. 1, 2015, vol. 195, No. 1, pp. 3160-3170.
Höfer et al., Competition for IL-2 Between Regulatory and Effector T Cells to Chisel Immune Responses, Frontiers in Immunology, Sep. 2012, vol. 3, Article 268, pp. 1-9.
Huisman et al., An Unbiased Characterization of the HLA-E and CD94/NKG2x Peptide Repertoire Reveals Peptide Ligands that Skew NK Cell Activation, bioRxiv preprint doi: https://doi.org/10.1101/2022.08.03.502719, pp.
International Preliminary Report on Patentability, International Application No. PCT/US2019/067676 (published under WO 2020/132366), 28 pages, Jan. 8, 2021.
International Preliminary Report on Patentability, International Application No. PCT/US2019/067679 (published under WO 2020/132368), 23 pages, Feb. 17, 2021.
International Preliminary Report on Patentability, International Application No. PCT/US2021/024201 (published under WO 2021/195411), 12 pages, Oct. 6, 2022.
International Preliminary Report on Patentability, International Application No. PCT/US2021/034371 (published under WO 2021/2429351), 4 pages, Apr. 19, 2022.
International Preliminary Report on Patentability, International Application No. PCT/US2021/041675 (published under WO 2022/015880), 18 pages, Nov. 23, 2022.
International Search Report and Written Opinion, International Application No. PCT/US2019/067676 (published under WO 2020/132366), 26 pages, Jun. 9, 2020.
International Search Report and Written Opinion, International Application No. PCT/US2019/067679 (published under WO 2020/132368), 12 pages, Apr. 14, 2020.
International Search Report and Written Opinion, International Application No. PCT/US2021/024201 (published under WO 2021/195411), 17 pages, Aug. 18, 2021.
International Search Report and Written Opinion, International Application No. PCT/US2021/034371 (published under WO 2021/242935), 17 pages, Nov. 10, 2021.
International Search Report and Written Opinion, International Application No. PCT/US2021/041675 (published under WO 2022/015880), 16 pages, Jan. 20, 2022.
International Search Report and Written Opinion, International Application No. PCT/US2021/058490 (published under WO 2022/099156), 14 pages, May 4, 2022.
International Search Report and Written Opinion, International Application No. PCT/US2021/058493 (published under WO 2022/099157), 16 pages, Mar. 24, 2022.
Jia et al., Identification of Two Novel HLA_A *0201-Restricted CTL Epitopes Derived from MAGE-A4, Clinical and Developmental Immunology, vol. 2010, Article ID 567594, 7 pgs.
Kageyama et al., Adoptive Transfer of MAGE-A4 T-Cell Receptor Gene-Transduced Lymphocytes in Patients with Recurrent Esophageal Cancer, American Association for Cancer Research, vol. 21, No. 10, pp. 2268-2277.
Kamiya Blocking Expression of Inhibitory Receptor NKG2A Overcomes Tumor Resistance to NK Cells, J. Clin Invest. (2019), vol. 129, No. 5, pp. 2094-2106.
Karaki et al., Is There Still Room for Cancer Vaccines at the Era of Checkpoint Inhibitors, Vaccines, (2016), vol. 4, No. 37, pp. 1-21.
Kerkar et al., MAGE-A is More Highly Expressed than NY-ESO-1 in a Systematic Immunohistochemical Analysis of 3668 Cases, J Immunother, (2016), vol. 39 No. 4, pp. 181-187.
Kotsiou et al., Dimerization of Soluble Disulfide Trap Single-Chain Major Histocompatibility Complex Class I Molecules Dependent on Peptide Binding Affinity; Antioxidants & Redox Signaling 15(3), 635-644 (2011).
Kotsiou et al., Properties and Applications of Single-Chain Major Histocompatibility Complex Class I Molecules; Antioxidants & Redox Signaling 15(3), 645-655 (2011).
Landry et al., Monoclonal Antibody 57B Stains Tumor Tissues that Express Gene MAGE-A4, Int. J. Cancer, (2000) vol. 86, pp. 835-841.
Li et al., Engineering Superior DNA Vaccines: MHC Class I Single Chain Trimers Bypass Antigen Processing and Enhance the Immune Response to Low Affinity Antigens, Vaccine, Feb. 2010, vol. 28, No. 8, pp. 1911-1918.
Lin et al., Human Leukocyte Antigen-G (HLA-G) Expression in Cancers: Roles in Immune Evasion, Metastasis and Target for Therapy, Molecular Medicine, (2015), vol. 21, pp. 782-791.
Lin et al., Melanoma-Associated Antigens in Esophageal Adenocarcinoma: Identification of Novel MAGE-A10 Splice Variants, American Association for Cancer Research, Sep. 1, 2004, vol. 10, pp. 5708-5716.
Liu et al., High Resolution Human Leukocyte Antigen Class I Allele Frequencies and HIV-1 Infection Associations in Chinese Han and Uyghur Cohorts, PLOS One, Dec. 2012, vol. 7, Issue 12, pp. 1-9.
Luimstra et al., "A Flexible MHC Class I Multimer Loading System for Large-Scale Detection of Antigen-Specific T cells", Journal of Experimental Medicine, May 7, 2018 (May 7, 2018), vol. 215, No. 5, pp. 1493-1504.

(56) References Cited

OTHER PUBLICATIONS

Marco et al., Unveiling the Peptide Motifs of HLA-C and HLA-G from Naturally Presented Peptides and Generation of Binding Prediction Matrices, The Journal of Immunology, Sep. 13, 2017, doi: 10.4049/Jimmunol.1700938, pp. 1-16.

McShan et al., TAPBPR promotes antigen loading on MHC-I molecules using a peptide trap; Nature Comms. 12 (Article No. 3174): 1-18 (2021), https://doi.org/10.1038/s41467-021-23225-6.

Meydan et al., Prediction of Peptides Binding to MHC Class I and Class II Alleles by Temporal Motif Mining, BMC Bioinformatics (2013), vol. 14 (Suppl 2), pp. 1-11.

Mitra et al., Interleukin-2 Activity Can Be Fine Tuned with Engineered Receptor Signaling Clamps, Cell Press Immunity, May 19, 2015, vol. 42, pp. 826-838.

Serge Muyldermans, A guide to: Generation and Design of Nanobodies, The FEBS Journal (2021) vol. 288, pp. 2084-2102.

NCBI Reference Sequence NP_004039.1 "beta-2-microglobulin precursor [*Homo sapiens*]", 25 (7-10, 13-16)/(1-2) Oct. 2020 [online]. [Retrieved on Jan. 4, 2020). Retrieved from the internet: <URL: https://www .ncbi.nlm.nih.gov/protein/NP 004039.1 />.

O'hUigin et al., The Molecular Origin and Consequences of Escape from miRNA Regulations by HLA-C Alleles, The American Journal of Human Genetics, Sep. 9, 2011, vol. 89, pp. 424-431.

Okazaki, et al., PD-1 and PD-1 Ligands: From Discovery to Clinical Application, International Immunology, (2007) vol. 19, No. 7, pp. 813-824.

Oved et al., Antibody-mediated targeting of human single-chain class I MHC with covalently linked peptides induces efficient killing of tumor cells by tumor or viral-specific cytotoxic T lymphocytes; Cancer Immunol Immunother 54: 867-879 (2005).

Paul et al., HLA Class I Alleles Are Associated with Peptide-Binding Repertoires of Different Size, Affinity, and Immunogenicity, The Journal of Immunology, (2013), vol. 191, pp. 5831-5839.

PhosphoSitePlus, Protein MAGE-A2 Melanoma-Associated Antigen 2, Cell Signaling Technology, pp. 1-2, available at http://www.phosphosite.org/ last accessed Jan. 12, 2022.

PhosphoSitePlus, Protein MAGE-A4 Melanoma-Associated Antigen 4, Cell Signaling Technology, pp. 1-2, available at http://www.phosphosite.org/ last accessed Jan. 12, 2022.

PhosphoSitePlus, Protein MAGE-A8 Melanoma-Associated Antigen 8, Cell Signaling Technology, pp. 1-2, available at http://www.phosphosite.org/ last accessed Jan. 12, 2022.

Roep, Islet Autoreactive CD9 T-cells in Type 1 Diabetes Licensed to Kill?, Diabetes, May 2008, vol. 57, pp. 1156-1157.

Saini et al., Dipeptides catalyze rapid peptide exchange on MHC class I molecules PNAS (USA) 112(1) 202-207 Jan. 6, 2015.

Sakurai et al., A Cleaved Form of MAGE-A4 Binds to Miz-1 and Induces Apoptosis in Human Cells, The Journal of Biological Chemistry, Apr. 9, 2004, vol. 279, No. 15, pp. 15505-15514.

Schmidt et al., "Reversible Major Histocompatibility Complex I-Peptide Multimers Containing Ni2+-Nitrilotriacetic Acid Peptides and Histidine Tags Improve Analysis and Sorting of CD8+ T Cells," Journal of Biological Chemistry, Oct. 11, 2011 (Oct. 11, 2011), vol. 286, No. 48. pp. 41723-41735.

Schumacher et al., Nanobodies: Chemical Functionalization Strategies and Intracellular Applications, Angewandte Chem. International Edition, (2018) vol. 57, pp. 2314-2333.

Seidel et al., Peptide-HLA-based Immunotherapeutics Platforms for Direct Modulation of Antigen-Specific T-Cells, Scientific Reports, (2021), vol. 11, 19220,doi, org/10.1038/s41598-021-98716-z, pp. 1-9.

Shields et al., High Resolution Mapping of the Binding Site on Human IgG1 for FcγRI, FcγRII, FcγRIII, and FcRn and Design of IgG1 Variants with Improved Binding to the FcγR*, The Journal of Biological Chemistry, Mar. 2, 2001, vol. 276, No. 9, pp. 6591-6604.

Shukla et al., Cancer-Germline Antigen Expression Discriminates Clinical Outcome to CTLA-4 Blockade, Cell. (2018), vol. 173, No. 3, pp. 624-633.

Sugita et al., NY-ESO-1 Expression and Immunogenicity in Malignant and Benign Breast Tumors, Cancer Research, Mar. 15, 2004, vol. 64, pp. 2199-2204.

Thomas et al., NY-ESO-1 Based Immunotherapy of Cancer: Current Perspectives, Frontiers in Immunology, May 2018, vol. 9, Article 947, pp. 1-14.

Truscott et al., Human Major Histocompatibility Complex (MHC) Class I Molecules with Disulfide Traps Secure Disease-related Antigenic Peptides and Exclude Competitor Peptides, J. Biol. Chem., 283(12): 7480-7490 (2008).

Verma et al., Not Just an Adhesion Molecule: LFA-1 Contact Tunes the T Lymphocyte Program, J. Immunology, (2017), vol. 199, pp. 1213-1221.

Volpe et al., Fas-Fas Ligand: Checkpoint of T Cell Functions in Multiple Sclerosis, Frontier in Immunology, Sep. 2016, vol. 7, Article 382, pp. 1-9.

Wang ZAP-70: An Essential Kinase in T-Cell Signaling, Cold Spring Harbor Perspective Biology, (2010), vol. 2: a002279, pp. 1-17.

Weon et al., The MAGE Protein Family and Cancer, Curr. Opin. Cell Biol., Dec. 2015, vol. 37, pp. 1-8.

Zarling et al., Identification of Class I MHC-Associated Phosphopeptides as Targets for Cancer Immunotherapy, PNAS, Oct. 3, 2006, vol. 103, No. 40, pp. 14889-14894.

Zhang et al., Expression of Tumor-Specific Antigen MAGE, GAGE and BAGE in Ovarian Cancer Tissues and Cell Lines, BMC Cancer (2010), vol. 10, No. 163, pp. 1-6.

International Preliminary Report on Patentability, International Application No. PCT/US2018/049803 (published under WO 2019/051127), 5 pages (Dec. 10, 2019).

International Search Report and Written Opinion, International Application No. PCT/US2018/049803 (published under WO 2019/051127), 13 pages (Nov. 26, 2018).

PCT/US2019/067675 & U.S. Appl. No. 17/342,501, filed Dec. 19, 2019, T-Cell Modulatory Multimeric Polypeptides With Conjugation Sites and Methods of Use Thereof.

PCT/US2019/067676 & U.S. Appl. No. 17/342,513, filed Dec. 19, 2019, T-Cell Modulatory Multimeric Polypeptides With Conjugation Sites and Methods of Use Thereof.

PCT/US2019/067679 & U.S. Appl. No. 17/342,518, filed Dec. 19, 2019, T-Cell Modulatory Multimeric Polypeptides With Conjugation Sites and Methods of Use Thereof.

PCT/US2021/034371 & U.S. Appl. No. 17/927,477, filed May 26, 2021, Antigen Presenting Polypeptide Complexes and Methods of Use Thereof.

PCT/US2021/024201 & U.S. Appl. No. 17/914,734, filed Mar. 25, 2021, T-Cell Modulatory Multimeric Polypeptides With Conjugation Sites and Methods of Use Thereof.

PCT/US2021/041675 & US Pat. Appln No., Jul. 14, 2021, T-Cell Modulatory Multimeric Polypeptides With Conjugation Sites and Methods of Use Thereof.

PCT/US2021/058490 & US Pat. Appln No., Nov. 8, 2021, T-Cell Modulatory Multimeric Polypeptides With Conjugation Sites and Methods of Use Thereof.

PCT/US2021/058493 & US Pat. Appln No., Nov. 8, 2021, Antigen Presenting Polypeptide Complexes and Methods of Use Thereof.

* cited by examiner

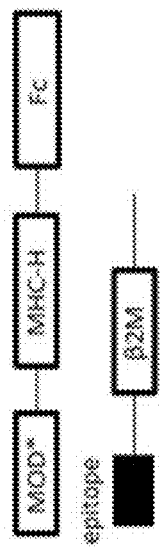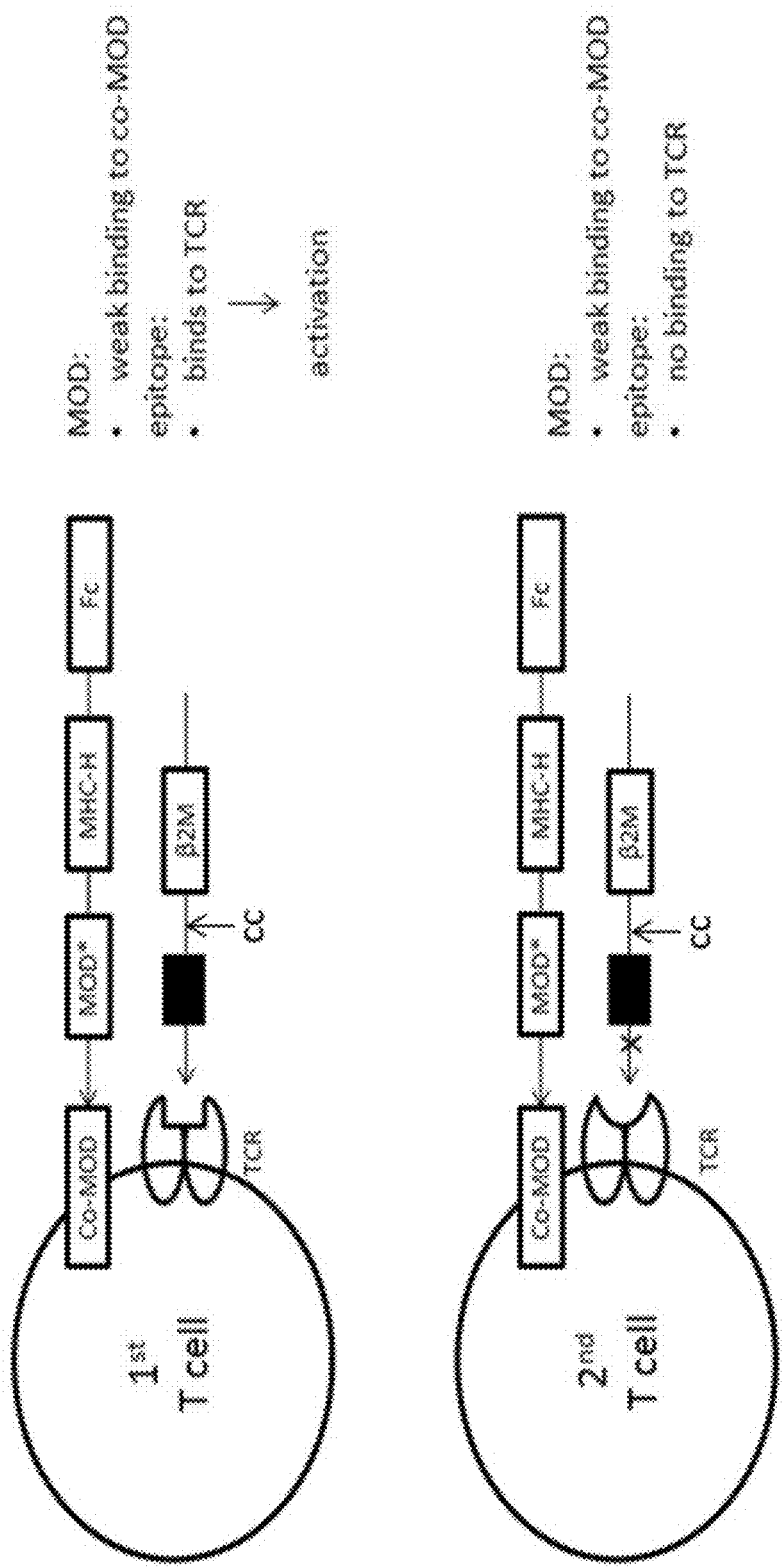
FIG. 1

Figure 2A

GenBank 3S7G_A
*Homo sapiens* IgG1 Fc (SEQ ID NO:1)
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325) (SEQ ID NO:2)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246) (SEQ ID NO:3)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

Figure 2B

GenBank AAA52770
*Homo sapiens* IgD Fc (amino acids 162-383) (SEQ ID NO:4)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srtlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank O308221A
*Homo sapiens* IgM Fc (SEQ ID NO:5)
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

Figure 2C

GenBank P01876
*Homo sapiens* IgA Fc (amino acids 120-353) (SEQ ID NO:6)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprislh rpaledlllg seanltctlt glrdasgvtf twtpssgksa vqgpperdlc
181 gcysvssvlp gcaepwnhgk tftctaaype sktpltatls ksgntfrpev hlpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222) (SEQ ID NO:7)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327) (SEQ ID NO:8)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 2D
WT Human IgG1 Fc Sequence (SEQ ID NO:9)
DKTHTCPPCPAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

FIG. 2E
Human IgG1 Fc Mutant: L234F/L235E/P331S (Triple Mutant "TM") (SEQ ID NO:10)
DKTHTCPPCPAPEFEGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPASIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

FIG. 2F
Human IgG1 Fc Mutant: N297A (SEQ ID NO:11)
DKTHTCPPCPAPELLGGPSVFLFPPKPKDTLMISRTPEVTCVVVDVSHEDPEVKFNWYVDGVEVHNAKTKPREEQYA STYRVVSVLTV
LHQDWLNGKEYKCKVSNKALPAPIEKTISKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

FIG. 2G
Human IgG1 Fc Mutant: L234A/L235A ("LALA") (SEQ ID NO:12)
DKTHTCPPCPAPEAAGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK Residue numbered according to EU index (Kabat Numbering)

Fig. 3A *Homo sapiens* HLA-A
Amino acids 25-365

**3A.1  HLA-A*01:01:01:01 NCBI (National Center for Biotechnology Information) Accession NP_001229687.1 (SEQ ID NO:134)**

```
  1 mavmaprtll llsgalalt qtwagshsmr yfftsvsrpg rgeprfiavg yvddtqfvrf
 61 dsdaasqkme prapwieqeg peywdqetrn mkahsqtdra nigtlrgyyn qsedgshtiq
121 imygcdvgpd grflrgyrqd aydgkdyial nedlrswtaa dmaaqitkrk weavhaaeqr
181 rvylegrcvd glrrylengk etlqrtdppk thmthhpisd heatlrcwal gfypaeitlt
241 wqrdgedgtq dtelvetrpa gdgtfqkwaa vvvpsgeeqr ytchvqhegl pkpltlrwel
301 ssqptipivg iiaglvllga vitgavvaav mwrrkssdrk ggsytqaass dsaqgsdvsl
361 tackv
```

**3A.2  HLA-A*1101 NCBI Accession P13746.1 (SEQ ID NO:135)**

```
  1 mavmaprtll llsgalalt qtwagshsmr yfytsvsrpg rgeprfiavg yvddtqfvrf
 61 dsdaasqrme prapwieqeg peywdqetrn vkaqsqtdrv dlgtlrgyyn qsedgshtiq
121 imygcdvgpd grflrgyrqd aydgkdyial nedlrswtaa dmaaqitkrk weaahaaeqq
181 raylegrcve wlrrylengk etlqrtdppk thmthhpisd heatlrcwal gfypaeitlt
241 wqrdgedgtq dtelvetrpa gdgtfqkwaa vvvpsgeeqr ytchvqhegl pkpltlrwel
301 ssqptipivg iiaglvllga vitgavvaav mwrrkssdrk ggsytqaass dsaqgsdvsl
361 tackv
```

**3A.3  HLA-A*2402  NCBI Accession P05534.2 (SEQ ID NO:136)**

```
  1 mavmaprtlv llsgalalt qtwagshsmr yfstsvsrpg rgeprfiavg yvddtqfvrf
 61 dsdaasqrme prapwieqeg peywdeetgk vkahsqtdre nlrialryyn qseagshtlq
121 mmfgcdvgsd grflrgyhqy aydgkdyial kedlrswtaa dmaaqitkrk weaahvaeqq
181 raylegtcvd glrrylengk etlqrtdppk thmthhpisd heatlrcwal gfypaeitlt
241 wqrdgedgtq dtelvetrpa gdgtfqkwaa vvvpsgeeqr ytchvqhegl pkpltlrwep
301 ssqptvpivg iiaglvllga vitgavvaav mwrrnssdrk ggsysqaass dsaqgsdvsl
361 tackv
```

**3A.4  HLA-A*3303 NCBI Accession AAA79865.1 SEQ ID NO:137**

```
  1 mavmaprtll llllgalalt qtwagshsmr yfttsvsrpg rgeprfiavg yvddtqfvrf
```

```
 61 dsdaasqrme prapwieqeg peywdrntrn vkahsqidrv dlgtlrgyyn qseagshtiq
121 mmygcdvgsd grflrgyyqd aydgkdyial nedlrswtaa dmaaqitqrk weaarvaeql
181 raylegtcve wlrrylengk etlqrtdppk thmthhavsd heatlrcwal sfypaeitlt
241 wqrdgedqtq dtelvetrpa gdgtfqkwas vvvpsgqeqr ytchvqhegl pkpltlrwep
301 ssqptipivg iiaglvlfga vfagavvaav rwrrkssdrk ggsysqaass dsaggsdmsl
361 tackv
```

Fig. 3B *Homo sapiens* HLA-B
HLA-B GenBank Accession NP_005505.2
Amino acids 25-362 (SEQ ID NO:138)

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grlirghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgqeqr ytchvqhegl pkpltlrwep
301 ssqstvpivg ivaglavlav vvigavvaav mcrrkssggk ggsysqaacs dsaggsdvsl
361 ta
```

Fig. 3C *Homo sapiens* HLA-C
HLA-C GenBank Accession NP_001229971.1,

Amino acids 25-366 (SEQ ID NO:139)

```
  1 mrvmaprall lllsgglalt etwacshsmr yfdtavsrpg rgeprfisvg yvddtqfvrf
 61 dsdaasprge prapwveqeg peywdretqn ykrqaqadrv slrnlrgyyn qsedgshtlq
121 rmygcdlgpd grlirgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaggsdes
361 litck
```

Fig. 3D.

```
HLA-A           GSHSMRYFFTSVSRPGRGEPRFIAVGYVDDTQFVRFDSDAASQRMEPRAPWIEQEGPEYW
HLA-B           GSHSMRYFYTSVSRPGRGEPRFISVGYVDDTQFVRFDSDAASPREEPRAPWIEQEGPEYW
HLA-C           CSHSMRYFDTAVSRPGRGEPRFISVGYVDDTQFVRFDSDAASPRGEPRAPWVEQEGPEYW
HLA-A*0201      GSHSMRYFFTSVSRPGRGEPRFIAVGYVDDTQFVRFDSDAASQRMEPRAPWIEQEGPEYW
Mouse H2K       GPHSLRYFVTAVSRPGLGEPRFIAVGYVDDTQFVRFDSDAENPRFEPRAPWMEQEGPEYW
HLA_A (var. 3)  GSHSMRYFFTSVSRPGRGEPRFIAVGYVDDTQFVRFDSDAASQRMEPRAPWIEQEGPEYW
HLA_A (var. 2C) GSHSMRYFFTSVSRPGRGEPRFIAVGYVDDTQFVRFDSDAASQRMEPRAPWIEQEGPEYW
HLA-A(var.2CP)  GSHSMRYFFTSVSRPGRGEPRFIAVGYVDDTQFVRFDSDAASQRMEPRAPWIEQEGPEYW
HLA-A*1101      GSHSMRYFYTSVSRPGRGEPRFIAVGYVDDTQFVRFDSDAASQRMEPRAPWIEQEGPEYW
HLA-A*2402      GSHSMRYFSTSVSRPGRGEPRFIAVGYVDDTQFVRFDSDAASQRMEPRAPWIEQEGPEYW
HLA-A*3303      GSHSMRYFTTSVSRPGRGEPRFIAVGYVDDTQFVRFDSDAASQRMEPRAPWIEQEGPEYW
                 *.***  *.****  ***** *.**************    * ******.********
```

84
```
HLA-A           DQETRNMKAQSQTDRANL|GTLRG|YYNQSE|GSHTIQIMYGCDVGPDGRFLRGYRQDAYDG
HLA-B           DRNTQIYKAQAQTDRESL|RNLRG|YYNQSE|GSHTLQSMYGCDVGPDGRLLRGHDQYAYDG
HLA-C           DRETQNYKRQAQADRVSL|RNLRG|YYNQSE|DSHTLQRMYGCDLGPDGRLLRGYDQSAYDG
HLA-A*0201      DGETRKVKAHSQTHRVDL|GTLRG|YYNQSE|AGSHTVQRMYGCDVGSDWRFLRGYHQYAYDG
MOUSE H2K       EEQTQRAKSDEQWFRVSL|RTAQR|YYNQSK|GSHTFQRMFGCDVGSDWRLLRGYQQFAYDG
HLA_A (var. 3)  DGETRKVKAHSQTHRVDL|GTLRG|YYNQSE|GSHTVQRMYGCDVGSDWRFLRGYHQYAYDG
HLA_A (var. 2C) DGETRKVKAHSQTHRVDL|GTLRG|YYNQSE|GSHTVQRMYGCDVGSDWRFLRGYHQYAYDG
HLA-A(var.2CP)  DGETRKVKAHSQTHRVDL|GTLRG|YYNQSE|GSHTVQRMYGCDVGSDWRFLRGYHQYAYDG
HLA-A*1101      DQETRNVKAQSQTDRVDL|GTLRG|YYNQSE|GSHTIQIMYGCDVGPDGRFLRGYRQDAYDG
HLA-A*2402      DEETGKVKAHSQTDRENL|RIALR|YYNQSE|GSHTLQRMFGCDVGSDGRFLRGYRQYAYDG
HLA-A*3303      DRNTRNVKAHSQIDRVDL|GTLRG|YYNQSE|GSHTIQRMYGCDVGSDGRFLRGYQQDAYDG
                 .*     . *  .*  .     *    ****. **** *  ****.* * ****.****
                                   |aac1 |aac2
```

139
```
HLA-A           KDYIALNEDLRSW|TAADM|AQITR|RKWEAVHAAEQRRVYLEGRCVDGLRRYLENGKETLQ
HLA-B           KDYIALNEDLRSW|TAADT|AQITR|RKWEAAREAEQRRAYLEGECVEWLRRYLENGKDKLE
HLA-C           KDYIALNEDLRSW|TAADT|AQITR|RKLEAARAAEQLRAYLEGTCVEWLRRYLENGKETLQ
HLA-A*0201      KDYIALKEDLRSW|TAADM|AQTTR|HKWEAAHVAEQLRAYLEGTCVEWLRRYLENGKETLQ
MOUSE H2K       KDYIALNEDLKTW|TAADT|AALIT|RKWEQAGEAEYYRAYLEGECVEWLRRYLELGNETLL
HLA_A (var. 3)  KDYIALKEDLRSW|TAADM|AQTTR|HKWEAAHVAEQLRAYLEGTCVEWLRRYLENGKETLQ
HLA_A (var. 2C) KDYIALKEDLRSW|TAADM|AQTTR|HKWEAAHVAEQLRAYLEGTCVEWLRRYLENGKETLQ
HLA-A(var.2CP)  KDYIALKEDLRSW|TAADM|AQTTR|HKWEAAHVAEQLRAYLEGTCVEWLRRYLENGKETLQ
HLA-A*1101      KDYIALNEDLRSW|TAADM|AQITR|RKWEAAHAAEQQRAYLEGRCVEWLRRYLENGKETLQ
HLA-A*2402      KDYIALKEDLRSW|TAADM|AQITR|RKWEAAHVAEQQRAYLEGTCVDGLRRYLENGKETLQ
HLA-A*3303      KDYIALNEDLRSW|TAADM|AQITR|RKWEAARVAEQLRAYLEGTCVEWLRRYLENGKETLQ
                 ******.****.|*****|* .   .*  *   **  ****  **  *****  .
                                   |aac3 |aac4
```

Fig. 3D. Continued

```
                                                                                    336
                                                                                     ↓
HLA-A            RTDPPKTHMTHHPISDHEATLRCWALGFYPAEITLTWQRDGEDQTQDTEL VETRP GDGTF
HLA-B            RADPPKTHVTHHPISDHEATLRCWALGFYPAEITLTWQRDGEDQTQDTEL VETRP GDRTF
HLA-C            RAEPPKTHVTHHPLSDHEATLRCWALGFYPAEITLTWQRDGEDQTQDTEL VETRP GDGTF
HLA-A*0201       RTDAPKTHMTHHAVSDHEATLRCWALSFYPAEITLTWQRDGEDQTQDTEL VETRP GDGTF
MOUSE H2K        RTDSPKAHVTYHPRSQVDVTLRCWALGFYPADITLTWQLNGEDLTQDMEL VETRP AGDGTF
HLA_A (var.2)    RTDAPKTHMTHHAVSDHEATLRCWALSFYPAEITLTWQRDGEDQTQDTEL VETRP GDGTF
HLA_A (var.2C)   RTDAPKTHMTHHAVSDHEATLRCWALSFYPAEITLTWQRDGEDQTQDTEL VETRP GDGTF
HLA-A(var.2CP)   RTDAPKTHMTHHAVSDHEATLRCWALSFYPAEITLTWQRDGEDQTQDTEL VETRP GDGTF
HLA-A*1101       RTDPPKTHMTHHPISDHEATLRCWALGFYPAEITLTWQRDGEDQTQDTEL VETRP GDGTF
HLA-A*2402       RTDPPKTHMTHHPISDHEATLRCWALGFYPAEITLTWQRDGEDQTQDTEL VETRP GDGTF
HLA-A*3303       RTDPPKTHMTHHAVSDHEATLRCWALSFYPAEITLTWQRDGEDQTQDTEL VETRP GDGTF
                 *:: **:*:*:*    *: :,*******,****;****** ;*** *** *******  ** **
                                                                   aac5   aac6

HLA-A            QKWAAVVVPSGEEQRYTCHVQHEGLPKPLTLRWE
HLA-B            QKWAAVVVPSGEEQRYTCHVQHEGLPKPLTLRWE
HLA-C            QKWAAVVVPSGQEQRYTCHMQHEGLQEPLTLSWE
HLA-A*0201       QKWAAVVVPSGQEQRYTCHVQHEGLPKPLTLRWEP
MOUSE H2K        QKWAAVVVPLGKEQNYTCHVHHKGLPEPLTLRW
HLA_A (var.2)    QKWAAVVVPSGQEQRYTCHVQHEGLPKPLTLRWE
HLA_A (var.2C)   QKWAAVVVPSGQEQRYTCHVQHEGLPKPLTLRWE
HLA-A(var.2CP)   QKWAAVVVPSGQEQRYTCHVQHEGLPKPLTLRWEP
HLA-A*1101       QKWAAVVVPSGEEQRYTCHVQHEGLPKPLTLRWEL
HLA-A*2402       QKWAAVVVPSGEEQRYTCHVQHEGLPKPLTLRWEP
HLA-A*3303       QKWASVVVPSGQEQRYTCHVQHEGLPKPLTLRWEP
                 ****;**** *;**,****;;*;**  ;**** *
```

FIG. 4

| | | |
|---|---|---|
| NP_004039.1 | MSRSVALAVLALLSLSGLEAIQRTPKIQVYSRHPAENGKSNFLNCYVSGFHPSDIEVDLL | 60 |
| NP_001009066.1 | MSRSVALAVLALLSLSGLEAIQRTPKIQVYSRHPAENGKSNFLNCYVSGFHPSDIEVDLL | 60 |
| NP_001040602.1 | MSRSVALAVLALLSLSGLEAIQRTPKIQVYSRHPENGEPNFLACYVSGFHPSDIEVDLL | 60 |
| NP_776318.1 | MARFVALVLIVTLGLLSSGLDAIQRPPKIQVYSRHPEDGSKPNTLACYVYGFHPQIEIDLL | 60 |
| NP_033865.2 | MARSVTLVFLVFLVLVSLTGLYAIQKTPLQVISRHPPENGKPNILNCYVTQFHPHIEIQML | 60 |
| | *:*.::*:: :: * :.** * *:**:*:::**: :* .*:.:*.*:*.*.::: | |

| | | |
|---|---|---|
| NP_004039.1 | KNGERIEKVEHSDLSFSKDWSFYLLYYTEFTPTEKDEYACRVNHVTLSQPKIVKWDRDM | 119 |
| NP_001009066.1 | KNGERIEKVEHSDLSFSKDWSFYLLYYTEFTPTEKDEYACRVNHVTLSQPKIVKWDRDM | 119 |
| NP_001040602.1 | KNGEKMGKVEHSDLSFSKDWSFYLLYYTEFTPNEKDEYACRVNHVTLSGPRTVKWDRDM | 119 |
| NP_776318.1 | KNGEKT-NSEQSDLSFSKDWSFYLLSHAEFTPMSKDQYSCRVKHVTLEQPRTVKWDRDT | 118 |
| NP_033865.2 | KNGEKIKTDRVEMSDWSFSKDWSFYILAHTEFTPFTDTTYACRVKHASMAEKTVVWDRDM | 119 |
| | ****:: .:.:*::****:* : .*.: : *:*.:*:*.***. | |

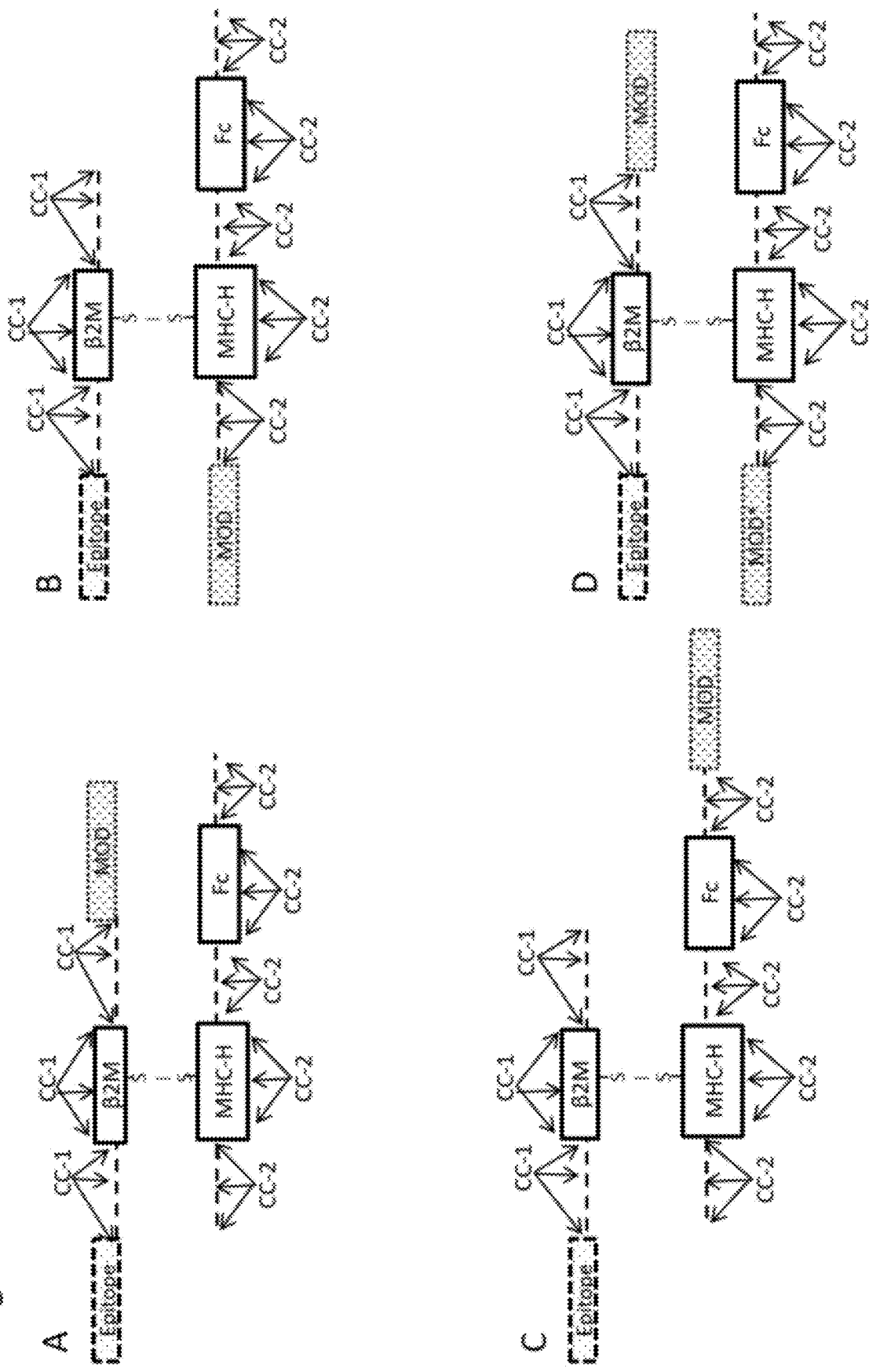

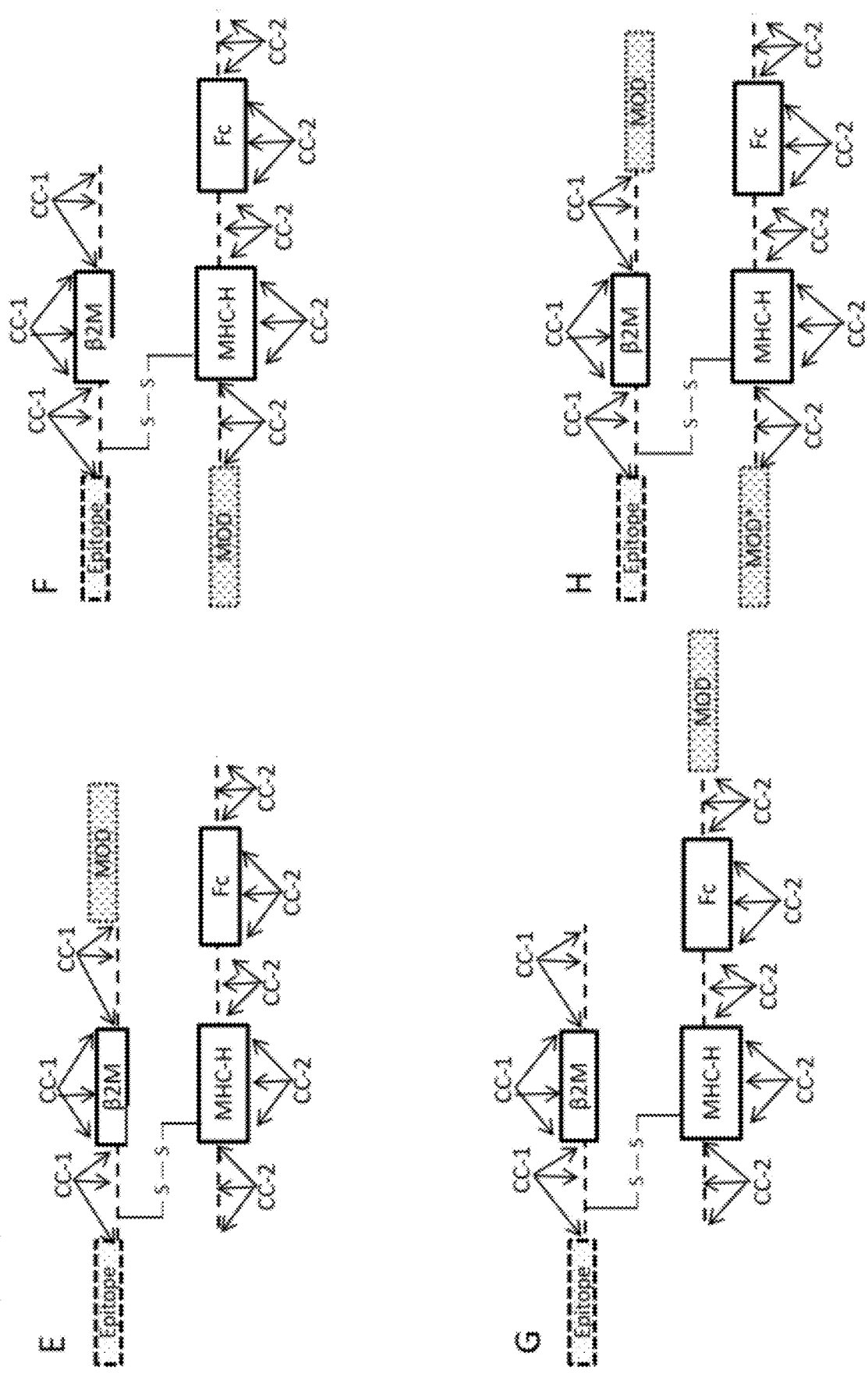

FIG. 9

A. (SEQ ID NO:160)

MSRSVALAVLALLSLSGLEAGGGGSLCTPSRGGGS*IQRTPKIQVYSCHPAENGKSNFLNCYVSGFHPSDIEVDLLKNGERIEKVEHSDLSFSKDWSFY LLYYTEFTPTEKDEYACRVNHVTLSQPKIVKWDRDM*

B. (SEQ ID NO:161)

MYRMQLLSCIALSLALVTNSAPTSSSTKKTQLQLFEALLLDLQMILNGINNYKNPKLTRMLTAKFYMPKKATELKHLQCLEEELKPLEEVLNLA QSKNFHLRPRDLISNINVIVLELKGSETTFMCEYADETATIVEFLNRWITFCQSIISTLTGGGSGGGGSGGGGSGGGGSAPTSSSTKKTQLQLEAL LLDLQMILNGINNYKNPKLTRMLTAKFYMPKKATELKHLQCLEEELKPLEEVLNLAQSKNFHLRPRDLISNINVIVLELKGSETTFMCEYADE TATIVEFLNRWITFCQSIISTLTGGGSGGGGSGGGGSGGGGSHSMRYFFTSVSRPGRGEPRFIAVGYVDDTQFVRFDSDAAS*QRMEPRAPWIEQ EGPEYWDGETRKVKAHSQTHRVDLGTLRGCYNQSEAGSHTVQRMYGCDVGSDWRFLRGYHQYAYDGKDYIALKEDLRSWTAADMCAQTTKHKWEA AHVAEQLRAYLEGTCVEWLRRYLENGKETLQRTDAPKTHMTHHAVSDHEATLRCWALSFYPAEITLTWQRDGEDQTQDTELVETRPCGDGTFQKWA AVVVPSGQEQRYTCHVQHEGLPKPLTLRWEAAAGGDKTHTCPPCPAPEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHNHYTQKSLSLSPGK

FIG. 10A

1775' hIL-2 signal; optional linker; immunomodulatory peptide (MOD); optional linker; HLA-A11 H chain (Y84C; A139C;A236C); AAAGG linker; hIgG1 Fc (L234A; L235A) (SEQ ID NO:162)

MYRMQLLSCIALSLALVTNS(optional linker)immunomodulatory peptide(optional linker)
GSHSMRYFYTSVSRPGRGEPRFIAVGYVDDTQFVRFDSDAASQRMEPRAPWIEQEGPE
YWDQETRNVKAQSQTDRVDLGTLRG*C*YNQSEDGSHTIQIMYGCDVGPDGRFLRGYR
QDAYDGKDYIALNEDLRSWTAADM*C*AQITKRKWEAAHAAEQQRAYLEGTCVEWLR
RYLENGKETLQRTDPPKTHMTHHPISDHEATLRCWALGFYPAEITLTWQRDGEDQTQD
TELVETRP*C*GDGTFQKWAAVVVPSGEEQRYTCHVQHEGLPKPLTLRWE*AAAGG*DKTH
TCPPCPAPE*AA*GGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK**

HLA-A11 (Y84C; A139C;A236C) (SEQ ID NO:163)

GSHSMRYFYTSVSRPGRGEPRFIAVGYVDDTQFVRFDSDAASQRMEPRAPWIEQEGPE
YWDQETRNVKAQSQTDRVDLGTLRG*C*YNQSEDGSHTIQIMYGCDVGPDGRFLRGYR
QDAYDGKDYIALNEDLRSWTAADM*C*AQITKRKWEAAHAAEQQRAYLEGTCVEWLR
RYLENGKETLQRTDPPKTHMTHHPISDHEATLRCWALGFYPAEITLTWQRDGEDQTQD
TELVETRP*C*GDGTFQKWAAVVVPSGEEQRYTCHVQHEGLPKPLTLRWE

FIG. 10B
1777' hIL-2 signal; hIL2 (H16A; F42A); (G4S)4 linker; hIL2 (H16A; F42A); (G4S)4 linker; HLA A11 H chain (Y84C; A139C; A236C); AAAGG linker; hIgG1 Fc (L234A; L235A) (SEQ ID NO:164)

MYRMQLLSCIALSLALVTNSAPTSSSTKKTQLQLE*A*LLLDLQMILNGINNYKNPKLTR
MLT*A*KFYMPKKATELKHLQCLEEELKPLEEVLNLAQSKNFHLRPRDLISNINVIVLELK
GSETTFMCEYADETATIVEFLNRWITFCQSIISTLT*GGGGSGGGGSGGGGSGGGGS*APTS
SSTKKTQLQLE*A*LLLDLQMILNGINNYKNPKLTRMLT*A*KFYMPKKATELKHLQCLEEE
LKPLEEVLNLAQSKNFHLRPRDLISNINVIVLELKGSETTFMCEYADETATIVEFLNRWI
TFCQSIISTLT*GGGGSGGGGSGGGGSGGGGS*GSHSMRYFYTSVSRPGRGEPRFIAVGYV
DDTQFVRFDSDAASQRMEPRAPWIEQEGPEYWDQETRNVKAQSQTDRVDLGTLRG*C*Y
NQSEDGSHTIQIMYGCDVGPDGRFLRGYRQDAYDGKDYIALNEDLRSWTAADM*C*AQI
TKRKWEAAHAAEQQRAYLEGTCVEWLRRYLENGKETLQRTDPPKTHMTHHPISDHEA
TLRCWALGFYPAEITLTWQRDGEDQTQDTELVETRP*C*GDGTFQKWAAVVVPSGEEQR
YTCHVQHEGLPKPLTLRWE*AAAGG*DKTHTCPPCPAPE*AA*GGPSVFLFPPKPKDTLMISR
TPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSV
MHEALHNHYTQKSLSLSPGK

FIG. 10C
1779' hIL-2 signal; optional linker; immunomodulatory peptide (MOD); optional linker; HLA-A A11 (Y84C; A139C;A236C); (G4S)6 linker; hIgG1 Fc (L234A; L235A) (SEQ ID NO:165)

<u>MYRMQLLSCIALSLALVTNS</u>(optional linker)immunomodulatory peptide(optional linker)
GSHSMRYFYTSVSRPGRGEPRFIAVGYVDDTQFVRFDSDAASQRMEPRAPWIEQEGPE
YWDQETRNVKAQSQTDRVDLGTLRG<u>C</u>YNQSEDGSHTIQIMYGCDVGPDGRFLRGYR
QDAYDGKDYIALNEDLRSWTAADM<u>C</u>AQITKRKWEAAHAAEQQRAYLEGTCVEWLR
RYLENGKETLQRTDPPKTHMTHHPISDHEATLRCWALGFYPAEITLTWQRDGEDQTQD
TELVETRP<u>C</u>GDGTFQKWAAVVVPSGEEQRYTCHVQHEGLPKPLTLRWE*GGGGSGGG*
*GSGGGGSGGGGSGGGGSGGGGS*DKTHTCPPCPAPE<u>AA</u>GGPSVFLFPPKPKDTLMISRTP
EVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHE
ALHNHYTQKSLSLSPGK

FIG. 10D
1781' hIL-2 signal; hIL2 (H16A; F42A); (G4S)4 linker; hIL2 (H16A; F42A); (G4S)4 linker; HLA-A A11 (Y84C; A139C; A236C); (G4S)6 linker; hIgG1 Fc (L234A; L235A) (SEQ ID NO:166)

<u>MYRMQLLSCIALSLALVTNS</u>APTSSSTKKTQLQLE<u>A</u>LLLDLQMILNGINNYKNPKLTR
MLT<u>A</u>KFYMPKKATELKHLQCLEEELKPLEEVLNLAQSKNFHLRPRDLISNINVIVLELK
GSETTFMCEYADETATIVEFLNRWITFCQSIISTLT*GGGGSGGGGSGGGGSGGGGS*APTS
SSTKKTQLQLE<u>A</u>LLLDLQMILNGINNYKNPKLTRMLT<u>A</u>KFYMPKKATELKHLQCLEEE
LKPLEEVLNLAQSKNFHLRPRDLISNINVIVLELKGSETTFMCEYADETATIVEFLNRWI
TFCQSIISTLT*GGGGSGGGGSGGGGSGGGGS*GSHSMRYFYTSVSRPGRGEPRFIAVGYV
DDTQFVRFDSDAASQRMEPRAPWIEQEGPEYWDQETRNVKAQSQTDRVDLGTLRG<u>C</u>Y
NQSEDGSHTIQIMYGCDVGPDGRFLRGYRQDAYDGKDYIALNEDLRSWTAADM<u>C</u>AQI
TKRKWEAAHAAEQQRAYLEGTCVEWLRRYLENGKETLQRTDPPKTHMTHHPISDHEA
TLRCWALGFYPAEITLTWQRDGEDQTQDTELVETRP<u>C</u>GDGTFQKWAAVVVPSGEEQR
YTCHVQHEGLPKPLTLRWE*GGGGSGGGGSGGGGSGGGGSGGGGS*DKTHTCP
PCPAPE<u>AA</u>GGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

FIG. 11A

1783' – β2M leader; (linker)$_{0-4}$X1Z1X2Z2X3Z3(linker)$_{0-4}$; human β2M (R12C)

<u>MSRSVALAVLALLSLSGLEA</u>(linker)$_{0-4}$X1Z1X2Z2X3Z3(linker)$_{0-4}$IQRTPKIQVYS<u>C</u>HPAENGKSNFLNCYVSGFHPSDIEVDLLKNGERIEKVEHSDLSFSKDWSFYLLYYTEFTPTEKDEYACRVNHVTLSQPKIVKWDRDM HBV epitope for conjugation: LIMPARFYPK (SEQ ID NO:91)

FIG. 11B

1784' – β2M leader; (linker)$_{0-4}$X1Z1X2Z2X3Z3(linker)$_{0-4}$; human β2M (R12C)

<u>MSRSVALAVLALLSLSGLEA</u>(linker)$_{0-4}$X1Z1X2Z2X3Z3(linker)$_{0-4}$IQRTPKIQVYS<u>C</u>HPAENGKSNFLNCYVSGFHPSDIEVDLLKNGERIEKVEHSDLSFSKDWSFYLLYYTEFTPTEKDEYACRVNHVTLSQPKIVKWDRDM HBV epitope for conjugation: AIMPARFYPK (SEQ ID NO:92)

FIG. 11C

1785' – β2M leader; (linker)$_{0-4}$X1Z1X2Z2X3Z3(linker)$_{0-4}$; human β2M (R12C)

<u>MSRSVALAVLALLSLSGLEA</u>(linker)$_{0-4}$X1Z1X2Z2X3Z3(linker)$_{0-4}$IQRTPKIQVYS<u>C</u>HPAENGKSNFLNCYVSGFHPSDIEVDLLKNGERIEKVEHSDLSFSKDWSFYLLYYTEFTPTEKDEYACRVNHVTLSQPKIVKWDRDM HBV epitope for conjugation: YVNVNMGLK (SEQ ID NO:93)

FIG. 11D

1938' – β2M leader; (linker)$_{0-4}$X1Z1X2Z2X3Z3(linker)$_{0-4}$; human β2M (R12C)

<u>MSRSVALAVLALLSLSGLEA</u>(linker)$_{0-4}$X1Z1X2Z2X3Z3(linker)$_{0-4}$IQRTPKIQVYS<u>C</u>HPAENGKSNFLNCYVSGFHPSDIEVDLLKNGERIEKVEHSDLSFSKDWSFYLLYYTEFTPTEKDEYACRVNHVTLSQPKIVKWDRDM HBV (C 18-27) epitope for conjugation: FLPSDFFPSV (SEQ ID NO:84)

FIG. 11E

1939' – β2M leader; (linker)$_{0-4}$X1Z1X2Z2X3Z3(linker)$_{0-4}$; human β2M (R12C)

<u>MSRSVALAVLALLSLSGLEA</u>(linker)$_{0-4}$X1Z1X2Z2X3Z3(linker)$_{0-4}$IQRTPKIQVYS<u>C</u>HPAENGKSNFLNCYVSGFHPSDIEVDLLKNGERIEKVEHSDLSFSKDWSFYLLYYTEFTPTEKDEYACRVNHVTLSQPKIVKWDRDM HBV (C 141-149) epitope epitope for conjugation: STLPETTVV (SEQ ID NO:90)

SEQUENCE LISTING

<160> NUMBER OF SEQ ID NOS: 170

<210> SEQ ID NO 1
<211> LENGTH: 227
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 2
<211> LENGTH: 325
<212> TYPE: PRT
<213> ORGANISM: Homo sapiens

<400> SEQUENCE: 2

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
            325

<210> SEQ ID NO 3

```
<211> LENGTH: 246
<212> TYPE: PRT
<213> ORGANISM: Homo sapiens

<400> SEQUENCE: 3

His Lys Pro Ser Asn Thr Lys Val Asp Lys Arg Val Glu Leu Lys Thr
1               5                   10                  15

Pro Leu Gly Asp Thr Thr His Thr Cys Pro Cys Pro Ala Pro Glu
            20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
            245

<210> SEQ ID NO 4
<211> LENGTH: 383
<212> TYPE: PRT
<213> ORGANISM: Homo sapiens

<400> SEQUENCE: 4

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
            20                  25                  30

His Pro Thr Ser Val Thr Val Thr Trp Tyr Met Gly Thr Gln Ser Gln
            35                  40                  45

Pro Gln Arg Thr Phe Pro Glu Ile Gln Arg Arg Asp Ser Tyr Tyr Met
    50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95
```

```
Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Glu Lys Lys Lys Glu
    130                 135                 140

Lys Glu Lys Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
    210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
    290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350

Thr Cys Val Val Ser His Glu Asp Ser Arg Thr Leu Leu Asn Ala Ser
        355                 360                 365

Arg Ser Leu Glu Val Ser Tyr Val Thr Asp His Gly Pro Met Lys
    370                 375                 380

<210> SEQ ID NO 5
<211> LENGTH: 276
<212> TYPE: PRT
<213> ORGANISM: Homo sapiens

<400> SEQUENCE: 5

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
            20                  25                  30

Ala Ser Ser Met Cys Val Pro Asp Gln Asp Thr Ala Ile Arg Val Phe
        35                  40                  45

Ala Ile Pro Pro Ser Phe Ala Ser Ile Phe Leu Thr Lys Ser Thr Lys
    50                  55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
```

```
                85                  90                  95
Ser Glu Ser His Pro Asn Ala Thr Phe Ser Ala Val Gly Glu Ala Ser
            100                 105                 110

Ile Cys Glu Asp Asx Asp Trp Ser Gly Glu Arg Phe Thr Cys Thr Val
            115                 120                 125

Thr His Thr Asp Leu Pro Ser Pro Leu Lys Gln Thr Ile Ser Arg Pro
            130                 135                 140

Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
                165                 170                 175

Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
            195                 200                 205

Pro Gln Ala Pro Gly Arg Tyr Phe Ala His Ser Ile Leu Thr Val Ser
        210                 215                 220

Glu Glu Glu Trp Asn Thr Gly Gly Thr Tyr Thr Cys Val Val Ala His
225                 230                 235                 240

Glu Ala Leu Pro Asn Arg Val Thr Glu Arg Thr Val Asp Lys Ser Thr
                245                 250                 255

Gly Lys Pro Thr Leu Tyr Asn Val Ser Leu Val Met Ser Asp Thr Ala
            260                 265                 270

Gly Thr Cys Tyr
            275

<210> SEQ ID NO 6
<211> LENGTH: 353
<212> TYPE: PRT
<213> ORGANISM: Homo sapiens

<400> SEQUENCE: 6

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
            130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175
```

```
Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
            245                 250                 255

Pro Lys Asp Val Leu Val Arg Trp Leu Gln Gly Ser Gln Glu Leu Pro
        260                 265                 270

Arg Glu Lys Tyr Leu Thr Trp Ala Ser Arg Gln Glu Pro Ser Gln Gly
    275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
            325                 330                 335

Thr His Val Asn Val Ser Val Val Met Ala Glu Val Asp Gly Thr Cys
        340                 345                 350

Tyr

<210> SEQ ID NO 7
<211> LENGTH: 222
<212> TYPE: PRT
<213> ORGANISM: Homo sapiens

<400> SEQUENCE: 7

Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
    50                  55                  60

Glu Lys Gln Arg Asn Gly Thr Leu Thr Val Thr Ser Thr Leu Pro Val
65                  70                  75                  80

Gly Thr Arg Asp Trp Ile Glu Gly Glu Thr Tyr Gln Cys Arg Val Thr
                85                  90                  95

His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
    130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190
```

```
Gln Lys Asp Glu Phe Ile Cys Arg Ala Val His Glu Ala Ala Ser Pro
            195                 200                 205
Ser Gln Thr Val Gln Arg Ala Val Ser Val Asn Pro Gly Lys
    210                 215                 220
```

<210> SEQ ID NO 8
<211> LENGTH: 327
<212> TYPE: PRT
<213> ORGANISM: Homo sapiens

<400> SEQUENCE: 8

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 9

<211> LENGTH: 227
<212> TYPE: PRT
<213> ORGANISM: Homo sapiens

<400> SEQUENCE: 9

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 10
<211> LENGTH: 227
<212> TYPE: PRT
<213> ORGANISM: Homo sapiens

<400> SEQUENCE: 10

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 11
<211> LENGTH: 227
<212> TYPE: PRT
<213> ORGANISM: Homo sapiens

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225
```

```
<210> SEQ ID NO 12
<211> LENGTH: 227
<212> TYPE: PRT
<213> ORGANISM: Homo sapiens

<400> SEQUENCE: 12

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 245
<212> TYPE: PRT
<213> ORGANISM: Homo sapiens

<400> SEQUENCE: 13

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
```

```
                100             105             110
Arg Cys Met Ile Ser Tyr Gly Gly Ala Asp Tyr Lys Arg Ile Thr Val
            115             120             125
Lys Val Asn Ala Pro Tyr Asn Lys Ile Asn Gln Arg Ile Leu Val Val
            130             135             140
Asp Pro Val Thr Ser Glu His Glu Leu Thr Cys Gln Ala Glu Gly Tyr
145             150             155             160
Pro Lys Ala Glu Val Ile Trp Thr Ser Ser Asp His Gln Val Leu Ser
            165             170             175
Gly Lys Thr Thr Thr Thr Asn Ser Lys Arg Glu Glu Lys Leu Phe Asn
            180             185             190
Val Thr Ser Thr Leu Arg Ile Asn Thr Thr Thr Asn Glu Ile Phe Tyr
            195             200             205
Cys Thr Phe Arg Arg Leu Asp Pro Glu Glu Asn His Thr Ala Glu Leu
            210             215             220
Val Ile Pro Gly Asn Ile Leu Asn Val Ser Ile Lys Ile Cys Leu Thr
225             230             235             240
Leu Ser Pro Ser Thr
            245

<210> SEQ ID NO 14
<211> LENGTH: 219
<212> TYPE: PRT
<213> ORGANISM: Homo sapiens

<400> SEQUENCE: 14

Phe Thr Val Thr Val Pro Lys Asp Leu Tyr Val Val Glu Tyr Gly Ser
1               5               10              15
Asn Met Thr Ile Glu Cys Lys Phe Pro Val Glu Lys Gln Leu Asp Leu
            20              25              30
Ala Ala Leu Ile Val Tyr Trp Glu Met Glu Asp Lys Asn Ile Ile Gln
            35              40              45
Phe Val His Gly Glu Glu Asp Leu Lys Val Gln His Ser Ser Tyr Arg
        50              55              60
Gln Arg Ala Arg Leu Leu Lys Asp Gln Leu Ser Leu Gly Asn Ala Ala
65              70              75              80
Leu Gln Ile Thr Asp Val Lys Leu Gln Asp Ala Gly Val Tyr Arg Cys
            85              90              95
Met Ile Ser Tyr Gly Gly Ala Asp Tyr Lys Arg Ile Thr Val Lys Val
            100             105             110
Asn Ala Pro Tyr Asn Lys Ile Asn Gln Arg Ile Leu Val Val Asp Pro
            115             120             125
Val Thr Ser Glu His Glu Leu Thr Cys Gln Ala Glu Gly Tyr Pro Lys
            130             135             140
Ala Glu Val Ile Trp Thr Ser Ser Asp His Gln Val Leu Ser Gly Lys
145             150             155             160
Thr Thr Thr Thr Asn Ser Lys Arg Glu Glu Lys Leu Phe Asn Val Thr
            165             170             175
Ser Thr Leu Arg Ile Asn Thr Thr Thr Asn Glu Ile Phe Tyr Cys Thr
            180             185             190
Phe Arg Arg Leu Asp Pro Glu Glu Asn His Thr Ala Glu Leu Val Ile
            195             200             205
Pro Gly Asn Ile Leu Asn Val Ser Ile Lys Ile
            210             215
```

```
<210> SEQ ID NO 15
<211> LENGTH: 268
<212> TYPE: PRT
<213> ORGANISM: Homo sapiens

<400> SEQUENCE: 15

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
            195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 16
<211> LENGTH: 208
<212> TYPE: PRT
<213> ORGANISM: Homo sapiens

<400> SEQUENCE: 16

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
    50                  55                  60
```

```
Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                 85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
        180                 185                 190

Gln Thr Phe Asn Trp Asn Thr Lys Gln Glu His Phe Pro Asp Asn
    195                 200                 205

<210> SEQ ID NO 17
<211> LENGTH: 220
<212> TYPE: PRT
<213> ORGANISM: Homo sapiens

<400> SEQUENCE: 17

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
         35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
        180                 185                 190

Asn Met Thr Pro Arg Arg Pro Gly Pro Thr Arg Lys His Tyr Gln Pro
    195                 200                 205

Tyr Ala Pro Pro Arg Asp Phe Ala Ala Tyr Arg Ser
210                 215                 220

<210> SEQ ID NO 18
```

```
<211> LENGTH: 123
<212> TYPE: PRT
<213> ORGANISM: Homo sapiens

<400> SEQUENCE: 18

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Trp Lys His Leu Cys Pro Ser Pro Leu
        35                  40                  45

Phe Pro Gly Pro Ser Lys Pro Phe Trp Val Leu Val Val Gly Gly
    50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
            100                 105                 110

Ala Pro Pro Arg Asp Phe Ala Ala Tyr Arg Ser
            115                 120

<210> SEQ ID NO 19
<211> LENGTH: 101
<212> TYPE: PRT
<213> ORGANISM: Homo sapiens

<400> SEQUENCE: 19

Met Leu Arg Leu Leu Leu Ala Leu Asn Leu Phe Pro Ser Ile Gln Val
1               5                   10                  15

Thr Gly Lys His Leu Cys Pro Ser Pro Leu Phe Pro Gly Pro Ser Lys
            20                  25                  30

Pro Phe Trp Val Leu Val Val Val Gly Gly Val Leu Ala Cys Tyr Ser
        35                  40                  45

Leu Leu Val Thr Val Ala Phe Ile Ile Phe Trp Val Arg Ser Lys Arg
    50                  55                  60

Ser Arg Leu Leu His Ser Asp Tyr Met Asn Met Thr Pro Arg Arg Pro
65                  70                  75                  80

Gly Pro Thr Arg Lys His Tyr Gln Pro Tyr Ala Pro Pro Arg Asp Phe
                85                  90                  95

Ala Ala Tyr Arg Ser
            100

<210> SEQ ID NO 20
<211> LENGTH: 224
<212> TYPE: PRT
<213> ORGANISM: Homo sapiens

<400> SEQUENCE: 20

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Asn Arg Thr Ser
    50                  55                  60
```

```
Phe Asp Ser Asp Ser Trp Thr Leu Arg Leu His Asn Leu Gln Ile Lys
 65                  70                  75                  80

Asp Lys Gly Leu Tyr Gln Cys Ile Ile His Lys Lys Pro Thr Gly
                 85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
            115                 120                 125

Tyr Ile Asn Leu Thr Cys Ser Ser Ile His Gly Tyr Pro Glu Pro Lys
        130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Asp His Ile Pro
    210                 215                 220

<210> SEQ ID NO 21
<211> LENGTH: 110
<212> TYPE: PRT
<213> ORGANISM: Homo sapiens

<400> SEQUENCE: 21

Ala Pro Leu Lys Ile Gln Ala Tyr Phe Asn Glu Thr Ala Asp Leu Pro
 1               5                  10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Asn Arg Thr Ser
 50                  55                  60

Phe Asp Ser Asp Ser Trp Thr Leu Arg Leu His Asn Leu Gln Ile Lys
 65                  70                  75                  80

Asp Lys Gly Leu Tyr Gln Cys Ile Ile His Lys Lys Pro Thr Gly
                 85                  90                  95

Met Ile Arg Ile His Gln Met Asn Ser Glu Leu Ser Val Leu
            100                 105                 110

<210> SEQ ID NO 22
<211> LENGTH: 254
<212> TYPE: PRT
<213> ORGANISM: Homo sapiens

<400> SEQUENCE: 22

Met Glu Tyr Ala Ser Asp Ala Ser Leu Asp Pro Glu Ala Pro Trp Pro
 1               5                  10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
 50                  55                  60
```

```
Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 23
<211> LENGTH: 174
<212> TYPE: PRT
<213> ORGANISM: Homo sapiens

<400> SEQUENCE: 23

Pro Ala Gly Leu Leu Asp Leu Arg Gln Gly Met Phe Ala Gln Leu Val
 1                5                  10                  15

Ala Gln Asn Val Leu Leu Ile Asp Gly Pro Leu Ser Trp Tyr Ser Asp
             20                  25                  30

Pro Gly Leu Ala Gly Val Ser Leu Thr Gly Gly Leu Ser Tyr Lys Glu
         35                  40                  45

Asp Thr Lys Glu Leu Val Val Ala Lys Ala Gly Val Tyr Tyr Val Phe
 50                  55                  60

Phe Gln Leu Glu Leu Arg Arg Val Val Ala Gly Glu Gly Ser Gly Ser
 65                  70                  75                  80

Val Ser Leu Ala Leu His Leu Gln Pro Leu Arg Ser Ala Ala Gly Ala
                 85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170

<210> SEQ ID NO 24
```

```
<211> LENGTH: 175
<212> TYPE: PRT
<213> ORGANISM: Homo sapiens

<400> SEQUENCE: 24

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 25
<211> LENGTH: 167
<212> TYPE: PRT
<213> ORGANISM: Homo sapiens

<400> SEQUENCE: 25

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala
                165
```

<210> SEQ ID NO 26
<211> LENGTH: 255
<212> TYPE: PRT
<213> ORGANISM: Homo sapiens

<400> SEQUENCE: 26

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 27
<211> LENGTH: 133
<212> TYPE: PRT
<213> ORGANISM: Homo sapiens

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 28
<211> LENGTH: 251
<212> TYPE: PRT
<213> ORGANISM: Homo sapiens

<400> SEQUENCE: 28

Glu Leu Cys Asp Asp Pro Pro Glu Ile Pro His Ala Thr Phe Lys
1               5                   10                  15

Ala Met Ala Tyr Lys Gly Thr Met Leu Asn Cys Glu Cys Lys Arg
            20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 29
<211> LENGTH: 524
<212> TYPE: PRT
<213> ORGANISM: Homo sapiens

<400> SEQUENCE: 29

Val Asn Gly Thr Ser Gln Phe Thr Cys Phe Tyr Asn Ser Arg Ala Asn
1               5                   10                  15
```

```
Ile Ser Cys Val Trp Ser Gln Asp Gly Ala Leu Gln Asp Thr Ser Cys
            20                  25                  30

Gln Val His Ala Trp Pro Asp Arg Arg Trp Asn Gln Thr Cys Glu
        35                  40                  45

Leu Leu Pro Val Ser Gln Ala Ser Trp Ala Cys Asn Leu Ile Leu Gly
50                  55                  60

Ala Pro Asp Ser Gln Lys Leu Thr Thr Val Asp Ile Val Thr Leu Arg
65                  70                  75                  80

Val Leu Cys Arg Glu Gly Val Arg Trp Arg Val Met Ala Ile Gln Asp
            85                  90                  95

Phe Lys Pro Phe Glu Asn Leu Arg Leu Met Ala Pro Ile Ser Leu Gln
            100                 105                 110

Val Val His Val Glu Thr His Arg Cys Asn Ile Ser Trp Glu Ile Ser
            115                 120                 125

Gln Ala Ser His Tyr Phe Glu Arg His Leu Glu Phe Glu Ala Arg Thr
130                 135                 140

Leu Ser Pro Gly His Thr Trp Glu Glu Ala Pro Leu Leu Thr Leu Lys
145                 150                 155                 160

Gln Lys Gln Glu Trp Ile Cys Leu Glu Thr Leu Thr Pro Asp Thr Gln
                165                 170                 175

Tyr Glu Phe Gln Val Arg Val Lys Pro Leu Gln Gly Glu Phe Thr Thr
                180                 185                 190

Trp Ser Pro Trp Ser Gln Pro Leu Ala Phe Arg Thr Lys Pro Ala Ala
            195                 200                 205

Leu Gly Lys Asp Thr Ile Pro Trp Leu Gly His Leu Leu Val Gly Leu
            210                 215                 220

Ser Gly Ala Phe Gly Phe Ile Ile Leu Val Tyr Leu Leu Ile Asn Cys
225                 230                 235                 240

Arg Asn Thr Gly Pro Trp Leu Lys Lys Val Leu Lys Cys Asn Thr Pro
                245                 250                 255

Asp Pro Ser Lys Phe Phe Ser Gln Leu Ser Ser Glu His Gly Gly Asp
            260                 265                 270

Val Gln Lys Trp Leu Ser Ser Pro Phe Pro Ser Ser Ser Phe Ser Pro
            275                 280                 285

Gly Gly Leu Ala Pro Glu Ile Ser Pro Leu Glu Val Leu Glu Arg Asp
290                 295                 300

Lys Val Thr Gln Leu Leu Leu Gln Gln Asp Lys Val Pro Glu Pro Ala
305                 310                 315                 320

Ser Leu Ser Ser Asn His Ser Leu Thr Ser Cys Phe Thr Asn Gln Gly
                325                 330                 335

Tyr Phe Phe Phe His Leu Pro Asp Ala Leu Glu Ile Glu Ala Cys Gln
                340                 345                 350

Val Tyr Phe Thr Tyr Asp Pro Tyr Ser Glu Glu Asp Pro Asp Glu Gly
            355                 360                 365

Val Ala Gly Ala Pro Thr Gly Ser Ser Pro Gln Pro Leu Gln Pro Leu
            370                 375                 380

Ser Gly Glu Asp Asp Ala Tyr Cys Thr Phe Pro Ser Arg Asp Asp Leu
385                 390                 395                 400

Leu Leu Phe Ser Pro Ser Leu Leu Gly Gly Pro Ser Pro Ser Thr
                405                 410                 415

Ala Pro Gly Gly Ser Gly Ala Gly Glu Glu Arg Met Pro Pro Ser Leu
            420                 425                 430
```

Gln Glu Arg Val Pro Arg Asp Trp Asp Pro Gln Pro Leu Gly Pro Pro
            435                 440                 445

Thr Pro Gly Val Pro Asp Leu Val Asp Phe Gln Pro Pro Glu Leu
450                 455                 460

Val Leu Arg Glu Ala Gly Glu Val Pro Asp Ala Gly Pro Arg Glu
465                 470                 475                 480

Gly Val Ser Phe Pro Trp Ser Arg Pro Pro Gly Gln Gly Glu Phe Arg
                485                 490                 495

Ala Leu Asn Ala Arg Leu Pro Leu Asn Thr Asp Ala Tyr Leu Ser Leu
            500                 505                 510

Gln Glu Leu Gln Gly Gln Asp Pro Thr His Leu Val
            515                 520

<210> SEQ ID NO 30
<211> LENGTH: 347
<212> TYPE: PRT
<213> ORGANISM: Homo sapiens

<400> SEQUENCE: 30

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

```
Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345
```

<210> SEQ ID NO 31
<211> LENGTH: 9
<212> TYPE: PRT
<213> ORGANISM: Artificial Sequence
<220> FEATURE:
<223> OTHER INFORMATION: Epitope tag

<400> SEQUENCE: 31

```
Tyr Pro Tyr Asp Val Pro Asp Tyr Ala
1               5
```

<210> SEQ ID NO 32
<211> LENGTH: 8
<212> TYPE: PRT
<213> ORGANISM: Artificial Sequence
<220> FEATURE:
<223> OTHER INFORMATION: Epitope tag

<400> SEQUENCE: 32

```
Asp Tyr Lys Asp Asp Asp Asp Lys
1               5
```

<210> SEQ ID NO 33
<211> LENGTH: 10
<212> TYPE: PRT
<213> ORGANISM: Artificial Sequence
<220> FEATURE:
<223> OTHER INFORMATION: Epitope tag

<400> SEQUENCE: 33

```
Glu Gln Lys Leu Ile Ser Glu Glu Asp Leu
1               5                   10
```

<210> SEQ ID NO 34
<211> LENGTH: 5
<212> TYPE: PRT
<213> ORGANISM: Artificial Sequence
<220> FEATURE:
<223> OTHER INFORMATION: 5x His Tag

<400> SEQUENCE: 34

```
His His His His His
1               5
```

<210> SEQ ID NO 35
<211> LENGTH: 6
<212> TYPE: PRT
<213> ORGANISM: Artificial Sequence
<220> FEATURE:
<223> OTHER INFORMATION: 6x His Tag

<400> SEQUENCE: 35

```
His His His His His His
1               5
```

```
<210> SEQ ID NO 36
<211> LENGTH: 8
<212> TYPE: PRT
<213> ORGANISM: Artificial Sequence
<220> FEATURE:
<223> OTHER INFORMATION: STREP TAG

<400> SEQUENCE: 36

Trp Ser His Pro Gln Phe Glu Lys
1               5

<210> SEQ ID NO 37
<211> LENGTH: 5
<212> TYPE: PRT
<213> ORGANISM: Artificial Sequence
<220> FEATURE:
<223> OTHER INFORMATION: cellulose binding domain

<400> SEQUENCE: 37

Arg Tyr Ile Arg Ser
1               5

<210> SEQ ID NO 38
<211> LENGTH: 4
<212> TYPE: PRT
<213> ORGANISM: Artificial Sequence
<220> FEATURE:
<223> OTHER INFORMATION: Phe-His-His-Thr

<400> SEQUENCE: 38

Phe His His Thr
1

<210> SEQ ID NO 39
<211> LENGTH: 16
<212> TYPE: PRT
<213> ORGANISM: Artificial Sequence
<220> FEATURE:
<223> OTHER INFORMATION: WEAAAREACCRECCAR PEPTIDE

<400> SEQUENCE: 39

Trp Glu Ala Ala Ala Arg Glu Ala Cys Cys Arg Glu Cys Cys Ala Arg
1               5                   10                  15

<210> SEQ ID NO 40
<211> LENGTH: 8
<212> TYPE: PRT
<213> ORGANISM: Artificial Sequence
<220> FEATURE:
<223> OTHER INFORMATION: LEVLFQGP CLEVAGE SITE

<400> SEQUENCE: 40

Leu Glu Val Leu Phe Gln Gly Pro
1               5

<210> SEQ ID NO 41
<211> LENGTH: 7
<212> TYPE: PRT
<213> ORGANISM: Artificial Sequence
<220> FEATURE:
<223> OTHER INFORMATION: ENLYTQS CLEAVAGE SITE

<400> SEQUENCE: 41

Glu Asn Leu Tyr Thr Gln Ser
1               5

<210> SEQ ID NO 42
```

```
<211> LENGTH: 5
<212> TYPE: PRT
<213> ORGANISM: Artificial Sequence
<220> FEATURE:
<223> OTHER INFORMATION: DDDDK CLEVAGE SITE

<400> SEQUENCE: 42

Asp Asp Asp Asp Lys
1               5

<210> SEQ ID NO 43
<211> LENGTH: 4
<212> TYPE: PRT
<213> ORGANISM: Artificial Sequence
<220> FEATURE:
<223> OTHER INFORMATION: LVPR CLEVAGE SITE

<400> SEQUENCE: 43

Leu Val Pro Arg
1

<210> SEQ ID NO 44
<211> LENGTH: 22
<212> TYPE: PRT
<213> ORGANISM: Artificial Sequence
<220> FEATURE:
<223> OTHER INFORMATION: GSGATNFSLLKQAGDVEENPGP CLEVAGE SITE

<400> SEQUENCE: 44

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 45
<211> LENGTH: 6
<212> TYPE: PRT
<213> ORGANISM: Artificial Sequence
<220> FEATURE:
<223> OTHER INFORMATION: SULFATASE MOTIF
<220> FEATURE:
<221> NAME/KEY: UNSURE
<222> LOCATION: (1)..(1)
<223> OTHER INFORMATION: Xaa is present or absent, and when present, can
      be any amino acid, though usually an aliphatic, a sulfur-
      containing, or a polar, uncharged amino acid (e.g.., other than
      an aromatic amino acid or a charged amino acid), usually L, M, V,
      S or T
<220> FEATURE:
<221> NAME/KEY: UNSURE
<222> LOCATION: (2)..(2)
<223> OTHER INFORMATION: Xaa is cysteine or serine
<220> FEATURE:
<221> NAME/KEY: UNSURE
<222> LOCATION: (3)..(3)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
<220> FEATURE:
<221> NAME/KEY: UNSURE
<222> LOCATION: (4)..(4)
<223> OTHER INFORMATION: Xaa is proline or alanine
<220> FEATURE:
<221> NAME/KEY: UNSURE
<222> LOCATION: (5)..(5)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
<220> FEATURE:
<221> NAME/KEY: UNSURE
```

-continued

```
<222> LOCATION: (6)..(6)
<223> OTHER INFORMATION: Xaa is a basic amino acid (arginine, lysine, or
      histidine, usually lysine), or an aliphatic amino acid (alanine,
      glycine, leucine, valine, isoleucine, or proline, usually A, G, L,
      V, or I.

<400> SEQUENCE: 45

Xaa Xaa Xaa Xaa Xaa Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: SULFATASE MOTIF
<220> FEATURE:
<221> NAME/KEY: UNSURE
<222> LOCATION: (1)..(1)
<223> OTHER INFORMATION: Xaa is cysteine or serine.
<220> FEATURE:
<221> NAME/KEY: UNSURE
<222> LOCATION: (2)..(2)
<223> OTHER INFORMATION: Xaa is any amino acid, though usually an
      aliphatic amino acid, a polar uncharged amino acid, or a sulfur
      containing amino acid (i.e., other than an aromatic amino acid or
      charged amino acid), usually S, T, A, V, G or C.
<220> FEATURE:
<221> NAME/KEY: UNSURE
<222> LOCATION: (2)..(2)
<223> OTHER INFORMATION: Xaa is proline or alanine.
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: UNSURE
<222> LOCATION: (4)..(4)
<223> OTHER INFORMATION: Xaa is any amino acid, though usually an
      aliphatic amino acid, a polar uncharged amino acid, or a sulfur
      containing amino acid (i.e., other than an aromatic amino acid or
      charged amino acid), usually S, T, A, V, G or C
<220> FEATURE:
<221> NAME/KEY: UNSURE
<222> LOCATION: (5)..(5)
<223> OTHER INFORMATION: Xaa is a basic amino acid (arginine, lysine, or
      histidine, usually lysine), or an aliphatic amino acid (alanine,
      glycine, leucine, valine, isoleucine, or proline, usually A, G, L,
      V, or I).

<400> SEQUENCE: 46

Xaa Xaa Xaa Xaa Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: SULFATASE MOTIF
<220> FEATURE:
<221> NAME/KEY: UNSURE
<222> LOCATION: (1)..(1)
<223> OTHER INFORMATION: Xaa is present or absent, and when present, can
      be any amino acid, though usually an aliphatic, a sulfur-
      containing, or a polar, uncharged amino acid (e.g.., other than
      an aromatic amino acid or a charged amino acid), usually L, M, V,
      S or T
<220> FEATURE:
<221> NAME/KEY: UNSURE
<222> LOCATION: (3)..(3)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
```

```
<220> FEATURE:
<221> NAME/KEY: UNSURE
<222> LOCATION: (5)..(5)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
<220> FEATURE:
<221> NAME/KEY: UNSURE
<222> LOCATION: (6)..(6)
<223> OTHER INFORMATION: Xaa is a basic amino acid (arginine, lysine, or
      histidine, usually lysine), or an aliphatic amino acid (alanine,
      glycine, leucine, valine, isoleucine, or proline, usually A, G, L,
      V, or I.

<400> SEQUENCE: 47

Xaa Cys Xaa Pro Xaa Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: SULFATASE MOTIF
<220> FEATURE:
<221> NAME/KEY: UNSURE
<222> LOCATION: (2)..(2)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
<220> FEATURE:
<221> NAME/KEY: UNSURE
<222> LOCATION: (4)..(4)
<223> OTHER INFORMATION: Xaa is any amino acid, though usually an
      aliphatic amino acid, a polar uncharged amino acid, or a sulfur
      containing amino acid (e.g., other than an aromatic amino acid or
      charged amino acid), usually S, T, A, V, G or C.
<220> FEATURE:
<221> NAME/KEY: UNSURE
<222> LOCATION: (5)..(5)
<223> OTHER INFORMATION: Xaa is a basic amino acid (arginine, lysine, or
      histidine, usually lysine), or an aliphatic amino acid (alanine,
      glycine, leucine, valine, isoleucine, or proline, usually A, G, L,
      V, or I.

<400> SEQUENCE: 48

Cys Xaa Pro Xaa Xaa
1               5

<210> SEQ ID NO 49
<211> LENGTH: 7
<212> TYPE: PRT
<213> ORGANISM: Artificial Sequence
<220> FEATURE:
<223> OTHER INFORMATION: AUXILIARY SULFATASE MOTIF

<400> SEQUENCE: 49

Ala Ala Leu Leu Thr Gly Arg
1               5

<210> SEQ ID NO 50
<211> LENGTH: 7
<212> TYPE: PRT
<213> ORGANISM: Artificial Sequence
<220> FEATURE:
<223> OTHER INFORMATION: AUXILIARY SULFATASE MOTIF

<400> SEQUENCE: 50

Ser Gln Leu Leu Thr Gly Arg
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: AUXILIARY SULFATASE MOTIF

<400> SEQUENCE: 51

Ala Ala Phe Met Thr Gly Arg
1               5

<210> SEQ ID NO 52
<211> LENGTH: 7
<212> TYPE: PRT
<213> ORGANISM: Artificial Sequence
<220> FEATURE:
<223> OTHER INFORMATION: AUXILIARY SULFATASE MOTIF

<400> SEQUENCE: 52

Ala Ala Phe Leu Thr Gly Arg
1               5

<210> SEQ ID NO 53
<211> LENGTH: 7
<212> TYPE: PRT
<213> ORGANISM: Artificial Sequence
<220> FEATURE:
<223> OTHER INFORMATION: AUXILIARY SULFATASE MOTIF

<400> SEQUENCE: 53

Gly Ser Leu Phe Thr Gly Arg
1               5

<210> SEQ ID NO 54
<211> LENGTH: 5
<212> TYPE: PRT
<213> ORGANISM: Artificial Sequence
<220> FEATURE:
<223> OTHER INFORMATION: SORTASE SITE
<220> FEATURE:
<221> NAME/KEY: UNSURE
<222> LOCATION: (3)..(3)
<223> OTHER INFORMATION: Xaa is any amino acide.
<220> FEATURE:
<221> NAME/KEY: UNSURE
<222> LOCATION: (5)..(5)
<223> OTHER INFORMATION: Xaa is glycine or alanine.

<400> SEQUENCE: 54

Leu Pro Xaa Thr Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: 5X Glycine

<400> SEQUENCE: 55

Gly Gly Gly Gly Gly
1               5

<210> SEQ ID NO 56
<211> LENGTH: 4
<212> TYPE: PRT
<213> ORGANISM: Artificial Sequence
```

```
<220> FEATURE:
<223> OTHER INFORMATION: 4X Glycine

<400> SEQUENCE: 56

Gly Gly Gly Gly
1

<210> SEQ ID NO 57
<211> LENGTH: 5
<212> TYPE: PRT
<213> ORGANISM: Artificial Sequence
<220> FEATURE:
<223> OTHER INFORMATION: 5X Alanine

<400> SEQUENCE: 57

Ala Ala Ala Ala Ala
1               5

<210> SEQ ID NO 58
<211> LENGTH: 4
<212> TYPE: PRT
<213> ORGANISM: Artificial Sequence
<220> FEATURE:
<223> OTHER INFORMATION: 4X Alanine

<400> SEQUENCE: 58

Ala Ala Ala Ala
1

<210> SEQ ID NO 59
<211> LENGTH: 6
<212> TYPE: PRT
<213> ORGANISM: Artificial Sequence
<220> FEATURE:
<223> OTHER INFORMATION: LPETGG  SORTASE SITE

<400> SEQUENCE: 59

Leu Pro Glu Thr Gly Gly
1               5

<210> SEQ ID NO 60
<211> LENGTH: 6
<212> TYPE: PRT
<213> ORGANISM: Artificial Sequence
<220> FEATURE:
<223> OTHER INFORMATION: LPETAA  SORTASE SITE

<400> SEQUENCE: 60

Leu Pro Glu Thr Ala Ala
1               5

<210> SEQ ID NO 61
<211> LENGTH: 5
<212> TYPE: PRT
<213> ORGANISM: Artificial Sequence
<220> FEATURE:
<223> OTHER INFORMATION: THROMBIN CLEAVAGE SITE

<400> SEQUENCE: 61

Leu Val Pro Arg Gly
1               5

<210> SEQ ID NO 62
<211> LENGTH: 5
<212> TYPE: PRT
<213> ORGANISM: Artificial Sequence
<220> FEATURE:
```

<223> OTHER INFORMATION: TRANSGLUTAMINASE SITE

<400> SEQUENCE: 62

Leu Leu Gln Gly Gly
1               5

<210> SEQ ID NO 63
<211> LENGTH: 4
<212> TYPE: PRT
<213> ORGANISM: Artificial Sequence
<220> FEATURE:
<223> OTHER INFORMATION: TRANSGLUTAMINASE SITE

<400> SEQUENCE: 63

Leu Leu Gln Gly
1

<210> SEQ ID NO 64
<211> LENGTH: 6
<212> TYPE: PRT
<213> ORGANISM: Artificial Sequence
<220> FEATURE:
<223> OTHER INFORMATION: TRANSGLUTAMINASE SITE

<400> SEQUENCE: 64

Leu Ser Leu Ser Gln Gly
1               5

<210> SEQ ID NO 65
<211> LENGTH: 6
<212> TYPE: PRT
<213> ORGANISM: Artificial Sequence
<220> FEATURE:
<223> OTHER INFORMATION: TRANSGLUTAMINASE SITE

<400> SEQUENCE: 65

Leu Leu Gln Leu Gln Gly
1               5

<210> SEQ ID NO 66
<211> LENGTH: 5
<212> TYPE: PRT
<213> ORGANISM: Artificial Sequence
<220> FEATURE:
<223> OTHER INFORMATION: GSGGS PEPTIDE

<400> SEQUENCE: 66

Gly Ser Gly Gly Ser
1               5

<210> SEQ ID NO 67
<211> LENGTH: 4
<212> TYPE: PRT
<213> ORGANISM: Artificial Sequence
<220> FEATURE:
<223> OTHER INFORMATION: GGGS PEPTIDE

<400> SEQUENCE: 67

Gly Gly Gly Ser
1

<210> SEQ ID NO 68
<211> LENGTH: 4
<212> TYPE: PRT
<213> ORGANISM: Artificial Sequence
<220> FEATURE:
<223> OTHER INFORMATION: GGSG PEPTIDE

```
<400> SEQUENCE: 68

Gly Gly Ser Gly
1

<210> SEQ ID NO 69
<211> LENGTH: 5
<212> TYPE: PRT
<213> ORGANISM: Artificial Sequence
<220> FEATURE:
<223> OTHER INFORMATION: GGSGG PEPTIDE

<400> SEQUENCE: 69

Gly Gly Ser Gly Gly
1               5

<210> SEQ ID NO 70
<211> LENGTH: 5
<212> TYPE: PRT
<213> ORGANISM: Artificial Sequence
<220> FEATURE:
<223> OTHER INFORMATION: GSGSG PEPTIDE

<400> SEQUENCE: 70

Gly Ser Gly Ser Gly
1               5

<210> SEQ ID NO 71
<211> LENGTH: 5
<212> TYPE: PRT
<213> ORGANISM: Artificial Sequence
<220> FEATURE:
<223> OTHER INFORMATION: GSGGG PEPTIDE

<400> SEQUENCE: 71

Gly Ser Gly Gly Gly
1               5

<210> SEQ ID NO 72
<211> LENGTH: 5
<212> TYPE: PRT
<213> ORGANISM: Artificial Sequence
<220> FEATURE:
<223> OTHER INFORMATION: GGGSG PEPTIDE

<400> SEQUENCE: 72

Gly Gly Gly Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: GSSSG PEPTIDE

<400> SEQUENCE: 73

Gly Ser Ser Ser Gly
1               5

<210> SEQ ID NO 74
<211> LENGTH: 5
<212> TYPE: PRT
<213> ORGANISM: Artificial Sequence
<220> FEATURE:
<223> OTHER INFORMATION: GSSSS PEPTIDE
```

```
<400> SEQUENCE: 74

Gly Ser Ser Ser Ser
1               5

<210> SEQ ID NO 75
<211> LENGTH: 5
<212> TYPE: PRT
<213> ORGANISM: Artificial Sequence
<220> FEATURE:
<223> OTHER INFORMATION: AAAGG PEPTIDE

<400> SEQUENCE: 75

Ala Ala Ala Gly Gly
1               5

<210> SEQ ID NO 76
<211> LENGTH: 5
<212> TYPE: PRT
<213> ORGANISM: Artificial Sequence
<220> FEATURE:
<223> OTHER INFORMATION: GGGGS PEPTIDE

<400> SEQUENCE: 76

Gly Gly Gly Gly Ser
1               5

<210> SEQ ID NO 77
<211> LENGTH: 15
<212> TYPE: PRT
<213> ORGANISM: Artificial Sequence
<220> FEATURE:
<223> OTHER INFORMATION: GCGASGGGGSGGGGS PEPTIDE

<400> SEQUENCE: 77

Gly Cys Gly Ala Ser Gly Gly Gly Gly Ser Gly Gly Gly Gly Ser
1               5                   10                  15

<210> SEQ ID NO 78
<211> LENGTH: 20
<212> TYPE: PRT
<213> ORGANISM: Artificial Sequence
<220> FEATURE:
<223> OTHER INFORMATION: GCGGSGGGGSGGGGSGGGGS PEPTIDE

<400> SEQUENCE: 78

Gly Cys Gly Gly Ser Gly Gly Gly Gly Ser Gly Gly Gly Gly Ser Gly
1               5                   10                  15

Gly Gly Gly Ser
            20

<210> SEQ ID NO 79
<211> LENGTH: 15
<212> TYPE: PRT
<213> ORGANISM: Artificial Sequence
<220> FEATURE:
<223> OTHER INFORMATION: GCGGSGGGGSGGGGS PEPTIDE

<400> SEQUENCE: 79

Gly Cys Gly Gly Ser Gly Gly Gly Gly Ser Gly Gly Gly Gly Ser
1               5                   10                  15

<210> SEQ ID NO 80
<211> LENGTH: 9
<212> TYPE: PRT
<213> ORGANISM: Human papillomavirus type 16
```

```
<400> SEQUENCE: 80

Leu Leu Met Gly Thr Leu Gly Ile Val
1               5

<210> SEQ ID NO 81
<211> LENGTH: 8
<212> TYPE: PRT
<213> ORGANISM: Human papillomavirus type 16

<400> SEQUENCE: 81

Thr Leu Gly Ile Val Cys Pro Ile
1               5

<210> SEQ ID NO 82
<211> LENGTH: 10
<212> TYPE: PRT
<213> ORGANISM: Human papillomavirus type 16

<400> SEQUENCE: 82

Tyr Met Leu Asp Leu Gln Pro Glu Thr Thr
1               5                   10

<210> SEQ ID NO 83
<211> LENGTH: 9
<212> TYPE: PRT
<213> ORGANISM: Human papillomavirus type 16

<400> SEQUENCE: 83

Tyr Met Leu Asp Leu Gln Pro Glu Thr
1               5

<210> SEQ ID NO 84
<211> LENGTH: 10
<212> TYPE: PRT
<213> ORGANISM: Hepatitis B virus

<400> SEQUENCE: 84

Phe Leu Pro Ser Asp Phe Phe Pro Ser Val
1               5                   10

<210> SEQ ID NO 85
<211> LENGTH: 10
<212> TYPE: PRT
<213> ORGANISM: Hepatitis B virus

<400> SEQUENCE: 85

Gly Leu Ser Arg Tyr Val Ala Arg Leu Gly
1               5                   10

<210> SEQ ID NO 86
<211> LENGTH: 9
<212> TYPE: PRT
<213> ORGANISM: Hepatitis B virus

<400> SEQUENCE: 86

Lys Leu His Leu Tyr Ser His Pro Ile
1               5

<210> SEQ ID NO 87
<211> LENGTH: 9
<212> TYPE: PRT
<213> ORGANISM: Hepatitis B virus

<400> SEQUENCE: 87
```

Phe Leu Leu Ser Leu Gly Ile His Leu
1               5

<210> SEQ ID NO 88
<211> LENGTH: 9
<212> TYPE: PRT
<213> ORGANISM: Hepatitis B virus

<400> SEQUENCE: 88

Ala Leu Met Pro Leu Tyr Ala Cys Ile
1               5

<210> SEQ ID NO 89
<211> LENGTH: 9
<212> TYPE: PRT
<213> ORGANISM: Hepatitis B virus

<400> SEQUENCE: 89

Ser Leu Tyr Ala Asp Ser Pro Ser Val
1               5

<210> SEQ ID NO 90
<211> LENGTH: 9
<212> TYPE: PRT
<213> ORGANISM: Hepatitis B virus

<400> SEQUENCE: 90

Ser Thr Leu Pro Glu Thr Thr Val Val
1               5

<210> SEQ ID NO 91
<211> LENGTH: 10
<212> TYPE: PRT
<213> ORGANISM: Hepatitis B virus

<400> SEQUENCE: 91

Leu Ile Met Pro Ala Arg Phe Tyr Pro Lys
1               5                   10

<210> SEQ ID NO 92
<211> LENGTH: 10
<212> TYPE: PRT
<213> ORGANISM: Hepatitis B virus

<400> SEQUENCE: 92

Ala Ile Met Pro Ala Arg Phe Tyr Pro Lys
1               5                   10

<210> SEQ ID NO 93
<211> LENGTH: 9
<212> TYPE: PRT
<213> ORGANISM: Hepatitis B virus

<400> SEQUENCE: 93

Tyr Val Asn Val Asn Met Gly Leu Lys
1               5

<210> SEQ ID NO 94
<211> LENGTH: 8
<212> TYPE: PRT
<213> ORGANISM: Hepatitis B virus

<400> SEQUENCE: 94

Pro Leu Gly Phe Phe Pro Asp His
1               5

<210> SEQ ID NO 95
<211> LENGTH: 15
<212> TYPE: PRT
<213> ORGANISM: Hepatitis B virus

<400> SEQUENCE: 95

Met Gln Trp Asn Ser Thr Ala Leu His Gln Ala Leu Gln Asp Pro
1               5                   10                  15

<210> SEQ ID NO 96
<211> LENGTH: 9
<212> TYPE: PRT
<213> ORGANISM: Hepatitis B virus

<400> SEQUENCE: 96

Leu Leu Asp Pro Arg Val Arg Gly Leu
1               5

<210> SEQ ID NO 97
<211> LENGTH: 10
<212> TYPE: PRT
<213> ORGANISM: Hepatitis B virus

<400> SEQUENCE: 97

Ser Ile Leu Ser Lys Thr Gly Asp Pro Val
1               5                   10

<210> SEQ ID NO 98
<211> LENGTH: 9
<212> TYPE: PRT
<213> ORGANISM: Hepatitis B virus

<400> SEQUENCE: 98

Val Leu Gln Ala Gly Phe Phe Leu Leu
1               5

<210> SEQ ID NO 99
<211> LENGTH: 9
<212> TYPE: PRT
<213> ORGANISM: Hepatitis B virus

<400> SEQUENCE: 99

Phe Leu Leu Thr Arg Ile Leu Thr Ile
1               5

<210> SEQ ID NO 100
<211> LENGTH: 9
<212> TYPE: PRT
<213> ORGANISM: Hepatitis B virus

<400> SEQUENCE: 100

Phe Leu Gly Gly Thr Pro Val Cys Leu
1               5

<210> SEQ ID NO 101
<211> LENGTH: 9
<212> TYPE: PRT
<213> ORGANISM: Hepatitis B virus

<400> SEQUENCE: 101

Leu Leu Cys Leu Ile Phe Leu Leu Val
1               5

```
<210> SEQ ID NO 102
<211> LENGTH: 10
<212> TYPE: PRT
<213> ORGANISM: Hepatitis B virus

<400> SEQUENCE: 102

Leu Val Leu Leu Asp Tyr Gln Gly Met Leu
1               5                   10

<210> SEQ ID NO 103
<211> LENGTH: 10
<212> TYPE: PRT
<213> ORGANISM: Hepatitis B virus

<400> SEQUENCE: 103

Leu Leu Asp Tyr Gln Gly Met Leu Pro Val
1               5                   10

<210> SEQ ID NO 104
<211> LENGTH: 9
<212> TYPE: PRT
<213> ORGANISM: Hepatitis B virus

<400> SEQUENCE: 104

Ile Pro Ile Pro Ser Ser Trp Ala Phe
1               5

<210> SEQ ID NO 105
<211> LENGTH: 9
<212> TYPE: PRT
<213> ORGANISM: Hepatitis B virus

<400> SEQUENCE: 105

Trp Leu Ser Leu Leu Val Pro Phe Val
1               5

<210> SEQ ID NO 106
<211> LENGTH: 10
<212> TYPE: PRT
<213> ORGANISM: Hepatitis B virus

<400> SEQUENCE: 106

Gly Leu Ser Pro Thr Val Trp Leu Ser Val
1               5                   10

<210> SEQ ID NO 107
<211> LENGTH: 10
<212> TYPE: PRT
<213> ORGANISM: Hepatitis B virus

<400> SEQUENCE: 107

Ser Ile Val Ser Pro Phe Ile Pro Leu Leu
1               5                   10

<210> SEQ ID NO 108
<211> LENGTH: 9
<212> TYPE: PRT
<213> ORGANISM: Hepatitis B virus

<400> SEQUENCE: 108

Ile Leu Ser Pro Phe Leu Pro Leu Leu
1               5

<210> SEQ ID NO 109
<211> LENGTH: 17
```

```
<212> TYPE: PRT
<213> ORGANISM: Hepatitis B virus

<400> SEQUENCE: 109

Ala Thr Val Glu Leu Leu Ser Phe Leu Pro Ser Asp Phe Phe Pro Ser
1               5                   10                  15

Val

<210> SEQ ID NO 110
<211> LENGTH: 9
<212> TYPE: PRT
<213> ORGANISM: Hepatitis B virus

<400> SEQUENCE: 110

Leu Pro Ser Asp Phe Phe Pro Ser Val
1               5

<210> SEQ ID NO 111
<211> LENGTH: 9
<212> TYPE: PRT
<213> ORGANISM: Hepatitis B virus

<400> SEQUENCE: 111

Cys Leu Thr Phe Gly Arg Glu Thr Val
1               5

<210> SEQ ID NO 112
<211> LENGTH: 10
<212> TYPE: PRT
<213> ORGANISM: Hepatitis B virus

<400> SEQUENCE: 112

Val Leu Glu Tyr Leu Val Ser Phe Gly Val
1               5                   10

<210> SEQ ID NO 113
<211> LENGTH: 9
<212> TYPE: PRT
<213> ORGANISM: Hepatitis B virus

<400> SEQUENCE: 113

Glu Tyr Leu Val Ser Phe Gly Val Trp
1               5

<210> SEQ ID NO 114
<211> LENGTH: 10
<212> TYPE: PRT
<213> ORGANISM: Hepatitis B virus

<400> SEQUENCE: 114

Ile Leu Ser Thr Leu Pro Glu Thr Thr Val
1               5                   10

<210> SEQ ID NO 115
<211> LENGTH: 11
<212> TYPE: PRT
<213> ORGANISM: Hepatitis B virus

<400> SEQUENCE: 115

Ser Thr Leu Pro Glu Thr Thr Val Val Arg Arg
1               5                   10

<210> SEQ ID NO 116
<211> LENGTH: 9
```

<212> TYPE: PRT
<213> ORGANISM: Hepatitis B virus

<400> SEQUENCE: 116

Asn Val Ser Ile Pro Trp Thr His Lys
1               5

<210> SEQ ID NO 117
<211> LENGTH: 9
<212> TYPE: PRT
<213> ORGANISM: Hepatitis B virus

<400> SEQUENCE: 117

Lys Val Gly Asn Phe Thr Gly Leu Tyr
1               5

<210> SEQ ID NO 118
<211> LENGTH: 9
<212> TYPE: PRT
<213> ORGANISM: Hepatitis B virus

<400> SEQUENCE: 118

Gly Leu Tyr Ser Ser Thr Val Pro Val
1               5

<210> SEQ ID NO 119
<211> LENGTH: 10
<212> TYPE: PRT
<213> ORGANISM: Hepatitis B virus

<400> SEQUENCE: 119

Thr Leu Trp Lys Ala Gly Ile Leu Tyr Lys
1               5                   10

<210> SEQ ID NO 120
<211> LENGTH: 10
<212> TYPE: PRT
<213> ORGANISM: Hepatitis B virus

<400> SEQUENCE: 120

Thr Pro Ala Arg Val Thr Gly Gly Val Phe
1               5                   10

<210> SEQ ID NO 121
<211> LENGTH: 10
<212> TYPE: PRT
<213> ORGANISM: Hepatitis B virus

<400> SEQUENCE: 121

Leu Val Val Asp Phe Ser Gln Phe Ser Arg
1               5                   10

<210> SEQ ID NO 122
<211> LENGTH: 9
<212> TYPE: PRT
<213> ORGANISM: Hepatitis B virus

<400> SEQUENCE: 122

Gly Leu Ser Arg Tyr Val Ala Arg Leu
1               5

<210> SEQ ID NO 123
<211> LENGTH: 9
<212> TYPE: PRT
<213> ORGANISM: Hepatitis B virus

<400> SEQUENCE: 123

Ser Ile Ala Cys Ser Val Val Arg Arg
1               5

<210> SEQ ID NO 124
<211> LENGTH: 9
<212> TYPE: PRT
<213> ORGANISM: Hepatitis B virus

<400> SEQUENCE: 124

Tyr Met Asp Asp Val Val Leu Gly Ala
1               5

<210> SEQ ID NO 125
<211> LENGTH: 10
<212> TYPE: PRT
<213> ORGANISM: Hepatitis B virus

<400> SEQUENCE: 125

Gln Ala Phe Thr Phe Ser Pro Thr Tyr Lys
1               5                   10

<210> SEQ ID NO 126
<211> LENGTH: 9
<212> TYPE: PRT
<213> ORGANISM: Hepatitis B virus

<400> SEQUENCE: 126

Lys Tyr Thr Ser Phe Pro Trp Leu Leu
1               5

<210> SEQ ID NO 127
<211> LENGTH: 10
<212> TYPE: PRT
<213> ORGANISM: Hepatitis B virus

<400> SEQUENCE: 127

Ile Leu Arg Gly Thr Ser Phe Val Tyr Val
1               5                   10

<210> SEQ ID NO 128
<211> LENGTH: 9
<212> TYPE: PRT
<213> ORGANISM: Hepatitis B virus

<400> SEQUENCE: 128

His Leu Ser Leu Arg Gly Leu Phe Val
1               5

<210> SEQ ID NO 129
<211> LENGTH: 9
<212> TYPE: PRT
<213> ORGANISM: Hepatitis B virus

<400> SEQUENCE: 129

Val Leu His Lys Arg Thr Leu Gly Leu
1               5

<210> SEQ ID NO 130
<211> LENGTH: 10
<212> TYPE: PRT
<213> ORGANISM: Hepatitis B virus

<400> SEQUENCE: 130

Gly Leu Ser Ala Met Ser Thr Thr Asp Leu
1               5                   10

<210> SEQ ID NO 131
<211> LENGTH: 9
<212> TYPE: PRT
<213> ORGANISM: Hepatitis B virus

<400> SEQUENCE: 131

Cys Leu Phe Lys Asp Trp Glu Glu Leu
1               5

<210> SEQ ID NO 132
<211> LENGTH: 9
<212> TYPE: PRT
<213> ORGANISM: Hepatitis B virus

<400> SEQUENCE: 132

Val Leu Gly Gly Cys Arg His Lys Leu
1               5

<210> SEQ ID NO 133
<211> LENGTH: 10
<212> TYPE: PRT
<213> ORGANISM: Artificial Sequence
<220> FEATURE:
<223> OTHER INFORMATION: LINKER SEQUENCE GCGGS(GGGGS)n where n is 1-9

<400> SEQUENCE: 133

Gly Cys Gly Gly Ser Gly Gly Gly Gly Ser
1               5                   10

<210> SEQ ID NO 134
<211> LENGTH: 365
<212> TYPE: PRT
<213> ORGANISM: Homo sapiens

<400> SEQUENCE: 134

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

```
Ala Glu Gln Arg Arg Val Tyr Leu Glu Gly Arg Cys Val Asp Gly Leu
                180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 135
<211> LENGTH: 365
<212> TYPE: PRT
<213> ORGANISM: Homo sapiens

<400> SEQUENCE: 135

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
                20                  25                  30

Tyr Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Gln Arg Met Glu Pro Arg Ala Pro Trp Ile Glu Gln Glu Gly
65                  70                  75                  80

Pro Glu Tyr Trp Asp Gln Glu Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Ala His Ala
                165                 170                 175

Ala Glu Gln Gln Arg Ala Tyr Leu Glu Gly Arg Cys Val Glu Trp Leu
```

```
            180                 185                 190
Arg Arg Tyr Leu Glu Asn Gly Lys Glu Thr Leu Gln Arg Thr Asp Pro
        195                 200                 205
Pro Lys Thr His Met Thr His His Pro Ile Ser Asp His Glu Ala Thr
        210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
        260                 265                 270
Val Pro Ser Gly Glu Glu Gln Arg Tyr Thr Cys His Val Gln His Glu
        275                 280                 285
Gly Leu Pro Lys Pro Leu Thr Leu Arg Trp Glu Leu Ser Ser Gln Pro
        290                 295                 300
Thr Ile Pro Ile Val Gly Ile Ile Ala Gly Leu Val Leu Leu Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Thr Gln Ala Ala Ser Ser Asp Ser
                340                 345                 350
Ala Gln Gly Ser Asp Val Ser Leu Thr Ala Cys Lys Val
        355                 360                 365

<210> SEQ ID NO 136
<211> LENGTH: 365
<212> TYPE: PRT
<213> ORGANISM: Homo sapiens

<400> SEQUENCE: 136

Met Ala Val Met Ala Pro Arg Thr Leu Val Leu Leu Leu Ser Gly Ala
1               5                   10                  15
Leu Ala Leu Thr Gln Thr Trp Ala Gly Ser His Ser Met Arg Tyr Phe
                20                  25                  30
Ser Thr Ser Val Ser Arg Pro Gly Arg Gly Glu Pro Arg Phe Ile Ala
            35                  40                  45
Val Gly Tyr Val Asp Asp Thr Gln Phe Val Arg Phe Asp Ser Asp Ala
        50                  55                  60
Ala Ser Gln Arg Met Glu Pro Arg Ala Pro Trp Ile Glu Gln Glu Gly
65                  70                  75                  80
Pro Glu Tyr Trp Asp Glu Glu Thr Gly Lys Val Lys Ala His Ser Gln
                85                  90                  95
Thr Asp Arg Glu Asn Leu Arg Ile Ala Leu Arg Tyr Tyr Asn Gln Ser
                100                 105                 110
Glu Ala Gly Ser His Thr Leu Gln Met Met Phe Gly Cys Asp Val Gly
            115                 120                 125
Ser Asp Gly Arg Phe Leu Arg Gly Tyr His Gln Tyr Ala Tyr Asp Gly
        130                 135                 140
Lys Asp Tyr Ile Ala Leu Lys Glu Asp Leu Arg Ser Trp Thr Ala Ala
145                 150                 155                 160
Asp Met Ala Ala Gln Ile Thr Lys Arg Lys Trp Glu Ala Ala His Val
                165                 170                 175
Ala Glu Gln Gln Arg Ala Tyr Leu Glu Gly Thr Cys Val Asp Gly Leu
            180                 185                 190
```

```
Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Val Pro Ile Val Gly Ile Ile Ala Gly Leu Val Leu Leu Gly Ala
305                 310                 315                 320

Val Ile Thr Gly Ala Val Val Ala Val Met Trp Arg Arg Asn Ser
                325                 330                 335

Ser Asp Arg Lys Gly Gly Ser Tyr Ser Gln Ala Ala Ser Ser Asp Ser
                340                 345                 350

Ala Gln Gly Ser Asp Val Ser Leu Thr Ala Cys Lys Val
            355                 360                 365

<210> SEQ ID NO 137
<211> LENGTH: 365
<212> TYPE: PRT
<213> ORGANISM: Homo sapiens

<400> SEQUENCE: 137

Met Ala Val Met Ala Pro Arg Thr Leu Leu Leu Leu Leu Gly Ala
1               5                   10                  15

Leu Ala Leu Thr Gln Thr Trp Ala Gly Ser His Ser Met Arg Tyr Phe
                20                  25                  30

Thr Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65              70                  75                  80

Pro Glu Tyr Trp Asp Arg Asn Thr Arg Asn Val Lys Ala His Ser Gln
                85                  90                  95

Ile Asp Arg Val Asp Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
        115                 120                 125

Ser Asp Gly Arg Phe Leu Arg Gly Tyr Gln Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Pro
        195                 200                 205
```

```
Pro Lys Thr His Met Thr His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ser Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Phe Ala Gly Ala Val Val Ala Ala Val Arg Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Met Ser Leu Thr Ala Cys Lys Val
        355                 360                 365

<210> SEQ ID NO 138
<211> LENGTH: 362
<212> TYPE: PRT
<213> ORGANISM: Homo sapiens

<400> SEQUENCE: 138

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
                20                  25                  30

Tyr Thr Ser Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
```

```
                  210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
            355                 360

<210> SEQ ID NO 139
<211> LENGTH: 365
<212> TYPE: PRT
<213> ORGANISM: Homo sapiens

<400> SEQUENCE: 139

Met Arg Val Met Ala Pro Arg Ala Leu Leu Leu Leu Leu Ser Gly Gly
1               5                   10                  15

Leu Ala Leu Thr Glu Thr Trp Ala Cys Ser His Ser Met Arg Tyr Phe
                20                  25                  30

Asp Thr Ala Val Ser Arg Pro Gly Arg Gly Glu Pro Arg Phe Ile Ser
                35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
                100                 105                 110

Glu Asp Gly Ser His Thr Leu Gln Arg Met Tyr Gly Cys Asp Leu Gly
            115                 120                 125

Pro Asp Gly Arg Leu Leu Arg Gly Tyr Asp Gln Ser Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Thr His Val Thr His His Pro Leu Ser Asp His Glu Ala Thr
    210                 215                 220
```

```
Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
        260                 265                 270

Val Pro Ser Gly Gln Glu Gln Arg Tyr Thr Cys His Met Gln His Glu
    275                 280                 285

Gly Leu Gln Glu Pro Leu Thr Leu Ser Trp Glu Pro Ser Ser Gln Pro
290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys
            355                 360                 365

<210> SEQ ID NO 140
<211> LENGTH: 275
<212> TYPE: PRT
<213> ORGANISM: Homo sapiens

<400> SEQUENCE: 140

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240
```

```
Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 141
<211> LENGTH: 275
<212> TYPE: PRT
<213> ORGANISM: Homo sapiens

<400> SEQUENCE: 141

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Gly Ser His Ser
    50                  55                  60

Met Arg Tyr Phe Tyr Thr Ser Val Ser Arg Pro Gly Arg Gly Glu Pro
65                  70                  75                  80

Arg Phe Ile Ser Val Gly Tyr Val Asp Asp Thr Gln Phe Val Arg Phe
                85                  90                  95

Asp Ser Asp Ala Ala Ser Pro Arg Glu Glu Pro Arg Ala Pro Trp Ile
            100                 105                 110

Glu Gln Glu Gly Pro Glu Tyr Trp Lys Asp Tyr Ile Ala Leu Asn Glu
        115                 120                 125

Asp Leu Arg Ser Trp Thr Ala Ala Asp Thr Ala Ala Gln Ile Thr Gln
130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 142
<211> LENGTH: 276
<212> TYPE: PRT
<213> ORGANISM: Homo sapiens

<400> SEQUENCE: 142
```

Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Ala Asp Arg Val Ser Leu Arg Asn
65              70                  75                  80

Leu Arg Gly Tyr Tyr Asn Gln Ser Glu Asp Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Leu Glu Ala Ala Arg Ala Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu Pro Pro Lys Thr His Val Thr His His
        180                 185                 190

Pro Leu Ser Asp His Glu Ala Thr Leu Arg Cys Trp Ala Leu Gly Phe
    195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Met Gln His Glu Gly Leu Gln Glu Pro Leu Thr Leu
            260                 265                 270

Ser Trp Glu Pro
        275

<210> SEQ ID NO 143
<211> LENGTH: 276
<212> TYPE: PRT
<213> ORGANISM: Homo sapiens

<400> SEQUENCE: 143

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65              70                  75                  80

Leu Arg Gly Tyr Tyr Asn Gln Ser Glu Ala Gly Ser His Thr Val Gln

```
                    85                  90                  95
Arg Met Tyr Gly Cys Asp Val Gly Ser Asp Trp Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 144
<211> LENGTH: 273
<212> TYPE: PRT
<213> ORGANISM: Mus musculus

<400> SEQUENCE: 144

Gly Pro His Ser Leu Arg Tyr Phe Val Thr Ala Val Ser Arg Pro Gly
1               5                   10                  15

Leu Gly Glu Pro Arg Phe Ile Ala Val Gly Tyr Val Asp Asp Thr Gln
                20                  25                  30

Phe Val Arg Phe Asp Ser Asp Ala Asp Asn Pro Arg Phe Glu Pro Arg
            35                  40                  45

Ala Pro Trp Met Glu Gln Glu Gly Pro Glu Tyr Trp Glu Glu Gln Thr
        50                  55                  60

Gln Arg Ala Lys Ser Asp Glu Gln Trp Phe Arg Val Ser Leu Arg Thr
65                  70                  75                  80

Ala Gln Arg Tyr Tyr Asn Gln Ser Lys Gly Gly Ser His Thr Phe Gln
                85                  90                  95

Arg Met Phe Gly Cys Asp Val Gly Ser Asp Trp Arg Leu Leu Arg Gly
                100                 105                 110

Tyr Gln Gln Phe Ala Tyr Asp Gly Arg Asp Tyr Ile Ala Leu Asn Glu
            115                 120                 125

Asp Leu Lys Thr Trp Thr Ala Ala Asp Thr Ala Ala Leu Ile Thr Arg
        130                 135                 140

Arg Lys Trp Glu Gln Ala Gly Asp Ala Glu Tyr Tyr Arg Ala Tyr Leu
145                 150                 155                 160

Glu Gly Glu Cys Val Glu Trp Leu Arg Arg Tyr Leu Glu Leu Gly Asn
                165                 170                 175
```

```
Glu Thr Leu Leu Arg Thr Asp Ser Pro Lys Ala His Val Thr Tyr His
            180                 185                 190

Pro Arg Ser Gln Val Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Lys Trp Ala Ala Val Val Pro Leu Gly Lys Glu Gln Asn Tyr
                245                 250                 255

Thr Cys His Val His His Lys Gly Leu Pro Glu Pro Leu Thr Leu Arg
            260                 265                 270

Trp

<210> SEQ ID NO 145
<211> LENGTH: 275
<212> TYPE: PRT
<213> ORGANISM: Homo sapiens

<400> SEQUENCE: 145

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Ala Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270
```

Arg Trp Glu
      275

<210> SEQ ID NO 146
<211> LENGTH: 275
<212> TYPE: PRT
<213> ORGANISM: Homo sapiens

<400> SEQUENCE: 146

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Cys Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
      275

<210> SEQ ID NO 147
<211> LENGTH: 275
<212> TYPE: PRT
<213> ORGANISM: Homo sapiens

<400> SEQUENCE: 147

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

```
Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
 50                      55                  60

Arg Lys Val Lys Ala His Ser Gln Thr His Arg Val Asp Leu Gly Thr
 65                  70                  75                  80

Leu Arg Gly Ala Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Lys Asp Tyr Ile Ala Leu Lys Glu Asp
        115                 120                 125

Leu Arg Ser Trp Thr Ala Ala Asp Met Ala Ala Gln Thr Thr Lys His
130                 135                 140

Lys Trp Glu Ala Ala His Val Ala Glu Gln Leu Arg Ala Tyr Leu Glu
145                 150                 155                 160

Gly Thr Cys Val Glu Trp Leu Arg Arg Tyr Leu Glu Asn Gly Lys Glu
                165                 170                 175

Thr Leu Gln Arg Thr Asp Ala Pro Lys Thr His Met Thr His His Ala
                180                 185                 190

Val Ser Asp His Glu Ala Thr Leu Arg Cys Trp Ala Leu Ser Phe Tyr
        195                 200                 205

Pro Ala Glu Ile Thr Leu Thr Trp Gln Arg Asp Gly Glu Asp Gln Thr
    210                 215                 220

Gln Asp Thr Glu Leu Val Glu Thr Arg Pro Cys Gly Asp Gly Thr Phe
225                 230                 235                 240

Gln Lys Trp Ala Ala Val Val Val Pro Ser Gly Gln Glu Gln Arg Tyr
                245                 250                 255

Thr Cys His Val Gln His Glu Gly Leu Pro Lys Pro Leu Thr Leu Arg
                260                 265                 270

Trp Glu Pro
        275

<210> SEQ ID NO 148
<211> LENGTH: 275
<212> TYPE: PRT
<213> ORGANISM: Homo sapiens

<400> SEQUENCE: 148

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gln Glu Thr
 50                      55                  60

Arg Asn Val Lys Ala Gln Ser Gln Thr Asp Arg Val Asp Leu Gly Thr
 65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125
```

```
Asp Leu Arg Ser Trp Thr Ala Ala Asp Met Ala Ala Gln Ile Thr Lys
        130                 135                 140

Arg Lys Trp Glu Ala Ala His Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                    165                 170                 175

Glu Thr Leu Gln Arg Thr Asp Pro Pro Lys Thr His Met Thr His His
                180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                    245                 250                 255

Tyr Thr Cys His Val Gln His Glu Gly Leu Pro Lys Pro Leu Thr Leu
                260                 265                 270

Arg Trp Glu
        275

<210> SEQ ID NO 149
<211> LENGTH: 341
<212> TYPE: PRT
<213> ORGANISM: Homo sapiens

<400> SEQUENCE: 149

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Glu Glu Thr
        50                  55                  60

Gly Lys Val Lys Ala His Ser Gln Thr Asp Arg Glu Asn Leu Arg Ile
65                  70                  75                  80

Ala Leu Arg Tyr Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Ile Thr Lys
        130                 135                 140

Arg Lys Trp Glu Ala Ala His Val Ala Glu Gln Gln Arg Ala Tyr Leu
145                 150                 155                 160

Glu Gly Thr Cys Val Asp Gly Leu Arg Arg Tyr Leu Glu Asn Gly Lys
                    165                 170                 175

Glu Thr Leu Gln Arg Thr Asp Pro Pro Lys Thr His Met Thr His His
                180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
```

```
             210                 215                 220
Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
                    260                 265                 270

Arg Trp Glu Pro Ser Ser Gln Pro Thr Val Pro Ile Val Gly Ile Ile
            275                 280                 285

Ala Gly Leu Val Leu Leu Gly Ala Val Ile Thr Gly Ala Val Val Ala
            290                 295                 300

Ala Val Met Trp Arg Arg Asn Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
                340

<210> SEQ ID NO 150
<211> LENGTH: 341
<212> TYPE: PRT
<213> ORGANISM: Homo sapiens

<400> SEQUENCE: 150

Gly Ser His Ser Met Arg Tyr Phe Thr Thr Ser Val Ser Arg Pro Gly
1               5                   10                  15

Arg Gly Glu Pro Arg Phe Ile Ala Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Arg Asn Thr
50                  55                  60

Arg Asn Val Lys Ala His Ser Gln Ile Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
                100                 105                 110

Tyr Gln Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Gln
130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
                180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240
```

```
Phe Gln Lys Trp Ala Ser Val Val Pro Ser Gly Gln Glu Gln Arg
                245                 250                 255

Tyr Thr Cys His Val Gln His Glu Gly Leu Pro Lys Pro Leu Thr Leu
        260                 265                 270

Arg Trp Glu Pro Ser Ser Gln Pro Thr Ile Pro Ile Val Gly Ile Ile
    275                 280                 285

Ala Gly Leu Val Leu Phe Gly Ala Val Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340

<210> SEQ ID NO 151
<211> LENGTH: 119
<212> TYPE: PRT
<213> ORGANISM: Homo sapiens

<400> SEQUENCE: 151

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115

<210> SEQ ID NO 152
<211> LENGTH: 119
<212> TYPE: PRT
<213> ORGANISM: Homo sapiens

<400> SEQUENCE: 152

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95
```

```
Glu Tyr Ala Cys Arg Val Asn His Val Thr Leu Ser Gln Pro Lys Ile
                100                 105                 110
Val Lys Trp Asp Arg Asp Met
            115
```

<210> SEQ ID NO 153
<211> LENGTH: 119
<212> TYPE: PRT
<213> ORGANISM: Homo sapiens

<400> SEQUENCE: 153

```
Met Ser Arg Ser Val Ala Leu Ala Val Leu Ala Leu Leu Ser Leu Ser
1               5                   10                  15
Gly Leu Glu Ala Ile Gln Arg Thr Pro Lys Ile Gln Val Tyr Ser Arg
            20                  25                  30
His Pro Pro Glu Asn Gly Lys Pro Asn Phe Leu Asn Cys Tyr Val Ser
        35                  40                  45
Gly Phe His Pro Ser Asp Ile Glu Val Asp Leu Leu Lys Asn Gly Glu
    50                  55                  60
Lys Met Gly Lys Val Glu His Ser Asp Leu Ser Phe Ser Lys Asp Trp
65                  70                  75                  80
Ser Phe Tyr Leu Leu Tyr Tyr Thr Glu Phe Thr Pro Asn Glu Lys Asp
                85                  90                  95
Glu Tyr Ala Cys Arg Val Asn His Val Thr Leu Ser Gly Pro Arg Thr
                100                 105                 110
Val Lys Trp Asp Arg Asp Met
            115
```

<210> SEQ ID NO 154
<211> LENGTH: 118
<212> TYPE: PRT
<213> ORGANISM: Homo sapiens

<400> SEQUENCE: 154

```
Met Ala Arg Phe Val Ala Leu Val Leu Leu Gly Leu Ser Leu Ser
1               5                   10                  15
Gly Leu Asp Ala Ile Gln Arg Pro Pro Lys Ile Gln Val Tyr Ser Arg
            20                  25                  30
His Pro Pro Glu Asp Gly Lys Pro Asn Tyr Leu Asn Cys Tyr Val Tyr
        35                  40                  45
Gly Phe His Pro Pro Gln Ile Glu Ile Asp Leu Leu Lys Asn Gly Glu
    50                  55                  60
Lys Ile Lys Ser Glu Gln Ser Asp Leu Ser Phe Ser Lys Asp Trp Ser
65                  70                  75                  80
Phe Tyr Leu Leu Ser His Ala Glu Phe Thr Pro Asn Ser Lys Asp Gln
                85                  90                  95
Tyr Ser Cys Arg Val Lys His Val Thr Leu Glu Gln Pro Arg Ile Val
                100                 105                 110
Lys Trp Asp Arg Asp Leu
        115
```

<210> SEQ ID NO 155
<211> LENGTH: 119
<212> TYPE: PRT
<213> ORGANISM: Homo sapiens

<400> SEQUENCE: 155

```
Met Ala Arg Ser Val Thr Leu Val Phe Leu Val Leu Val Ser Leu Thr
```

```
                1               5                      10                      15
            Gly Leu Tyr Ala Ile Gln Lys Thr Pro Gln Ile Gln Val Tyr Ser Arg
                        20                      25                      30
            His Pro Pro Glu Asn Gly Lys Pro Asn Ile Leu Asn Cys Tyr Val Thr
                        35                      40                      45
            Gln Phe His Pro Pro His Ile Glu Ile Gln Met Leu Lys Asn Gly Lys
                        50                      55                      60
            Lys Ile Pro Lys Val Glu Met Ser Asp Met Ser Phe Ser Lys Asp Trp
             65                     70                      75                      80
            Ser Phe Tyr Ile Leu Ala His Thr Glu Phe Thr Pro Thr Glu Thr Asp
                                85                      90                      95
            Thr Tyr Ala Cys Arg Val Lys His Ala Ser Met Ala Glu Pro Lys Thr
                            100                     105                     110
            Val Tyr Trp Asp Arg Asp Met
                    115

<210> SEQ ID NO 156
<211> LENGTH: 276
<212> TYPE: PRT
<213> ORGANISM: Artificial Sequence
<220> FEATURE:
<223> OTHER INFORMATION: MHC Class I heavy chain sequence with variable
      regions
<220> FEATURE:
<221> NAME/KEY: Unsure
<222> LOCATION: (79)..(79)
<223> OTHER INFORMATION: Xaa is (i) any amino acid or (ii) any amino
      acid except proline or glycine
<220> FEATURE:
<221> NAME/KEY: Unsure
<222> LOCATION: (80)..(80)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (81)..(81)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (82)..(82)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (83)..(83)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (85)..(85)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (86)..(86)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (87)..(87)
<223> OTHER INFORMATION: Xaa is present or absent, and when present is
      (i) any amino acid or (ii) any amino acid except proline or
      glycine
<220> FEATURE:
```

```
<221> NAME/KEY: Unsure
<222> LOCATION: (88)..(88)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (89)..(89)
<223> OTHER INFORMATION: Xaa is (i) any amino acid or (ii) or ii) any
      amino acid except proline or glycine
<220> FEATURE:
<221> NAME/KEY: Unsure
<222> LOCATION: (134)..(134)
<223> OTHER INFORMATION: Xaa is (i) any amino acid or (ii) or ii) any
      amino acid except proline or glycine
<220> FEATURE:
<221> NAME/KEY: Unsure
<222> LOCATION: (135)..(135)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (136)..(136)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (137)..(137)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (138)..(138)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (138)..(138)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (140)..(140)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (141)..(141)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (142)..(142)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (143)..(143)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (144)..(144)
<223> OTHER INFORMATION: Xaa is (i) any amino acid or (ii) any amino
      acid except proline or glycine

<400> SEQUENCE: 156

Gly Ser His Ser Met Arg Tyr Phe Phe Thr Ser Val Ser Arg Pro Gly
1               5                   10                  15
```

-continued

```
Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Xaa Xaa
65                  70                  75                  80

Xaa Xaa Xaa Cys Xaa Xaa Xaa Xaa Ala Gly Ser His Thr Val Gln
                85                  90                  95

Arg Met Tyr Gly Cys Asp Val Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Xaa Xaa Xaa Xaa Cys Xaa Xaa Xaa Xaa
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275

<210> SEQ ID NO 157
<211> LENGTH: 99
<212> TYPE: PRT
<213> ORGANISM: Homo sapiens

<400> SEQUENCE: 157

Ile Gln Arg Thr Pro Lys Ile Gln Val Tyr Ser Cys His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

```
<210> SEQ ID NO 158
<211> LENGTH: 276
<212> TYPE: PRT
<213> ORGANISM: Artificial Sequence
<220> FEATURE:
<223> OTHER INFORMATION: MHC Class 1 heavy chain sequence with variable
      regions
<220> FEATURE:
<221> NAME/KEY: Unsure
<222> LOCATION: (79)..(79)
<223> OTHER INFORMATION: Xaa is (i) any amino acid or (ii) any amino
      acid except proline or glycine
<220> FEATURE:
<221> NAME/KEY: Unsure
<222> LOCATION: (79)..(79)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (80)..(80)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (81)..(81)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (82)..(82)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (83)..(83)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (85)..(85)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (86)..(86)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (87)..(87)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (88)..(88)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (89)..(89)
<223> OTHER INFORMATION: Xaa is (i) any amino acid or (ii) any amino
      acid except proline or glycine
<220> FEATURE:
<221> NAME/KEY: Unsure
<222> LOCATION: (134)..(134)
<223> OTHER INFORMATION: Xaa  is (i) any amino acid or (ii) any amino
      acid except proline or glycine
<220> FEATURE:
```

```
<221> NAME/KEY: Unsure
<222> LOCATION: (135)..(135)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (136)..(136)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (137)..(137)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (138)..(138)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (140)..(140)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (141)..(141)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (142)..(142)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (143)..(143)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (144)..(144)
<223> OTHER INFORMATION: Xaa is (i) any amino acid or (ii) any amino
      acid except proline or glycine
<220> FEATURE:
<221> NAME/KEY: Unsure
<222> LOCATION: (231)..(231)
<223> OTHER INFORMATION: Xaa  is (i) any amino acid or (ii) any amino
      acid except proline or glycine
<220> FEATURE:
<221> NAME/KEY: Unsure
<222> LOCATION: (232)..(232)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (233)..(233)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (234)..(234)
<223> OTHER INFORMATION: Xaa is present or absent, and when present is
      (i) any amino acid or (ii) any amino acid except proline or
      glycine
<220> FEATURE:
<221> NAME/KEY: Unsure
<222> LOCATION: (235)..(235)
<223> OTHER INFORMATION: Xaa is present or absent, and when present is
```

(i) any amino acid or (ii) any amino acid except proline or
glycine
<220> FEATURE:
<221> NAME/KEY: Unsure
<222> LOCATION: (237)..(237)
<223> OTHER INFORMATION: Xaa is present or absent, and when present is
(i) any amino acid or (ii) any amino acid except proline or
glycine
<220> FEATURE:
<221> NAME/KEY: Unsure
<222> LOCATION: (238)..(238)
<223> OTHER INFORMATION: Xaa is present or absent, and when present is
(i) any amino acid or (ii) any amino acid except proline or
glycine
<220> FEATURE:
<221> NAME/KEY: Unsure
<222> LOCATION: (239)..(239)
<223> OTHER INFORMATION: Xaa is present or absent, and when present is
(i) any amino acid or (ii) any amino acid except proline or
glycine
<220> FEATURE:
<221> NAME/KEY: Unsure
<222> LOCATION: (240)..(240)
<223> OTHER INFORMATION: Xaa is (i) any amino acid or (ii) any amino
acid except proline or glycine
<220> FEATURE:
<221> NAME/KEY: misc_feature
<222> LOCATION: (241)..(241)
<223> OTHER INFORMATION: Xaa can be any naturally occurring amino acid

<400> SEQUENCE: 158

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Xaa Xaa
65                  70                  75                  80

Xaa Xaa Xaa Cys Xaa Xaa Xaa Xaa Xaa Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Xaa Xaa Xaa Xaa Xaa Cys Xaa Xaa Xaa Xaa Xaa
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
            165                 170                 175

Glu Thr Leu Gln Arg Thr Asp Ala Pro Lys Thr His Met Thr His His
        180                 185                 190

Ala Val Ser Asp His Glu Ala Thr Leu Arg Cys Trp Ala Leu Ser Phe
    195                 200                 205

Tyr Pro Ala Glu Ile Thr Leu Thr Trp Gln Arg Asp Gly Glu Asp Gln
210                 215                 220

Thr Gln Asp Thr Glu Leu Xaa Xaa Xaa Xaa Cys Xaa Xaa Xaa Xaa
225                 230                 235                 240

Xaa Gln Lys Trp Ala Ala Val Val Val Pro Ser Gly Gln Glu Gln Arg
            245                 250                 255

-continued

```
Tyr Thr Cys His Val Gln His Glu Gly Leu Pro Lys Pro Leu Thr Leu
            260                 265                 270

Arg Trp Glu Pro
        275

<210> SEQ ID NO 159
<211> LENGTH: 5
<212> TYPE: PRT
<213> ORGANISM: Artificial Sequence
<220> FEATURE:
<223> OTHER INFORMATION: Val-Pro-Gly-X-Gly pentapeptide
<220> FEATURE:
<221> NAME/KEY: unsure
<222> LOCATION: (4)..(4)
<223> OTHER INFORMATION: Xaa is any amino acid other than proline

<400> SEQUENCE: 159

Val Pro Gly Xaa Gly
1               5

<210> SEQ ID NO 160
<211> LENGTH: 135
<212> TYPE: PRT
<213> ORGANISM: Artificial Sequence
<220> FEATURE:
<223> OTHER INFORMATION: PEPTIDE COSTRUCT

<400> SEQUENCE: 160

Met Ser Arg Ser Val Ala Leu Ala Val Leu Ala Leu Leu Ser Leu Ser
1               5                   10                  15

Gly Leu Glu Ala Gly Gly Gly Ser Leu Cys Thr Pro Ser Arg Gly
            20                  25                  30

Gly Gly Gly Ser Ile Gln Arg Thr Pro Lys Ile Gln Val Tyr Ser Cys
        35                  40                  45

His Pro Ala Glu Asn Gly Lys Ser Asn Phe Leu Asn Cys Tyr Val Ser
    50                  55                  60

Gly Phe His Pro Ser Asp Ile Glu Val Asp Leu Leu Lys Asn Gly Glu
65                  70                  75                  80

Arg Ile Glu Lys Val Glu His Ser Asp Leu Ser Phe Ser Lys Asp Trp
                85                  90                  95

Ser Phe Tyr Leu Leu Tyr Tyr Thr Glu Phe Thr Pro Thr Glu Lys Asp
            100                 105                 110

Glu Tyr Ala Cys Arg Val Asn His Val Thr Leu Ser Gln Pro Lys Ile
        115                 120                 125

Val Lys Trp Asp Arg Asp Met
    130                 135

<210> SEQ ID NO 161
<211> LENGTH: 833
<212> TYPE: PRT
<213> ORGANISM: Artificial Sequence
<220> FEATURE:
<223> OTHER INFORMATION: PEPTIDE CONSTRUCT

<400> SEQUENCE: 161

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu Ala Leu Leu Leu Asp Leu Gln Met Ile Leu Asn Gly Ile
        35                  40                  45
```

```
Asn Asn Tyr Lys Asn Pro Lys Leu Thr Arg Met Leu Thr Ala Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Ser Gly Gly Gly Ser Ala Pro Thr
                165                 170                 175

Ser Ser Ser Thr Lys Lys Thr Gln Leu Gln Leu Glu Ala Leu Leu Leu
            180                 185                 190

Asp Leu Gln Met Ile Leu Asn Gly Ile Asn Asn Tyr Lys Asn Pro Lys
        195                 200                 205

Leu Thr Arg Met Leu Thr Ala Lys Phe Tyr Met Pro Lys Lys Ala Thr
    210                 215                 220

Glu Leu Lys His Leu Gln Cys Leu Glu Glu Glu Leu Lys Pro Leu Glu
225                 230                 235                 240

Glu Val Leu Asn Leu Ala Gln Ser Lys Asn Phe His Leu Arg Pro Arg
                245                 250                 255

Asp Leu Ile Ser Asn Ile Asn Val Ile Val Leu Glu Leu Lys Gly Ser
            260                 265                 270

Glu Thr Thr Phe Met Cys Glu Tyr Ala Asp Glu Thr Ala Thr Ile Val
        275                 280                 285

Glu Phe Leu Asn Arg Trp Ile Thr Phe Cys Gln Ser Ile Ile Ser Thr
    290                 295                 300

Leu Thr Gly Gly Gly Gly Ser Gly Gly Gly Ser Gly Gly Gly Gly
305                 310                 315                 320

Ser Gly Gly Gly Ser Gly Ser His Ser Met Arg Tyr Phe Phe Thr
                325                 330                 335

Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
        355                 360                 365

Gln Arg Met Glu Pro Arg Ala Pro Trp Ile Glu Gln Glu Gly Pro Glu
    370                 375                 380

Tyr Trp Asp Gly Glu Thr Arg Lys Val Lys Ala His Ser Gln Thr His
385                 390                 395                 400

Arg Val Asp Leu Gly Thr Leu Arg Gly Cys Tyr Asn Gln Ser Glu Ala
                405                 410                 415

Gly Ser His Thr Val Gln Arg Met Tyr Gly Cys Asp Val Gly Ser Asp
            420                 425                 430

Trp Arg Phe Leu Arg Gly Tyr His Gln Tyr Ala Tyr Asp Gly Lys Asp
        435                 440                 445

Tyr Ile Ala Leu Lys Glu Asp Leu Arg Ser Trp Thr Ala Ala Asp Met
    450                 455                 460
```

```
Cys Ala Gln Thr Thr Lys His Lys Trp Glu Ala His Val Ala Glu
465                 470                 475                 480

Gln Leu Arg Ala Tyr Leu Glu Gly Thr Cys Val Glu Trp Leu Arg Arg
                485                 490                 495

Tyr Leu Glu Asn Gly Lys Glu Thr Leu Gln Arg Thr Asp Ala Pro Lys
                500                 505                 510

Thr His Met Thr His His Ala Val Ser Asp His Glu Ala Thr Leu Arg
            515                 520                 525

Cys Trp Ala Leu Ser Phe Tyr Pro Ala Glu Ile Thr Leu Thr Trp Gln
530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
                565                 570                 575

Ser Gly Gln Glu Gln Arg Tyr Thr Cys His Val Gln His Glu Gly Leu
                580                 585                 590

Pro Lys Pro Leu Thr Leu Arg Trp Glu Ala Ala Gly Gly Asp Lys
                595                 600                 605

Thr His Thr Cys Pro Pro Cys Pro Ala Pro Glu Ala Ala Gly Gly Pro
            610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
                660                 665                 670

Ala Lys Thr Lys Pro Arg Glu Glu Gln Tyr Asn Ser Thr Tyr Arg Val
            675                 680                 685

Val Ser Val Leu Thr Val Leu His Gln Asp Trp Leu Asn Gly Lys Glu
            690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
                740                 745                 750

Cys Leu Val Lys Gly Phe Tyr Pro Ser Asp Ile Ala Val Glu Trp Glu
            755                 760                 765

Ser Asn Gly Gln Pro Glu Asn Asn Tyr Lys Thr Thr Pro Pro Val Leu
770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys
```

<210> SEQ ID NO 162
<211> LENGTH: 527
<212> TYPE: PRT
<213> ORGANISM: Artificial Sequence
<220> FEATURE:
<223> OTHER INFORMATION: PEPTIDE CONSTRUCT

```
<400> SEQUENCE: 162

Met Tyr Arg Met Gln Leu Leu Ser Cys Ile Ala Leu Ser Leu Ala Leu
1               5                   10                  15

Val Thr Asn Ser Gly Ser His Ser Met Arg Tyr Phe Tyr Thr Ser Val
            20                  25                  30

Ser Arg Pro Gly Arg Gly Glu Pro Arg Phe Ile Ala Val Gly Tyr Val
        35                  40                  45

Asp Asp Thr Gln Phe Val Arg Phe Asp Ser Asp Ala Ala Ser Gln Arg
    50                  55                  60

Met Glu Pro Arg Ala Pro Trp Ile Glu Gln Glu Gly Pro Glu Tyr Trp
65                  70                  75                  80

Asp Gln Glu Thr Arg Asn Val Lys Ala Gln Ser Gln Thr Asp Arg Val
                85                  90                  95

Asp Leu Gly Thr Leu Arg Gly Cys Tyr Asn Gln Ser Glu Asp Gly Ser
            100                 105                 110

His Thr Ile Gln Ile Met Tyr Gly Cys Asp Val Gly Pro Asp Gly Arg
        115                 120                 125

Phe Leu Arg Gly Tyr Arg Gln Asp Ala Tyr Asp Gly Lys Asp Tyr Ile
    130                 135                 140

Ala Leu Asn Glu Asp Leu Arg Ser Trp Thr Ala Ala Asp Met Cys Ala
145                 150                 155                 160

Gln Ile Thr Lys Arg Lys Trp Glu Ala His Ala Ala Glu Gln Gln
                165                 170                 175

Arg Ala Tyr Leu Glu Gly Thr Cys Val Glu Trp Leu Arg Arg Tyr Leu
            180                 185                 190

Glu Asn Gly Lys Glu Thr Leu Gln Arg Thr Asp Pro Pro Lys Thr His
        195                 200                 205

Met Thr His His Pro Ile Ser Asp His Glu Ala Thr Leu Arg Cys Trp
    210                 215                 220

Ala Leu Gly Phe Tyr Pro Ala Glu Ile Thr Leu Thr Trp Gln Arg Asp
225                 230                 235                 240

Gly Glu Asp Gln Thr Gln Asp Thr Glu Leu Val Glu Thr Arg Pro Cys
                245                 250                 255

Gly Asp Gly Thr Phe Gln Lys Trp Ala Ala Val Val Pro Ser Gly
            260                 265                 270

Glu Glu Gln Arg Tyr Thr Cys His Val Gln His Glu Gly Leu Pro Lys
        275                 280                 285

Pro Leu Thr Leu Arg Trp Glu Ala Ala Gly Gly Asp Lys Thr His
    290                 295                 300

Thr Cys Pro Pro Cys Pro Ala Pro Glu Ala Ala Gly Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415
```

```
Ser Lys Ala Lys Gly Gln Pro Arg Glu Pro Gln Val Tyr Thr Leu Pro
            420                 425                 430

Pro Ser Arg Glu Glu Met Thr Lys Asn Gln Val Ser Leu Thr Cys Leu
        435                 440                 445

Val Lys Gly Phe Tyr Pro Ser Asp Ile Ala Val Glu Trp Glu Ser Asn
450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
                500                 505                 510

His Asn His Tyr Thr Gln Lys Ser Leu Ser Leu Ser Pro Gly Lys
            515                 520                 525

<210> SEQ ID NO 163
<211> LENGTH: 275
<212> TYPE: PRT
<213> ORGANISM: Artificial Sequence
<220> FEATURE:
<223> OTHER INFORMATION: PEPTIDE CONSTRUCT

<400> SEQUENCE: 163

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
50                  55                  60

Arg Asn Val Lys Ala Gln Ser Gln Thr Asp Arg Val Asp Leu Gly Thr
65                  70                  75                  80

Leu Arg Gly Cys Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Cys Ala Gln Ile Thr Lys
130                 135                 140

Arg Lys Trp Glu Ala Ala His Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Cys Gly Asp Gly Thr
225                 230                 235                 240

Phe Gln Lys Trp Ala Ala Val Val Val Pro Ser Gly Glu Glu Gln Arg
                245                 250                 255
```

-continued

Tyr Thr Cys His Val Gln His Glu Gly Leu Pro Lys Pro Leu Thr Leu
            260                 265                 270
Arg Trp Glu
        275

<210> SEQ ID NO 164
<211> LENGTH: 833
<212> TYPE: PRT
<213> ORGANISM: Artificial Sequence
<220> FEATURE:
<223> OTHER INFORMATION: PEPTIDE CONSTRUCT

<400> SEQUENCE: 164

Met Tyr Arg Met Gln Leu Leu Ser Cys Ile Ala Leu Ser Leu Ala Leu
1               5                   10                  15
Val Thr Asn Ser Ala Pro Thr Ser Ser Thr Lys Lys Thr Gln Leu
            20                  25                  30
Gln Leu Glu Ala Leu Leu Leu Asp Leu Gln Met Ile Leu Asn Gly Ile
        35                  40                  45
Asn Asn Tyr Lys Asn Pro Lys Leu Thr Arg Met Leu Thr Ala Lys Phe
    50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
    130                 135                 140
Cys Gln Ser Ile Ile Ser Thr Leu Thr Gly Gly Gly Gly Ser Gly Gly
145                 150                 155                 160
Gly Gly Ser Gly Gly Gly Gly Ser Gly Gly Gly Gly Ser Ala Pro Thr
                165                 170                 175
Ser Ser Ser Thr Lys Lys Thr Gln Leu Gln Leu Glu Ala Leu Leu Leu
            180                 185                 190
Asp Leu Gln Met Ile Leu Asn Gly Ile Asn Asn Tyr Lys Asn Pro Lys
        195                 200                 205
Leu Thr Arg Met Leu Thr Ala Lys Phe Tyr Met Pro Lys Lys Ala Thr
    210                 215                 220
Glu Leu Lys His Leu Gln Cys Leu Glu Glu Glu Leu Lys Pro Leu Glu
225                 230                 235                 240
Glu Val Leu Asn Leu Ala Gln Ser Lys Asn Phe His Leu Arg Pro Arg
                245                 250                 255
Asp Leu Ile Ser Asn Ile Asn Val Ile Val Leu Glu Leu Lys Gly Ser
            260                 265                 270
Glu Thr Thr Phe Met Cys Glu Tyr Ala Asp Glu Thr Ala Thr Ile Val
        275                 280                 285
Glu Phe Leu Asn Arg Trp Ile Thr Phe Cys Gln Ser Ile Ile Ser Thr
    290                 295                 300
Leu Thr Gly Gly Gly Gly Ser Gly Gly Gly Gly Ser Gly Gly Gly Gly
305                 310                 315                 320
Ser Gly Gly Gly Gly Ser Gly Ser His Ser Met Arg Tyr Phe Tyr Thr
                325                 330                 335

```
Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
            355                 360                 365

Gln Arg Met Glu Pro Arg Ala Pro Trp Ile Glu Gln Glu Gly Pro Glu
            370                 375                 380

Tyr Trp Asp Gln Glu Thr Arg Asn Val Lys Ala Gln Ser Gln Thr Asp
385                 390                 395                 400

Arg Val Asp Leu Gly Thr Leu Arg Gly Cys Tyr Asn Gln Ser Glu Asp
            405                 410                 415

Gly Ser His Thr Ile Gln Ile Met Tyr Gly Cys Asp Val Gly Pro Asp
            420                 425                 430

Gly Arg Phe Leu Arg Gly Tyr Arg Gln Asp Ala Tyr Asp Gly Lys Asp
            435                 440                 445

Tyr Ile Ala Leu Asn Glu Asp Leu Arg Ser Trp Thr Ala Ala Asp Met
            450                 455                 460

Cys Ala Gln Ile Thr Lys Arg Lys Trp Glu Ala Ala His Ala Ala Glu
465                 470                 475                 480

Gln Gln Arg Ala Tyr Leu Glu Gly Thr Cys Val Glu Trp Leu Arg Arg
            485                 490                 495

Tyr Leu Glu Asn Gly Lys Glu Thr Leu Gln Arg Thr Asp Pro Pro Lys
            500                 505                 510

Thr His Met Thr His His Pro Ile Ser Asp His Glu Ala Thr Leu Arg
            515                 520                 525

Cys Trp Ala Leu Gly Phe Tyr Pro Ala Glu Ile Thr Leu Thr Trp Gln
            530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
            565                 570                 575

Ser Gly Glu Glu Gln Arg Tyr Thr Cys His Val Gln His Glu Gly Leu
            580                 585                 590

Pro Lys Pro Leu Thr Leu Arg Trp Glu Ala Ala Ala Gly Gly Asp Lys
            595                 600                 605

Thr His Thr Cys Pro Pro Cys Pro Ala Pro Glu Ala Ala Gly Gly Pro
            610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
            645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
            675                 680                 685

Val Ser Val Leu Thr Val Leu His Gln Asp Trp Leu Asn Gly Lys Glu
            690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
            725                 730                 735

Leu Pro Pro Ser Arg Glu Glu Met Thr Lys Asn Gln Val Ser Leu Thr
            740                 745                 750
```

```
Cys Leu Val Lys Gly Phe Tyr Pro Ser Asp Ile Ala Val Glu Trp Glu
            755                 760                 765

Ser Asn Gly Gln Pro Glu Asn Asn Tyr Lys Thr Thr Pro Pro Val Leu
        770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys

<210> SEQ ID NO 165
<211> LENGTH: 552
<212> TYPE: PRT
<213> ORGANISM: Artificial Sequence
<220> FEATURE:
<223> OTHER INFORMATION: PROTEIN CONSTRUCT

<400> SEQUENCE: 165

Met Tyr Arg Met Gln Leu Leu Ser Cys Ile Ala Leu Ser Leu Ala Leu
1               5                   10                  15

Val Thr Asn Ser Gly Ser His Ser Met Arg Tyr Phe Tyr Thr Ser Val
            20                  25                  30

Ser Arg Pro Gly Arg Gly Glu Pro Arg Phe Ile Ala Val Gly Tyr Val
        35                  40                  45

Asp Asp Thr Gln Phe Val Arg Phe Asp Ser Asp Ala Ala Ser Gln Arg
50                  55                  60

Met Glu Pro Arg Ala Pro Trp Ile Glu Gln Glu Gly Pro Glu Tyr Trp
65                  70                  75                  80

Asp Gln Glu Thr Arg Asn Val Lys Ala Gln Ser Gln Thr Asp Arg Val
                85                  90                  95

Asp Leu Gly Thr Leu Arg Gly Cys Tyr Asn Gln Ser Glu Asp Gly Ser
            100                 105                 110

His Thr Ile Gln Ile Met Tyr Gly Cys Asp Val Gly Pro Asp Gly Arg
        115                 120                 125

Phe Leu Arg Gly Tyr Arg Gln Asp Ala Tyr Asp Gly Lys Asp Tyr Ile
130                 135                 140

Ala Leu Asn Glu Asp Leu Arg Ser Trp Thr Ala Ala Asp Met Cys Ala
145                 150                 155                 160

Gln Ile Thr Lys Arg Lys Trp Glu Ala Ala His Ala Ala Glu Gln Gln
                165                 170                 175

Arg Ala Tyr Leu Glu Gly Thr Cys Val Glu Trp Leu Arg Arg Tyr Leu
            180                 185                 190

Glu Asn Gly Lys Glu Thr Leu Gln Arg Thr Asp Pro Pro Lys Thr His
        195                 200                 205

Met Thr His His Pro Ile Ser Asp His Glu Ala Thr Leu Arg Cys Trp
210                 215                 220

Ala Leu Gly Phe Tyr Pro Ala Glu Ile Thr Leu Thr Trp Gln Arg Asp
225                 230                 235                 240

Gly Glu Asp Gln Thr Gln Asp Thr Glu Leu Val Glu Thr Arg Pro Cys
                245                 250                 255

Gly Asp Gly Thr Phe Gln Lys Trp Ala Ala Val Val Val Pro Ser Gly
            260                 265                 270

Glu Glu Gln Arg Tyr Thr Cys His Val Gln His Glu Gly Leu Pro Lys
```

```
                275                 280                 285
Pro Leu Thr Leu Arg Trp Glu Gly Gly Gly Ser Gly Gly Gly Gly
    290                 295                 300

Ser Gly Gly Gly Ser Gly Gly Gly Ser Gly Gly Gly Ser
305                 310                 315                 320

Gly Gly Gly Gly Ser Asp Lys Thr His Thr Cys Pro Pro Cys Pro Ala
                325                 330                 335

Pro Glu Ala Ala Gly Gly Pro Ser Val Phe Leu Phe Pro Pro Lys Pro
                340                 345                 350

Lys Asp Thr Leu Met Ile Ser Arg Thr Pro Glu Val Thr Cys Val Val
                355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
                420                 425                 430

Leu Pro Ala Pro Ile Glu Lys Thr Ile Ser Lys Ala Lys Gly Gln Pro
                435                 440                 445

Arg Glu Pro Gln Val Tyr Thr Leu Pro Pro Ser Arg Glu Glu Met Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
                500                 505                 510

Ser Lys Leu Thr Val Asp Lys Ser Arg Trp Gln Gln Gly Asn Val Phe
    515                 520                 525

Ser Cys Ser Val Met His Glu Ala Leu His Asn His Tyr Thr Gln Lys
530                 535                 540

Ser Leu Ser Leu Ser Pro Gly Lys
545                 550
```

<210> SEQ ID NO 166
<211> LENGTH: 858
<212> TYPE: PRT
<213> ORGANISM: Artificial Sequence
<220> FEATURE:
<223> OTHER INFORMATION: PEPTIDE CONSTRUCT

<400> SEQUENCE: 166

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu Ala Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
```

```
                  85                  90                  95
Asn Phe His Leu Arg Pro Arg Asp Leu Ile Ser Asn Ile Asn Val Ile
                100                 105                 110
Val Leu Glu Leu Lys Gly Ser Glu Thr Thr Phe Met Cys Glu Tyr Ala
                115                 120                 125
Asp Glu Thr Ala Thr Ile Val Glu Phe Leu Asn Arg Trp Ile Thr Phe
            130                 135                 140
Cys Gln Ser Ile Ile Ser Thr Leu Thr Gly Gly Gly Ser Gly Gly
145                 150                 155                 160
Gly Gly Ser Gly Gly Gly Ser Gly Gly Gly Ser Ala Pro Thr
                165                 170                 175
Ser Ser Ser Thr Lys Lys Thr Gln Leu Gln Leu Glu Ala Leu Leu Leu
                180                 185                 190
Asp Leu Gln Met Ile Leu Asn Gly Ile Asn Asn Tyr Lys Asn Pro Lys
                195                 200                 205
Leu Thr Arg Met Leu Thr Ala Lys Phe Tyr Met Pro Lys Lys Ala Thr
            210                 215                 220
Glu Leu Lys His Leu Gln Cys Leu Glu Glu Leu Lys Pro Leu Glu
225                 230                 235                 240
Glu Val Leu Asn Leu Ala Gln Ser Lys Asn Phe His Leu Arg Pro Arg
                245                 250                 255
Asp Leu Ile Ser Asn Ile Asn Val Ile Val Leu Glu Leu Lys Gly Ser
            260                 265                 270
Glu Thr Thr Phe Met Cys Glu Tyr Ala Asp Glu Thr Ala Thr Ile Val
            275                 280                 285
Glu Phe Leu Asn Arg Trp Ile Thr Phe Cys Gln Ser Ile Ile Ser Thr
            290                 295                 300
Leu Thr Gly Gly Gly Gly Ser Gly Gly Gly Ser Gly Gly Gly Gly
305                 310                 315                 320
Ser Gly Gly Gly Ser Gly Ser His Ser Met Arg Tyr Phe Tyr Thr
                325                 330                 335
Ser Val Ser Arg Pro Gly Arg Gly Glu Pro Arg Phe Ile Ala Val Gly
            340                 345                 350
Tyr Val Asp Asp Thr Gln Phe Val Arg Phe Asp Ser Asp Ala Ala Ser
            355                 360                 365
Gln Arg Met Glu Pro Arg Ala Pro Trp Ile Glu Gln Glu Gly Pro Glu
            370                 375                 380
Tyr Trp Asp Gln Glu Thr Arg Asn Val Lys Ala Gln Ser Gln Thr Asp
385                 390                 395                 400
Arg Val Asp Leu Gly Thr Leu Arg Gly Cys Tyr Asn Gln Ser Glu Asp
                405                 410                 415
Gly Ser His Thr Ile Gln Ile Met Tyr Gly Cys Asp Val Gly Pro Asp
            420                 425                 430
Gly Arg Phe Leu Arg Gly Tyr Arg Gln Asp Ala Tyr Asp Gly Lys Asp
            435                 440                 445
Tyr Ile Ala Leu Asn Glu Asp Leu Arg Ser Trp Thr Ala Ala Asp Met
            450                 455                 460
Cys Ala Gln Ile Thr Lys Arg Lys Trp Glu Ala Ala His Ala Ala Glu
465                 470                 475                 480
Gln Gln Arg Ala Tyr Leu Glu Gly Thr Cys Val Glu Trp Leu Arg Arg
                485                 490                 495
Tyr Leu Glu Asn Gly Lys Glu Thr Leu Gln Arg Thr Asp Pro Pro Lys
                500                 505                 510
```

```
Thr His Met Thr His His Pro Ile Ser Asp His Glu Ala Thr Leu Arg
        515                 520                 525
Cys Trp Ala Leu Gly Phe Tyr Pro Ala Glu Ile Thr Leu Thr Trp Gln
530                 535                 540
Arg Asp Gly Glu Asp Gln Thr Gln Asp Thr Glu Leu Val Glu Thr Arg
545                 550                 555                 560
Pro Cys Gly Asp Gly Thr Phe Gln Lys Trp Ala Ala Val Val Val Pro
                565                 570                 575
Ser Gly Glu Glu Gln Arg Tyr Thr Cys His Val Gln His Glu Gly Leu
                580                 585                 590
Pro Lys Pro Leu Thr Leu Arg Trp Glu Gly Gly Gly Ser Gly Gly
        595                 600                 605
Gly Gly Ser Gly Gly Gly Gly Ser Gly Gly Gly Gly Ser Gly Gly Gly
        610                 615                 620
Gly Ser Gly Gly Gly Ser Asp Lys Thr His Thr Cys Pro Pro Cys
625                 630                 635                 640
Pro Ala Pro Glu Ala Ala Gly Gly Pro Ser Val Phe Leu Phe Pro Pro
                645                 650                 655
Lys Pro Lys Asp Thr Leu Met Ile Ser Arg Thr Pro Glu Val Thr Cys
                660                 665                 670
Val Val Val Asp Val Ser His Glu Asp Pro Glu Val Lys Phe Asn Trp
                675                 680                 685
Tyr Val Asp Gly Val Glu Val His Asn Ala Lys Thr Lys Pro Arg Glu
                690                 695                 700
Glu Gln Tyr Asn Ser Thr Tyr Arg Val Val Ser Val Leu Thr Val Leu
705                 710                 715                 720
His Gln Asp Trp Leu Asn Gly Lys Glu Tyr Lys Cys Lys Val Ser Asn
                725                 730                 735
Lys Ala Leu Pro Ala Pro Ile Glu Lys Thr Ile Ser Lys Ala Lys Gly
                740                 745                 750
Gln Pro Arg Glu Pro Gln Val Tyr Thr Leu Pro Pro Ser Arg Glu Glu
        755                 760                 765
Met Thr Lys Asn Gln Val Ser Leu Thr Cys Leu Val Lys Gly Phe Tyr
        770                 775                 780
Pro Ser Asp Ile Ala Val Glu Trp Glu Ser Asn Gly Gln Pro Glu Asn
785                 790                 795                 800
Asn Tyr Lys Thr Thr Pro Pro Val Leu Asp Ser Asp Gly Ser Phe Phe
                805                 810                 815
Leu Tyr Ser Lys Leu Thr Val Asp Lys Ser Arg Trp Gln Gln Gly Asn
                820                 825                 830
Val Phe Ser Cys Ser Val Met His Glu Ala Leu His Asn His Tyr Thr
                835                 840                 845
Gln Lys Ser Leu Ser Leu Ser Pro Gly Lys
        850                 855

<210> SEQ ID NO 167
<211> LENGTH: 20
<212> TYPE: PRT
<213> ORGANISM: Homo sapiens

<400> SEQUENCE: 167

Met Ser Arg Ser Val Ala Leu Ala Val Leu Ala Leu Leu Ser Leu Ser
1                 5                  10                  15

Gly Leu Glu Ala
```

-continued

```
                20

<210> SEQ ID NO 168
<211> LENGTH: 20
<212> TYPE: PRT
<213> ORGANISM: Homo sapiens

<400> SEQUENCE: 168

Met Tyr Arg Met Gln Leu Leu Ser Cys Ile Ala Leu Ser Leu Ala Leu
1               5                   10                  15

Val Thr Asn Ser
            20

<210> SEQ ID NO 169
<211> LENGTH: 833
<212> TYPE: PRT
<213> ORGANISM: Artificial Sequence
<220> FEATURE:
<223> OTHER INFORMATION: PROTEIN CONSTRUCT

<400> SEQUENCE: 169

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu Ala Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Ser Gly Gly
145                 150                 155                 160

Gly Gly Ser Gly Gly Gly Gly Ser Gly Gly Gly Gly Ser Ala Pro Thr
                165                 170                 175

Ser Ser Ser Thr Lys Lys Thr Gln Leu Gln Leu Glu Ala Leu Leu Leu
            180                 185                 190

Asp Leu Gln Met Ile Leu Asn Gly Ile Asn Asn Tyr Lys Asn Pro Lys
        195                 200                 205

Leu Thr Arg Met Leu Thr Ala Lys Phe Tyr Met Pro Lys Lys Ala Thr
    210                 215                 220

Glu Leu Lys His Leu Gln Cys Leu Glu Glu Glu Leu Lys Pro Leu Glu
225                 230                 235                 240

Glu Val Leu Asn Leu Ala Gln Ser Lys Asn Phe His Leu Arg Pro Arg
                245                 250                 255

Asp Leu Ile Ser Asn Ile Asn Val Ile Val Leu Glu Leu Lys Gly Ser
            260                 265                 270

Glu Thr Thr Phe Met Cys Glu Tyr Ala Asp Glu Thr Ala Thr Ile Val
        275                 280                 285
```

```
Glu Phe Leu Asn Arg Trp Ile Thr Phe Cys Gln Ser Ile Ile Ser Thr
    290                 295                 300

Leu Thr Gly Gly Gly Gly Ser Gly Gly Gly Gly Ser Gly Gly Gly Gly
305                 310                 315                 320

Ser Gly Gly Gly Gly Ser Gly Ser His Ser Met Arg Tyr Phe Tyr Thr
                325                 330                 335

Ser Val Ser Arg Pro Gly Arg Gly Glu Pro Arg Phe Ile Ala Val Gly
            340                 345                 350

Tyr Val Asp Asp Thr Gln Phe Val Arg Phe Asp Ser Asp Ala Ala Ser
        355                 360                 365

Gln Arg Met Glu Pro Arg Ala Pro Trp Ile Glu Gln Glu Gly Pro Glu
370                 375                 380

Tyr Trp Asp Gln Glu Thr Arg Asn Val Lys Ala Gln Ser Gln Thr Asp
385                 390                 395                 400

Arg Val Asp Leu Gly Thr Leu Arg Gly Cys Tyr Asn Gln Ser Glu Asp
                405                 410                 415

Gly Ser His Thr Ile Gln Ile Met Tyr Gly Cys Asp Val Gly Pro Asp
            420                 425                 430

Gly Arg Phe Leu Arg Gly Tyr Arg Gln Asp Ala Tyr Asp Gly Lys Asp
        435                 440                 445

Tyr Ile Ala Leu Asn Glu Asp Leu Arg Ser Trp Thr Cys Ala Asp Met
450                 455                 460

Cys Ala Gln Ile Thr Lys Arg Lys Trp Glu Ala Ala His Ala Ala Glu
465                 470                 475                 480

Gln Gln Arg Ala Tyr Leu Glu Gly Thr Cys Val Glu Trp Leu Arg Arg
                485                 490                 495

Tyr Leu Glu Asn Gly Lys Glu Thr Leu Gln Arg Thr Asp Pro Pro Lys
            500                 505                 510

Thr His Met Thr His His Pro Ile Ser Asp His Glu Ala Thr Leu Arg
        515                 520                 525

Cys Trp Ala Leu Gly Phe Tyr Pro Ala Glu Ile Thr Leu Thr Trp Gln
530                 535                 540

Arg Asp Gly Glu Asp Gln Thr Gln Asp Thr Glu Leu Val Glu Thr Arg
545                 550                 555                 560

Pro Cys Gly Asp Gly Thr Phe Gln Lys Trp Ala Ala Val Val Val Pro
                565                 570                 575

Ser Gly Glu Glu Gln Arg Tyr Thr Cys His Val Gln His Glu Gly Leu
            580                 585                 590

Pro Lys Pro Leu Thr Leu Arg Trp Glu Ala Ala Ala Gly Gly Asp Lys
        595                 600                 605

Thr His Thr Cys Pro Pro Cys Pro Ala Pro Glu Ala Ala Gly Gly Pro
610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
        675                 680                 685

Val Ser Val Leu Thr Val Leu His Gln Asp Trp Leu Asn Gly Lys Glu
690                 695                 700
```

```
Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
    770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys

<210> SEQ ID NO 170
<211> LENGTH: 9
<212> TYPE: PRT
<213> ORGANISM: cytomegalovirus

<400> SEQUENCE: 170

Asn Leu Val Pro Met Val Ala Thr Val
1               5
```

T-CELL MODULATORY MULTIMERIC POLYPEPTIDE WITH CONJUGATION SITES AND METHODS OF USE THEREOF

This application is a continuation of International Application No. PCT/US2018/049803, filed Sep. 6, 2018, which claims the benefit of U.S. Provisional Patent Application No. 62/555,559, filed Sep. 7, 2017, U.S. Provisional Patent Application No. 62/609,082, filed Dec. 21, 2017, and U.S. Provisional Patent Application No. 62/615,402, filed Jan. 9, 2018.

This application contains a sequence listing submitted electronically via EFS-web, which serves as both the paper copy and the computer readable form (CRF) and consists of a file entitled "123640-8001US03_seqlist.txt", which was created on Mar. 6, 2020, which is 196,228 bytes in size, and which is herein incorporated by reference in its entirety.

INTRODUCTION

An adaptive immune response involves the engagement of the T-cell receptor (TCR), present on the surface of a T-cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T-cell modulation (activation or inhibition) and effector function. Following epitope-specific cell targeting, the targeted T-cells are activated through engagement of costimulatory proteins found on the APC with counterpart costimulatory proteins on the T-cells. Both signals—epitope/TCR binding and engagement of APC costimulatory proteins with T-cell costimulatory proteins—are required to drive T-cell specificity and activation or inhibition. The TCR is specific for a given epitope; however, the costimulatory protein is not epitope specific and instead is generally expressed on all T-cells or on large T-cell subsets.

SUMMARY

The present disclosure provides T-cell modulatory multimeric polypeptides (a "T-Cell-MMP" or multiple "T-Cell-MMPs") that in one embodiment comprise a portion of a MHC receptor and at least one immunomodulatory polypeptide (also referred to herein as a "MOD polypeptide" or simply, a "MOD"). Any one or more of the MODs present in the T-Cell-MMP may be wild-type or a variant that exhibits reduced binding affinity to its cellular (e.g., T-cell surface) binding partner/receptor (generally referred to as a "Co-MOD"). The T-Cell-MMPs comprise at least one chemical conjugation site at which a molecule comprising a target epitope (e.g., a peptide or non-peptide such as a carbohydrate) may be covalently bound for presentation to a cell bearing a T-cell receptor. T-Cell-MMPs comprising a chemical conjugation site for linking an epitope are useful for rapidly preparing T-Cell-MMP-epitope conjugates that can modulate the activity of T-cells specific to the epitope presented and, accordingly, for modulating an immune response in an individual involving those T-cells. The T-Cell-MMPs and their epitope conjugates may additionally comprise sites for the conjugation of bioactive substances (payloads) such as chemotherapeutic agents for co-delivery with a specific target epitope. As such, T-Cell-MMP-epitope conjugates may be considered a means by which to deliver immunomodulatory peptides (e.g., IL-2, 4-1BBL, FasL, TGFβ, CD70, CD80, CD86, OX40L, ICOS-L, ICAM, JAG1 or fragments thereof, or altered (mutated) variants thereof) and/or payloads (e.g., chemotherapeutics) to cells in an epitope specific manner.

In embodiments described herein the T-Cell-MMPs may comprise modifications that assist in the stabilization of the T-Cell-MMP during intracellular trafficking and/or following secretion by cells expressing the multimeric polypeptide even in the absence of an associated epitope peptide. In embodiments described herein the T-Cell-MMPs may include modifications that link the carboxyl end of the MHC-I $\alpha_1$ helix and the amino end of the MHC-I $\alpha_{2-1}$ helix. Such modifications include the insertion of cysteine residues that result in the formation of disulfide linkages linking the indicated regions of those helices. For example, the insertion of cysteine residues at amino acid 84 (Y84C substitution) and 139 (A139C substitution) of MHC-I, or the equivalent positions relative to the sequences forming the helices, may form a disulfide linkage that helps stabilize the T-Cell-MMP. See, e.g., Z. Hein et al. (2014), Journal of Cell Science 127:2885-2897.

BRIEF DESCRIPTION OF THE DRAWINGS

FIG. 1 depicts preferential activation of an epitope-specific T-cell to an epitope non-specific T-cell by an embodiment of a T-Cell-MMP of the present disclosure bearing a epitope attached by chemical coupling (denoted by "CC") to a β-2 microglobulin (β2M) polypeptide sequence.

FIGS. 2A-2G provide amino acid sequences of immunoglobulin Fc polypeptides (SEQ ID NOs. 1-12).

FIGS. 3A, 3B and 3C provide amino acid sequences of human leukocyte antigen (HLA) Class I heavy chain polypeptides. Signal sequences, amino acids 1-24, are bolded and underlined. FIG. 3A entry: 3A.1 is the HLA-A alpha chain (HLA-A*01:01:01:01) (NCBI accession NP_001229687.1), SEQ ID NO:134; entry 3A.2 is from HLA-A*1101 SEQ ID NO:135; entry 3A.3 is from HLA-A*2402 SEQ ID NO:136 and entry 3A.4 is from HLA-A*3303 SEQ ID NO:137.

FIG. 3D shows an alignment of eleven mature MHC Class I heavy chain peptide sequences without their leader sequences and without transmembrane domain regions. The aligned sequences include huma HLA-A, SEQ ID NO:140 (see also SEQ ID NO:134); HLA-B, SEQ ID NO:141 (see SEQ ID NO:138); HLA-C, SEQ ID NO:142 (see SEQ ID NO:139); HLA-A*0201, SEQ ID NO:143; a mouse H2K protein sequence, SEQ ID NO:144; three variants of HLA-A (var.2, var. 2C, and var.2CP, SEQ ID NOs:145-147); 3 huma HLA-A variants (HLA-A*1101 (HLA-A11), SEQ ID NO:148; HLA-A*2402 (HLA-A24), SEQ ID NO:149; and HLA-A*3303 (HLA-A33), SEQ ID NO:150)). HLA-A*0201 is a variant of HLA-A. Marked as HLA-A (var. 2) is the Y84A and A236C variant of HLA-A. The seventh HLA-A sequence, marked as HLA-A (var. 2C), shows HLA-A substituted with C residues at positions 84, 139 and 236, and the 8th sequence adds one additional proline to the C-terminus of the preceding sequence. The 9th through the 11th sequences are from HLA-A11 (HLA-A*1101), HLA-A24 (HLA-A*2402); and HLA-A33 (HLA-A*3303), respectively, which are prevalent in certain Asian populations. Indicated in the alignment are the locations (84 and 139 of the mature proteins) where cysteine residues may be inserted in place of the amino acid at that position for the formation of a disulfide bond to stabilize the MHC—β2M complex in the absence of a bound epitope peptide. Also shown in the alignment is position 236 (of the mature polypeptide), which may be replaced by a cysteine residue that can form an intra-chain disulfide bond with β2M (e.g., at aa 12 of the mature polypeptide). An arrow appears above each of those locations and the residues are bolded. The boxes flanking residues 84, 139 and 236 show the groups of five amino acids on either side of those six sets of five residues, denoted aa cluster 1, aa cluster 2, aa cluster 3, aa cluster 4, aa cluster 5, and aa cluster 6 (shown in the figure as aac 1 through aac 6, respectively), that may be replaced by 1 to 5 amino acids selected independently from (i) any naturally occurring amino acid or (ii) any naturally occurring amino acid except proline or glycine.

FIG. 4 provides a multiple amino acid sequence alignment of β2M precursors (i.e., including the leader sequence) from Homo sapiens (NP_004039.1; SEQ ID NO:151), Pan troglodytes (NP_001009066.1; SEQ ID NO:152), Macaca mulatta (NP_001040602.1; SEQ ID NO:153), Bos Taurus (NP_776318.1; SEQ ID NO:154) and Mus musculus (NP_033865.2; SEQ ID NO:155). Underlined amino acids 1-20 are the signal peptide (sometime referred to as a leader sequence).

FIG. 6 provides eight embodiments of T-Cell-MMP epitope conjugates, marked as A through H, that parallel the embodiments in FIG. 5. As in FIG. 5, the first polypeptide has an N-terminus and C-terminus with the first MHC polypeptide given as comprising a β-2-microglobulin polypeptide (β2M capable of interacting with the MHC Class I heavy chain (MHC-H) and presenting the epitope to a T-Cell receptor. The second polypeptide has an N-terminus and C-terminus, a MHC-H polypeptide, and optionally comprises an immunoglobulin (Fc) polypeptide or a non-Ig polypeptide scaffold. The optional disulfide bond joining the first and second polypeptide of the T-Cell-MMP epitope conjugates is shown connecting the β2M peptide sequence and MHC-H peptide sequence in A to D, and the independently selected optional linker sequences, indicated by the dashed line (- - -), are not required. In E to H, the complexes in A to D are repeated, however a disulfide bond joining the first and second polypeptide is shown joining the MHC-H peptide sequence to a linker sequence interposed between the epitope and β2M peptide sequence (e.g., a bond from a Cys residue at position 84 of a MHC-H chain sequence (see FIG. 3) to the interposed linker). The first polypeptide, the second polypeptide, or both the first and second polypeptides of the T-Cell-MMP may also comprise one or more chemical conjugation sites in addition to the site employed for the conjugation of the epitope. The potential locations for such CC-1 and CC-2 are shown by arrows. The one or more immunomodulatory polypeptides (either MODs or variant MODs) are as described in FIG. 5.

FIG. 9 shows in part A a map of a T-Cell-MMP with the first polypeptide having a sulfatase motif as the location for developing a chemical conjugation site (an fGly residue) through the action of an FGE enzyme. At B, FIG. 9 shows a second polypeptide of a T-Cell-MMP having tandem IL-2 MODs attached to the amino end of a human MHC Class I HLA-A heavy chain polypeptide followed by a human IgG1 Fc polypeptide.

FIG. 10A to FIG. 10 D show a series of HLA A*1101 heavy chain constructs having, from N-terminus to C-terminus, a human IL-2 signal sequence, shown in underline and bold. The signal (leader) sequence is followed by a MOD, which is indicated as a human IL-2 or an "optional peptide linker-immunomodulatory polypeptide-optional peptide linker." Where the MOD is not specified, it may be any desired MOD. The remainder of the sequence is HLA A*1101 H chain sequence with three cysteine substitutions (Y84C; A139C; A236C); a linker; and a hIgG1 Fc with two amino acid substitutions (L234A; L235A). The asterisk indicates stop to the sequence.

FIG. 11A to FIG. 11E shows a series of constructs comprising a human β2M polypeptide sequence. The constructs comprise from N-terminus to C-terminus: the leader sequence MSRSVALAVLALLSLSGLEA (bolded and underlined), an optional linker and sulfatase site and another independently selected linker as described in Examples 1 and 2, (linker)$_{0-4}$X1Z1X2Z2X3Z3(linker)$_{0-4}$, and a human β2M sequence with an R12C amino acid modification (IQRTPKIQVYSCHPAENGKSNFLNCYVSGFHPSDI-EVDLLKNGERIEKVEHS DLSFSKDWSFYLLY-YTEFTPTEKDEYACRVNHVTLSQPKIVKWDRDM). Following co-expression in a mammalian cell with a MHC Class I heavy chain containing polypeptide, such as the peptides in FIG. 10, to yield a T-Cell-MMP, the sulfatase sequence is enzymatically modified to contain a formyl glycine residue. A T-Cell-MMP conjugate can then be prepared by reacting the formyl glycine of the T-Cell-MMP with an HBV peptide (e.g., as shown in FIGS. 11A-11E) that have been modified to bear a hydrazinyl group (e.g., a hydrazinyl indole group) at, for example, their carboxyl terminus.

DEFINITIONS

Figure 5:
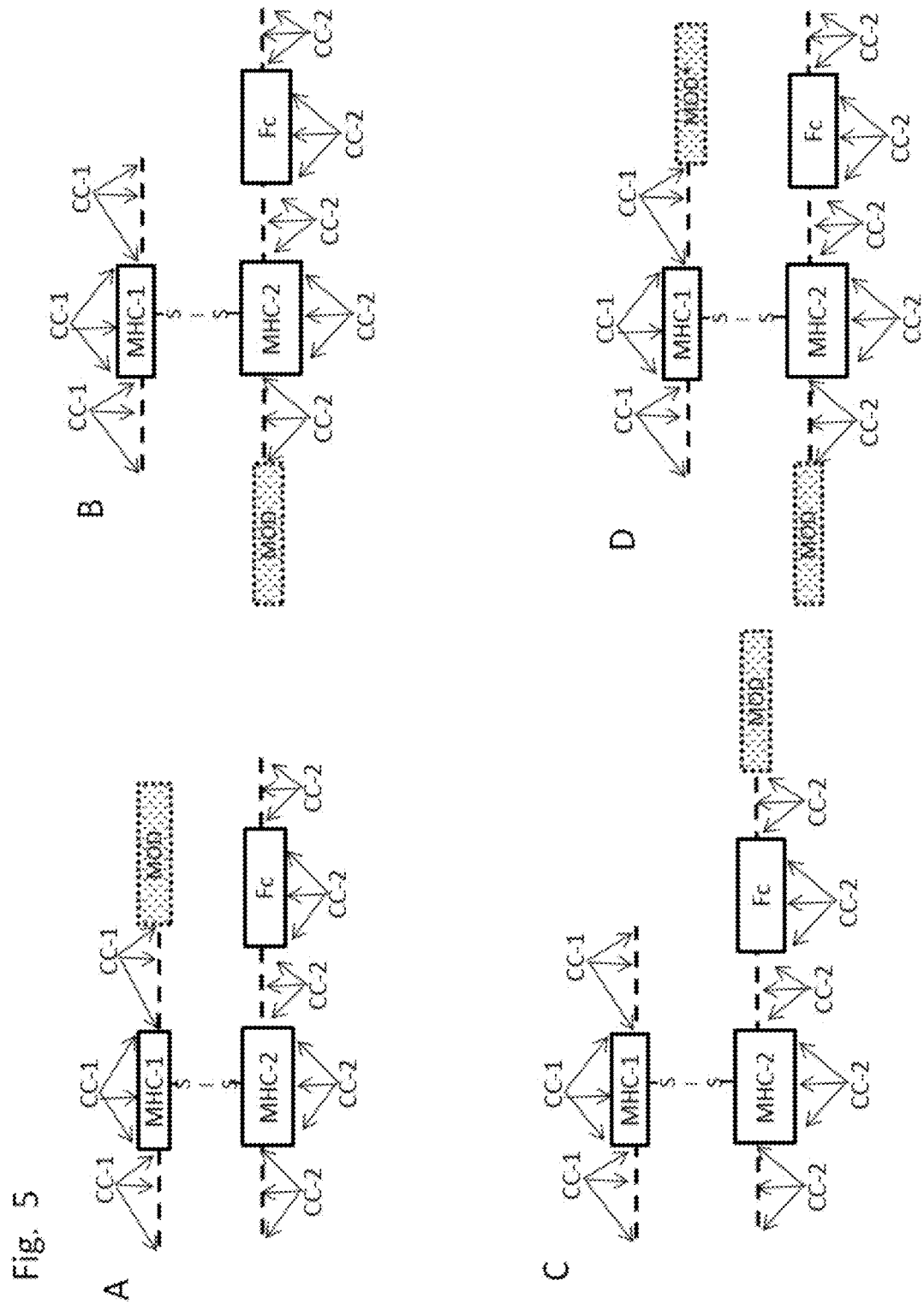
FIG. 5 provides four T-Cell-MMP embodiments marked as A through D. In each case the T-Cell-MMPs comprise: a first polypeptide having an N-terminus and C-terminus and which comprises a first major histocompatibility complex (MHC) polypeptide (MHC-1); and a second polypeptide having an N-terminus and C-terminus and a second MHC polypeptide (MHC-2), and optionally comprising an immunoglobulin (Fc) polypeptide or a non-Ig polypeptide scaffold. In the embodiments shown the first and second polypeptides are shown linked by a disulfide bond; however, the T-Cell-MMPs do not require a disulfide linkage or any other covalent linkage between the first and second polypeptides. The T-Cell-MMPs may also comprise independently selected linker sequences indicated by the dashed line (- - -). The first polypeptide, the second polypeptide, or both the first and second polypeptides of the T-Cell-MMP comprise at least one chemical conjugation site. Some potential locations for the first polypeptide chemical conjugation sites (CC-1) and second polypeptide chemical conjugation sites (CC-2) are shown by arrows. Locations for one or more MODs that are selected independently (e.g., a sequence comprising one, two, three or more MODs connected in sequence with optional amino acid linkers between the MODs) are shown by "MOD" in the stippled box. The MODs may contain variant MODs denoted by MOD* elsewhere in this disclosure. In A the MOD(s) are located at the C-terminus of the first polypeptide, in B the MOD(s) are located at the N-terminus of the second polypeptide, in C the MOD(s) are located at the C-terminus of the second polypeptide, and in D the MODs, which may be the same or different, are located at the C-terminus of the first polypeptide and at the N-terminus of the second polypeptide.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi nlm nili.gov/BLAST, ebi.ac.uk/Tools/msa/tcoffee/, ebi.ac.uk/Tools/msa/muscle/, and mafft.cbrc.jp/alignment/software/. See, e.g., Altschul et al. (1990), J. Mol. Biol. 215:403-10. Unless stated otherwise, sequence alignments are prepared using BLAST.

The terms "amino acid" and "amino acids" are abbreviated as "aa" and "aas," respectively. Naturally occurring amino acid or naturally occurring amino acids, unless stated otherwise, means: L (Leu, leucine), A (Ala, alanine), G (Gly, glycine), S (Ser, serine), V (Val, valine), F (Phe, phenylalanine), Y (Tyr, tyrosine), H (His, histidine), R (Arg, arginine), N (Asn, asparagine), E (Glu, glutamic acid), D (Asp, asparagine), C (Cys, cysteine), Q (Gln, glutamine), I (Ile, isoleucine), M (Met, methionine), P (Pro, proline), T (Thr, threonine), K (Lys, lysine), and W (Trp, tryptophan); all of the L-configuration. Both selenocysteine and hydroxyproline are naturally occurring amino acids that are specifically referred to in any instance where they are intended to be encompassed.

Non-natural amino acids are any amino acid other than the naturally occurring amino acids recited above, selenocysteine, and hydroxyproline.

"Chemical conjugation" as used herein means formation of a covalent bond. "Chemical conjugation site" as used herein means a location in a polypeptide at which a covalent bond can be formed, including any contextual elements (e.g., surrounding amino acid sequences) that are required or assist in the formation of a covalent bond to the polypeptide. Accordingly, a site comprising a group of amino acids that direct enzymatic modification, and ultimately covalent bond formation at an amino acid within the group, may also be referred to a chemical conjugation site. In some instances, as will be clear from the context, the term chemical conjugation site may be used to refer to a location where covalent bond formation or chemical modification has already occurred.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consists of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

The terms "immunological synapse" or "immune synapse" as used herein generally refer to the natural interface between two interacting immune cells of an adaptive immune response including, e.g., the interface between an APC, or target T-cell, and an effector cell, e.g., a lymphocyte, an effector T-cell, a natural killer cell, or the like. An immunological synapse between an APC and a T-cell is generally initiated by the interaction of a T-cell antigen receptor and one or more MHC molecules, e.g., as described in Bromley et al., Ann Rev Immunol. 2001; 19:375-96; the disclosure of which is incorporated herein by reference in its entirety.

"T-cell" includes all types of immune cells expressing CD3, including T-helper cells ($CD4^+$ cells), cytotoxic T-cells ($CD8^+$ cells), T-regulatory cells (Treg), and NK-T-cells.

Unless stated otherwise, as used herein, the terms "first major histocompatibility complex (MHC) polypeptide" or "first MHC polypeptide", and the terms "second MHC polypeptide", "MHC heavy chain", and "MHC-H", refer to MHC Class I receptor elements.

A "MOD" (also termed a co-immunomodulatory or co-stimulatory polypeptide), as the term is used herein, includes a polypeptide on an APC (e.g., a dendritic cell, a B cell, and the like), or a portion of the polypeptide on an APC, that specifically binds a "Co-MOD" (also termed a cognate co-immunomodulatory polypeptide or a cognate co-stimulatory polypeptide) on a T-cell, thereby providing a signal which, in addition to the primary signal provided by, for instance, binding of a TCR/CD3 complex with a MHC polypeptide loaded with peptide, mediates a T-cell response including, but not limited to, proliferation, activation, differentiation, and the like. MODs include, but are not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds the Toll ligand receptor, and a ligand that specifically binds with B7-H3. A MOD also encompasses, inter alia, an antibody (or an antigen binding portion thereof such as an Fab) that specifically binds with a Co MOD present on a T-cell, such as, but not limited to, CD27, CD28, 4-1BB, OX40, CD30, CD40, PD-1, ICOS, lymphocyte function-associated antigen-1 (LFA-1), CD2, LIGHT, NKG2C, B7-H3, and a ligand that specifically binds to CD83.

An "immunomodulatory domain" ("MOD") of a T-Cell-MMP is a polypeptide of the T-Cell-MMP that acts as a MOD.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments, or from a series of synthetic oligonucleotides, to provide a synthetic nucleic acid which is capable of being expressed from a recombinant transcriptional unit contained in a cell or in a cell-free transcription and translation system.

The terms "recombinant expression vector" and "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

"Binding" as used herein (e.g., with reference to binding of a molecule such as a T-cell-MMP comprising one or more MODs or its epitope conjugate to one or more polypeptide (e.g., a T-cell receptor and a cognate co-immunomodulatory polypeptide (Co-MOD) on a T-cell) refers to a non-covalent interaction(s) between the molecules. Non-covalent binding refers to a direct association between two molecules, due to, for example, electrostatic, hydrophobic, ionic, and/or hydrogen-bond interactions, including interactions such as salt bridges and water bridges. Non-covalent binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, or less than $10^{-12}$ M. "Affinity" refers to the strength of non-covalent binding, increased binding affinity being correlated with a lower $K_D$. "Specific binding" generally refers to, e.g., binding between a ligand molecule and its binding site or "receptor" with an affinity of at least about $10^{-7}$ M or greater, (e.g., less than $5 \times 10^{-7}$ M, less than $10^{-8}$ M, less than $5 \times 10^{-8}$ M, less than $10^{-9}$ M, less than $10^{-10}$ M, less than $10^{-11}$ M, or less than $10^{-12}$ M and greater affinity, or in a range from $10^{-7}$ to $10^{-9}$ or from $10^{-9}$ to $10^{-12}$). "Non-specific binding" generally refers to the binding of a ligand to something other than its designated binding site or "receptor," typically with an affinity of less than about $10^{-7}$ M (e.g., binding with an affinity of less than about $10^{-6}$ M, less than about $10^{-5}$ M, less than about $10^{-4}$ M). However, in some contexts, e.g., binding between a TCR and a peptide/MHC complex, "specific binding" can be in the range of from 1 μM to 100 μM, or from 100 μM to 1 mM. "Covalent binding" as used herein means the formation of one or more covalent chemical bonds between two different molecules The terms "treatment," "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal and includes: (a) preventing the disease or symptom from occurring in a subject which may be predisposed to acquiring the disease or symptom but has not yet been diagnosed as having it; (b) inhibiting the disease or symptom, i.e., arresting its development; and/or (c) relieving the disease, i.e., causing regression of the disease. The therapeutic agent may be administered before, during and/or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient" are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that the range includes each intervening value, to the tenth of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where a range includes upper and lower limits, ranges excluding either or both of those limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that, as used herein and in the appended claims, the singular forms "a," "an," and "the" include plural referents unless the context clearly dictates otherwise. Thus, for example, reference to "multimeric T-cell modulatory polypeptide" includes a plurality of such polypeptides and reference to "the immunomodulatory polypeptide" or "the MOD" includes reference to one or more immunomodulatory polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

I. T-Cell Modulatory Multimeric Polypeptides (T-Cell-MMPs) with Chemical Conjugation Sites for Epitope Binding The present disclosure provides T-Cell-MMPs and their epitope conjugates that are useful for modulating the activity of a T-cell, and methods of their preparation and use in modulating an immune response in an individual. The T-Cell-MMPs may comprise one or more independently selected wild-type and/or variant MOD polypeptides that exhibit reduced binding affinity to their Co-MODs and chemical conjugation sites for coupling epitopes and payloads. Included in this disclosure are T-Cell-MMPs that are heterodimeric, comprising two types of polypeptides (a first polypeptide and a second polypeptide), wherein at least one of those polypeptides comprises a chemical conjugation site for the attachment (e.g., covalent attachment) of payloads such as chemotherapeutic agents and/or materials (e.g., epitope peptides and null peptides) that can bind a TCR. Also included in this disclosure are T-Cell-MMPs which have been chemically conjugated to an epitope and/or a payload (e.g., a chemotherapeutic). Depending on the type of MOD(s) present in the T-Cell-MMP, when an epitope specific to a TCR is present on a T-Cell-MMP, the T-cell can respond by undergoing activation including, for example, clonal expansion (e.g., when activating MODs such as IL-2, 4-1BBL and/or CD80 are incorporated into the T-Cell-MMP). Alternatively, the T-cell may undergo inhibition that down regulates T-cell activity (e.g., blocking autoimmune reactions) when MODs such as CD86 and/or PD-L1 are incorporated into the T-Cell-MMPs. Because MODs are not specific to any epitope, activation or inhibition of T-cells can be biased toward epitope-specific interactions by incorporating variant MODs having reduced affinity for their Co-MOD into the T-Cell-MMPs such that the binding of a T-Cell-MMP to a T-cell is strongly affected by, or even dominated by, the MHC-epitope-TCR interaction.

In embodiments described herein, a T-Cell-MMP-epitope conjugate functions as a surrogate APC, and mimics the adaptive immune response. The T-Cell-MMP-epitope conjugate does so by engaging a TCR present on the surface of a T-cell with a covalently bound epitope presented in the T-Cell-MMP-epitope conjugate complex. This engagement provides the T-Cell-MMP-epitope conjugate with the ability to achieve epitope-specific cell targeting. In embodiments described herein, T-Cell-MMP-epitope conjugates also possess at least one MOD that engages a counterpart costimulatory protein (Co-MOD) on the T-cell. Both signals—epitope/MHC binding to a TCR and MOD binding to a Co-MOD—then drive both the desired T-cell specificity and either inhibition or activation/proliferation.

The T-Cell-MMPs having chemical conjugation sites find use as a platform into which different epitopes and/or payloads may be inserted to prepare materials for therapeutic, diagnostic and research applications. Such T-Cell-MMPs comprising a chemical conjugation site permit the rapid preparation of diagnostics and therapeutics as they permit the epitope containing material (e.g., a peptide) to be rapidly inserted into the T-Cell-MMP and tested for activation or inhibition of T-cells bearing TCRs specific to the epitope.

In an embodiment, a chemical conjugation site of such a T-Cell-MMP may be utilized to attach a payload such as a chemotherapeutic agent or enzyme to the T-Cell-MMP. In the absence of an added epitope, the resulting complex may be used in a fashion similar to an antibody to deliver the payload, particularly when the T-Cell-MMPs form multimers (e.g., dimers or higher order structures) due to the incorporation of an Fc scaffold. Due to the lack of an epitope, the MODs of T-Cell-MMP-payload conjugates will dictate the cells that will receive the payload by their binding specificity and the avidity of the complex for different cells.

In an embodiment, where variant MODs that stimulate T-cell proliferation and an epitope are incorporated into a T-Cell-MMP, contacting the T-cells with at least one concentration of the T-Cell-MMP induces at least a twofold (e.g., at least a 2, 3, 4, 5, 10, 20, 30, 50, 75, or 100 fold) difference in the activation of T-cells (as measured by T-cell proliferation or ZAP-70 activity, see e.g., Wang, et al., *Cold Spring Harbor perspectives in biology* 2.5 (2010): a002279) having a TCR specific to the epitope, as compared to T-cells contacted with the same concentration of the T-Cell-MMP that do not have a TCR specific to the epitope.

In an embodiment where variant MODs that inhibit T-cell activation and an epitope is incorporated into a T-Cell-MMP, contacting the T-cells with at least one concentration of the T-Cell-MMP prevents activation of T-cells in an epitope specific manner as measured by T-cell proliferation).

The specificity of T-Cell-MMPs into which an epitope has been incorporated will depend on the relative contributions of the epitope and MODs to the binding. Where the MODs dominate the binding interactions the specificity of the T-Cell-MMP of T-cells specific to the epitope will be reduced relative to T-Cell-MMP complexes where the epitope dominates the binding interactions by contributing more to the overall binding energy than the MODs. The greater the contribution of the epitope to a TCR specific to the epitope, the greater the specificity of the T-Cell-MMP will be for that T-cell type. Where an epitope has strong affinity for its TCR, the use of variant MODs with reduced affinity for their Co-MODs will favor epitope selective interactions of the T-Cell-MMP-epitope conjugates, and also facilitate selective delivery of any payload that may be conjugated to the T-Cell-MMP-epitope conjugate.

In addition to being useful as a structure into which to incorporate epitopes and prepare T-Cell-MMPs that are epitope specific, the T-Cell-MMPs described as either lacking an epitope or containing a null peptide may be employed to deliver a payload to target cells bearing receptors for the MODs and/or variant MODs present in the T-Cell-MMPs.

In an embodiment, T-Cell-MMPs bearing MODs inhibitory to T-cell activation and/or proliferation that lack an epitope (or contain a null peptide) may be used as simulators of T-cells that contain one or more receptors for the MOD or variant MODs present in the T-Cell-MMP. Such stimulatory T-Cell-MMPs may be used to simultaneously deliver a payload (e.g., a chemically conjugated chemotherapeutic) to the T-cells to which it binds.

In an embodiment, T-Cell-MMPs bearing MODs inhibitory to T-cell activation and/or proliferation that lack an epitope (or that contain a null peptide) may be used as an immunosuppressant alone or in conjunction with other immunosuppressants such as cyclosporine to suppress immune reactions (e.g., prevent graft-v-host or host-v-graft rejection). Such inhibitory T-Cell-MMPs may be used to simultaneously deliver a payload (e.g., a chemically conjugated chemotherapeutic) to the T-cells to which it binds The present disclosure provides T-Cell-MMPs that are useful for modulating the activity of a T-cell and, accordingly, for modulating an immune response in an individual. The T-Cell-MMPs comprise a MOD that exhibits reduced binding affinity to a Co-MOD.

I.A. T-Cell-MMPs

The T-Cell-MMP frameworks described herein comprise at least one chemical conjugation site on either the first polypeptide chain or the second polypeptide chain.

In an embodiment, the present disclosure provides a T-Cell-MMP comprising a heterodimer comprising: a) a first polypeptide comprising: a first MHC polypeptide; b) a second polypeptide comprising a second MHC polypeptide; c) at least one of first or second polypeptides comprises a chemical conjugation site, and d) at least one MOD, where the first and/or the second polypeptide comprises the at least one MOD (e.g., one, two, three, or more). Optionally, the first or the second polypeptide comprises an Ig Fc polypeptide or a non-Ig scaffold. One or more of the MODs, which are selected independently, may be a variant MOD that exhibits reduced affinity to a Co-MOD compared to the affinity of a corresponding wild-type MOD for the Co-MOD. The disclosure also provides T-Cell-MMPs in which an epitope (e.g., a peptide bearing an epitope) is covalently bound (directly or indirectly) to the chemical conjugation site forming a T-Cell-MMP-epitope conjugate. In such an embodiment, the epitope (e.g., epitope peptide) present in a T-Cell-MMP epitope conjugate of the present disclosure may bind to a T-cell receptor (TCR) on a T-cell with an affinity of at least 100 μM (e.g., at least 10 μM, at least 1 μM, at least 100 nM, at least 10 nM, or at least 1 nM). A T-Cell-MMP epitope conjugate may bind to a first T-cell with an affinity that is at least 25% higher than the affinity with which the T-Cell-MMP epitope conjugate binds to a second T-cell, where the first T-cell expresses on its surface the Co-MOD and a TCR that binds the epitope with an affinity of at least 100 μM, and where the second T-cell expresses on its surface the Co-MOD but does not express on its surface a TCR that binds the epitope with an affinity of at least 100 μM (e.g., at least 10 μM, at least 1 μM, at least 100 nM, at least 10 nM, or at least 1 nM).

In an embodiment, the present disclosure provides a heterodimeric T-Cell-MMP (which may form higher level multimers, dimers, trimers, etc. of the heterodimers) comprising:

a) a first polypeptide comprising, i) a first MHC polypeptide;
b) a second polypeptide comprising, in order from N-terminus to C-terminus: i) a second MHC polypeptide and ii) an optional immunoglobulin (Ig) Fc polypeptide scaffold or a non-Ig polypeptide scaffold;
c) one or more first polypeptide chemical conjugation sites attached to or within the first polypeptide, and/or one or more second polypeptide chemical conjugation sites attached to or within the second polypeptide; and
d) one or more immunomodulatory polypeptides (MODs), wherein at least one of the one or more MODs is
   A) at the C-terminus of the first polypeptide (see, e.g., A in FIG. 5 or 6),
   B) at the N-terminus of the second polypeptide (see, e.g., B in FIG. 5 or 6),
   C) at the C-terminus of the second polypeptide (see, e.g., C in FIG. 5 or 6), or
   D) at the C-terminus of the first polypeptide and at the N-terminus of the second polypeptide (see, e.g., D in FIG. 5 or 6);

wherein each of the one or more MODs is an independently selected wild-type or variant MOD.

Such T-Cell-MMP frameworks act as a platform on which epitopes (e.g., polypeptide epitopes) can be covalently attached through a linkage to one of the first or second chemical conjugation sites bound to at least one of the first and second MHC polypeptides forming a T-Cell-MMP-epitope conjugate. This permits facile introduction of different epitopes into the framework for presentation in the context of the T-Cell-MMP to a T-cell receptor (TCR) on a T-cell. Payload (e.g., chemotherapeutics) can similarly be attached to a T-Cell-MMP by covalent attachment to one of the first or second chemical conjugation sites (e.g., a site not employed for attachment of an epitope).

Where an immunoglobulin (Ig) Fc polypeptide or a non-Ig polypeptide scaffold that can multimerize is employed, the T-Cell-MMPs may multimerize. The complexes may be in the form of dimers (see, e.g., FIG. 7), trimers, tetramers, or pentamers. Compositions comprising multimers of T-Cell-MMPs may also comprise monomers and, accordingly may comprise monomers, dimers, trimers, tetramers, pentamers, or combinations of any thereof (e.g., a mixture of monomers and dimers).

In an embodiment, the MODs are independently selected wild-type MODs or variant MODs presented in a T-Cell-MMP that optionally comprises an epitope. In an embodiment, the MODs are one or more MODs or variant MODs capable of stimulating epitope-specific T-cell activation/proliferation (e.g., IL-2, 4-1BBL and/or CD80). In another embodiment, the MODs are one or more MODs or variant MODs capable of inhibiting T-cell activation/proliferation (e.g., FAS-L and/or PD-L1). When used in conjunction with a T-Cell-MMP bearing a suitable epitope, such activating or inhibitory MODs are capable of epitope-specific T-cell action, particularly where the MODs are variant MODs and the MHC-epitope-TCR interaction is sufficiently strong to dominate the interaction of the T-Cell-MMP with the T-cells.

Figure 7:
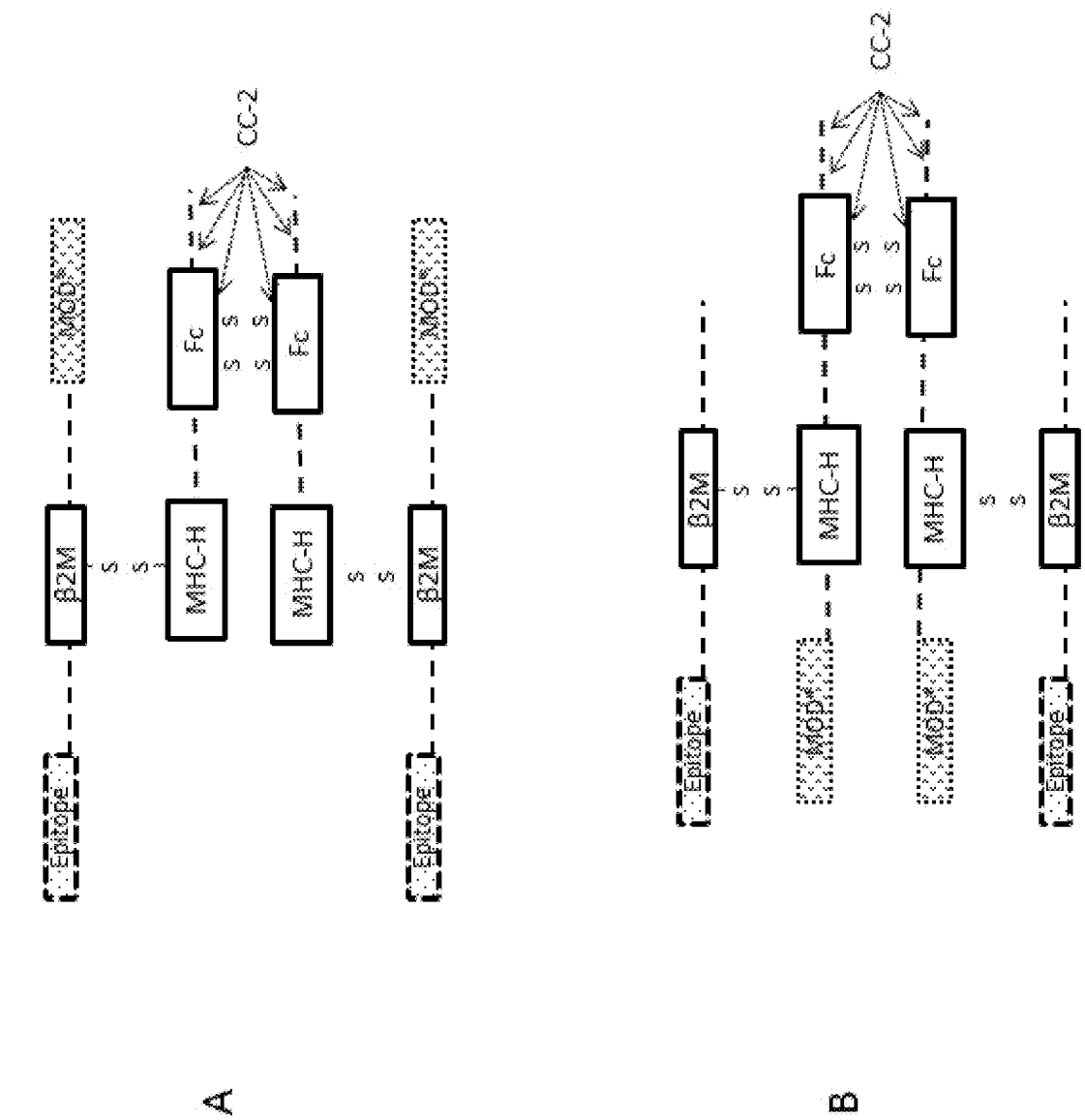
FIG. 7 provides examples of two dimers formed from T-Cell-MMPs. The dimer labeled "A" is the result of dimerizing two of the T-Cell-MMPs labeled "A" in FIG. 6. The dimer labeled "B" is the result of dimerizing two of the T-Cell-MMPs labeled "B" in FIG. 6. The embodiment as shown includes one or more disulfide bonds between the polypeptides, each of which are optional. In addition, only a subset of CC-2 sites in the Fc region or the attached optional linker are shown.

I.A.1 Locations of the First and Second Chemical Conjugation Sites in T-Cell-MMPs Prior to being subject to chemical conjugation reactions that incorporate an epitope (e.g., an epitope containing peptide) and/or payload, the T-Cell-MMPs described herein comprise at least one chemical conjugation site. Where the T-Cell-MMPs comprise more than one chemical conjugation site, there may be two or more conjugation sites on the first polypeptide (first polypeptide chemical conjugation sites), two or more conjugation sites on the second polypeptide (second polypeptide chemical conjugation sites), or at least one first polypeptide chemical conjugation site and at least one second polypeptide chemical conjugation site. In each instance where more than one chemical conjugation site is present in a T-Cell-MMP molecule, the sites are independently selected and may employ the same or different chemistries, amino acid sequences, or chemical groups for conjugation. Some examples of the locations for first polypeptide chemical conjugation sites (indicated as CC-1) and second polypeptide chemical conjugation sites (indicated as CC-1) are shown in FIGS. 5-7.

In embodiments, the first polypeptide of the T-Cell-MMPs comprise: a first MHC polypeptide without a linker on its N-terminus and C-terminus; a first MHC polypeptide bearing a linker on its N-terminus; a first MHC polypeptide bearing a linker on its C-terminus, or a first MHC polypeptide bearing a linker on its N-terminus and C-terminus. At least one of the one or more first polypeptide chemical conjugation sites is: a) attached to (e.g., at the N- or C-terminus), or within, the sequence of the first MHC polypeptide when the first MHC polypeptide is without a linker on its N- and C-terminus; b) attached to, or within, the sequence of the first MHC polypeptide, where the first MHC polypeptide comprises a linker on its N- and C-terminus; c) attached to, or within, the sequence of a linker on the N-terminus of the first MHC polypeptide; and/or d) attached to, or within, the sequence of a linker on the C-terminus of the first MHC polypeptide. Additional first polypeptide chemical conjugation sites of a T-Cell-MMP may be present at (attached to or within) any location on the first polypeptide (e.g., more than one enzyme modification sequence serving as a site for chemical conjugation), including the first MHC polypeptide or in any linker attached to it. In such embodiments, the first MHC polypeptide may comprise a β2M polypeptide sequence as described below.

In embodiments, the second polypeptide of the T-Cell-MMPs comprise: a second MHC polypeptide without a linker on its N-terminus and C-terminus; a second MHC polypeptide bearing a linker on its N-terminus; a second MHC polypeptide bearing a linker on its C-terminus, or a second MHC polypeptide bearing a linker on its N-terminus and C-terminus. At least one of the one or more second polypeptide chemical conjugation sites is: a) attached to (e.g., at the N- or C-terminus), or within, the sequence of the second MHC polypeptide when the second MHC polypeptide is without a linker on its N- and C-terminus; b) attached to, or within, the sequence of the second MHC polypeptide where the second MHC polypeptide comprises a linker on its N- and C-terminus; c) attached to, or within, the sequence of the linker on the N-terminus of the second MHC polypeptide; and/or d) attached to, or within, the sequence of the linker on the C-terminus of the second MHC polypeptide. In addition, when the second polypeptide contains an immunoglobulin (Fc) polypeptide aa sequence or a non-Ig polypeptide scaffold, along with an additional linker attached thereto, the second polypeptide chemical conjugation sites may be attached to or within the second MHC polypeptide, the immunoglobulin polypeptide, the polypeptide scaffold, or the attached linker. Additional second polypeptide chemical conjugation sites of a T-Cell-MMP may be present at (attached to or within) any location on the second polypeptide (e.g., more than one enzyme modification sequence serving as a site for chemical conjugation), including the second MHC polypeptide or in any linker attached to it. In such embodiments, the second MHC polypeptide may comprise a MHC heavy chain (MHC-H) polypeptide sequence as described below.

In an embodiment, the first and second MHC polypeptides may be selected to be Class I MHC polypeptides, with the first MHC polypeptide comprising a β2M polypeptide sequence and the second polypeptide comprising a MHC heavy chain sequence, wherein there is at least one chemical conjugation site on the first or second polypeptide. In an embodiment, at least one of the one or more first chemical conjugation sites in the T-Cell-MMP may be attached to (including at the N- or C-terminus) or within either the β2M polypeptide or the linker attached to its N-terminus or C-terminus. In an embodiment, at least one of the one or more second polypeptide chemical conjugation sites in the T-Cell-MMP may be attached to (including at the N- or C-terminus) or within: the MHC-H polypeptide; a linker attached to the N-terminus or C-terminus of the MHC-H polypeptide; or, when present, attached to or within an immunoglobulin (Fc) polypeptide (or a non-Ig polypeptide scaffold) or a linker attached thereto. In another embodiment of such a Class I MHC polypeptide construct, both the first and second polypeptides comprise at least one chemical conjugation site.

Where the T-Cell-MMP comprises a β2M polypeptide sequence, the sequence may have at least 85% amino acid sequence identity (e.g., at least 90%, 95%, 98% or 99% identity, or even 100% identity) to one of the amino acid sequences set forth in FIG. 4. The β2M polypeptide may comprise an amino acid sequence having at least 20, 30, 40, 50, 80, 100, or 110 contiguous amino acids with identity to a portion of an amino acid sequence set forth in FIG. 4. The chemical conjugation sequences can be attached to the β2M polypeptide (e.g., at the N- and/or C-termini or linkers attached thereto) or within the β2M polypeptide.

Where the T-Cell-MMP comprises a MHC-H polypeptide, it may be a HLA-A, a HLA-B, or a HLA-C heavy chain. In an embodiment, the MHC-H polypeptide may comprise an amino acid sequence having at least 85% amino acid sequence identity (e.g., at least 90%, 95%, 98% or 99% identity, or even 100% identity) to the amino acid sequence set forth in one of FIGS. 3A-3D. The MHC Class I heavy chain polypeptides may comprise an amino acid sequence having at least 20, 30, 40, 50, 80, 100, 150, 200, 250, 300, or 330 contiguous amino acids with identity to a portion of an amino acid sequence set forth in FIGS. 3A-3D. The chemical conjugation sequences can be attached (e.g., at the N- and/or C-termini or linkers attached thereto) or within the MHC-H polypeptides.

The second polypeptide of the T-Cell-MMP may comprise an Ig Fc polypeptide sequence that can act as part of a molecule scaffold providing structure and the ability to multimerize to the T-Cell-MMP (or its epitope conjugate) and, in addition, potential locations for chemical conjugation. In some embodiments the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In such embodiments the Ig Fc polypeptide may comprise an amino acid sequence that has at least 85%, 90%, 95%, 98, or 99%, or even 100%, amino acid sequence identity to an amino acid sequence depicted in one of FIGS. 2A-2D. Ig Fc polypeptides may comprise a sequence having at least 20, 30, 40, 50, 60, 80, 100, 120, 140, 160, 180, 200, or 220 contiguous amino acids with identity to a portion of an amino acid sequence in FIG. 2. In an embodiment where the second polypeptide comprises an IgG1 Fc polypeptide, the polypeptide may also comprise one or more amino acid substitutions selected from N297A, L234A, L235A, L234F, L235E, and P331S. In one such embodiment, the IgG1 Fc polypeptide comprises L234A and L235A substitutions either alone or in combination with a second polypeptide chemical conjugation site. The chemical conjugation sites can be located/attached at the N- and/or C-termini or to linkers attached thereto, or within the Ig Fc polypeptides.

I.A.2 Chemical Conjugation Sites of T-Cell-MMPs

The first and second polypeptide chemical conjugation sites of the T-Cell-MMPs may be any suitable site that can be modified upon treatment with a reagent and/or catalyst such as an enzyme that permits the formation of a covalent linkage to either one or both of the T-Cell-MMP polypeptides. In an embodiment, there is only one chemical conjugation site that has been introduced into either the first or second polypeptide of a T-Cell-MMP. In another embodiment, each first and second polypeptide chemical conjugation site is selected such that there is only one type of conjugation site (different conjugation sites) on the respective polypeptides, permitting different molecules to be selectively conjugated to each of the polypeptides. In other embodiments, such as where both an epitope molecule and one or more payload molecules are to be incorporated into a T-Cell-MMP, more than one copy of a first and/or second polypeptide chemical conjugation may be introduced into the T-Cell-MMP. For example, a T-Cell-MMP may have one first polypeptide chemical conjugation site (e.g., for conjugating an epitope) and multiple second polypeptide chemical conjugation sites for delivering molecules of payload.

In embodiments, the first and second chemical conjugation sites may be selected independently from:
a) peptide sequence attached to or within the first or second polypeptide that acts as an enzyme modification sequence (e.g., sulfatase, sortase, and/or transglutaminase sequences);
b) non-natural amino acids and/or selenocysteines attached to or within the first or second polypeptide;
c) engineered amino acid chemical conjugation sites;
d) carbohydrate or oligosaccharide moieties attached to the first or second polypeptide; and
e) IgG nucleotide binding sites attached to or within the first or second polypeptide.

I.A.2.1 Sulfatase Motifs

In those embodiments where enzymatic modification is chosen as the means of providing a chemical conjugation site, at least one of the one or more first and second chemical conjugation sites may comprise a sulfatase motif. Sulfatase motifs are usually 5 or 6 amino acids in length, and are described, for example, in U.S. Pat. No. 9,540,438 and U.S. Pat. Pub. No. 2017/0166639 A1, which are incorporated by reference. Insertion of the motif results in the formation of a protein or polypeptide that is sometimes referred to as aldehyde tagged or having an aldehyde tag. The motif may be acted on by formylglycine generating enzyme(s) ("FGE" or "FGEs") to convert a cysteine or serine in the motif to a formylglycine residue ("fGly" although sometimes denoted "FGly"), which is an aldehyde containing amino acid that may be utilized for selective (e.g., site specific) chemical conjugation reactions. Accordingly, as used herein, "aldehyde tag" or "aldehyde tagged" polypeptides refer to an amino acid sequence comprising an unconverted sulfatase motif, as well as to an amino acid sequence comprising a sulfatase motif in which the cysteine or the serine residue of the motif has been converted to fGly by action of an FGE. In addition, where a sulfatase motif is provided in the context of an amino acid sequence, it is understood as providing disclosure of both the amino acid sequence (e.g., polypeptide) containing the unconverted motif as well as its fGly containing counterpart. Once incorporated into a polypeptide (e.g, of a T-Cell-MMP), a fGly residue may be reacted with molecules (e.g., epitope peptides) comprising a variety of reactive groups including, but not limited to thiosemicarbazide, aminooxy, hydrazide, and hydrazino groups to form a conjugate (e.g., a T-Cell-MMP epitope conjugate) having a covalent bond between the peptide and the molecule via the fGly residue.

In embodiments, the sulfatase motif is at least 5 or 6 aa residues, but can be, for example, from 5 to 16 (e.g., 6-16, 5-14, 6-14, 5-12, 6-12, 5-10, 6-10, 5-8, or 6-8) aa in length. The sulfatase motif may be limited to a length less than 16, 14, 12, 10, or 8 amino acid residues.

In an embodiment, the sulfatase motif contains the sequence shown in Formula (I):

$$X1Z1X2Z2X3Z3 \qquad \text{(I) (SEQ ID NO:45), where}$$

Z1 is cysteine or serine;
Z2 is either a proline or alanine residue (which can also be represented by "P/A");
Z3 is a basic amino acid (arginine, lysine, or histidine, usually lysine), or an aliphatic amino acid (alanine, glycine, leucine, valine, isoleucine, or proline, usually A, G, L, V, or I);
X1 is present or absent and, when present, can be any amino acid, though usually an aliphatic amino acid, a sulfur-containing amino acid, or a polar uncharged amino acid (e.g., other than an aromatic amino acid or a charged amino acid), usually L, M, V, S or T, more usually L, M, S or V, with the proviso that, when the sulfatase motif is at the N-terminus of the target polypeptide, X1 is present; and
X2 and X3 independently can be any amino acid, though usually an aliphatic amino acid, a polar, uncharged amino acid, or a sulfur containing amino acid (e.g., other than an aromatic amino acid or a charged amino acid), usually S, T, A, V, G or C, more usually S, T, A, V or G.

Accordingly, in one embodiment, FGly containing polypeptides may be prepared using a sulfatase motif having Formula I, where:
Z1 is cysteine or serine;
Z2 is a proline or alanine residue;
Z3 is an aliphatic amino acid or a basic amino acid;
X1 is present or absent and, when present, is any amino acid, with the proviso that, when the sulfatase motif is at an N-terminus of the polypeptide, X1 is present; and
X2 and X3 are each independently any amino acid, wherein the sequence is within or adjacent to a solvent accessible loop region of the Ig constant region, and wherein the sequence is not at the C-terminus of the Ig heavy chain.

Where the aldehyde tag is present at a location other than the N-terminus of a target polypeptide, X1 of the sulfatase motif may be provided by an amino acid of the sequence in which the target polypeptide is incorporated. Accordingly, in some embodiments, where the motif is present at a location other than the N-terminus of a target polypeptide, the sulfatase motif may be of the formula:

(C/S)X2(P/A)X3Z3,    Formula (II) (SEQ ID NO:46), where: X1 is absent; X2, X3 and Z3 are as defined above.

Where peptides containing a sulfatase motif are being prepared for conversion into fGly-containing peptides by a eukaryotic FGE, for example by expression and conversion of the peptide in a eukaryotic cell or cell free system using a eukaryotic FGE, sulfatase motifs amenable to conversion by a eukaryotic FGE may advantageously be employed. In general, sulfatase motifs amenable to conversion by a eukaryotic FGE contain a cysteine and proline at Z1 and Z2 respectively in Formula (I) above (e.g., X1CX2PX3Z3, SEQ ID NO:47); and in CX2PX3Z3, SEQ ID NO:48 (encompassed by Formula (II) above). Peptides bearing those motifs can be modified by "SUMF1-type" FGEs.

In an embodiment where the FGE is a eukaryotic FGE, the sulfatase motif may comprise an amino acid sequence selected from the group consisting of:

X1CX2PX3R or CX2PX3R (SEQ ID NOs:47 and 48, where Z3 is R, and X1 is present or absent);
X1CX2PX3K or CX2PX3K (SEQ ID NOs:47 and 48, where Z3 is K, and X1 is present or absent);
X1CX2PX3H or CX2PX3H (SEQ ID NOs:47 and 48, where Z3 is H, and X1 is present or absent);
X1CX2PX3L or CX2PX3L (SEQ ID NOs:47 and 48, where Z3 is L, and X1 is present or absent);
where X1, X2 and X3 are as defined above.

In an embodiment, the sulfatase motif comprises the sequence: X1C(X2)P(X3)Z3 (see SEQ ID NO:47), where:
X1 is present or absent and, when present, is any amino acid, provided that, when the sulfatase motif is at an N-terminus of a polypeptide, X1 is present; and
X2 and X3 are independently selected serine, threonine, alanine or glycine residues.

Sulfatase motifs of Formula (I) and Formula (II) amenable to conversion by a prokaryotic FGE often contain a cysteine or serine at Z1 and a proline at Z2 that may be modified either by the "SUMP I-type" FGE or the "AtsB-type" FGE, respectively. Other sulfatase motifs of Formula (I) or (II) susceptible to conversion by a prokaryotic FGE contain a cysteine or serine at Z1, and a proline or alanine at Z2 (each of which are selected independently), with the remaining amino acids of the sequence as described for Formulas (I) and (II); and are susceptible to modification by, for example, a FGE from *Clostridium perfringens* (a cysteine type enzyme), *Klebsiella pneumoniae* (a Serine-type enzyme) or a FGE of *Mycobacterium tuberculosis*.

Sulfatase motifs may be incorporated into any desired location on the first or second polypeptide of the T-Cell-MMP (or its epitope conjugate). Sulfatase motifs may be used to incorporate not only epitopes (e.g., epitope presenting peptides), but also to incorporate payloads (e.g., in the formation of conjugates with drugs and diagnostic molecules). In an embodiment, a sulfatase motif may be added at or near the terminus of any element in the first or second polypeptide of the T-Cell-MMP (or its epitope conjugate), including the first and second MHC polypeptides (e.g., MHC-H and β2M polypeptides), the scaffold or Ig Fc, and the linkers adjoining those elements. In embodiments, a sulfatase motif may be incorporated into a β2M, class I MHC heavy chain, and/or a Fc Ig polypeptide. In an embodiment, a sulfatase motif may be incorporated into the first polypeptide near or at the amino terminal end of the first MHC polypeptide (e.g., a β2M polypeptide) or a linker attached to it. In an embodiment, where the first polypeptide comprises a β2M polypeptide sequence, the sulfatase motif X1(C/S)X2PX3Z3 (SEQ ID NO:45 where Z1 is C or S and Z2 is P) may be incorporated at or near the N-terminus of a β2M sequence, permitting the chemical conjugation of, for example, an epitope either directly or through a linker. By way of example, the mature sequences of β2-microglobulin as shown in FIG. 4 begin with a 20 amino acid leader sequence, and the mature polypeptides begin with the initial sequence IQ(R/K)TP(K/Q)IQVYS . . . (aa residues 21-31 of SEQ ID NOs:151-155) and continues through the remainder of the β2M polypeptide. Accordingly, the sulfatase motif linked to an amino acid in the N-terminal region of β2M (with or without a linker) can be shown as, for example:

| | |
|---|---|
| X1Z1X2Z2X3Z3-IQ(R/K)TP(K/Q)IQVYS...; SEQ ID NO: 45 linked to a β2M sequence | X1Z1X2Z2X3Z3-linker-IQ(R/K)TP(K/Q)IQ VYS...; SEQ ID NO: 45 linked to a β2M sequence with an intervenin linker |
| X1Z1X2Z2X3Z3-(R/K)TP(K/Q)IQVYS...; SEQ ID NO: 45 linked to a β2M sequence | X1CX2PX3Z3-(RTP(K/Q)IQVYS...; SEQ ID NO: 47 linked to a β2M sequence |
| X1CX2PX3Z3-IQ(R/K)TP(K/Q)IQVYS...; SEQ ID NO: 47 linked to a β2M sequence | X1CX2PX3Z3-linker-IQ(R/K)TP(K/Q)IQVYS...; SEQ ID NO: 47 linked to a β2M sequence with an intervenin linker | or as shown with the human β2M leader sequences MSRSVALAVLALLSLSGLEA (aas 1-20 of SEQ ID NO:151) and an optional linker (e.g., a linker peptide) sequence having at least 85% (e.g., at least 90%, 95%, 98% or 99%, or even 100%) amino acid sequence identity relative to the corresponding portion of a sequence shown in FIG. 2

```
(aa 1-20 of SEQ ID NO: 151)-Linker-(SEQ ID NO:45 or 47)-(a β2M sequence)
MSRSVALAVLALLSLSGLEA-linker-X1Z1X2Z2X3Z3IQRTP(K/Q)IQVYS . . . ;

MSRSVALAVLALLSLSGLEA-linker-X1Z1X2Z2X3Z3-linker-IQRTP(K/Q)IQVYS . . . ;

MSRSVALAVLALLSLSGLEA-linker-X1Z1X2Z2X3RTP(K/Q)IQVYS . . . ;

MSRSVALAVLALLSLSGLEA-linker-X1CX2PX3IQRTP(K/Q)IQVYS . . . ;

MSRSVALAVLALLSLSGLEA-linker-X1CX2PX3Z3-linker-IQRTP(K/Q)IQVYS . . . ;
or

MSRSVALAVLALLSLSGLEA-linker-X1CX2PX3RTP(K/Q)IQVYS . . . ;
``` where the linkers, when present, may comprise independently selected amino acid sequences (e.g., from 1 to 50 aa, such as polyglycine, polyalanine, polyserine and poly-Gly, such as AAAGG (SEQ ID NO:75) or (GGGGS)$_n$ where n is 1, 2, 3, 4, 5, 6, 7, 8, 9, or 10, (SEQ ID NO:76)). The linkers shown may be present or absent, and when two are shown they may be the same or different.

In an embodiment a sulfatase motif is incorporated into, or attached to (e.g., via a peptide linker), a T-Cell-MMP (or its epitope conjugate) in the first or second polypeptide having a β2M polypeptide with a sequence having at least 85% (e.g., at least 90%, 95%, 98% or 99%, or even 100%) amino acid sequence identity to a sequence shown in FIG. 4 (e.g., any of the full length sequences shown in FIG. 4, or the sequence of any of the mature β2M polypeptides starting at amino acid 21 and ending at their C-terminus). For the purposes of this embodiment sequence identity of the β2M polypeptide is determined relative to the corresponding portion of a β2M polypeptide in FIG. 4 without consideration of the added sulfatase motif and any linker sequences present.

In an embodiment a sulfatase motif is incorporated into, or attached to (e.g., via one or more independently selected peptide linkers at the N-, C-, or both the N- and C-termini) a T-Cell-MMP (or its epitope conjugate) having a first or second polypeptide having a β2M polypeptide sequence with 1 to 15 (e.g., 1, 2, 3, 4, 5, 6, 7, 8, 9, 10, 11, 12, 13, 14, or 15) amino acid deletions, insertions, and/or changes compared with a sequence shown in FIG. 4 (e.g., any of the full length sequences shown in FIG. 4, or the sequence of any of the mature β2M polypeptides starting at amino acid 21 and ending at their C-terminus) with amino acid deletions, insertions and/or changes assessed without consideration of the added $A_{2-5}$ or a $G_{2-5}$ motif and any linker sequences present. For the purposes of this embodiment amino acid deletions, insertions, and/or changes in the β2M polypeptide are determined relative to the corresponding portion of a β2M polypeptide in FIG. 4 without consideration of the amino acids of the sulfatase motif and any linker sequences present. In one such embodiment, a sulfatase motif (e.g., of the formula X1Z1X2Z2X3Z3, (C/S)X2(P/A)X3Z3, X1CX2PX3R or X1CX2PX3L described above) may either replace and/or be inserted between any of the amino terminal 15 amino acids of a mature β2M sequence, such as those shown in FIG. 4.

In another embodiment, the sulfatase motif of Formula (I) SEQ ID NO:45 or (II) SEQ ID NO:46 may be incorporated into, or attached to (e.g., via a peptide linker), an Ig Fc region as a second polypeptide chemical conjugation site. In an embodiment a sulfatase motif is incorporated into a before the addition of the sulfatase motif sequence. In one such embodiment the sulfatase motifs may be utilized as sites for the conjugation of, for example, epitopes and/or payloads either directly or indirectly through a peptide or chemical linker.

In another embodiment, the sulfatase motif of SEQ ID NO:45 (Formula (I)) or SEQ ID NO:46 (Formula II) may be incorporated into a MHC-H polypeptide sequence as a chemical conjugation site. In an embodiment the sulfatase motif is incorporated into a MHC-H sequence having at least 85% (e.g., at least 90%, 95%, 98% or 99%, or even 100%) amino acid sequence identity relative to the corresponding portion of a sequence shown in FIG. 3 before the addition of the sulfatase motif sequence. In one such embodiment the sulfatase motifs may be utilized as sites for the conjugation of, for example, epitopes and/or payloads either directly or indirectly through a peptide or chemical linker.

In another embodiment, the one or more copies of the sulfatase motif of SEQ ID NO:45 (Formula (I)) or SEQ ID NO:46 (Formula II) may be incorporated into the IgFc region as one or more second polypeptide chemical conjugation sites. In one such embodiment they may be utilized as sites for the conjugation of, for example, epitopes and/or payloads either directly or indirectly through a peptide or chemical linker.

As indicated above, a sulfatase motif of an aldehyde tag is at least 5 or 6 amino acid residues, but can be, for example, from 5 to 16 amino acids in length. The motif can contain additional residues at one or both of the N- and C-termini, such that the aldehyde tag includes both a sulfatase motif and an "auxiliary motif." In an embodiment, the sulfatase motif includes a C-terminal auxiliary motif (i.e., following the Z3 position of the motif), and may include 1, 2, 3, 4, 5, 6, or all 7 of the contiguous residues of an amino acid sequence selected from the group consisting of AALLTGR (SEQ ID NO:49), SQLLTGR (SEQ ID NO:50), AAFMTGR (SEQ ID NO:51), AAFLTGR (SEQ ID NO:52), and GSLFTGR (SEQ ID NO:53); numerous other auxiliary moifs have been described. The auxiliary motif amino acid residues are not required for FGE mediated conversion of the sulfatase motif of the aldehyde tag, and thus are only optional and may be specifically excluded from the aldehyde tags described herein.

U.S. Pat. No. 9,540,438 discusses the incorporation of sulfatase motifs into the various immunoglobulin sequences, including Fc region polypeptides, and is herein incorporated by reference for its teachings on sulfatase motifs and modification of Fc polypeptides and other polypeptides. That patent is also incorporated by reference for its guidance on FGE enzymes, and their use in forming fGly residues, as well as the chemistry related to the coupling of molecules such as epitopes and payloads to fGly residues.

The incorporation of the sulfatase motif may be accomplished by incorporating a nucleic acid sequence encoding the motif at the desired location in a nucleic acid encoding the first and/or second polypeptide of the T-Cell-MMP. As discussed below, the nucleic acid sequence may be placed under the control of a transcriptional regulatory sequence(s) (a promoter), and provided with regulatory elements that direct its expression. The expressed protein may be treated with one or more FGEs after expression and partial or complete purification. Alternatively, expression of the nucleic acid in cells that express a FGE recognizing the sulfatase motif results in the conversion of the cysteine or serine of the motif to fGly, which is sometimes called oxoalanine. Where two or more different sulfatase motifs are present (e.g., a first and second sulfatase motif) it is also possible to conduct the conversion of each motif during cellular expression, or each motif after cellular expression and partial or complete purification. Using two or more FGE enzymes with different motif selectivity and motifs preferentially converted by each of the FGEs, it is also possible to sequentially convert at least one sulfatase motif during cellular expression and at least one sulfatase motif after partial or complete purification, or to separately convert sulfatase motifs to fGly residues after expression. As discussed below, the ability to separately convert different sulfatase motifs and chemically couple them to epitopes and/or payloads in a sequential fashion permits the use of sulfatase coupling to incorporate different epitopes or payloads at the locations of different motifs.

Host cells for production of polypeptides with unconverted sulfatase motifs, or where the cell expresses a suitable FGE for converting fGly-containing polypeptide sequences, include those of a prokaryotic and eukaryotic organism. Non-limiting examples include *Escherichia coli* strains, *Bacillus* spp. (e.g., *B. subtilis*, and the like), yeast or fungi (e.g., *S. cerevisiae, Pichia* spp., and the like). Examples of other host cells, including those derived from a higher organism such as insects and vertebrates, particularly mammals, include, but are not limited to, CHO cells, HEK cells, and the like (e.g., American Type Culture Collection (ATCC) No. CCL-2), CHO cells (e.g., ATCC Nos. CRL9618 and CRL9096), CHO DG44 cells, CHO-K1 cells (ATCC CCL-61), 293 cells (e.g., ATCC No. CRL-1573), Vero cells, NIH 3T3 cells (e.g., ATCC No. CRL-1658), Hnh-7 cells, BHK cells (e.g., ATCC No. CCL1O), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

A variety of FGEs may be employed for the conversion (oxidation) of cysteine or serine in a sulfatase motif to fGly. As used herein, the term formylglycine generating enzyme, or FGE, refers to fGly-generating enzymes that catalyze the conversion of a cysteine or serine of a sulfatase motif to fGly. As discussed in U.S. Pat. No. 9,540,438, the literature often uses the term formylglycine-generating enzymes for those enzymes that convert a cysteine of the motif to fGly, whereas enzymes that convert a serine in a sulfatase motif to fGly are referred to as Ats-B-like.

FGEs may be divided into two categories, aerobic and anaerobic. The aerobic enzymes, which include the eukaryotic enzyme (e.g., the human enzyme), convert a cysteine residue to fGly, where the cysteine is generally in the context of a sulfatase motif of the formula X1CX2PX3Z3 (SEQ ID NO:47). Eukaryotic FGEs are of the "SUMF1-type" and are encoded in humans by the SUMF1 gene. The anaerobic enzymes are of the AtsB type most often from prokaryotic sources (e.g., *Clostridium perfringens, Klebsiella pneumoniae,* or *Mycobacterium tuberculosis*) and appear to be able to convert a cysteine or a serine in their sulfatase motif to fGly using a mechanism that is different from the aerobic form.

The ability to catalyze serine or cysteine conversion to fGly depends on the enzyme and the sulfatase motifs. Because of the differences in the ability of FGEs to convert serine and cysteine, it is possible that different sulfatase motifs may be used as different chemical conjugation sites. For example, it may be possible to incorporate into a T-Cell-MMP a sequence encoding both a cysteine containing site amenable to conversion by the eukaryotic aerobic SUMF1-type FGE and a serine containing site amenable to conversion by an AtsB-type FGE. After expression in a eukaryotic cell expressing a SumF1-type FGE, the cysteine motif will bear a fGly residue that may be subject to a first chemical conjugation with an epitope or payload. Following the first chemical conjugation, the T-Cell-MMP conjugate would be treated with an AtsB-type serine-type enzyme in a cell free system, and the fGly produced from the serine containing motif can then be subjected to chemical conjugation with a molecule that is the same as or different from the molecule used in the first chemical conjugation.

In view of the foregoing, this disclosure provides for T-Cell-MMPs comprising one or more fGly residues incorporated into the sequence of the first or second polypeptide chain as discussed above. The fGly residues may, for example, be in the context of the sequence X1(fGly)X2Z2X3Z3, where: fGly is the formylglycine residue; and Z2, Z3, X1, X2 and X3 are as defined in Formula (I) above.

After chemical conjugation the T-Cell-MMPs comprise one or more fGly' residues incorporated into the sequence of the first or second polypeptide chain in the context of the sequence X1(fGly')X2Z2X3Z3, where the fGly' residue is formylglycine that has undergone a chemical reaction and now has a covalently attached moiety (e.g., epitope or payload).

A number of chemistries and commercially available reagents can be utilized to conjugate a molecule (e.g., an epitope or payload) to a fGly residue, including, but not limited to, the use of thiosemicarbazide, aminooxy, hydrazide, or hydrazino, derivatives of the molecules to be coupled at a fGly-containing chemical conjugation site. For example, epitopes (e.g., epitope peptides) and/or payloads bearing thiosemicarbazide, aminooxy, hydrazide, hydrazino or hydrazinyl functional groups (e.g., attached directly to an amino acid of a peptide or via a linker such as a PEG) can be reacted with fGly-containing first or second polypeptides of the T-Cell-MMP to form a covalently linked epitope. Similarly, payloads such as drugs and therapeutics can be incorporated using, for example, biotin hydrazide as a linking agent.

In an embodiment, a peptide (e.g., an epitope containing peptide) is modified to incorporate a nucleophile-containing moiety (e.g., an aminooxy or hydrazide moiety) that reacts with the fGly residues incorporated into the first and/or second polypeptides of a T-Cell-MMP. The reaction results in the formation of a conjugate in which the T-Cell-MMP and peptide (e.g., epitope or payload) are covalently linked (e.g., by hydrazone or oxime linkage). (See, e.g., U.S. Pat. Nos. 9,238,878 and 7,351,797; Interchem, Aminooxy & Aldehyde PEO/PEG reagents for Biorthogonal Conjugation and Labeling Featuring Oxime Formation (undated), available at http://www.interchim.fr/ft/J/JV2290.pdf (accessed Sep. 2, 2017).

In an embodiment, an epitope (e.g., peptide epitope) and/or payload bearing a thiosemicarbazide, aminooxy, hydrazide, or hydrazino group is reacted with a fGly-containing first and/or second polypeptides of a T-Cell-MMP. The reaction results in the formation of a covalent bond between the T-Cell-MMP and the epitope and/or payload. As discussed in U.S. Pat. No. 9,540,438 and U.S. Pat. Pub. No. 2017/0166639 A1, the resulting conjugates may contain a structure (modified amino acid residue) of the form:

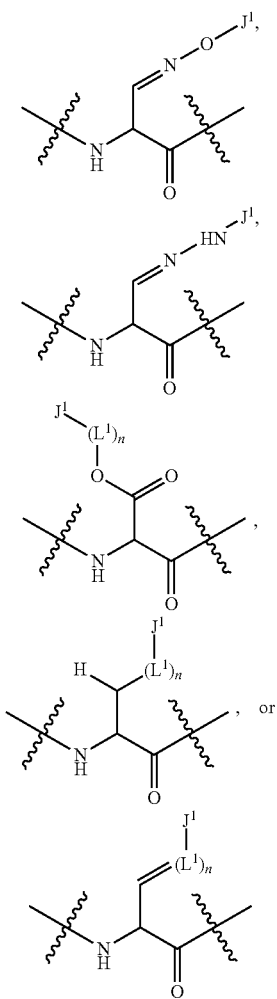

where:
J1 is a covalently bound moiety;
each L1 is a divalent moiety independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine; and n is a number selected from zero to 40 (e.g., 1-5, 5-10, 10-20, 20-30, or 30-40).

In an embodiment, epitopes and/or payloads may be modified to include a covalently bound hydrazinyl group, including those bearing cyclic substituents (e.g., indoles), that permits their covalent attachment to T-Cell-MMPs bearing fGly amino acid residues. In one embodiment the hydrazinal compounds are compounds of Formula (III):

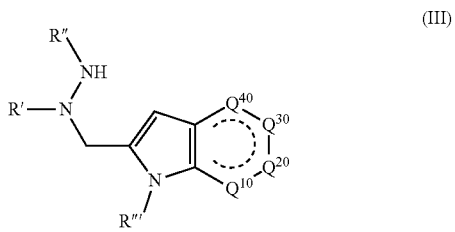

(III)

wherein, for the purpose of Fomula (III):
R''' may be a payload or epitope of interest that is to be conjugated to the fGly containing polypeptide;
R' and R'' may each independently be any desired substituent including, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$Q^{10}$, $Q^{20}$, $Q^{30}$ and $Q^{40}$ may be $CR^{11}$, $NR^{12}$, N, O or S;
wherein one of $Q^{10}$, $Q^{20}$, $Q^{30}$ and $Q^{40}$ is optional, and $R^{11}$ and $R^{12}$ may be any desired substituent (e.g., alkyl). See U.S. Pat. Pub. No. 2015/0352225.

In other embodiments the hydrazinyl group of modified epitopes and payloads (e.g., drugs and/or diagnostic agents) have a structure given by Formula (IV), (V), (Va), (VI), or (VIa). See U.S. Pat. No. 9,310,374, which is incorporated by reference for its teachings on the preparation and use of hydrazinyl compounds in the formation of biological conjugates including conjugates involving peptides and polypeptides.

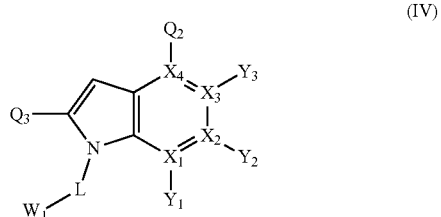

(IV)

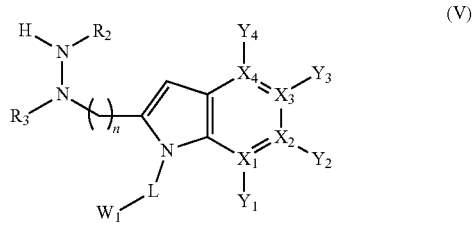

(V)

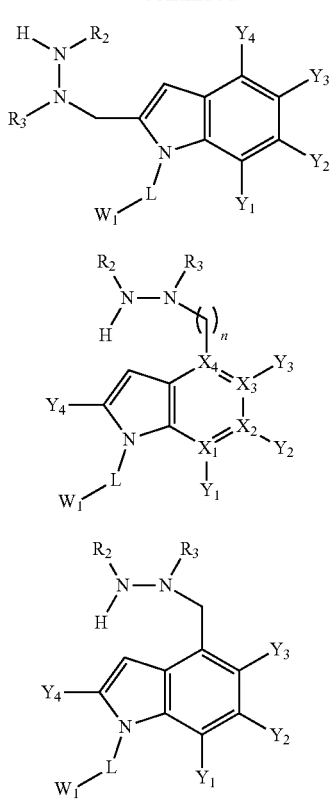

wherein, for the purpose of Formulas (IV), (V), (Va), (VI), or (VIa) recited in this section: one of $Q^2$ and $Q^3$ is —(CH$_2$)$_n$NR$_3$NHR$_2$ and the other is $Y_4$;

n is 0 or 1;

R$_2$ and R$_3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

X$_1$, X$_2$, X$_3$ and X$_4$ are each independently selected from C, N, O and S;

Y$_1$, Y$_2$, Y$_3$ and Y$_4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is an optional linker; and

W$_1$ is selected from an epitope (e.g., epitope polypeptide), a drug, a diagnostic agent, or other payload.

Figure 8:
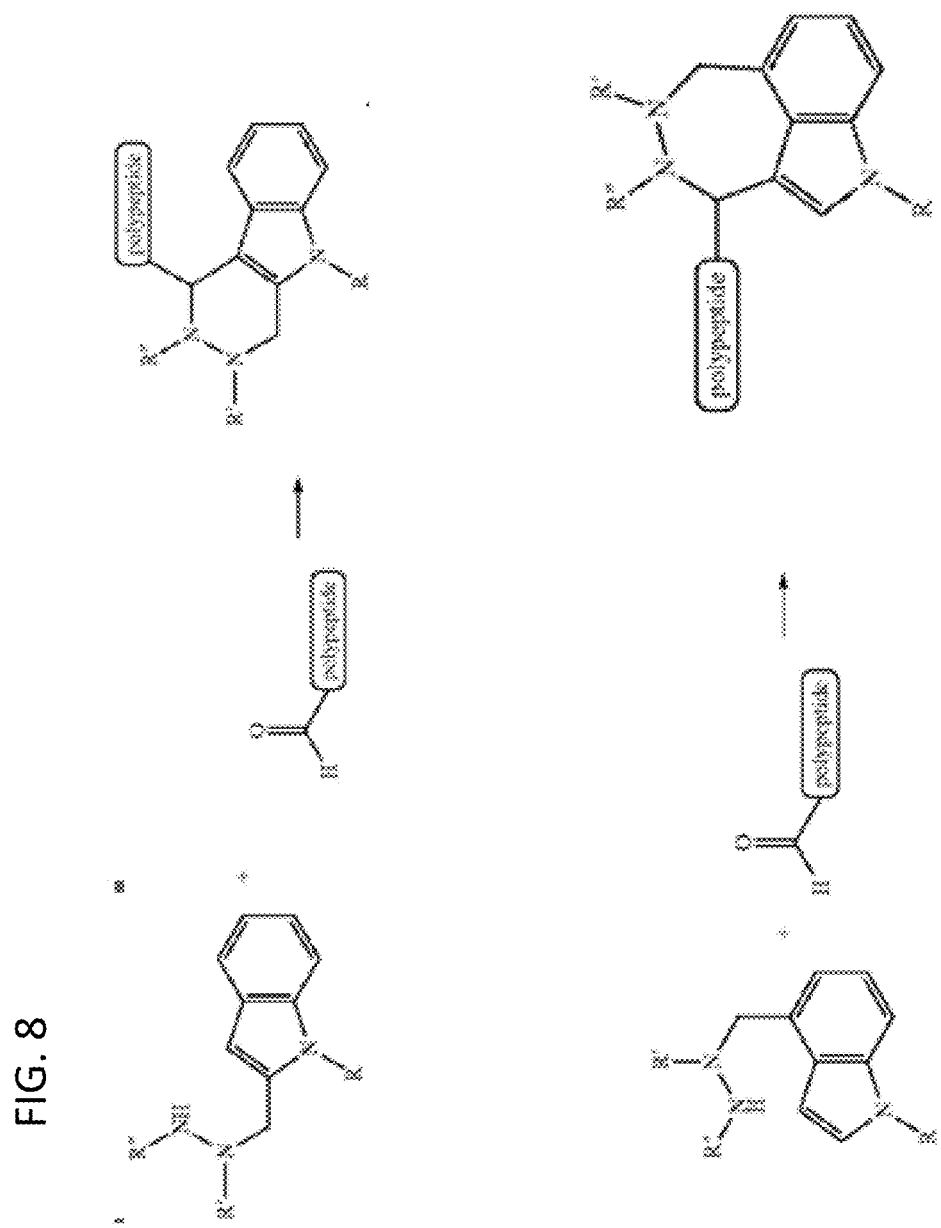
FIG. 8 shows a schematic of hydrazinyl indoles reacting with an aldehyde containing polypeptide adapted from U.S. Pat. No. 9,310,374.

Exemplary reactions of hydrazinyl indoles, which fall within those structures, with aldehyde functionalized peptides are shown schematically in FIG. 8.

In an embodiment, $Q^2$ is —(CH$_2$)$_n$NR$_3$NHR$_2$ and $Q_3$ is $Y_4$. In an embodiment, $Q_3$ is —(CH2)$_n$NR$_3$NHR$_2$ and $Q_2$ is $Y_4$. In an embodiment, n is 1. In an embodiment, R$_2$ and R$_3$ are each independently selected from alkyl and substituted alkyl. In some embodiments, R$_2$ and R$_3$ are each methyl. In an embodiment, X$_1$, X$_2$, X$_3$ and X$_4$ are each C. In an embodiment, Y$_1$, Y$_2$, Y$_3$ and Y$_4$ are each H.

In an embodiment, L is present and includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In some embodiments, L is present and includes a polymer. In some embodiments, the polymer is a polyethylene glycol.

For the purposes of Formulas (IV), (V), (Va), (VI), or (VIa):

1. "Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$-).

2. The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), or —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

3. "Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)$_n$, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH (CH$_3$)—), (—C(CH$_3$)$_2$CH$_2$CH$_2$—), (—C(CH$_3$)$_2$CH$_2$C (O)$_n$), (—C(CH$_3$)$_2$CH$_2$C(O)NH—), (—CH(CH$_3$) CH$_2$—), and the like.

4. R$^{10}$ is H or alkyl (e.g., H, —CH$_3$, —CH$_2$CH$_3$ or —CH$_2$CH$_2$CH$_3$).

5. "Substituted alkylene" refers to an alkylene group having from 1 to 3 hydrogens replaced with substituents as described for carbons in the definition of "substituted" below.

6. The term "alkane" refers to alkyl group and alkylene group, as defined herein.
7. The terms "alkylaminoalkyl," "alkylaminoalkenyl" and "alkylaminoalkynyl" refer to the groups R'NHR"— where R' is an alkyl group as defined herein and R" is an alkylene, alkenylene or alkynylene group as defined herein.
8. The term "alkaryl" or "aralkyl" refers to the groups -alkylene-aryl and -substituted alkylene-aryl where alkylene, substituted alkylene and aryl are defined herein.
9. "Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.
10. The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.
11. The term "alkoxyamino" refers to the group —NH-alkoxy, wherein alkoxy is defined herein.
12. The term "haloalkoxy" refers to the group alkyl-O— wherein one or more hydrogen atoms on the alkyl group have been substituted with a halo group and include, by way of examples, groups such as trifluoromethoxy, and the like.
13. The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.
14. The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.
15. The term "alkylthioalkoxy" refers to the groups -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.
16. "Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.
17. The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.
18. "Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).
19. The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.
20. "Alkynyloxy" refers to the group —O-alkynyl, wherein alkynyl is as defined herein. Alkynyloxy includes, by way of example, ethynyloxy, propynyloxy, and the like.
21. "Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.
22. "Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O)alkenyl, —NR$^{20}$C(O) substituted alkenyl, —NR$^{20}$C(O)alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.
23. "Aminocarbonyl" or the term "aminoacyl" refers to the group —C(O)NR$^{21}$R$^{22}$, wherein R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

24. "Aminocarbonylamino" refers to the group —$NR_{21}C(O)NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

25. The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

26. The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

27. "Aminosulfonyl" refers to the group —$SO_2NR_{21}R^{22}$, wherein $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

28. "Sulfonylamino" refers to the group —$NR^{21}SO_2R^{22}$, wherein $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

29. "Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl), which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted to form "substituted aryl" groups with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

30. "Aryloxy" refers to the group —O-aryl, wherein aryl is as defined herein, including, by way of example, phenoxy, naphthoxy, and the like, including optionally substituted aryl groups as also defined herein.

31. "Amino" refers to the group —$NH_2$.

32. The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

33. The term "azido" refers to the group —$N_3$.

34. "Carboxyl," "carboxy" or "carboxylate" refers to —$CO_2H$ or salts thereof.

35. "Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

36. "(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

37. "Cyano" or "nitrile" refers to the group —CN.

38. "Cycloalkyl" refers to cyclic alkyl groups of from 3 to 10 carbon atoms having single or multiple cyclic rings including fused, bridged, and spiraling systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

39. The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

40. "Cycloalkenyl" refers to non-aromatic cyclic alkyl groups of from 3 to 10 carbon atoms having single or multiple rings and having at least one double bond and preferably from 1 to 2 double bonds.

41. The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

42. "Cycloalkynyl" refers to non-aromatic cycloalkyl groups of from 5 to 10 carbon atoms having single or multiple rings and having at least one triple bond.

43. "Cycloalkoxy" refers to —O-cycloalkyl.

44. "Cycloalkenyloxy" refers to —O-cycloalkenyl.

45. "Halo" or "halogen" refers to fluoro, chloro, bromo, and iodo.

46. "Hydroxy" or "hydroxyl" refers to the group —OH.

47. "Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as pyridinyl, imidazolyl or furyl) or multiple condensed rings in a ring system (for example as in groups such as indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N->O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted to form "substituted heteroaryl" groups with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

48. The term "heteroaralkyl" refers to the group -alkylene-heteroaryl where alkylene and heteroaryl are defined herein. This term includes, by way of example, pyridylmethyl, pyridylethyl, indolylmethyl, and the like.

49. "Heteroaryloxy" refers to —O-heteroaryl.

50. "Heterocycle," "heterocyclic," "heterocycloalkyl," and "heterocyclyl" refer to a saturated or unsaturated group having a single ring or multiple condensed rings, including fused, bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

51. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

52. Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

53. "Heterocyclyloxy" refers to the group —O-heterocyclyl.
54. The term "heterocyclylthio" refers to the group heterocyclic-S—.
55. The term "heterocyclene" refers to the diradical group formed from a heterocycle, as defined herein.
56. The term "hydroxyamino" refers to the group —NHOH.
57. "Nitro" refers to the group —NO$_2$.
58. "Oxo" refers to the atom (═O).
59. "Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.
60. "Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.
61. The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.
62. "Thiol" refers to the group —SH.
63. "Thioxo" or the term "thioketo" refers to the atom (═S).
64. "Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.
65. The term "substituted thioalkoxy" refers to the group —S-substituted alkyl.
66. The term "thioaryloxy" refers to the group aryl-S— wherein the aryl group is as defined herein including optionally substituted aryl groups also defined herein.
67. The term "thioheteroaryloxy" refers to the group heteroaryl-S— wherein the heteroaryl group is as defined herein including optionally substituted aryl groups as also defined herein.
68. The term "thioheterocyclooxy" refers to the group heterocyclyl-S— wherein the heterocyclyl group is as defined herein including optionally substituted heterocyclyl groups as also defined herein.
69. In addition to the disclosure herein, the term "substituted," when used to modify a specified group or radical, can also mean that one or more hydrogen atoms of the specified group or radical are each, independently of one another, replaced with the same or different substituent groups as defined below.
70. In addition to the groups disclosed with respect to the individual terms herein, substituent groups for substituting for one or more hydrogens (any two hydrogens on a single carbon can be replaced with ═O, ═NR$^{70}$, ═N—OR$^{70}$, ═N$_2$ or ═S) on saturated carbon atoms in the specified group or radical are, unless otherwise specified, —R$^{60}$, halo, ═O, —OR$^{70}$, —SR$^{70}$, —NR$^{80}$R$^{80}$, trihalomethyl, —CN, —OCN, —SCN, —NO, —NO$_2$, ═N$_2$, —N$_3$, —SO$_2$R$^{70}$, —SO$_2$O$^-$M$^+$, —SO$_2$R$^{70}$, —OSO$_2$O$^-$R$^{70}$, —OSO$_2$O$^-$M$^+$, —OSO$_2$OR$^{70}$, —P(O)(O$^-$)$_2$(O$^-$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or, alternatively, two R$^{80}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as +N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("$_{0.5}$" means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.
71. In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^-$2(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that, in the case of substituted alkene or alkyne, the substituents are not —O⁻M⁺, —OR⁷⁰, —SR⁷⁰, or —S⁻M⁺.

72. In addition to the groups disclosed with respect to the individual terms herein, substituent groups for hydrogens on nitrogen atoms in "substituted" heteroalkyl and cycloheteroalkyl groups are, unless otherwise specified, —R⁶⁰, -O⁻M⁺, —OR⁷⁰, —SR⁷⁰, —S⁻M⁺, —NR⁸⁰R⁸⁰, trihalomethyl, —CF₃, —CN, —NO, —NO₂, —S(O)₂R⁷⁰, —S(O)₂O⁻M⁺, —S(O)₂R⁷⁰, —OS(O)₂R⁷⁰, —OS(O)₂O⁻M⁺, —OS(O)₂R⁷⁰, —P(O)(O⁻)₂(M⁺)₂, —P(O)(OR⁷⁰)O⁻M⁺, —P(O)(OR⁷⁰)(OR⁷⁰), —C(O)R⁷⁰, —C(S)R⁷⁰, —C(NR⁷⁰)R⁷⁰, —C(O)OR⁷⁰, —C(S)OR⁷⁰, —C(O)NR⁸⁰R⁸⁰, —C(NR⁷⁰)NR⁸⁰R⁸⁰, OC(O)R⁷⁰, —OC(S)R⁷⁰, —OC(O)OR⁷⁰, —OC(S)OR⁷⁰, —NR⁷⁰C(O)R⁷⁰, —NR⁷⁰C(S)R⁷⁰, —NR⁷⁰C(O)OR⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where R⁶⁰, R⁷⁰, R⁸⁰ and M⁺ are as previously defined.

In an embodiment, an epitope (e.g., peptide epitope) and/or payload to be conjugated with a fGly containing polypeptide has the form of Formula (III), (IV), (V), (Va), (VI), or (VIa). In some embodiments an epitope is covalently bound in a compound of Formula (III), (IV), (V), (Va), (VI), or (VIa). In one such embodiment the epitope is a peptide comprising the aa sequence of an epitope (e.g., a viral or cancer epitope). In an embodiment the peptide epitope has a length from about 4 aa to about 20 aa (e.g., 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, or 20 aa) in length.

The disclosure provides for methods of preparing T-Cell-MMP-epitope conjugates and/or T-Cell-MMP-payload conjugates comprising:

a) incorporating a sequence encoding a sulfatase motif including a serine or cysteine (e.g., a sulfatase motif of Formula (I) or (II) such as X1CX2PX3Z3 (SEQ ID NO:47); CX1PX2Z3 (SEQ ID NO:48) discussed above) into a nucleic acid encoding a first polypeptide and/or second polypeptide of a T-Cell-MMP;

b) expressing the sulfatase motif-containing first polypeptide and/or second polypeptide in a cell that
  i) expresses a FGE and converts the serine or cysteine of the sulfatase motif to a fGly and partially or completely purifying the fGly-containing first polypeptide and/or second polypeptide separately or as the T-Cell-MMP, or
  ii) does not express a FGE that converts a serine or cysteine of the sulfatase motif to a fGly, purifying or partially purifying the T-Cell-MMP containing the fGly residue and contacting the purified or partially purified T-Cell-MMP with a FGE that converts the serine or cysteine of the sulfatase motif into a fGly residue; and c) contacting the fGly-containing first and/or second polypeptides separately, or as part of a T-Cell-MMP, with an epitope and/or payload that has been functionalized with a group that forms a covalent bond between the aldehyde of the fGly and epitope and/or payload;
thereby forming T-Cell-MMP-epitope conjugate and/or T-Cell-MMP payload conjugate.

In such methods the epitope (epitope containing molecule) and/or payload may be functionalized by any suitable function group that reacts selectively with an aldehyde group. Such groups may, for example, be selected from the group consisting of thiosemicarbazide, aminooxy, hydrazide, and hydrazino. In embodiments, epitope and or payload is part of a hydrazinyl compound of Formula (III), (IV), (V), (Va), (VI), or (VIa). In one such embodiment the sulfatase motif is incorporated into a T-Cell-MMP first polypeptide comprising a β2M aa sequence, either within the β2M sequence or a linker attached thereto (e.g., within 10, 20, 30, 40, 50, 60, 70, 80, 90, or 100 aa of the N-terminus. In an embodiment a sulfatase motif is incorporated into a first or second polypeptide comprising a β2M aa sequence with at least 85% (e.g., at least 90%, 95%, 98% or 99%, or even 100%) sequence identity to a β2M sequence shown in FIG. 4, (e.g., with identity calculated without including or before the addition of the sulfatase motif sequence). For example, the sulfatase motif may be placed between the signal sequence and the sequence of the mature peptide, or at the N-terminus of the mature peptide, and the motif may be separated from the β2M sequence(s) by peptide linkers, In other embodiments for methods of preparing T-Cell-MMP-epitope conjugates and/or T-Cell-MMP payload conjugates, a sulfatase motif of SEQ ID NO:45 (Formula (I)) or SEQ ID NO:46 may be incorporated into an IgFc region of a second polypeptide as a second polypeptide chemical conjugation site. In an embodiment, a sulfatase motif is incorporated into a sequence comprising a sequence having at least 85% (e.g., at least 90%, 95%, 98% or 99%, or even 100%) amino acid sequence identity to a sequence shown in FIG. 2 before the addition of the sulfatase motif sequence.

In another embodiment of the method of preparing a T-Cell-MMP-epitope conjugate and/or T-Cell-MMP payload conjugate, the sulfatase motif of SEQ ID NO:45 (Formula (I)) or SEQ ID NO:46 may be incorporated into a MHC Class I heavy chain polypeptide as a chemical conjugation site.

In an embodiment of the method of preparing a T-Cell-MMP-epitope conjugate and/or T-Cell-MMP payload conjugate, a sulfatase motif is incorporated into a sequence having at least 85% (e.g., at least 90%, 95%, 98% or 99%, or even 100%) amino acid sequence identity to a sequence shown in FIG. 3 (e.g., with sequence identity calculated without including or before the addition of the sulfatase motif sequence). In one such embodiment, the sulfatase motifs may be utilized as sites for the conjugation of, for example, epitopes and/or payloads either directly or indirectly through a peptide or chemical linker.

I.A.2.2 Sortase A Enzyme Sites

Epitopes (e.g., peptides comprising the sequence of an epitope) and payloads may be attached at the N- and/or C-termini of the first and/or second polypeptides of a T-Cell-MMP by incorporating sites for Sortase A conjugation at those locations.

Sortase A recognizes a C-terminal pentapeptide sequence LP(X5)TG/A (SEQ ID NO 54, with X5 being any single amino acid, and G/A being a glycine or alanine), and creates an amide bond between the threonine within the sequence and glycine or alanine in the N-terminus of the conjugation partner. Advantageously, the recognition sequences can be incorporated into either conjugation partner permitting either the amino or carboxyl terminus of the first or second polypeptide to serve as a chemical conjugation site. Further, the LP(X5)TG/A sequence does not require any non-natural amino acids, allowing expression to the T-Cell-MMPs to be carried out under a wide variety of conditions in diverse cell types. A potential disadvantage of Sortase A enzymatic ligation is that it employs bacterial transglutaminases (mTGs) that can also catalyze the coupling of glutamine side chains to alkyl primary amines, such as lysine. Bacterial mTGs appear unable to modify glutamine residues in native IgG1, but may result in secondary modifications of the polypeptide sequences when employed.

For attachment of epitopes or payloads to the carboxy terminus of the first or second polypeptide of the T-Cell-MMP, an LP(X5)TG/A is engineered into the carboxy terminal portion of the desired peptide(s). An exposed stretch of glycines or alanines (e.g., (G)$_{3-5}$ (SEQ ID NOs:55 and 56) when using Sortase A from *Staphylococcus aureus* or (A)$_{3-5}$ (SEQ ID NOs:57 and 58) when using Sortase A from *Streptococcus pyogenes*) is engineered into the N-terminus of a peptide that comprises an epitope (or a linker attached thereto), a peptide payload (or a linker attached thereto), or a peptide covalently attached to a non-peptide epitope or payload.

For attachment of epitopes or payloads to the amino terminus of the first or second polypeptide of the T-Cell-MMP, an exposed stretch of glycines (e.g., (G)$_{2, 3, 4, or 5}$) or alanines (e.g., (A)$_{2, 3, 4, or 5}$) is engineered to appear at the N-terminus of the desired polypeptide(s), and a LP(X5)TG/A is engineered into the carboxy terminal portion of a peptide that comprises an epitope (or a linker attached thereto), a peptide payload (or a linker attached thereto), or a peptide covalently attached to a non-peptide epitope or payload.

Combining Sortase A with the amino and carboxy engineered peptides results in a cleavage between the Thr and Gly/Ala residues in the LP(X5)TG/A sequence, forming a thioester intermediate with the carboxy labeled peptide. Nucleophilic attack by the N-terminally modified polypeptide results in the formation of a covalently coupled complex of the form: carboxy-modified polypeptide-LP(X5)T*G/A-amino-modified polypeptide, where the "*" represents the bond formed between the threonine of the LP(X5)TG/A motif and the glycine or alanine of the N-terminal modified peptide. In view of the foregoing, this disclosure contemplates compositions containing, and the use of, T-Cell-MMPs having:

- at least one LP(X5)TG/A amino acid sequence at the carboxy terminus of the first and/or second polypeptides (e.g., for coupling with an epitope peptide modified with oligoglycine or oligo alanine at its N-terminus);
- at least one LP(X5)TA (e.g., LPETA, SEQ ID NO:54 where X5 is E and the end position is A) amino acid sequence in the first and/or second polypeptides (e.g., for coupling with an epitope peptide modified with oligoglycine or oligo alanine at its N-terminus); and/or
- at least one LP(X5)TG (e.g., LPETG, SEQ ID NO:54 where X5 is E and the end position is G) amino acid sequence in the first and/or second polypeptides (e.g., for coupling with an epitope peptide modified with oligoglycine or oligo alanine at its N-terminus).

In place of LP(X5)TG/A, a LPETGG (SEQ ID NOs:59) peptide may be used for *S. aureus* Sortase A coupling, or a LPETAA (SEQ ID NOs:60) peptide may be used for *S. pyogenes* Sortase A coupling. The conjugation reaction is still between the threonine and the amino terminal oligoglycine or oligoalanine peptide to yield a carboxy-modified polypeptide-LP(X5)T*G/A-amino-modified polypeptide, where the "*" represents the bond formed between the threonine and the glycine or alanine of the N-terminal modified peptide.

In one embodiment, where the first polypeptide of the T-Cell-MMP comprises a β2M polypeptide, the first polypeptide contains an oligoglycine (e.g., (G)$_{2, 3, 4, or 5}$) or an oligoalanine (e.g., (A)$_{2, 3, 4, or 5}$) at the N-terminus of the polypeptide, or at the N-terminus of a polypeptide linker attached to the first polypeptide (e.g., the linker is co-translated with, and at the N-terminus of the first polypeptide). The oligoglycine or oligoalanine may be used as a Sortase A chemical conjugation site to introduce an epitope molecule into the T-Cell-MMP by conjugating it with an epitope comprising a polypeptide bearing a LP(X5)TG/A in its carboxy terminal region. By way of example, the sequences of β2M as shown in FIG. 4 begin with a 20 amino acid leader sequence, and the mature polypeptide begins with the initial sequence IQRTP(K/Q)IQVYS and continues through the remainder of the polypeptide. The sortase motifs of SEQ ID NOs:54, 59, and 69 may be incorporated therein, for example as:

```
A2-5 or G2-5-linker-IQ(R/K)TP(K/Q)IQVYS . . . ,

A2-5 or G2-5-linker-Q(R/K)TP(K/Q)IQVYS . . . ,
or

A2-5 or G2-5-linker-(R/K)TP(K/Q)IQVYS . . . , (see SEQ ID NOs: 55 to 58 for A2-5 or G2-5, and SEQ ID NOs: 151-155 and
FIG. 4 for the β2M sequences);
or as shown with the human leader sequences
MSRSVALAVLALLSLSGLEA (see SEQ ID NO: 151 and FIG. 4)

MSRSVALAVLALLSLSGLEA (A2-5 or G2-5)-linker-IQ(R/K)TP(K/Q)IQVYS . . . ,

MSRSVALAVLALLSLSGLEA (A2-5 or G2-5)-linker-Q(R/K)TP(K/Q)IQVYS . . . ,
or

MSRSVALAVLALLSLSGLEA (A2-5 or G2-5)-linker-(R/K)TP(K/Q)IQVYS . . . ,
```

- at least one oligoglycine (e.g., (G)$_{2, 3, 4, or 5}$) at the amino terminus of the first and/or second polypeptides (e.g., for coupling with an epitope polypeptide modified with LP(X5)TG/A amino acid sequence at its N-terminus);
- at least one oligo alanine (e.g., (A)$_{2, 3, 4, or 5}$) at the amino terminus of the first and/or second polypeptides (e.g., for coupling with an epitope polypeptide modified with LP(X5)TG/A amino acid sequence at its N-terminus);

where the linkers, when present, may comprise independently selected amino acid sequences (e.g., from 1 to 50 amino acids, such as polyglycine, polyalanine, polyserine and poly-Gly, such as AAAGG (SEQ ID NO:75) or (GGGGS)$_n$ where n is 1, 2, 3, 4, 5, 6, 7, 8, 9, or 10, (SEQ ID NO:76)), or chemical group (e.g., polyethylene oxide, polyethylene glycol, etc.). Linkers may be present or absent and when two are shown they may be the same or different.

Where a polypeptide bearing an oligoglycine at its N-terminus is prepared by expression in a cell based system, and any part of the leader sequence and/or linker is not removed or not completely removed by the expressing cell, a thrombin cleavage site (Leu-Val-Pro-Arg-Gly, SEQ ID NO:61) may be inserted to precede the glycine. As thrombin cleaves between the Arg and Gly residues, it ensures that upon cleavage the glycines are exposed on the protein molecule to be labeled with oligo glycine and conjugated, provided there are no other thrombin sites in the polypeptide.

In an embodiment, a $A_{2-5}$ or a $G_{2-5}$ motif is incorporated into a polypeptide comprising a sequence having at least 85% (e.g., at least 90%, 95%, 98% or 99%, or even 100%) amino acid sequence identity to a sequence shown in FIG. 4 (e.g., either the entire sequences shown in FIG. 4, or the sequence of the mature polypeptides starting at amino acid 21 and ending at their C-terminus), with sequence identity assessed without consideration of the added $A_{2-5}$ or a $G_{2-5}$ motif and any linker sequences present.

In an embodiment, an $A_{2-5}$ or a $G_{2-5}$ motif is incorporated into a polypeptide comprising a β2M sequence having 1 to 15 (e.g., 1, 2, 3, 4, 5, 6, 7, 8, 9, 10, 11, 12, 13, 14, or 15) amino acid deletions, insertions and/or changes compared with a sequence shown in FIG. 4 (e.g., any of the full length sequences shown in FIG. 4, or any of the mature polypeptide sequences starting at amino acid 21 and ending at their C-terminus), with amino acid deletions, insertions and/or changes assessed without consideration of the added $A_{2-5}$ or a $G_{2-5}$ motif and any linker sequences present. In one such embodiment an $A_{2-5}$ or a $G_{2-5}$ motif may either replace and/or be inserted between any of the amino terminal 15 (e.g., 1-5, 5-10 or 10-15) amino acids of a mature β2M sequence, such as those shown in FIG. 4.

I.A.2.3 Transglutaminase Enzyme Sites

Transglutaminases (mTGs) catalyze the formation of a covalent bond between the amide group on the side chain of a glutamine residue and a primary amine donor (e.g., a primary alkyl amine, such as is found on the side chain of a lysine residue in a polypeptide). Transglutaminases may be employed to conjugate epitopes and payloads to T-Cell-MMPs, either directly or indirectly via a linker comprising a free primary amine. As such, glutamine residues present in the first and/or second polypeptides of the T-Cell-MMP may be considered as chemical conjugation sites when they can be accessed by enzymes such as *Streptoverticillium mobaraense* transglutaminase. That enzyme (EC 2.3.2.13) is a stable, calcium-independent enzyme catalyzing the γ-acyl transfer of glutamine to the ε-amino group of lysine. Glutamine residues appearing in a sequence are, however, not always accessible for enzymatic modification. The limited accessibility can be advantageous as it limits the number of locations where modification may occur. For example, bacterial mTGs are generally unable to modify glutamine residues in native IgG1s; however, Schibli and co-workers (Jeger, S., et al. Angew Chem (Int Engl). 2010; 49:99957 and Dennler P, et al. Bioconjug Chem. 2014; 25(3):569-78) found that deglycosylating IgG1 s at N297 rendered glutamine residue Q295 accessible and permitted enzymatic ligation to create an antibody drug conjugate. Further, by producing a N297 to Q297 IgG1 mutant, they introduce two sites for enzymatic labeling by transglutaminase.

Where a first and/or second polypeptide of the T-Cell-MMP does not contain a glutamine that may be employed as a chemical conjugation site (e.g., it is not accessible to a transglutaminase or not placed in the desired location), a glutamine residue, or a sequence comprising an accessible glutamine that can act as a substrate of a transglutaminase (sometimes referred to as a "glutamine tag" or a "Q-tag"), may be incorporated into the polypeptide. The added glutamine or Q-tag may act as a first polypeptide chemical conjugation site or a second polypeptide chemical conjugation site. US Patent Publication 2017/0043033 A1 describes the incorporation of glutamine residues and Q-tags and the use of transglutaminase for modifying polypeptides, and is incorporated herein for those teachings.

Incorporation of glutamine residues and Q-tags may be accomplished chemically where the peptide is synthesized, or by modifying a nucleic acid that encodes the polypeptide and expressing the modified nucleic acid in a cell or cell free system.

In an embodiment where a first polypeptide chemical conjugation site is a glutamine or Q-tag, the glutamine or Q-tag may be at any of the locations indicated for first polypeptide chemical conjugation sites or second polypeptide chemical conjugation sites described above.

In an embodiment, the added glutamine residue or Q-tag is attached to (e.g., at the N- or C-terminus), or within, the sequence of the first MHC polypeptide, or, if present, a linker attached to the first MHC polypeptide. Additional first polypeptide chemical conjugation sites may be present (attached to or within) any location on the first polypeptide of the T-Cell-MMP. In one such embodiment, the first MHC polypeptide of a T-Cell-MMP is a β2M polypeptide, and an added glutamine or Q-tag is incorporated within 20, 15, or 10 amino acids of the N-terminus of a mature β2M polypeptide sequence, which exclude the 20 base pair signal sequence, provided in FIG. 4 (or a peptide having at least 85%, 90%, 95%, 98%, 99, or even 100% sequence identity to a mature β2M polypeptide in FIG. 4). In another embodiment, the glutamine or Q-tag is present in a polypeptide linker attached to the N-terminus of one of the mature β2M polypeptides provided in FIG. 4.

In an embodiment the added glutamine residue or Q-tag is attached to (e.g., at the N- or C-terminus), or within, the sequence of the second polypeptide of a T-Cell-MMP, for example a terminus or within a second MHC polypeptide (e.g., a MHC-H peptide), or, if present, a Fc, scaffold peptide or linker attached directly or indirectly to the second MHC polypeptide. Additional second polypeptide chemical conjugation sites may be present (attached to or within) any location on the second polypeptide of the T-Cell-MMP. In one embodiment, the second MHC polypeptide is a MHC-H polypeptide, the second polypeptide comprises a Fc polypeptide, and an added glutamine or Q-tag is incorporated within the MHC-H or the Fc polypeptide sequence. In another embodiment, the glutamine or Q-tag is present within a polypeptide linker between the MHC-H and Fc polypeptides, or within a linker attached to the carboxyl terminus of the Fc polypeptide.

In embodiments, the glutamine-containing tag comprises an amino acid sequence selected from the group consisting of LQG, LLQGG (SEQ ID NO:62), LLQG (SEQ ID NO:63), LSLSQG (SEQ ID NO:64), and LLQLQG (SEQ ID NO:65) (numerous others are available).

Payloads and epitopes that contain, or have been modified to contain, a primary amine group may be used as the amine donor in a transglutaminase catalyzed reaction forming a covalent bond between a glutamine residue (e.g., a glutamine residue in a Q-tag) and the epitope or payload.

Where an epitope or payload does not comprise a suitable primary amine to permit it to act as the amine donor, the epitope or payload may be chemically modified to incorporate an amine group (e.g., modified to incorporate a primary amine by linkage to a lysine, aminocaproic acid, cadaverine etc.). Where an epitope or payload comprises a peptide, and requires a primary amine to act as the amine donor, a lysine, or other amine containing compound that a primary amine with a transglutaminase can act on, may be incorporated into the peptide. Other amine containing compounds that may provide a primary amine group and that may be incorporated into, or at the end of, an alpha amino acid chain include, but are not limited to, homolysine, 2,7-diaminoheptanoic acid, and aminoheptanoic acid. Alternatively, the epitope or payload may be attached to a peptide or non-peptide linker that comprises a suitable amine group. Examples of suitable non-peptide linkers include an alkyl linker and a PEG (polyethylene glycol) linker.

Transglutaminase can be obtained from a variety of sources, and include enzymes from: mammalian liver (e.g., guinea pig liver); fungi (e.g., *Oomycetes, Actinomycetes, Saccharomyces, Candida, Cryptococcus, Monascus,* or *Rhizopus* transglutaminases); myxomycetes (e.g., *Physarum polycephalum* transglutaminase); and/or bacteria (e.g., *Streptoverticillium mobarensis, Streptoverticillium griseocarneum, Streptoverticillium ladakanum, Streptomyces mobarensis, Streptomyces viridis, Streptomyces ladakanum, Streptomyces caniferus, Streptomyces platensis, Streptomyces hygroscopius, Streptomyces netropsis, Streptomyces fradiae, Streptomyces roseovertivillatus, Streptomyces cinnamaoneous, Streptomyces griseocarneum, Streptomyces lavendulae, Streptomyces lividans, Streptomyces lydicus, S. mobarensis, Streptomyces sioyansis, Actinomadura* sp., *Bacillus circulans, Bacillus subtilis, Corynebacterium ammoniagenes, Corynebacterium glutamicum, Clostridium, Enterobacter* sp., *Micrococcus*). In some embodiments, the transglutaminase is a calcium independent transglutaminase which does not require calcium to induce enzyme conformational changes and allow enzyme activity.

As discussed above for other first polypeptide chemical conjugation sites and second polypeptide chemical conjugation sites, a glutamine or Q-tag may be incorporated into any desired location on the first or second polypeptide of the T-Cell-MMP. In an embodiment, a glutamine or Q-tag may be added at or near the terminus of any element in the first or second polypeptide of the T-Cell-MMP, including the first and second MHC polypeptides (e.g., MHC-H and β2M polypeptides), the scaffold or Ig Fc, and the linkers adjoining those elements.

In one embodiment, where the first polypeptide of the T-Cell-MMP comprises a β2M polypeptide sequence, the first polypeptide contains a glutamine or Q-tag at the N-terminus of the polypeptide, or at the N-terminus of a polypeptide linker attached to the first polypeptide (e.g., the linker is attached to the N-terminus of the first polypeptide). The glutamine or Q-tag may be used as a chemical conjugation site to introduce an epitope molecule into the T-Cell-MMP by conjugating it with a primary amine bearing epitope, or an epitope bound to a linker comprising a primary amine, that can be used as an amide donor by a transglutaminase. By way of example, the sequences of β2M as shown in FIG. 4 begin with a 20 amino acid leader sequence, and the mature polypeptide begins with the initial sequence IQRTP(K/Q)IQVYS and continues through the remainder of the polypeptide. A Q-tag with the amino acid sequence LLQG (SEQ ID NO:63), which is representative of, and substitutable by, the other Q-tags shown above, can be incorporated at the N-terminus of β2M as shown:

```
Q-tag-linker-IQRTP(K/Q)IQVYS . . . ;

LLQG-linker-IQRTP(K/Q)IQVYS . . . ;

LLQG-linker-QRTP(K/Q)IQVYS . . . ;
or

LLQG-linker-RTP(K/Q)IQVYS . . . ;
(see SEQ ID NOs: 151-155 for the β2M sequences)
``` or as shown with the human leader sequences MSRSVA-LAVLALLSLSGLEA (see SEQ ID NO:151 and FIG. 4),

```
MSRSVALAVLALLSLSGLEA-linker-Q-tag-linker-

IQRTP(K/Q)IQVYS . . . ;

MSRSVALAVLALLSLSGLEA-linker-LLQG-linker-

IQRTP(K/Q)IQVYS . . . ;

MSRSVALAVLALLSLSGLEA-linker-LLQG-linker-

QRTP(K/Q)IQVYS . . . ;
or

MSRSVALAVLALLSLSGLEA-linker-LLQG-linker-

RTP(K/Q)IQVYS . . . .
``` where the linkers, when present, may comprise independently selected amino acid sequences (e.g., from 1 to 50 amino acids, such as polyglycine, polyalanine, polyserine and poly-Gly, such as AAAGG (SEQ ID NO:75) or (GGGGS)$_n$ where n is 1, 2, 3, 4, 5, 6, 7, 8, 9, or 10 (SEQ ID NO:76), or a chemical group (e.g., polyethylene oxide, polyethylene glycol, etc.). Linkers may be present or absent and when two are shown they may be the same or different.

In an embodiment a Q-tag motif is incorporated into a polypeptide comprising a β2M sequence having at least 85% (e.g., at least 90%, 95%, 98% or 99%, or even 100%) amino acid sequence identity to a sequence shown in FIG. 4 (e.g., any of the full-length sequences shown in FIG. 4, or the sequence of any of the mature β2M polypeptide starting at amino acid 21 and ending at their C-terminus), with identity assessed without consideration of the added Q-tag motif and any linker sequences present.

In an embodiment a Q-tag motif is incorporated into a sequence having 1 to 15 (e.g., 1, 2, 3, 4, 5, 6, 7, 8, 9, 10, 11, 12, 13, 14, or 15) amino acid deletions, insertions and/or changes compared with a sequence shown in FIG. 4 (either the entire sequences shown in FIG. 4, or the sequence of the mature polypeptides starting at amino acid 21 and ending at their C-terminus). Changes are assessed without consideration of the amino acids of the Q-tag motif and any linker sequences present. In one such embodiment a Q-tag motif may replace and/or be inserted between any of the amino terminal 15 (e.g., 1-5, 5-10, or 10-15) amino acids of a mature β2M sequence, such as those shown in FIG. 4.

Alternatively, the sequence around any one, two, or three of the glutamine residues appearing in a MHC-H chain sequence appearing in a T-Cell-MMP may be modified to match that of a Q-tag and used as a chemical conjugation site for addition of an epitope or payload.

In another embodiment, glutamines or Q-tags may be incorporated into the IgFc region as second polypeptide chemical conjugation sites. In one such embodiment they may be utilized as sites for the conjugation of, for example, epitopes and/or payloads either directly or indirectly through a peptide or chemical linker bearing primary amine.

I.A.2.4 Selenocysteine and Non-Natural Amino Acids as Chemical Conjugation Sites One strategy for providing site-specific chemical conjugation sites in the first and/or second polypeptides of a T-Cell-MMP employs the insertion of amino acids with reactivity distinct from the other amino acids present in the polypeptide. Such amino acids include, but are not limited to, the non-natural amino acids, acetylphenylalanine (p-acetyl-L-phenylalanine, pAcPhe), parazido phenylalanine, and propynyl-tyrosine, and the naturally occurring amino acid, selenocysteine (Sec).

Thanos et al. in US Pat. Publication No. 20140051836 A1 discuss some other non-natural amino acids including O-methyl-L-tyrosine, L-3-(2-naphthyl)alanine, a 3-methylphenylalanine, an O-4-allyl-L-tyrosine, a 4-propyl-L-tyrosine, a tri-O-acetyl-GlcNAcβ-serine, L-Dopa, a fluorinated phenylalanine, an isopropyl-L-phenylalanine, a p-acyl-L-phenylalanine, a p-benzoyl-L-phenylalanine, L-phosphoserine, a phosphonoserine, a phosphonotyrosine, a p-iodophenylalanine, a p-bromophenylalanine, a p-amino-L-phenylalanine, an isopropyl-L-phenylalanine, and a p-propargyloxy-phenylalanine. Other non-natural amino acids include reactive groups including amino, carboxy, acetyl, hydrazino, hydrazido, semicarbazido, sulfanyl, azido and alkynyl. See, e.g., US Pat. Publication No. 20140046030 A1.

In addition to directly synthesizing polypeptides in the laboratory, two methods utilizing stop codons have been developed to incorporate non-natural amino acids into proteins and polypeptides utilizing transcription-translation systems. The first incorporates selenocysteine (Sec) by pairing the opal stop codon, UGA, with a Sec insertion sequence. The second incorporates non-natural amino acids into a polypeptide generally through the use of amber, ochre, or opal stop codons. The use of other types of codons such as a unique codon, a rare codon, an unnatural codon, a five-base codon, and a four-base codon, and the use of nonsense and frameshift suppression have also been reported. See, e.g., US Pat. Publication No. 20140046030 A1 and Rodriguez et al., PNAS 103(23)8650-8655(2006). By way of example, the non-natural amino acid acetylphenylalanine may be incorporated at an amber codon using a tRNA/ aminoacyl tRNA synthetase pair in an in vivo or cell free transcription-translation system.

Incorporation of both selenocysteine and non-natural amino acids requires engineering the necessary stop codon(s) into the nucleic acid coding sequence of the first and/or second polypeptide of the T-Cell-MMP at the desired location(s), after which the coding sequence is used to express the first or second polypeptide strand of the T-Cell-MMP in an in vivo or cell free transcription-translation system.

In vivo systems generally rely on engineered cell-lines to incorporate non-natural amino acids that act as bio-orthogonal chemical conjugation sites into polypeptides and proteins. See, e.g., International Published Application No. 2002/085923 entitled "In vivo incorporation of unnatural amino acids." In vivo non-natural amino acid incorporation relies on a tRNA and an aminoacyl tRNA synthetase (aaRS) pair that is orthogonal to all the endogenous tRNAs and synthetases in the host cell. The non-natural amino acid of choice is supplemented to the media during cell culture or fermentation, making cell-permeability and stability important considerations.

Various cell-free synthesis systems provided with the charged tRNA may also be utilized to incorporate non-natural amino acids. Such systems include those described in US Published Pat. Application No. 20160115487A1; Gubens et al., RNA. 2010 August; 16(8): 1660-1672; Kim, D M. and Swartz, J. R. Biotechnol. Bioeng. 66:180-8 (1999); Kim, D M. and Swartz, J. R. Biotechnol. Prog. 16:385-90 (2000); Kim, D M. and Swartz, J. R. Biotechnol. Bioeng. 74:309-16 (2001); Swartz et al, Methods Mol. Biol. 267: 169-82 (2004); Kim, D M. and Swartz, J. R. Biotechnol. Bioeng. 85:122-29 (2004); Jewett, M. C. and Swartz, J. R., Biotechnol. Bioeng. 86:19-26 (2004); Yin, G. and Swartz, J. R., Biotechnol. Bioeng. 86:188-95 (2004); Jewett, M. C. and Swartz, J. R., Biotechnol. Bioeng. 87:465-72 (2004); Voloshin, A. M. and Swartz, J. R., Biotechnol. Bioeng. 91:516-21 (2005).

Once incorporated into the first or second polypeptide of the T-Cell-MMP, epitopes and/or payload bearing groups reactive with the incorporated selenocysteine or non-natural amino acid are brought into contact with the T-Cell-MMP under suitable conditions to form a covalent bond. By way of example, the keto group of the pAcPhe is reactive towards alkoxy-amines, via oxime coupling, and can be conjugated directly to alkoxyamine containing epitopes and/or payloads or indirectly to epitopes and payloads via an alkoxyamine containing linker. Selenocysteine reacts with, for example, primary alkyl iodides (e.g., iodoacetamide which can be used as a linker), maleimides, and methylsulfone phenyloxadiazole groups. Accordingly, epitopes and/or payloads bearing those groups or bound to linkers bearing those groups can be covalently bound to polypeptide chains bearing selenocysteines.

As discussed above for other first polypeptide chemical conjugation sites and second polypeptide chemical conjugation sites, selenocysteines and/or non-natural amino acids may be incorporated into any desired location in the first or second polypeptide of the T-Cell-MMP. In an embodiment, selenocysteines and/or non-natural amino acids may be added at or near the terminus of any element in the first or second polypeptide of the T-Cell-MMP, including the first and second MHC polypeptides (e.g., MHC-H and β2M polypeptides), the scaffold or Ig Fc, and the linkers adjoining those elements. In embodiments selenocysteines and/or non-natural amino acids may be incorporated into a β2M, class I MHC heavy chain, and/or a Fc Ig polypeptide. In an embodiment, selenocysteines and/or non-natural amino acids may be incorporated into the first polypeptide near or at the amino terminal end of the first MHC polypeptide (e.g., the β2M polypeptide) or a linker attached to it. For example, where the first polypeptide comprises a β2M sequence, selenocysteines and/or non-natural amino acids may be incorporated at or near the N-terminus of a β2M sequence, permitting the chemical conjugation of, for example, an epitope either directly or through a linker. By way of example, the sequences of β2M as shown in FIG. 4 begin with a 20 amino acid leader sequence, and the mature polypeptide begins with the initial sequence IQRTP(K/Q) IQVYS and continues through the remainder of the polypeptide. Selenocysteines and/or non-natural amino acids (denoted by "ψ") may be incorporated therein, for example as:

ψ IQRTP(K/Q)IQVYS . . . ;

ψ-linker-IQRTP(K/Q)IQVYS . . . ;

-continued

```
ψ-linker-QRTP(K/Q)IQVYS . . . ;
or

ψ-linker-RTP(K/Q)IQVYS . . . ;
``` or as shown with the human leader sequences MSRSVA-LAVLALLSLSGLEA (see SEQ ID NOs:151-155 and FIG. 4 for the β2M sequences),

```
MSRSVALAVLALLSLSGLEA-linker-ψ IQRTP(K/Q)

IQVYS . . . ;

MSRSVALAVLALLSLSGLEA-linker-ψ-linker-IQRTP(K/Q)

IQVYS . . . ;

MSRSVALAVLALLSLSGLEA-linker-ψ-linker-QRTP(K/Q)

IQVYS . . . ;
or

MSRSVALAVLALLSLSGLEA-linker-ψ-linker-RTP(K/Q)

IQVYS . . . ,
``` where the linkers, when present, may comprise independently selected amino acid sequences (e.g., from 1 to 50 amino acids such as polyglycine, polyalanine, polyserine and poly-Gly, such as AAAGG (SEQ ID NO:75) or $(GGGGS)_n$ where n is 1, 2, 3, 4, 5, 6, 7, 8, 9, or 10 (SEQ ID NO:76)), or a chemical group (e.g., polyethylene oxide, polyethylene glycol, etc.). Linkers may be present or absent and when two are shown they may be the same or different.

In an embodiment selenocysteines and/or non-natural amino acids are incorporated into a polypeptide comprising a β2M sequence having at least 85% (e.g., at least 90%, 95%, 98% or 99%, or even 100%) amino acid sequence identity to a β2M sequence shown in FIG. 4 (e.g., any of the full length sequences shown in FIG. 4, or the sequence of any of the mature β2M polypeptides starting at amino acid 21 and ending at their C-terminus), with sequence identity assessed without consideration of the added selenocysteines and/or non-natural amino acids and any linker sequences present.

In an embodiment selenocysteines and/or non-natural amino acids are incorporated into a polypeptide comprising a β2M sequence having 1 to 15 (e.g., 1, 2, 3, 4, 5, 6, 7, 8, 9, 10, 11, 12, 13, 14, or 15) amino acid deletions, insertions and/or changes compared with a β2M sequence shown in FIG. 4 (e.g., any of the full-length sequences shown in FIG. 4, or the sequence of any of the mature β2M polypeptides starting at amino acid 21 and ending at their C-terminus). Changes are assessed without consideration of the amino acids of the selenocysteines and/or non-natural amino acids and any linker sequences present. In one such embodiment a selenocysteine and/or non-natural amino acid may replace and/or be inserted between any of the amino terminal 15 amino acids of a mature β2M sequence, such as those shown in FIG. 4.

In other embodiments, selenocysteines and/or non-natural amino acids may be incorporated into polypeptides comprising a MHC-H chain or IgFc polypeptide sequences (including linkers attached thereto) as chemical conjugation sites. In one such embodiment they may be utilized as sites for the conjugation of, for example, epitopes and/or payloads conjugated to the T-Cell-MMP either directly or indirectly through a peptide or chemical linker.

I.A.2.5 Engineered Amino Acid Chemical Conjugation Sites

Any of the variety of functionalities (e.g., —SH, —NH₃, —OH, —COOH and the like) present in the side chains of naturally occurring amino acids, or at the termini of polypeptides, can be used as chemical conjugation sites. This includes the side chains of lysine and cysteine which are readily modifiable by reagents including N-hydroxysuccinimide and maleimide functionalities, respectively. The main disadvantages of utilizing such amino acid residues is the potential variability and heterogeneity of the products. For example, an IgG has over 80 lysines, with over 20 at solvent-accessible sites. See, e.g., McComb and Owen, AAPS J. 117(2): 339-351. Cysteines tend to be less widely distributed; they tend to be engaged in disulfide bonds and may be inaccessible and not located where it is desirable to place a chemical conjugation site. Accordingly, it is possible to engineer the first and/or second polypeptide to incorporate non-naturally occurring amino acids at the desired locations for selective modification of the T-Cell-MMP first and/or second polypeptides. Engineering may take the form of direct chemical synthesis of the polypeptides (e.g., by coupling appropriately blocked amino acids) and/or by modifying the sequence of a nucleic acid encoding the polypeptide and expressing it in a cell or cell free system. Accordingly, the specification includes and provides for the preparation of all or part of the first and/or second polypeptide of a T-Cell-MMP by transcription/translation, and joining to the C- or N-terminus of the translated portion of the first and/or second polypeptide an engineered polypeptide bearing a non-natural or natural (including selenocysteine) amino acid to be used as a chemical conjugation site (e.g., for epitopes or peptides). The engineered peptide may be joined by any suitable method, including the use of a sortase as described for epitope peptides above and may include a linker peptide sequence. In an embodiment the engineered peptide may comprise a sequence of 2, 3, 4, or 5 alanines or glycines that may serve for sortase conjugation and/or as part of a linker sequence.

In one embodiment, a first or second polypeptide of a T-Cell-MMP contains at least one naturally occurring amino acid to be used as a chemical conjugation site engineered into a β2M sequence as shown in FIG. 4, an IgFc sequence as shown in FIG. 2, or a MHC Class I heavy chain polypeptide as shown in FIG. 3. In an embodiment, at least one naturally occurring amino acid to be used as a chemical conjugation site is engineered into a polypeptide having at least 85% (e.g., at least 90%, 95%, 98% or 99%, or even 100%) amino acid sequence identity to a β2M sequence as shown in FIG. 4, an IgFc sequence as shown in FIG. 2, or a MHC Class I heavy chain polypeptide as shown in FIG. 3. In an embodiment, at least one naturally occurring amino acid to be used as a chemical conjugation site is engineered into a T-Cell-MMP first or second polypeptide comprising: a β2M amino acid sequence having at least 90% (e.g., at least 93%, 95%, 98% or 99%, or even 100%) amino acid sequence identity with at least the amino terminal 10, 20, 30, 40, 50 60 or 70 amino acids of a mature β2M sequence as shown in FIG. 4; an IgFc sequence as shown in FIG. 2; or a MHC Class I heavy chain polypeptide as shown in FIG. 3. In another embodiment, at least one naturally occurring amino acid to be used as a chemical conjugation site is engineered into a polypeptide comprising a contiguous sequence of at least 30, 40, 50, 60, 70, 80, 90, or 100 amino acids having 100% amino acid sequence identity to a β2M sequence as shown in FIG. 4, an IgFc sequence as shown in FIG. 2, or a MHC Class I heavy chain sequence as shown in FIG. 3. In any of the embodiments mentioned above where a naturally occurring amino acid is engineered into a polypeptide, the amino acid may be selected from the group consisting of arginine, lysine, cysteine, serine, threonine, glutamic acid, glutamine, aspartic acid, and asparagine. In another such embodiment, the amino acid is selected from the group consisting of lysine, cysteine, serine, threonine, and glutamine. In another such embodiment, the amino acid is selected from the group consisting of lysine, glutamine, and cysteine. In an embodiment the amino acid is cysteine. In an embodiment the amino acid is lysine; in another embodiment the amino acid is glutamine.

Any method known in the art may be used to couple payloads or epitopes to amino acids engineered into the first or second polypeptides of the T-Cell-MMP. By way of example, maleimides may be utilized to couple to sulfhydryls, N-hydroxysuccinimide may be utilized to couple to amine groups, acid anhydrides or chlorides may be used to couple to alcohols or amines, and dehydrating agents may be used to couple alcohols or amines to carboxylic acid groups. Accordingly, using such chemistry an epitope or payload may be coupled directly, or indirectly through a linker (e.g., a homo- or hetero-bifunctional crosslinker), to a location on a first and/or second polypeptide. By way of example, an epitope peptide (or a peptide-containing payload) including a maleimide amino acid can be conjugated to a sulfhydryl of a chemical conjugation site (e.g., a cysteine residue) that is naturally occurring or engineered into a T-Cell-MMP. Using a Diels-Alder/retro-Diels-Alder protecting scheme, it is possible to directly incorporate maleimide amino acid into a peptide (e.g., an epitope peptide) using solid phase peptide synthetic techniques. See, e.g., Koehler, Kenneth Christopher (2012), "Development and Implementation of Clickable Amino Acids," *Chemical & Biological Engineering Graduate Theses & Dissertations,* 31, https://scholar.colorado.edu/chbe_gradetds/31. Accordingly, in one embodiment an epitope peptide comprises a maleimide amino acid that is coupled to a cysteine present in the binding pocket of a T-Cell-MMP. A maleimide may also be appended to an epitope peptide using a crosslinker that attaches a maleimide to the peptide (e.g., a heterobifunctional N-hydroxysuccinimide—maleimide crosslinker, which can attach maleimide to an amine group on, for example, a peptide lysine). In an embodiment, an epitope peptide having at least one (e.g., 1 or 2) maleimide amino acid is conjugated to a MHC heavy chain having cysteine residues at any one or more (e.g., 1 or 2) amino acid positions selected from positions 5, 7, 59, 84, 116, 139, 167, 168, 170, and/or 171 (e.g., Y7C, Y59C, Y84C, Y116C, A139C, W167C, L168C, R170C, and Y171C substitutions) with the numbering as in FIG. 3D. In an embodiment, an epitope peptide having at least one (e.g., 1 or 2) maleimide amino acids is conjugated to a MHC heavy chain having cysteine residues at any one or more (e.g., 1 or 2) amino acid positions selected from positions 7, 84 and/or 116, (e.g., Y7C, Y84C, and Y116C substitutions) with the numbering as in FIG. 3D. In an embodiment, an epitope peptide having at least one (e.g., 1 or 2) maleimide amino acids is conjugated to a MHC heavy chain having cysteine residues at any one or more (e.g., 1 or 2) amino acid positions selected from positions 84 and/or 116 (e.g., Y84C and/or Y116C substitutions) with the numbering as in FIG. 3D.

A pair of sulfhydryl groups may be employed simultaneously to create a chemical conjugate to a T-Cell-MMP. In such an embodiment a T-Cell-MMP that has a disulfide bond, or has two cysteines (or selenocysteines) engineered into locations proximate to each other, may be utilized as a chemical conjugation site through the use of bis-thiol linkers. Bis-thiol linkers, described by Godwin and co-workers, avoid the instability associated with reducing a disulfide bond by forming a bridging group in its place and at the same time permit the incorporation of another molecule, which can be an epitope or payload. See, e.g., Badescu G, et al., (2014), Bioconjug Chem., 25(6):1124-36, entitled *Bridging disulfides for stable and defined antibody drug conjugates*, describing the use of bis-sulfone reagents, which incorporate a hydrophilic linker (e.g., PEG (polyethyleneglycol) linker).

Where a T-Cell-MMP comprises a disulfide bond, the bis-thiol linker may be used to incorporate an epitope or payload by reducing the bond, generally with stoichiometric or near stoichiometric amounts of dithiol reducing agents (e.g., dithiothreitol) and allowing the linker to react with both cysteine residues. Where multiple disulfide bonds are present, the use of stoichiometric or near stoichiometric amounts of reducing agents may allow for selective modification at one site. See, e.g., Brocchini, et al., Adv. Drug. Delivery Rev. (2008) 60:3-12. Where the first and/or second polypeptides of the T-Cell-MMP do not comprise a pair of cysteines and/or selenocysteines (e.g., a selenocysteine and a cysteine), they may be engineered into the polypeptide (by introducing one or both of the cysteines or selenocysteines) to provide a pair of residues that can interact with a bis-thiol linker. The cysteines and/or selenocysteines should be located such that a bis-thiol linker can bridge them (e.g., at a location where two cysteines could form a disulfide bond). Any combination of cysteines and selenocysteines may be employed (i.e. two cysteines, two selenocysteines, or a selenocysteine and a cysteine). The cysteines and/or selenocysteines may both be present on the first and/or second polypeptide of a T-Cell-MMP. Alternatively, the cysteines and/or selenocysteines may be present on the first polypeptide and their counterpart for bis-thiol linker reaction present on the second polypeptide of a T-Cell-MMP.

In an embodiment, a pair of cysteines and/or selenocysteines is incorporated into a first or second polypeptide of a T-Cell-MMP comprising a β2M sequence having at least 85% (e.g., at least 90%, 95%, 98% or 99%, or even 100%) amino acid sequence identity to a sequence shown in FIG. 4 before the addition of the pair of cysteines and/or selenocysteines, or into a peptide linker attached to one of those sequences. In one such embodiment the pair of cysteines and/or selenocysteines may be utilized as a bis-thiol linker coupling site for the conjugation of, for example, epitopes and/or payloads either directly or indirectly through a peptide or chemical linker. In one embodiment, the pair of cysteines and/or selenocysteines is located within 10, 20, 30, 40 or 50 amino acids of the amino terminus of the first polypeptide of the T-Cell-MMP.

In another embodiment, a pair of cysteines and/or selenocysteines is incorporated into an IgFc sequence incorporated into a second polypeptide to provide a chemical conjugation site. In an embodiment a pair of cysteines and/or selenocysteines is incorporated into a polypeptide comprising an IgFc sequence having at least 85% (e.g., at least 90%, 95%, 98% or 99%, or even 100%) amino acid sequence identity to a sequence shown in FIG. 2 before the addition of the pair of cysteines or selenocysteines, or into a peptide linker attached to one of those sequences. In one such embodiment the pair of cysteines and/or selenocysteines may be utilized as a bis-thiol linker coupling site for the conjugation of, for example, epitopes and/or payloads either directly or indirectly through a peptide or chemical linker.

In another embodiment, a pair of cysteines and/or selenocysteines is incorporated into a polypeptide comprising a MHC Class I heavy chain polypeptide sequence as a chemical conjugation site. In an embodiment, a pair of cysteines and/or selenocysteines is incorporated into a polypeptide comprising a sequence having at least 85% (e.g., at least 90%, 95%, 98% or 99%, or even 100%) amino acid sequence identity to a sequence shown in FIG. 3 before the addition of a pair of cysteines or selenocysteines, or into a peptide linker attached to one of those sequences. In one such embodiment the pair of cysteines and/or selenocysteines may be utilized as a bis-thiol linker coupling site for the conjugation of, for example, epitopes and/or payloads either directly or indirectly through a peptide or chemical linker.

A pair of sulfhydryl groups may be employed simultaneously to create a chemical conjugate to a T-Cell-MMP. In such an embodiment a T-Cell-MMP that has a disulfide bond, or has two cysteines (or selenocysteines) engineered into locations proximate to each other may be utilized as a chemical conjugation site through the use of bis-thiol linkers.

I.A.2.6 Other Chemical Conjugation Sites
Carbohydrate Chemical Conjugation Sites Many proteins prepared by cellular expression contain added carbohydrates (e.g., oligosaccharides of the type added to antibodies expressed in mammalian cells). Accordingly, where first and/or second polypeptides of a T-Cell-MMP are prepared by cellular expression, carbohydrates may be present and available as site selective chemical conjugation sites in glycol-conjugation reactions. McCombs and Owen, AAPS Journal, (2015) 17(2): 339-351, and references cited therein describe the use of carbohydrate residues for glycol-conjugation of molecules to antibodies.

The addition and modification of carbohydrate residues may also be conducted ex vivo, through the use of chemicals that alter the carbohydrates (e.g., periodate, which introduces aldehyde groups), or by the action of enzymes (e.g., fucosyltransferases) that can incorporate chemically reactive carbohydrates or carbohydrate analogs for use as chemical conjugation sites.

In an embodiment, the incorporation of an IgFc scaffold with known glycosylation sites may be used to introduce site specific chemical conjugation sites.

This disclosure includes and provides for T-Cell-MMPs and their epitope conjugates having carbohydrates as chemical conjugation (glycol-conjugation) sites. The disclosure also includes and provides for the use of such molecules in forming conjugates with epitopes and with other molecules such as drugs and diagnostic agents, and the use of those molecules in methods of medical treatment and diagnosis.

Nucleotide Binding Sites

Nucleotide binding sites offer site-specific functionalization through the use of a UV-reactive moiety that can covalently link to the binding site. Bilgicer et al., Bioconjug Chem. 2014; 25(7):1198-202, reported the use of an indole-3-butyric acid (IBA) moiety that can be covalently linked to an IgG at a nucleotide binding site. By incorporation of the sequences required to form a nucleotide binding site, chemical conjugates of T-Cell-MMP with suitably modified epitopes and/or other molecules (e.g., drugs or diagnostic agents) bearing a reactive nucleotide may be employed to prepare T-Cell-MMP-epitope conjugates.

This disclosure includes and provides for T-Cell-MMPs having nucleotide binding sites as chemical conjugation sites. The disclosure also includes and provides for the use of such molecules in forming conjugates with epitopes and with other molecules such as drugs and diagnostic agents, and the use of those molecules in methods of treatment and diagnosis.

I.A.2.7 Binding and Properties of T-Cell-MMPs, Epitopes and MOD

The present disclosure provides T-Cell-MMP-epitope conjugates. In one embodiment the disclosure provides for a T-Cell-MMP epitope conjugate comprising: a) a first polypeptide; and b) a second polypeptide, wherein the first and second polypeptides of the multimeric polypeptide comprise an epitope; a first MHC polypeptide; a second MHC polypeptide; and optionally an immunoglobulin (Ig) Fc polypeptide or a non-Ig scaffold. In another embodiment, the present disclosure also provides a T-Cell-MMP-epitope conjugate comprising: a) a first polypeptide comprising, in order from N-terminus to C-terminus: i) an epitope; ii) a first MHC polypeptide; and b) a second polypeptide comprising, in order from N-terminus to C-terminus: i) a second MHC polypeptide; and ii) optionally an Ig Fc polypeptide or a non-Ig scaffold. In addition to those components recited above, at least one of the first and second polypeptides of the T-Cell-MMP-epitope conjugates of the present disclosure comprise one or more (e.g., at least one) MODs. The one or more MODs are located at: A) the C-terminus of the first polypeptide; B) the N-terminus of the second polypeptide; C) the C-terminus of the second polypeptide; and/or D) at the C-terminus of the first polypeptide and at the N-terminus of the second polypeptide. In an embodiment, at least one (e.g., at least two, or at least three) of the one or more MODs is a variant MOD that exhibits reduced affinity to a Co-MOD compared to the affinity of a corresponding wild-type MOD for the Co-MOD.

In an embodiment, the epitope present in a T-Cell-MMP-epitope conjugate of the present disclosure binds to a T-cell receptor (TCR) on a T-cell with an affinity of at least 100 μM (e.g., at least 10 μM, at least 1 μM, at least 100 nM, at least 10 nM or at least 1 nM). In an embodiment, a T-Cell-MMP-epitope conjugate of the present disclosure binds to a first T-cell with an affinity that is at least 25% higher than the affinity with which the T-Cell-MMP-epitope conjugate binds to a second T-cell, where the first T-cell expresses on its surface the Co-MOD and a TCR that binds the epitope with an affinity of at least 100 μM, and where the second T-cell expresses on its surface the Co-MOD but does not express on its surface a TCR that binds the epitope with an affinity of at least 100 μM (e.g., at least 10 μM, at least 1 μM, at least 100 nM, at least 10 nM, or at least 1 nM).

In some cases, the epitope present in a T-Cell-MMP-epitope conjugate of the present disclosure binds to a TCR on a T-cell with an affinity of from about $10^{-4}$ M to about $5 \times 10^{-4}$ M, from about $5 \times 10^{-4}$ M to about $10^{-5}$ M, from about $10^{-5}$ M to about $5 \times 10^{-5}$ M, from about $5 \times 10^{-5}$ M to about $10^{-6}$ M, from about $10^{-6}$ M to about $5 \times 10^{-6}$ M, from about $5 \times 10^{-6}$ M to about $10^{-7}$ M, from about $10^{-7}$ M to about $10^{-8}$ M or from about $10^{-8}$ M to about $10^{-9}$ M. Expressed another way, in some cases, the epitope present in a T-Cell-MMP-epitope conjugate of the present disclosure binds to a TCR on a T-cell with an affinity of from about 0.1 μM to about 0.5 μM, from about 0.5 μM to about 1 μM, from about 1 μM to about 5 μM, from about 5 μM to about 10 μM, from about 10 μM to about 25 μM, from about 25 μM to about 50 μM, from about 50 μM to about 75 μM, or from about 75 μM to about 100 μM.

In an embodiment, a variant MOD present in a T-Cell-MMP-epitope conjugate of the present disclosure binds to its Co-MOD with an affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the affinity of a corresponding wild-type MOD for the Co-MOD.

In some cases, a variant MOD present in a T-Cell-MMP-epitope conjugate of the present disclosure has a binding affinity for a Co-MOD that is from 1 nM to 100 nM, or from 100 nM to 100 µM. For example, in some cases, a variant MOD present in a T-Cell-MMP-epitope conjugate of the present disclosure has a binding affinity for a Co-MOD that is from about 1 nM to about 5 nM, from about 5 nM to about 10 nM, from about 10 nM to about 50 nM, from about 50 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, a variant MOD present in a T-Cell-MMP of the present disclosure has a binding affinity for a Co-MOD that is from about 1 nM to about 5 nM, from about 5 nM to about 10 nM, from about 10 nM to about 50 nM, from about 50 nM to about 100 nM.

The combination of the reduced affinity of the MOD for its Co-MOD, and the affinity of the epitope for a TCR, provides for enhanced selectivity of a T-Cell-MMP-epitope conjugate of the present disclosure, while still allowing for activity of the MOD. For example, a T-Cell-MMP-epitope conjugate of the present disclosure binds selectively to a first T-cell that displays both: i) a TCR specific for the epitope present in the T-Cell-MMP-epitope conjugate; and ii) a Co-MOD that binds to the MOD present in the T-Cell-MMP-epitope conjugate, compared to binding to a second T-cell that displays: i) a TCR specific for an epitope other than the epitope present in the T-Cell-MMP-epitope conjugate; and ii) a Co-MOD that binds to the MOD present in the T-Cell-MMP-epitope conjugate. For example, a T-Cell-MMP-epitope conjugate of the present disclosure binds to the first T-cell with an affinity that is at least 10%, at least 15%, at least 20%, at least 25%, at least 30%, at least 40%, at least 50%, at least 60%, at least 70%, at least 80%, at least 90%, at least 200% (2-fold), at least 250% (2.5-fold), at least 500% (5-fold), at least 1,000% (10-fold), at least 1,500% (15-fold), at least 2,000% (20-fold), at least 2,500% (25-fold), at least 5,000% (50-fold), at least 10,000% (100-fold), or more than 100-fold, higher than the affinity to which it binds the second T-cell.

In some cases, a T-Cell-MMP epitope conjugate of the present disclosure, when administered to an individual in need thereof, induces both an epitope-specific T-cell response and an epitope non-specific T-cell response. The T-Cell-MMP epitope conjugate of the present disclosure, when administered to an individual in need thereof, induces an epitope-specific T-cell response by modulating the activity of a first T-cell that displays both: i) a TCR specific for the epitope present in the T-Cell-MMP-epitope conjugate; and ii) a Co-MOD that binds to the MOD present in the T-Cell-MMP-epitope conjugate. The T-Cell-MMP epitope conjugate also induces an epitope non-specific T-cell response by modulating the activity of a second T-cell that displays: i) a TCR specific for an epitope other than the epitope present in the T-Cell-MMP-epitope conjugate; and ii) a Co-MOD that binds to the MOD present in the T-Cell-MMP-epitope conjugate. The ratio of the epitope-specific T-cell response to the epitope-non-specific T-cell response is at least 2:1, at least 5:1, at least 10:1, at least 15:1, at least 20:1, at least 25:1, at least 50:1, or at least 100:1. The range of the epitope-specific T-cell response to the epitope-non-specific T-cell response is from about 2:1 to about 5:1, from about 5:1 to about 10:1, from about 10:1 to about 15:1, from about 15:1 to about 20:1, from about 20:1 to about 25:1, from about 25:1 to about 50:1, from about 50:1 to about 100:1, or more than 100:1. "Modulating the activity" of a T-cell can include one or more of: i) activating a cytotoxic (e.g., $CD8^+$) T-cell; ii) inducing cytotoxic activity of a cytotoxic (e.g., $CD8^+$) T-cell; iii) inducing production and release of a cytotoxin (e.g., a perforin; a granzyme; a granulysin) by a cytotoxic (e.g., $CD8^+$) T-cell; and iv) inhibiting activity of an autoreactive T-cell; and the like.

The combination of the reduced affinity of the MOD for its Co-MOD, and the affinity of the epitope for a TCR, provides for enhanced selectivity of a T-Cell-MMP-epitope conjugate of the present disclosure. Thus, for example, a T-Cell-MMP-epitope conjugate of the present disclosure binds with higher avidity to a first T-cell that displays both: i) a TCR specific for the epitope present in the T-Cell-MMP-epitope conjugate; and ii) a Co-MOD that binds to the MOD present in the T-Cell-MMP-epitope conjugate, compared to the avidity with which it binds to a second T-cell that displays: i) a TCR specific for an epitope other than the epitope present in the T-Cell-MMP-epitope conjugate; and ii) a Co-MOD that binds to the MOD present in the T-Cell-MMP-epitope conjugate.

I.A.2.8 Determining Binding Affinity

Binding affinity between a MOD and its Co-MOD can be determined by bio-layer interferometry (BLI) using purified MOD and purified Co-MOD. Binding affinity between a T-Cell-MMP-epitope conjugate and its Co-MOD can be determined by BLI using purified T-Cell-MMP-epitope conjugate and the Co-MOD. BLI methods are well known to those skilled in the art. See, e.g., Lad et al. (2015) *J. Biomol. Screen.*, 20(4):498-507; and Shah and Duncan (2014) *J. Vis. Exp.* 18:e51383. The specific and relative binding affinities described in this disclosure between a Co-MOD and a MOD, or between a Co-MOD and a T-Cell-MMP (or its epitope conjugate), can be determined using the following procedures.

A BLI assay can be carried out using an Octet RED 96 (Pal FortéBio) instrument, or a similar instrument, as follows. For example, to determine binding affinity of a Co-MOD for a T-Cell-MMP (or its epitope conjugate) (e.g., a T-Cell-MMP epitope conjugate of the present disclosure with a variant MOD; or a control T-Cell-MMP-epitope conjugate comprising a wild-type MOD), the T-Cell-MMP (or its epitope conjugate) is immobilized onto an insoluble support (a "biosensor"). The immobilized T-Cell-MMP (or its epitope conjugate) is the "target" Immobilization can be effected by immobilizing a capture antibody onto the insoluble support, where the capture antibody immobilizes the T-Cell-MMP (or its epitope conjugate). For example, where the T-Cell-MMP comprises an IgFc polypeptide, immobilization can be effected by immobilizing anti-Fc (e.g., anti-human IgG Fc) antibodies onto the insoluble support, and contacting the T-Cell-MMP epitope conjugate with the immobilized anti-Fc antibodies which will bind to and immobilize it. A Co-MOD is applied, at several different concentrations, to the immobilized T-Cell-MMP (or its immobilized epitope conjugate), and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the Co-MOD to the immobilized T-Cell-MMP (or its epitope conjugate) is conducted at 30° C. As a positive control for binding affinity, an anti-MHC Class I monoclonal antibody can be used. For example, anti-HLA Class I monoclonal antibody (mAb) W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The Co-MOD, or the anti-MHC Class I mAb, is the "analyte." BLI analyzes the interference pattern of white light reflected from two surfaces: i) from the immobilized polypeptide ("target"); and ii) from an internal reference layer. A change in the number of molecules ("analyte"; e.g., Co-MOD; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/k_a$) gives rise to the affinity constant $K_D$. The assay can also be conducted with purified wild-type or its variant MOD immobilized on the biosensor while the Co-MOD is applied, at several different concentrations, to determine the binding parameters between a MOD and its Co-MOD.

Determining the binding affinity of a Co-MOD (e.g., IL-2R) with both a wild-type MOD (e.g., IL-2) and a variant MOD (e.g., an IL-2 variant as disclosed herein), or with a T-Cell-MMP (or its epitope conjugate) containing wild-type or variant MODs, thus allows one to determine the relative binding affinity of the wild-type and variant molecules. That is, one can determine whether the binding affinity of a variant MOD for its receptor (its Co-MOD) is reduced as compared to the binding affinity of the wild-type MOD for the same Co-MOD, and, if so, what is the percentage reduction from the binding affinity of the wild-type Co-MOD.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008), *J. Anal. Biochem.,* 377:209.

Unless otherwise stated herein, the affinity of a T-Cell-MMP-epitope conjugate of the present disclosure for a Co-MOD, or the affinity of a control T-Cell-MMP-epitope conjugate (where a control T-Cell-MMP-epitope conjugate comprises a wild-type MOD) for a Co-MOD, is determined using BLI, as described above. Likewise, the affinity of a MOD and its Co-MOD polypeptide can be determined using BLI as described above.

In some cases, the ratio of: i) the binding affinity of a control T-Cell-MMP-epitope conjugate (where the control comprises a wild-type MOD) to a Co-MOD to ii) the binding affinity of a T-Cell-MMP-epitope conjugate of the present disclosure comprising a variant of the wild-type MOD to the Co-MOD, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control T-Cell-MMP-epitope conjugate (where the control comprises a wild-type MOD) to a Co-MOD to ii) the binding affinity of a T-Cell-MMP-epitope conjugate of the present disclosure comprising a variant of the wild-type MOD to the Co-MOD, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

As an example, where a control T-Cell-MMP-epitope conjugate comprises a wild-type IL-2 polypeptide, and where a T-Cell-MMP-epitope conjugate of the present disclosure comprises a variant IL-2 polypeptide (comprising from 1 to 10 amino acid substitutions relative to the amino acid sequence of the wild-type IL-2 polypeptide) as the MOD, the ratio of: i) the binding affinity of the control T-Cell-MMP-epitope conjugate to an IL-2 receptor (i.e., the Co-MOD) to ii) the binding affinity of the T-Cell-MMP-epitope conjugate of the present disclosure to the IL-2 receptor (i.e., the Co-MOD), when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, where a control T-Cell-MMP-epitope conjugate comprises a wild-type IL-2 polypeptide, and where a T-Cell-MMP-epitope conjugate of the present disclosure comprises a variant IL-2 polypeptide (comprising from 1 to 10 amino acid substitutions relative to the amino acid sequence of the wild-type IL-2 polypeptide) as the MOD, the ratio of: i) the binding affinity of the control T-Cell-MMP-epitope conjugate to IL-2 receptor (i.e., the Co-MOD) to ii) the binding affinity of the T-Cell-MMP-epitope conjugate of the present disclosure to the IL-2 receptor, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

As another example, where a control T-Cell-MMP-epitope conjugate comprises a wild-type PD-L1 polypeptide, and where a T-Cell-MMP-epitope conjugate of the present disclosure comprises a variant PD-L1 polypeptide (comprising from 1 to 10 amino acid substitutions relative to the amino acid sequence of the wild-type PD-L1 polypeptide) as the MOD, the ratio of: i) the binding affinity of the control T-Cell-MMP-epitope conjugate to a PD-1 polypeptide (i.e., the Co-MOD) to ii) the binding affinity of the T-Cell-MMP-epitope conjugate of the present disclosure to the PD-1 polypeptide, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1.

As another example, where a control T-Cell-MMP-epitope conjugate comprises a wild-type CD80 polypeptide, and where a T-Cell-MMP-epitope conjugate of the present disclosure comprises a variant CD80 polypeptide (comprising from 1 to 10 amino acid substitutions relative to the amino acid sequence of the wild-type CD80 polypeptide) as the MOD, the ratio of: i) the binding affinity of the control T-Cell-MMP-epitope conjugate to CTLA4 polypeptide (i.e., the Co-MOD) to ii) the binding affinity of the T-Cell-MMP-epitope conjugate of the present disclosure to the CTLA4 polypeptide, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1.

As another example, where a control T-Cell-MMP-epitope conjugate comprises a wild-type CD80 polypeptide, and where a T-Cell-MMP-epitope conjugate of the present disclosure comprises a variant CD80 polypeptide (comprising from 1 to 10 amino acid substitutions relative to the amino acid sequence of the wild-type CD80 polypeptide) as the MOD, the ratio of: i) the binding affinity of the control T-Cell-MMP-epitope conjugate to CD28 polypeptide (i.e., the Co-MOD) to ii) the binding affinity of the T-Cell-MMP-epitope conjugate of the present disclosure to the CD28 polypeptide, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1.

As another example, where a control T-Cell-MMP-epitope conjugate comprises a wild-type 4-1BBL polypeptide, and where a T-Cell-MMP-epitope conjugate of the present disclosure comprises a variant 4-1BBL polypeptide (comprising from 1 to 10 amino acid substitutions relative to the amino acid sequence of the wild-type 4-1BBL polypeptide) as the MOD, the ratio of: i) the binding affinity of the control T-Cell-MMP-epitope conjugate to 4-1BB polypeptide (i.e., the Co-MOD) to ii) the binding affinity of the T-Cell-MMP-epitope conjugate of the present disclosure to the 4-1BB polypeptide, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1.

As another example, where a control T-Cell-MMP-epitope conjugate comprises a wild-type CD86 polypeptide, and where a T-Cell-MMP-epitope conjugate of the present disclosure comprises a variant CD86 polypeptide (comprising from 1 to 10 amino acid substitutions relative to the amino acid sequence of the wild-type CD86 polypeptide) as the MOD, the ratio of: i) the binding affinity of the control T-Cell-MMP-epitope conjugate to CD28 polypeptide (i.e., the Co-MOD) to ii) the binding affinity of the T-Cell-MMP-epitope conjugate of the present disclosure to the CD28 polypeptide, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1.

Binding affinity of a T-Cell-MMP-epitope conjugate of the present disclosure to a target T-cell can be measured in the following manner: A) contacting a T-Cell-MMP-epitope conjugate of the present disclosure with a target T-cell expressing on its surface: i) a Co-MOD that binds to the parental wild-type MOD; and ii) a TCR that binds to the epitope, where the T-Cell-MMP-epitope conjugate comprises an epitope tag or fluorescent label, such that the T-Cell-MMP-epitope conjugate binds to the target T-cell; B) if the T-Cell-MMP epitope conjugate is unlabeled, contacting the target T-cell-bound T-Cell-MMP-epitope conjugate with a fluorescently labeled binding agent (e.g., a fluorescently labeled antibody) that binds to the epitope tag, generating a T-Cell-MMP-epitope conjugate/target T-cell/binding agent complex; C) measuring the mean fluorescence intensity (MFI) of the T-Cell-MMP-epitope conjugate/target T-cell/binding agent complex using flow cytometry. The epitope tag can be, e.g., a FLAG tag, a hemagglutinin tag, a c-myc tag, a poly(histidine) tag, etc. The MFI measured over a range of concentrations of the T-Cell-MMP-epitope conjugate (library member) provides a measure of the affinity. The MFI measured over a range of concentrations of the T-Cell-MMP-epitope conjugate (library member) provides a half maximal effective concentration ($EC_{50}$) of the T-Cell-MMP-epitope conjugate. In some cases, the $EC_{50}$ of a T-Cell-MMP-epitope conjugate of the present disclosure for a target T-cell is in the nM range; and the $EC_{50}$ of the T-Cell-MMP-epitope conjugate for a control T-cell (where a control T-cell expresses on its surface: i) a Co-MOD that binds the parental wild-type MOD; and ii) a T-cell receptor that does not bind to the epitope present in the T-Cell-MMP-epitope conjugate) is in the μM range. In some cases, the ratio of the $EC_{50}$ of a T-Cell-MMP-epitope conjugate of the present disclosure for a control T-cell to the $EC_{50}$ of the T-Cell-MMP-epitope conjugate for a target T-cell is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at lease $10^5$:1, or at least $10^6$:1. The ratio of the $EC_{50}$ of a T-Cell-MMP-epitope conjugate of the present disclosure for a control T-cell to the $EC_{50}$ of the T-Cell-MMP-epitope conjugate for a target T-cell is an expression of the selectivity of the T-Cell-MMP-epitope conjugate.

In some cases, when measured as described in the preceding paragraph, a T-Cell-MMP-epitope conjugate of the present disclosure exhibits selective binding to a target T-cell, compared to binding of the T-Cell-MMP-epitope conjugate (library member) to a control T-cell that comprises: i) the Co-MOD that binds the parental wild-type MOD; and ii) a TCR that binds to an epitope other than the epitope present in the T-Cell-MMP-epitope conjugate library member.

Dimerized Multimeric T-Cell Modulatory Polypeptides

T-Cell-MMPs of the present disclosure, including those having an epitope chemically conjugated to them, can be dimerized, i.e., the present disclosure provides a multimeric polypeptide comprising a dimer of a multimeric T-Cell-MMP of the present disclosure. Thus, the present disclosure provides a multimeric T-Cell-MMP comprising: A) a first heterodimer comprising: a) a first polypeptide comprising: i) a peptide epitope; and ii) a first MHC polypeptide; and b) a second polypeptide comprising a second MHC polypeptide, wherein the first heterodimer comprises one or more MODs; and B) a second heterodimer comprising: a) a first polypeptide comprising: i) a peptide epitope; and ii) a first MHC polypeptide; and b) a second polypeptide comprising a second MHC polypeptide, wherein the second heterodimer comprises one or more MODs, and wherein the first heterodimer and the second heterodimer are covalently linked to one another. In some cases, the two multimeric T-Cell-MMPs are identical to one another in amino acid sequence. In some cases, the first heterodimer and the second heterodimer are covalently linked to one another via a C-terminal region of the second polypeptide of the first heterodimer and a C-terminal region of the second polypeptide of the second heterodimer. In some cases, the first heterodimer and the second heterodimer are covalently linked to one another via the C-terminal amino acid of the second polypeptide of the first heterodimer and the C-terminal region of the second polypeptide of the second heterodimer; for example, in some cases, the C-terminal amino acid of the second polypeptide of the first heterodimer and the C-terminal region of the second polypeptide of the second heterodimer are linked to one another, either directly or via a linker. The linker can be a peptide linker. The peptide linker can have a length of from 1 aa to 200 aa (e.g., from 1 aa to 5 aa, from 5 aa to 10 aa, from 10 aa to 25 aa, from 25 aa to 50 aa, from 50 aa to 100 aa, from 100 aa to 150 aa, or from 150 aa to 200 aa). In some cases, the peptide epitope of the first heterodimer and the peptide epitope of the second heterodimer comprise the same amino acid sequence. In some cases, the first MHC polypeptides of the first and second heterodimers are MHC Class I β2M, and the second MHC polypeptides of the first and second heterodimers are MHC Class I heavy chain. In some cases, the MOD of the first heterodimer and the MOD of the second heterodimer comprise the same amino acid sequence. In some cases, the MOD of the first heterodimer and the MOD of the second heterodimer are variant MODs that comprise from 1 to 10 amino acid substitutions compared to a corresponding parental wild-type MOD, wherein from 1 to 10 amino acid substitutions result in reduced affinity binding of the variant MOD to a Co-MOD. In some cases, the MOD of the first heterodimer and the MOD of the second heterodimer are selected from the group consisting of IL-2, 4-1BBL, PD-L1, CD70, CD80, CD86, ICOS-L, OX-40L, FasL, JAG1(CD339), TGFβ, ICAM, and variant MODs thereof (e.g., variant MODs having 1 to 10 amino acid substitutions compared to a corresponding parental wild-type MOD). Examples of suitable MHC polypeptides, MODs, and peptide epitopes are described below.

In addition to dimers, the T-Cell-MMPs and T-Cell-MMP epitope conjugates of the present disclosure may form higher order complexes including trimers, tetramers, or pentamers. Compositions comprising multimers of T-Cell-MMPs may also comprise lower order complexes such as monomers and, accordingly, may comprise monomers, dimers, trimers, tetramers, pentamers, or combinations of any thereof (e.g., a mixture of monomers and dimers).

I.B. MHC Polypeptides of T-Cell-MMPs

As noted above, T-Cell-MMPs and T-Cell-MMP-epitope conjugates include MHC polypeptides. For the purposes of the instant disclosure, the term "major histocompatibility complex (MHC) polypeptides" is meant to include MHC Class I polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC Class I heavy chain and/or portions thereof).

As noted above, the first and second MHC polypeptides of the T-Cell-MMPs and T-Cell-MMP-epitope conjugates described herein are Class I MHC polypeptides (e.g., in some cases, the first MHC polypeptide is a MHC Class I β2M (β2M) polypeptide, and the second MHC polypeptide is a MHC Class I heavy chain (H chain) ("MHC-H")). In an embodiment, both the β2M and MHC-H chain sequences in a T-Cell-MMP (or its epitope conjugate) are of human origin. Unless expressly stated otherwise, the T-Cell-MMPs described herein are not intended to include membrane anchoring domains (transmembrane regions) of the MHC Class I molecule, or a part of that molecule sufficient to anchor the resulting T-Cell-MMP, or a peptide thereof, to a cell (e.g., eukaryotic cell such as a mammalian cell) in which it is expressed.

In some cases, a MHC polypeptide of a T-Cell-MMP, or a T-Cell-MMP-epitope conjugate is a Class I HLA polypeptide, e.g., a β2M polypeptide, or a Class I HLA heavy chain polypeptide. Class I HLA heavy chain polypeptides that can be included in a T-Cell-MMP or their epitope conjugates include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides, or polypeptides comprising a sequence having at least 75%, at least 80%, at least 85%, at least 90%, at least 95%, at least 98%, at least 99%, or 100% amino acid sequence identity (e.g., they may comprise 1-30, 1-5, 5-10, 10-15, 15-20, 20-25 or 25-30 amino acid insertions, deletions, and/or substitutions) to amino acids 25-365 of the amino acid sequence of any of the human HLA heavy chain polypeptides depicted in FIGS. 3A, 3B, 3C, and/or 3D.

As an example, a MHC Class I heavy chain polypeptide of a multimeric polypeptide can comprise an amino acid sequence having at least 75%, at least 80%, at least 85%, at least 90%, at least 95%, at least 98%, at least 99%, or 100% amino acid sequence identity to amino acids 25-365 of the amino acid sequence of any of the human HLA-A heavy chain polypeptides depicted in FIG. 3A.

I.B.1 MHC Class I Heavy Chains

HLA-A (HLA-A*01:01:01:01)

In an embodiment, a MHC Class I heavy chain polypeptide of a T-Cell-MMP or a T-Cell-MMP-epitope conjugate comprises an amino acid sequence of HLA-A*01:01:01:01 (HLA-A in FIG. 3D (SEQ ID NO:140)), or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-A heavy chain polypeptide of a T-Cell-MMP or its epitope conjugate has less than 100% identity to the sequence labeled HLA-A in FIG. 3D, it may comprise a substitution at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). The Y84A substitution opens one end of the MHC binding pocket, allows a linker (if present) to "thread" through the end of the pocket, and permits greater variation in epitope sizes (e.g., longer peptides bearing epitope sequences) to fit into the pocket and be presented by the T-Cell-MMP. In an embodiment, the HLA-A heavy chain polypeptide of a T-Cell-MMP or its epitope conjugate comprises the Y84A and A236C mutations. In an embodiment, the HLA-A heavy chain polypeptide of a T-Cell-MMP or its epitope conjugate comprises the Y84C and A139C mutations. In an embodiment, the HLA-A heavy chain polypeptide of a T-Cell-MMP or its epitope conjugate comprises the Y84C, A139C and A236C mutations.

HLA-A*0201

In an embodiment, a MHC Class I heavy chain polypeptide of a T-Cell-MMP or a T-Cell-MMP-epitope conjugate comprises an amino acid sequence of HLA-A*0201 (SEQ ID NO:143) provided in FIG. 3D, or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-A*0201 heavy chain polypeptide of a T-Cell-MMP or its epitope conjugate has less than 100% identity to the sequence labeled HLA-A*0201 in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-A*0201 heavy chain polypeptide of a T-Cell-MMP or its epitope conjugate comprises the Y84A and A236C mutations. In an embodiment, the HLA-A*0201 heavy chain polypeptide of a T-Cell-MMP or its epitope conjugate comprises the Y84C and A139C mutations. In an embodiment, the HLA-A*0201 heavy chain polypeptide of a T-Cell-MMP or its epitope conjugate comprises the Y84C, A139C and A236C mutations.

HLA-A*1101

In an embodiment, a MHC Class I heavy chain polypeptide of a T-Cell-MMP or a T-Cell-MMP-epitope conjugate comprises an amino acid sequence of HLA-A*1101 (SEQ ID NO:148) provided in FIG. 3D, or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-A*1101 heavy chain polypeptide of a T-Cell-MMP or its epitope conjugate has less than 100% identity to the sequence labeled HLA-A*1101 in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-A*1101 heavy chain polypeptide of a T-Cell-MMP or its epitope conjugate comprises the Y84A and A236C mutations. In an embodiment, the HLA-A*1101 heavy chain polypeptide of a T-Cell-MMP or its epitope conjugate comprises the Y84C and A139C mutations. In an embodiment, the HLA-A*1101 heavy chain polypeptide of a T-Cell-MMP or its epitope conjugate comprises the Y84C, A139C and A236C mutations.

HLA-A*2402

In an embodiment, a MHC Class I heavy chain polypeptide of a T-Cell-MMP or a T-Cell-MMP-epitope conjugate comprises an amino acid sequence of HLA-A*2402 (SEQ ID NO:149) provided in FIG. 3D, or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-A*2402 heavy chain polypeptide of a T-Cell-MMP or its epitope conjugate has less than 100% identity to the sequence labeled HLA-A*2402 in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-A*2402 heavy chain polypeptide of a T-Cell-MMP or its epitope conjugate comprises the Y84A and A236C mutations. In an embodiment, the HLA-A*2402 heavy chain polypeptide of a T-Cell-MMP or its epitope conjugate comprises the Y84C and A139C mutations. In an embodiment, the HLA-A*2402 heavy chain polypeptide of a T-Cell-MMP or its epitope conjugate comprises the Y84C, A139C and A236C mutations.

HLA-A*3303

In an embodiment, a MHC Class I heavy chain polypeptide of a T-Cell-MMP or a T-Cell-MMP-epitope conjugate comprises an amino acid sequence of HLA-A*3303 (SEQ ID NO:150) provided in FIG. 3D, or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-A*3303 heavy chain polypeptide of a T-Cell-MMP or its epitope conjugate has less than 100% identity to the sequence labeled HLA-A*3303 in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-A*3303 heavy chain polypeptide of a T-Cell-MMP or its epitope conjugate comprises the Y84A and A236C mutations. In an embodiment, the HLA-A*3303 heavy chain polypeptide of a T-Cell-MMP or its epitope conjugate comprises the Y84C and A139C mutations. In an embodiment, the HLA-A*3303 heavy chain polypeptide of a T-Cell-MMP or its epitope conjugate comprises the Y84C, A139C and A236C mutations.

HLA-B

In an embodiment, a MHC Class I heavy chain polypeptide of a T-Cell-MMP or a T-Cell-MMP-epitope conjugate comprises an amino acid sequence of HLA-B (SEQ ID NO:141) (HLA-B in FIG. 3D), or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-B heavy chain polypeptide of a T-Cell-MMP or its epitope conjugate has less than 100% identity to the sequence labeled HLA-B in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-B heavy chain polypeptide of a T-Cell-MMP or its epitope conjugate comprises the Y84A and A236C mutations. In an embodiment, the HLA-B heavy chain polypeptide of a T-Cell-MMP or its epitope conjugate comprises the Y84C and A139C mutations. In an embodiment, the HLA-B heavy chain polypeptide of a T-Cell-MMP or its epitope conjugate comprises the Y84C, A139C and A236C mutations.

HLA-C

In an embodiment, a MHC Class I heavy chain polypeptide of a T-Cell-MMP or a T-Cell-MMP-epitope conjugate comprises an amino acid sequence of HLA-C (SEQ ID NO:142) (HLA-C in FIG. 3D), or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the HLA-C heavy chain polypeptide of a T-Cell-MMP or its epitope conjugate has less than 100% identity to the sequence labeled HLA-C in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the HLA-C heavy chain polypeptide of a T-Cell-MMP or its epitope conjugate comprises the Y84A and A236C mutations. In an embodiment, the HLA-C heavy chain polypeptide of a T-Cell-MMP or its epitope conjugate comprises the Y84C and A139C mutations. In an embodiment, the HLA-C heavy chain polypeptide of a T-Cell-MMP or its epitope conjugate comprises the Y84C, A139C and A236C mutations.

Mouse H2K

In an embodiment, a MHC Class I heavy chain polypeptide of a T-Cell-MMP or a T-Cell-MMP-epitope conjugate comprises an amino acid sequence of MOUSE H2K (SEQ ID NO:144) (MOUSE H2K in FIG. 3D), or a sequence having at least 75%, at least 80%, at least 85%, at least 90%, at least 95%, at least 98%, at least 99%, or 100% amino acid sequence identity to that sequence (e.g., it may comprise 1-25, 1-5, 5-10, 10-15, 15-20, 20-25, or 25-30 amino acid insertions, deletions, and/or substitutions). In an embodiment, where the MOUSE H2K heavy chain polypeptide of a T-Cell-MMP or its epitope conjugate has less than 100% identity to the sequence labeled MOUSE H2K in FIG. 3D, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In an embodiment, the MOUSE H2K heavy chain polypeptide of a T-Cell-MMP or its epitope conjugate comprises the Y84A and A236C mutations. In an embodiment, the MOUSE H2K heavy chain polypeptide of a T-Cell-MMP or its epitope conjugate comprises the Y84C and A139C mutations. In an embodiment, the MOUSE H2K heavy chain polypeptide of a T-Cell-MMP or its epitope conjugate comprises the Y84C, A139C and A236C mutations.

Substitutions at Positions 116 and 167

Any MHC Class I heavy chain sequences (including those disclosed above for: HLA-A (HLA-A*01:01:01:01); HLA-A*0201; HLA-A*1101; HLA-A*2402; HLA-A*3303; HLA-B; HLA-C; and Mouse H2K, may further comprise a cysteine substitution at position 116 (Y116C, providing thiol for anchoring an epitope peptide such as by reaction with a maleimide peptide) and/or one of an alanine (W167A) or cysteine (W167C) at position 167. As with substitutions that open one end of the MHC-H binding pocket (e.g., at position 84 or its equivalent such as Y84A), substitution of an alanine or glycine at position 167 or its equivalent (e.g., a W167A substitution) opens the other end of the MHC binding pocket, creating a groove that permits greater variation (e.g., longer length) epitope peptides that may be presented by the T-Cell-MMP epitope conjugates. Substitutions at positions 84 and 167 or their equivalent (e.g., Y84A in combination with W167A or W167G) may be used in combination to modify the binding pocket of MHC-H chains. The placement of a cysteine at position 167 (e.g., a W167C mutation) or its equivalent provides a thiol residue for anchoring an epitope peptide). Cysteine substitutions at positions 116 and 167 may be used separately to anchor epitopes (e.g., epitope peptides), or in combination to anchor the epitope in two locations (e.g., the ends of the epitope containing peptide. Mutations at positions 116 and/or 167 may be combined with any one or more mutations at positions 84, 139 and/or 236 described above.

Combinations of Substitutions

When amino acids 84 and 139 are both cysteines they may form an intrachain disulfide bond which can stabilize the MHC Class 1 protein and permit translation and excretion by eukaryotic cells, even when not loaded with an epitope peptide. When position 84 is a C residue, it can also form an intrachain disulfide bond with a linker attached to the N-terminus of a β2M polypeptide (e.g., epitope-GCGGS (G4S)n (SEQ ID NO:133) mature β2M polypeptide, see SEQ ID NOs:151 to 155). When amino acid 236 is a cysteine it can form an interchain disulfide bond with cysteine at amino acid 12 of a variant β2M polypeptide that comprises R12 C substitution at that position. Some possible combinations of MHC Class 1 heavy chain sequence modifications that may be incorporated into a T-Cell-MMP or its epitope conjugate are shown in the Table that follows. Any combination of substitutions provided in the table at residues 84, 139 and 236 may be combined with any combination of substitutions at positions 116 and 167 provided in the table.

SOME COMBINATIONS OF MHC CLASS 1 HEAVY CHAIN SEQUENCE MODIFICATIONS THAT MAY BE INCORPORATED INTO A T-CELL-MMP OR ITS EPITOPE CONJUGATE

| Entry | Base sequence (from FIG. 3D) | SEQ ID NO. | Sequence Identity Range* | Specific Substitutions at aa positions 84, 139 and/or 236 | Substitutions at positions 116 and/or 167 |
|---|---|---|---|---|---|
| 1 | HLA-A | 140 | 100% | None | None |
| 2 | HLA-A | 140 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |
| 3 | HLA-B | 141 | 100% | None | None |
| 4 | HLA-B | 141 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |
| 5 | HLA-C | 142 | 100% | None | None |
| 6 | HLA-C | 142 | 75%-99.8%, 80%-99.8%, 85%-99.8%, 90%-99.8%, 95%-99.8%, 98%-99.8%, or 99%-99.8%; or 1- | None; Y84C; Y84A; A139C; A236C; (Y84A & A236C); | None; Y116C; W167A; |

SOME COMBINATIONS OF MHC CLASS 1 HEAVY CHAIN SEQUENCE MODIFICATIONS THAT MAY BE INCORPORATED INTO A T-CELL-MMP OR ITS EPITOPE CONJUGATE

| Entry | Base sequence (from FIG. 3D) | SEQ ID NO. | Sequence Identity Range⁂ | Specific Substitutions at aa positions 84, 139 and/or 236 | Substitutions at positions 116 and/or 167 |
|---|---|---|---|---|---|
| | | | 25, 1-5, 5-10, 10-15, 15-20, or 20-25 aa insertions, deletions, and/or substitutions) | (Y84C & A139C); or (Y84C, A139C & A236C) | W167C; or (Y116C & W167C) |
| 7 | HLA-A*0201 | 143 | 100% | None | None |
| 8 | HLA-A*0201 | 143 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |
| 9 | MOUSE H2K | 144 | 100% | None | None |
| 10 | MOUSE H2K | 144 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |
| 11 | HLA-A*1101 | 148 | 100% | None | None |
| 12 | HLA-A*1101 | 148 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20- | None; Y84C; Y84A; A139C; A236C; (Y84A & A236C); (Y84C & A139C); or | None; Y116C; W167A; W167C; or |
| 13 | HLA-A*2402 | 149 | 100% | None | None |
| 14 | HLA-A*2402 | 149 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |
| 15 | HLA-A*3303 | 150 | 100% | None | None |
| 16 | HLA-A*3303 | 150 | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions) | None; Y84C; Y84A; A139C; A236C; (Y84A & A236C); (Y84C & A139C); or (Y84C, A139C & A236C) | None; Y116C; W167A; W167C; or (Y116C & W167C) |

⁂The Sequence Identity Range is the permissible range in sequence identity of a MHC-H polypeptide sequence incorporated into a T-Cell-MMP relative to the corresponding portion of the sequences listed in FIG. 3D.

I.B.2 MHC Class I β2-Microglobins and Combinations with MHC-H Polypeptides

A β2M polypeptide of a multimeric polypeptide can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100% amino acid sequence identity to a β2M amino acid sequence depicted in FIG. 4. In some instances, a β2M polypeptide comprises an amino acid sequence having at least 75%, at least 80%, at least 85%, at least 90%, at least 95%, at least 98%, at least 99%, or 100% amino acid sequence identity to amino acids 21 to 119 of a β2M amino acid sequence depicted in FIG. 4.

In some cases, a MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in a MHC polypeptide of a first polypeptide of a T-Cell-MMP, or its epitope conjugate, can form a disulfide bond with a cysteine residue present in a second polypeptide chain.

In some cases, a first MHC polypeptide in a first polypeptide of a multimeric polypeptide, and/or a second MHC polypeptide in a second polypeptide of a multimeric polypeptide, include an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in a HLA β2M and a HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 3A, which includes a signal peptide, Gly120 is Gly144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 3A) is substituted with a Cys. In some cases, residue 236 of the mature HLA-B amino acid sequence (i.e., residue 260 of the amino acid sequence depicted in FIG. 3B) is substituted with a Cys. In some cases, residue 236 of the mature HLA-C amino acid sequence (i.e., residue 260 of the amino acid sequence depicted in FIG. 3C) is substituted with a Cys. In some cases, residue 32 (corresponding to Arg-12 of mature β2M) of an amino acid sequence depicted in FIG. 4 is substituted with a Cys.

Separately, or in addition to, the pairs of cysteine residues in a β2M and HLA Class I heavy chain polypeptide that may be used to form interchain disulfide bonds between the first and second polypeptides of a T-Cell-MMP (discussed above), the HLA-heavy chain of a T-Cell-MMP or its epitope conjugate may be substituted with cysteines to form an intrachain disulfide bond between a cysteine substituted into the carboxyl end portion of the α1 helix and a cysteine in the amino end portion of the α2-1 helix. Such disulfide bonds stabilize the T-Cell-MMP and permit its cellular processing and excretion from eukaryotic cells in the absence of a bound epitope peptide (or null peptide). In one embodiment the carboxyl end portion of the α1 helix is from about amino acid position 79 to about amino acid position 89 and the amino end portion of the α2-1 helix is from about amino acid position 134 to amino acid position 144 of the MHC Class I heavy chain (the amino acid positions are determined based on the sequence of the heavy chains without their leader sequence (see, e.g., FIG. 3D). In one such embodiment the disulfide bond is between a cysteine located at positions 83, 84, or 85 and a cysteine located at any of positions 138, 139 or 140 of the MHC Class I heavy chain. For example, a disulfide bond may be formed from cysteines incorporated into the MHC Class I heavy chain at amino acid 83 and a cysteine at an amino acid located at any of positions 138, 139 or 140. Alternatively, a disulfide bond may be formed between a cysteine inserted at position 84 and a cysteine inserted at any of positions 138, 139 or 140, or between a cysteine inserted at position 85 and a cysteine at any one of positions 138, 139 or 140. In an embodiment, the MHC Class 1 heavy chain intrachain disulfide bond is between cysteines substituted into a heavy chain sequence at positions 84 and 139 (e.g., the heavy chain sequence may be one of the heavy chain sequences set forth in FIG. 3D). As noted above, any of the MHC Class I intrachain disulfide bonds, including a disulfide bond between cysteines at 84 and 139, may be combined with intrachain disulfide bonds including a bond between MHC Class 1 heavy position 236 and position 12 of a mature β2M polypeptide sequence (lacking its leader) as shown, for example, in FIG. 4.

In another embodiment, an intrachain disulfide bond may be formed in a MHC-H sequence of a T-Cell-MMP, or its epitope conjugate, between a cysteine substituted into the region between amino acid positions 79 and 89 and a cysteine substituted into the region between amino acid positions 134 and 144 of the sequences given in FIG. 3D. In such an embodiment, the MHC Class I heavy chain sequence may have insertions, deletions and/or substitutions of 1 to 5 amino acids preceding or following the cysteines forming the disulfide bond between the carboxyl end portion of the α1 helix and the amino end portion of the α2-1 helix. Any inserted amino acids may be selected from the naturally occurring amino acids or the naturally occurring amino acids except proline and alanine.

In an embodiment, the β2M polypeptide of a T-Cell-MMP or its epitope conjugate comprises a mature β2M polypeptide sequence (aas 21-119) of any one of NP_004039.1, NP_001009066.1, NP_001040602.1, NP_776318.1, or NP_033865.2 (SEQ ID NOs 151 to 155).

In some cases, a HLA Class I heavy chain polypeptide of a T-Cell-MMP or its epitope conjugate comprises any one of the HLA-A, B or C sequences set forth in FIG. 3D. Any of the heavy chain sequences may further comprise cysteine substitutions at positions 84 and 139, which may form an intrachain disulfide bond.

In an embodiment, the β2M polypeptide of a T-Cell-MMP, or its epitope conjugate, comprises a mature β2M polypeptide sequence (aas 21-119) of any one of the sequences in FIG. 4, which further comprises a R12C substitution.

In an embodiment, a T-Cell-MMP, or its epitope conjugate, comprises a first polypeptide comprising a mature β2M polypeptide sequence (e.g., aas 21-119 of any one of the sequences in FIG. 4) having a R12C substitution, and a second polypeptide comprising any one of the HLA-A, B or C heavy chain sequences in FIG. 3D bearing a cysteine at position 236. In such embodiments an intrachain disulfide bond may form between the cysteines at positions 12 and 236. In addition, any of the heavy chain sequences may further comprise cysteine substitutions at positions 84 and 139, which may form an intrachain disulfide bond.

In some cases, a HLA Class I heavy chain polypeptide of a T-Cell-MMP, or its epitope conjugate, comprises the amino acid sequence of HLA-A*0201 (FIG. 3D). In some cases, a HLA Class I heavy chain polypeptide of a T-Cell-MMP, or its epitope conjugate, comprises the amino acid sequence of HLA-A*0201 having an A236C substitution (FIG. 3D). In some cases, a HLA Class I heavy chain polypeptide of a T-Cell-MMP, or its epitope conjugate, comprises the amino acid sequence of HLA-A*0201 having a Y84A and a A236C substitution (FIG. 3D).

In an embodiment, a T-Cell-MMP, or its epitope conjugate, comprises a first polypeptide comprising amino acid residues 21-119 of NP_004039.1 with a R12C substitution (see FIG. 4), and a second polypeptide comprising a HLA- A0201 (HLA-A2) sequence in FIG. 3D. In one such embodiment the HLA-A0201 sequence has an A236C substitution. In another such embodiment, the HLA-A0201 sequence has a Y84C and A139C substitution. In another such embodiment, the HLA-A0201 sequence has a Y84C, A139C, and A236C substitution. As indicated, MHC-H sequences with Y84C and A139C substitutions may form a stabilizing intrachain disulfide bond, and cysteines at position 236 may bond to cysteines at position 12 of a mature β2M polypeptide.

In an embodiment, a T-Cell-MMP, or its epitope conjugate, comprises a first polypeptide comprising amino acid residues 21-119 of NP_004039.1 with a R12C substitution (see FIG. 4), and a second polypeptide, a HLA Class I heavy chain polypeptide comprises the amino acid sequence GSHSMRYFFTSVSRPGRGEPRFIAVGYVDDTQFVRFDSDAASQRMEPRAPWIEQEGPEYWDGE TRKVKAHSQTHRVDL(aa cluster 1){C}(aa cluster 2)AGSHTVQRMYGCDVGSDWRFLRGYHQYAYDGKDYIALKEDLRSW(aa cluster 3){C}(aa cluster 4)HKWEAAHVAEQLRAYLEGTCVEWLRRYLENGKETLQRTDAPKTHMTHHAVSDHEATLRCWALSFYPAEITLTWQRDGEDQTQDTELVET RPAGDGTFQK-WAAVVVPSGQEQRYTCHVQHEGLPKPLTLRWEP (SEQ ID NO:156); or, the first polypeptide comprises the sequence IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:157), and the second polypeptide comprises the amino acid sequence, GSHSMRYFFTSVSRPGRGEPRFIAVGYVDDTQFVRFDSDAASQRMEPRAPWIEQEGPEYWDGE TRKVKAHSQTHRVDL(aa cluster 1){C}(aa cluster 2)AGSHTVQRMYGCDVGSDWRFLRGYHQYAYDGKDYIALKEDLRSW(aa cluster 3){C}(aa cluster 4))HKWEAAHVAEQLRAYLEGTCVEWLRRYLENGKETLQRTDAPKTHMTHHAVSDHEATLRCWALSFYPAEITLTWQRDGEDQTQDTEL(aa cluster 5)(C)(aa cluster 6)QK-WAAVVVPSGQEQRYTCHVQHEGLPKPLTLRWEP (SEQ ID NO:158); where the cysteine residues indicated as {C} form a disulfide bond between the α1 and α2-1 helices and the (C) residue forms a disulfide bond with the β2M polypeptide cysteine at position 12.

Each occurrence of aa cluster 1, aa cluster 2, aa cluster 3, aa cluster 4, aa cluster 5, and aa cluster 6 is independently selected to be 1-5 amino acid residues, wherein the amino acid residues are each selected independently from i) any naturally occurring (proteogenic) amino acid or ii) any naturally occurring amino acid except proline or glycine.

In an embodiment:

aa cluster 1 may be the amino acid sequence GTLRG or that sequence with one or two amino acids deleted or substituted with other naturally occurring amino acids (e.g., L replaced by I, V, A or F);

aa cluster 2 may be the amino acid sequence YNQSE or that sequence with one or two amino acids deleted or substituted with other naturally occurring amino acids (e.g., N replaced by Q, Q replaced by N, and/or E replaced by D);

aa cluster 3 may be the amino acid sequence TAADM or that sequence with one or two amino acids deleted or substituted with other naturally occurring amino acids (e.g., T replaced by S, A replaced by G, D replaced by E, and/or M replaced by L, V, or I);

aa cluster 4 may be the amino acid sequence AQTTK or that sequence with one or two amino acids deleted or substituted with other naturally occurring amino acids (e.g., A replaced by G, Q replaced by N, or T replaced by S, and or K replaced by R or Q);

aa cluster 5 may be the amino acid sequence VETRP or that sequence with one or two amino acids deleted or substituted with other naturally occurring amino acids (e.g., V replaced by I or L, E replaced by D, T replaced by S, and/or R replaced by K); and/or aa cluster 6 may be the amino acid sequence GDGTF or that sequence with one or two amino acids deleted or substituted with other naturally occurring amino acids (e.g., D replaced by E, T replaced by S, or F replaced by L, W, or Y).

In some cases, the β2M polypeptide comprises the amino acid sequence:

(SEQ ID NO: 157)
IQRTPKIQVYSCHPAENGKSNFLNCYVSGFHPSDIEVDLLKNGERIE

KVEHSDLSFSKDWSFYLLYYTEFTPTEKDEYACRVNHVTLSQPKIVK

WDRDM.

In some cases, the first polypeptide and the second polypeptide of a T-Cell-MMP of the present disclosure are disulfides linked to one another through: i) a Cys residue present in a linker connecting the peptide epitope and a β2M polypeptide in the first polypeptide chain (e.g., with the epitope placed in the N-terminal to the linker and the β2M sequences); and ii) a Cys residue present in a MHC Class I heavy chain in the second polypeptide chain. In some cases, the Cys residue present in the MHC Class I heavy chain is a Cys introduce as a Y84C substitution. In some cases, the linker connecting the peptide epitope and the β2M polypeptide in the first polypeptide chain is GCGGS(G$_4$S)n, where n is 1, 2, 3, 4, 5, 6, 7, 8, or 9 (SEQ ID NO:133) (e.g., epitope-GCGGS(G$_4$S)n-mature β2M polypeptide). For example, in some cases, the linker comprises the amino acid sequence GCGGSGGGGSGGGGSGGGGS (SEQ ID NO:78). As another example, the linker comprises the amino acid sequence GCGGSGGGGSGGGGS (SEQ ID NO:79). Examples of such a disulfide-linked first and second polypeptide are depicted schematically in FIGS. 6E-6H.

I.C. Scaffold Polypeptides

T-Cell-MMPs and T-Cell-MMP-epitope conjugates can comprise a Fc polypeptide, or can comprise another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, a Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:159), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, a Fc polypeptide increases the in vivo half-life (serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

I.D. Fc Polypeptides

In some cases, the first and/or the second polypeptide chains of a T-Cell-MMP (or its corresponding T-Cell-MMP-epitope conjugate) comprise a Fc polypeptide which may be modified to include one or more chemical conjugation sites within or attached (e.g., at a terminus or attached by a linker) to the polypeptide. The Fc polypeptide of a T-Cell-MMP or T-Cell-MMP-epitope conjugate can be, for example, from an IgA, IgD, IgE, IgG, or IgM, which may contain a human polypeptide sequence, a humanized polypeptide sequence, a Fc region polypeptide of a synthetic heavy chain constant region, or a consensus heavy chain constant region. In embodiments, the Fc polypeptide can be from a human IgG1 Fc, a human IgG2 Fc, a human IgG3 Fc, a human IgG4 Fc, a human IgA Fc, a human IgD Fc, a human IgE Fc, a human IgM Fc, etc. Unless stated otherwise, the Fc polypeptides used in the T-Cell-MMPs and their epitope conjugates do not comprise a trans-membrane anchoring domain or a portion thereof sufficient to anchor the T-Cell-MMP or its epitope conjugate to a cell membrane. In some cases, the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to an amino acid sequence of a Fc region depicted in FIGS. 2A-2G. In some cases, the Fc region comprises an amino acid sequence having at least about 70%, at least about 75%, at least about 80%, at least about 85%, at least about 90%, at least about 95%, at least about 98%, at least about 99%, or 100% amino acid sequence identity to the human IgG1 Fc polypeptide depicted in FIG. 2A. In some cases, the Fc region comprises an amino acid sequence having at least about 70%, at least about 75%, at least about 80%, at least about 85%, at least about 90%, at least about 95%, at least about 98%, at least about 99%, or 100% amino acid sequence identity to the human IgG1 Fc polypeptide depicted in FIG. 2A; and comprises a substitution of N77; e.g., the Fc polypeptide comprises a N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to the human IgG2 Fc polypeptide depicted in FIG. 2A; e.g., the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to amino acids 99-325 of the human IgG2 Fc polypeptide depicted in FIG. 2A. In some cases, the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to the human IgG3 Fc polypeptide depicted in FIG. 2A; e.g., the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to amino acids 19-246 of the human IgG3 Fc polypeptide depicted in FIG. 2A. In some cases, the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to the human IgM Fc polypeptide depicted in FIG. 2B; e.g., the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to amino acids 1-276 to the human IgM Fc polypeptide depicted in FIG. 2B. In some cases, the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to the human IgA Fc polypeptide depicted in FIG. 2C; e.g., the Fc polypeptide comprises an amino acid sequence having at least about 70%, at least about 75%, at least about 80%, at least about 85%, at least about 90%, at least about 95%, at least about 98%, at least about 99%, or 100% amino acid sequence identity to amino acids 1-234 to the human IgA Fc polypeptide depicted in FIG. 2C.

In some cases, the Fc polypeptide present in a multimeric polypeptide comprises the amino acid sequence depicted in FIG. 2A (human IgG1 Fc). In some cases, the Fc polypeptide present in a multimeric polypeptide comprises the amino acid sequence depicted in FIG. 2A (human IgG1 Fc), except for a substitution of N297 with an amino acid other than asparagine. In some cases, the Fc polypeptide present in a multimeric polypeptide comprises the amino acid sequence depicted in FIG. 2C (human IgG1 Fc comprising an N297A substitution). In some cases, the Fc polypeptide present in a multimeric polypeptide comprises the amino acid sequence depicted in FIG. 2A (human IgG1 Fc), except for a substitution of L234 with an amino acid other than leucine. In some cases, the Fc polypeptide present in a multimeric polypeptide comprises the amino acid sequence depicted in FIG. 2A (human IgG1 Fc), except for a substitution of L235 with an amino acid other than leucine.

In some cases, the Fc polypeptide present in a multimeric polypeptide comprises the amino acid sequence depicted in FIG. 2E. In some cases, the Fc polypeptide present in a multimeric polypeptide comprises the amino acid sequence depicted in FIG. 2F. In some cases, the Fc polypeptide present in a multimeric polypeptide comprises the amino acid sequence depicted in FIG. 2G (human IgG1 Fc comprising an L234A substitution and an L235A substitution). In some cases, the Fc polypeptide present in a multimeric polypeptide comprises the amino acid sequence depicted in FIG. 2A (human IgG1 Fc), except for a substitution of P331 with an amino acid other than proline; in some cases, the substitution is a P331S substitution. In some cases, the Fc polypeptide present in a multimeric polypeptide comprises the amino acid sequence depicted in FIG. 2A (human IgG1 Fc), except for substitutions at L234 and L235 with amino acids other than leucine. In some cases, the Fc polypeptide present in a multimeric polypeptide comprises the amino acid sequence depicted in FIG. 2A (human IgG1 Fc), except for substitutions at L234 and L235 with amino acids other than leucine, and a substitution of P331 with an amino acid other than proline. In some cases, the Fc polypeptide present in a multimeric polypeptide comprises the amino acid sequence depicted in FIG. 2B (human IgG1 Fc comprising L234F, L235E, and P331S substitutions). In some cases, the Fc polypeptide present in a multimeric polypeptide is an IgG1 Fc polypeptide that comprises L234A and L235A substitutions.

I.E. Linkers

T-Cell-MMPs (and their T-Cell-MMP-epitope conjugates) can include one or more independently selected linker peptides interposed between, for example, any one or more of: i) a MHC polypeptide and an Ig Fc polypeptide, where such a linker is referred to herein as a "L1 linker"; ii) a MHC polypeptide and a MOD, where such a linker is referred to herein as a "L2 linker"; iii) a first MOD and a second MOD, where such a linker is referred to herein as a "L3 linker" (e.g., between a first variant 4-1BBL polypeptide and a second variant 4-1BBL polypeptide; or between a second variant 4-1BBL polypeptide and a third variant 4-1BBL polypeptide); iv) a conjugation site or a peptide antigen (conjugated "epitope" peptide) and a MHC Class I polypeptide (e.g., β2M); v) a MHC Class I polypeptide and a dimerization polypeptide (e.g., a first or a second member of a dimerizing pair); and vi) a dimerization polypeptide (e.g., a first or a second member of a dimerizing pair) and an IgFc polypeptide.

Suitable linkers (also referred to as "spacers") can be readily selected and can be of any of a number of suitable lengths, such as from 1 aa to 25 aa, from 3 aa to 20 aa, from 2 aa to 15 aa, from 3 aa to 12 aa, from 4 aa to 10 aa, from 5 aa to 9 aa, from 6 aa to 8 aa, or from 7 aa to 8 aa. In embodiments, a suitable linker can be 1, 2, 3, 4, 5, 6, 7, 8, 9, 10, 11, 12, 13, 14, 15, 16, 17, 18, 19, 20, 21, 22, 23, 24, or 25 aa in length. In some cases, a linker has a length of from 25 aa to 50 aa, e.g., from 25 to 30, from 30 to 35, from 35 to 40, from 40 to 45, or from 45 to 50 aa in length.

Exemplary linkers include glycine polymers $(G)_n$, glycine-serine polymers (including, for example, $(GS)_n$, $(GSGGS)_n$ (SEQ ID NO:66) and $(GGGS)_n$ (SEQ ID NO:67), where n is an integer of at least one (e.g., 1, 2, 3, 4, 5, 6, 7, 8, 9, or 10) glycine-alanine polymers, alanine-serine polymers, and other flexible linkers known in the art. Glycine and glycine-serine polymers can both be used; both Gly and Ser are relatively unstructured, and therefore can serve as a neutral tether between components. Glycine polymers access significantly more phi-psi space than even alanine, and are much less restricted than residues with longer side chains (see Scheraga, Rev. Computational Chem. 11173-142 (1992)). Exemplary linkers can also comprise amino acid sequences including, but not limited to, GGSG (SEQ ID NO:68), GGSGG (SEQ ID NO:69), GSGSG (SEQ ID NO:70), GSGGG (SEQ ID NO:71), GGGSG (SEQ ID NO:72), GSSSG (SEQ ID NO:73), and the like. Exemplary linkers can include, e.g., Gly(Ser₄)n (SEQ ID NO:74), where n is 1, 2, 3, 4, 5, 6, 7, 8, 9, or 10. In one embodiment the linker comprises the amino acid sequence AAAGG (SEQ ID NO:75).

In some cases, a linker comprises the amino acid sequence $(GGGGS)_n$ (SEQ ID NO:76), where n is 1, 2, 3, 4, 5, 6, 7, 8, 9, or 10. In some cases, a linker polypeptide, present in a first polypeptide of a T-Cell-MMP or its epitope conjugate, includes a cysteine residue that can form a disulfide bond with a cysteine residue present in an epitope or a second polypeptide of a T-Cell-MMP or its epitope conjugate. In some cases, for example, the linker comprises the amino acid sequence GCGGS($G_4$S)n where n is 1, 2, 3, 4, 5, 6, 7, 8, or 9 (SEQ ID NO:133), GCGASGGGGSGGGGS (SEQ ID NO:77), the sequence GCGGSGGGGSGGGGSGGGGS (SEQ ID NO:78) or the sequence GCGGSGGGGSGGGGS (SEQ ID NO:79).

Linkers, including the polypeptide linkers described above, may be present between a payload coupled to the first or second polypeptide of a T-Cell-MMP (or its epitope conjugate). In addition to the polypeptide linkers recited above, the linkers used to attach a payload or epitope (e.g., peptide) to the first and/or second polypeptide can be non-peptides. Such non-peptide linkers include polymers comprising, for example, polyethylene glycol (PEG). Other linkers, including those resulting from coupling with a bifunctional crosslinking agent, such as those recited below, may also be utilized.

I.F. Epitopes

The chemical conjugation sites and chemistries described herein permit the incorporation of both peptide (epitope-presenting peptides) and non-peptide epitopes into a T-Cell-MMP. In addition to polypeptide epitopes, epitopes may include for example glycopeptides.

In an embodiment, an epitope present in a multimeric polypeptide can have a length of from about 4 aa to about 25 aa, e.g., the epitope can have a length of from 4 aa to 10 aa, from 10 aa to 15 aa, from 15 aa to 20 aa, or from 20 aa to 25 aa. For example, an epitope present in a T-Cell-MMP-epitope conjugate can have a length of 4 aa, 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide has a length of from 5 aa to 10 aa, e.g., 5 aa, 6 aa, 7 aa, 8 aa, 9 aa, or 10 aa.

In an embodiment, an epitope present in a multimeric polypeptide is specifically bound by a T-cell, i.e., the epitope is specifically bound by an epitope-specific T-cell. An epitope-specific T-cell binds an epitope having a reference amino acid sequence, but does not substantially bind an epitope that differs from the reference amino acid sequence. For example, an epitope-specific T-cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T-cell can bind an epitope for which it is specific with an affinity of at least $10^{-7}$ M, at least $10^{-8}$ M, at least $10^{-9}$ M, or at least $10^{-10}$ M.

Suitable peptide/polypeptide epitopes include, but are not limited to, epitopes present in a cancer-associated antigen. Cancer-associated antigens are known in the art; see, e.g., Cheever et al. (2009) Clin. Cancer Res. 15:5323. Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1;

mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); vascular endothelial growth factor receptor-2 (VEGF-R2) (see, e.g., Vigneron et al. (2013) *Cancer Immunity* 13:15; and Vigneron (2015) *BioMed Res. Int'l* Article ID 948501); and epidermal growth factor receptor (EGFR) vIII polypeptide (see, e.g., Wong et al. (1992) *Proc. Natl. Acad. Sci. USA* 89:2965; and Miao et al. (2014) *PLoSOne* 9:e94281). In some cases, the epitope is a human papilloma virus E7 antigen epitope; (see, e.g., Ramos et al. (2013) *J. Immunother.* 36:66).

In some cases, a suitable peptide epitope is a peptide fragment of from about 4 aa to about 20 aa (e.g., 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, or 20 aa) in length of a MUC1 polypeptide, a human papillomavirus (HPV) E6 polypeptide, a LMP2 polypeptide, a HPV E7 polypeptide, an epidermal growth factor receptor (EGFR) vIII polypeptide, a HER-2/neu polypeptide, a melanoma antigen family A, 3 (MAGE A3) polypeptide, a p53 polypeptide, a mutant p53 polypeptide, a NY-ESO-1 polypeptide, a folate hydrolase (prostate-specific membrane antigen; PSMA) polypeptide, a carcinoembryonic antigen (CEA) polypeptide, a melanoma antigen recognized by T-cells (melanA/MART1) polypeptide, a Ras polypeptide, a gp100 polypeptide, a proteinase3 (PR1) polypeptide, a bcr-abl polypeptide, a tyrosinase polypeptide, a survivin polypeptide, a prostate specific antigen (PSA) polypeptide, an hTERT polypeptide, a sarcoma translocation breakpoints polypeptide, a synovial sarcoma X (SSX) breakpoint polypeptide, an EphA2 polypeptide, an acid phosphatase, prostate (PAP) polypeptide, a melanoma inhibitor of apoptosis (ML-IAP) polypeptide, an alpha-fetoprotein (AFP) polypeptide, an epithelial cell adhesion molecule (EpCAM) polypeptide, an ERG (TMPRSS2 ETS fusion) polypeptide, a NA17 polypeptide, a paired-box-3 (PAX3) polypeptide, an anaplastic lymphoma kinase (ALK) polypeptide, an androgen receptor polypeptide, a cyclin B1 polypeptide, an N-myc proto-oncogene (MYCN) polypeptide, a Ras homolog gene family member C (RhoC) polypeptide, a tyrosinase-related protein-2 (TRP-2) polypeptide, a mesothelin polypeptide, a prostate stem cell antigen (PSCA) polypeptide, a melanoma associated antigen-1 (MAGE A1) polypeptide, a cytochrome P450 1B1 (CYP1B1) polypeptide, a placenta-specific protein 1 (PLAC1) polypeptide, a BORIS polypeptide (also known as CCCTC-binding factor or CTCF), an ETV6-AML polypeptide, a breast cancer antigen NY-BR-1 polypeptide (also referred to as ankyrin repeat domain-containing protein 30A), a regulator of G-protein signaling (RGSS) polypeptide, a squamous cell carcinoma antigen recognized by T-cells (SART3) polypeptide, a carbonic anhydrase IX polypeptide, a paired box-5 (PAX5) polypeptide, an OY-TES1 (testis antigen; also known as acrosin binding protein) polypeptide, a sperm protein 17 polypeptide, a lymphocyte cell-specific protein-tyrosine kinase (LCK) polypeptide, a high molecular weight melanoma associated antigen (HMW-MAA), an A-kinase anchoring protein-4 (AKAP-4), a synovial sarcoma X breakpoint 2 (SSX2) polypeptide, an X antigen family member 1 (XAGE1) polypeptide, a B7 homolog 3 (B7H3; also known as CD276) polypeptide, a legumain polypeptide (LGMN1; also known as asparaginyl endopeptidase), a tyrosine kinase with Ig and EGF homology domains-2 (Tie-2; also known as angiopoietin-1 receptor) polypeptide, a P antigen family member 4 (PAGE4) polypeptide, a vascular endothelial growth factor receptor 2 (VEGF2) polypeptide, a MAD-CT-1 polypeptide, a fibroblast activation protein (FAP) polypeptide, a platelet derived growth factor receptor beta (PDGFβ) polypeptide, a MAD-CT-2 polypeptide, a Fos-related antigen-1 (FOSL) polypeptide, or a Wilms tumor-1 (WT-1) polypeptide.

Amino acid sequences of cancer-associated antigens are known in the art; see, e.g., MUC1 (GenBank CAA56734); LMP2 (GenBank CAA47024); HPV E6 (GenBank AAD33252); HPV E7 (GenBank AHG99480); EGFRvIII (GenBank NP_001333870); HER-2/neu (GenBank AAI67147); MAGE-A3 (GenBank AAH11744); p53 (GenBank BAC16799); NY-ESO-1 (GenBank CAA05908); PSMA (GenBank AAH25672); CEA (GenBank AAA51967); melan/MART1 (GenBank NP_005502); Ras (GenBank NP_001123914); gp100 (GenBank AAC60634); bcr-abl (GenBank AAB60388); tyrosinase (GenBank AAB60319); survivin (GenBank AAC51660); PSA (GenBank CAD54617); hTERT (GenBank BAC11010); SSX (GenBank NP_001265620); Eph2A (GenBank NP_004422); PAP (GenBank AAH16344); ML-IAP (GenBank AAH14475); AFP (GenBank NP_001125); EpCAM (GenBank NP_002345); ERG (TMPRSS2 ETS fusion) (GenBank ACA81385); PAX3 (GenBank AAI01301); ALK (GenBank NP_004295); androgen receptor (GenBank NP_000035); cyclin B1 (GenBank CAO99273); MYCN (GenBank NP_001280157); RhoC (GenBank AAH52808); TRP-2 (GenBank AAC60627); mesothelin (GenBank AAH09272); PSCA (GenBank AAH65183); MAGE A1 (GenBank NP_004979); CYP1B1 (GenBank AAM50512); PLAC1 (GenBank AAG22596); BORIS (GenBank NP_001255969); ETV6 (GenBank NP_001978); NY-BR1 (GenBank NP_443723); SART3 (GenBank NP_055521); carbonic anhydrase IX (GenBank EAW58359); PAX5 (GenBank NP_057953); OY-TES1 (GenBank NP_115878); sperm protein 17 (GenBank AAK20878); LCK (GenBank NP_001036236); HMW-MAA (GenBank NP_001888); AKAP-4 (GenBank NP_003877); SSX2 (GenBank CAA60111); XAGE1 (GenBank NP_001091073; XP_001125834; XP_001125856; and XP_001125872); B7H3 (GenBank NP_001019907; XP_947368; XP_950958; XP_950960; XP_950962; XP_950963; XP_950965; and XP_950967); LGMN1 (GenBank NP_001008530); TIE-2 (GenBank NP_000450); PAGE4 (GenBank NP_001305806); VEGFR2 (GenBank NP_002244); MAD-CT-1 (GenBank NP_005893 NP_056215); FAP (GenBank NP_004451); PDGFβ (GenBank NP_002600); MAD-CT-2 GenBank NP_001138574); FOSL (GenBank NP_005429); and WT-1 (GenBank NP_000369).). These polypeptides are also discussed in, e.g., Cheever et al. (2009) *Clin. Cancer Res.* 15:5323, and references cited therein; Wagner et al. (2003) *J. Cell. Sci.* 116:1653; Matsui et al. (1990) *Oncogene* 5:249; Zhang et al. (1996) *Nature* 383:168.

In some cases, the epitope is an epitope of an infectious disease agent such as a virus, mycoplasma (e.g., *Mycoplasma pneumoniae*), or bacterial agent. In some cases where the epitope is a viral epitope, the epitope is from a core protein, early protein, late protein, DNA or RNA polymerase, or coat protein. For example, in some cases, the viral epitope is a peptide epitope from a papilloma virus (e.g., a human papilloma virus (HPV)) or a hepatitis virus (e.g., hepatitis A virus or hepatitis B virus (HBV)). In another embodiment the epitopes are from Cytomegalovirus ("CMV").

In an embodiment where the epitope is an HPV virus it is derived from Human Papiloma early proteins. In one such embodiment the epitope is from HPV E6 polypeptide, HPV E7 polypeptide, HPV 16 Early Protein 7 (HPV16E7) amino acids 82-90 (HPV16E7/82-90, LLMGTLGIV; SEQ ID NO:80). In an embodiment, the epitope is HPV16E7 amino acids 86-93 (TLGIVCPI; SEQ ID NO:81). In an embodiment, the epitope is HPV16E7 amino acids 11-20 (YMLDLQPETT; SEQ ID NO:82). In an embodiment, the epitope isHPV16E7 amino acids 11-19 (YMLDLQPET; SEQ ID NO:83). See, e.g., Ressing et al. ((1995) *J. Immunol.* 154: 5934) for additional suitable HPV epitopes.

In some cases, the epitope is a hepatitis B virus (HBV) epitope. A number of HBV epitopes are known in the art. See, e.g., Desmond et al. (2008) *Antiviral Therapy* 13:161; Lumley et al. (2016) *Wellcome Open Res.* 1:9; and Kefalakes et al. (2015) *Hepatology* 62:47. A HBV peptide suitable for inclusion in a T-Cell-MMP epitope conjugate of the present disclosure can be a HBV peptide from any of various HBV genotypes, including HBV genotype A, HBV genotype B, HBV genotype C, or HBV genotype D. A HBV peptide suitable for inclusion in a T-cell-MMP of the present disclosure can be a HBV peptide from any of various HBV sub-genotypes. A HBV peptide suitable for inclusion in a T-cell-MMP of the present disclosure may bind to a MHC complex with an affinity of at least $10^{-7}$ M, at least $10^{-8}$ M, at $5\times10^{-9}$ M, at least $10^{-9}$ M, at $5\times10^{-10}$ M, or at least $10^{-10}$ M; and is bound by a TCR when complexed with the MHC complex.

A HBV peptide suitable for inclusion in a T-cell-MMP of the present disclosure can have a length of from about 4 aa to about 25 aa, e.g., the epitope can have a length of from 4 aa to 10 aa, from 9 aa to 15 aa, from 10 aa to 15 aa, from 15 aa to 20 aa, or from 20 aa to 25 aa. For example, a HBV peptide suitable for inclusion in a T-cell-MMP of the present disclosure can have a length of 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa.

In some cases, a HBV peptide suitable for inclusion in a T-cell-MMP of the present disclosure is a MHC Class I-restricted HBV peptide (e.g., it is restricted to a particular HLA class I allele). For example, in some cases, a HBV peptide suitable for inclusion in a T-cell-MMP of the present disclosure is restricted to HLA-A, e.g., HLA-A2, HLA-A11 (HLA-A*1101), HLA-A*2402 or HLA-A3303 (see e.g., FIG. 3). As another example, in some cases, a HBV peptide suitable for inclusion in a T-Cell-MMP epitope conjugate of the present disclosure is restricted to a HLA-B. As another example, in some cases, a HBV peptide suitable for inclusion in a T-Cell-MMP epitope conjugate of the present disclosure is restricted to a HLA-C.

Among the HBV peptides suitable for inclusion in a T-Cell-MMP epitope conjugate described herein are: HBV envelope peptides; HBV precore/core peptides; polymerase peptides and HBV X-protein peptides. Some HBV epitopes are known in the art. See, e.g., Desmond et al. (2008) *Antiviral Therapy* 13:161; Lumley et al. (2016) *Wellcome Open Res.* 1:9; and Kefalakes et al. (2015) *Hepatology* 62:47. HBV peptides suitable for inclusion in T-Cell-MMP epitope conjugates of the present disclosure may bind to a MHC Class I complex with an affinity of at least $10^{-7}$ M, at least $10^{-8}$ M, at $5\times10^{-9}$ M, at least $10^{-9}$ M, at $5\times10^{-10}$ M, or at least $10^{-10}$ M; and are bound by a TCR when complexed with the MHC complex. The Table of HBV Epitopes provided herein sets forth non-limiting embodiments of HBV epitope containing peptide sequences that may form all or part of an epitope peptide incorporated into an T-Cell-MMP-epitope conjugate.

Table of HBV Epitopes

| No. | Sequence | Length in aa residues | SEQ ID NO. |
|---|---|---|---|
| 1 | FLPSDFFPSV from HBV core protein | 10-12 | 84 |
| 2 | GLSRYVARLG from HBV polymerase | 10-12 | 85 |
| 3 | KLHLYSHPI from HBV polymerase | 9-11 | 86 |
| 4 | FLLSLGIHL from HBV polymerase | 9-11 | 87 |
| 5 | ALMPLYACI from HBV polymerase | 9-11 | 88 |
| 6 | SLYADSPSV from HBV polymerase | 9-11 | 89 |
| 7 | STLPETTVV | 9-11 | 90 |
| 8 | LIMPARFYPK | 10-12 | 91 |
| 9 | AIMPARFYPK | 10-12 | 92 |
| 10 | YVNVNMGLK | 9-11 | 93 |
| 11 | PLGFFPDH | 8-10 | 94 |
| 12 | MQWNSTALHQALQDP | 15-17 | 95 |
| 13 | LLDPRVRGL | 9-11 | 96 |
| 14 | SILSKTGDPV | 10-12 | 97 |
| 15 | VLQAGFFLL | 9-11 | 98 |
| 16 | FLLTRILTI | 9-11 | 99 |
| 17 | FLGGTPVCL | 9-11 | 100 |
| 18 | LLCLIFLLV | 9-11 | 101 |
| 19 | LVLLDYQGML | 10-11 | 102 |
| 20 | LLDYQGMLPV | 10-12 | 103 |
| 21 | IPIPSSWAF | 9-11 | 104 |
| 22 | WLSLLVPFV | 9-11 | 105 |
| 23 | GLSPTVWLSV | 10-12 | 106 |
| 24 | SIVSPFIPLL | 9-11 | 107 |
| 25 | ILSPFLPLL | 9-11 | 108 |
| 26 | ATVELLSFLPSDFFPSV | 17-19 | 109 |
| 27 | LPSDFFPSV | 9-11 | 110 |
| 28 | CLTFGRETV | 9-11 | 111 |
| 29 | VLEYLVSFGV | 10-12 | 112 |
| 30 | EYLVSFGVW | 9-11 | 113 |
| 31 | ILSTLPETTV | 10-12 | 114 |

Table of HBV Epitopes -continued

| No. | Sequence | Length in aa residues | SEQ ID NO. |
|---|---|---|---|
| 32 | STLPETTVVRR | 11-13 | 115 |
| 33 | NVSIPWTHK | 9-11 | 116 |
| 34 | KVGNFTGLY | 9-11 | 117 |
| 35 | GLYSSTVPV |  | 118 |
| 36 | TLWKAGILYK | 10-12 | 119 |
| 37 | TPARVTGGVF | 10-12 | 120 |
| 38 | LVVDFSQFSR | 10-12 | 121 |
| 39 | GLSRYVARL | 9-11 | 122 |
| 40 | SIACSVVRR | 9-11 | 123 |
| 41 | YMDDVVLGA | 9-11 | 124 |
| 42 | QAFTFSPTYK | 9-11 | 125 |
| 43 | KYTSFPWLL | 9-11 | 126 |
| 44 | ILRGTSFVYV | 10-12 | 127 |
| 45 | HLSLRGLFV | 9-11 | 128 |
| 46 | VLHKRTLGL | 9-11 | 129 |
| 47 | GLSAMSTTDL | 10-12 | 130 |
| 48 | CLFKDWEEL | 9-11 | 131 |
| 49 | VLGGCRHKL | 9-11 | 132 |
| 50 | STLPETTVV | 9-11 | 167 |

I.G. Immunomodulatory Polypeptides (MODs)

Suitable MOD polypeptides may be incorporated into T-Cell-MMPs as domains that exhibit reduced affinity for Co-MODs. The MOD polypeptides can have from 1 aa to 10 aa differences from a wild-type immunomodulatory domain. For example, in some cases, a variant MOD polypeptide present in a T-Cell-MMP of the present disclosure may differ in amino acid sequence by, for example. 1 aa, 2 aa, 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, or 20 aa (e.g., from laa to 5 aa, from 5 aa to 10 aa, or from 10 aa to 20 aa) from a corresponding wild-type MOD. As an example, in some cases, a variant MOD polypeptide present in a T-Cell-MMP of the present disclosure has and/or includes 1, 2, 3, 4, 5, 6, 7, 8, 9, 10, 11, 12, 13, 14, 15, 16, 17, 18, 19, or 20 (e.g., from 1 to 5, from 2 to 5, from 3 to 5, from 5 to 10, or from 10 to 20) amino acid substitutions, compared to a corresponding reference (e.g., wild-type) MOD. In some cases, variant MOD polypeptides present in a T-Cell-MMP include a single amino acid substitution compared to a corresponding reference (e.g., wild-type) MOD. In some cases, a variant MOD present in a T-Cell-MMP includes, relative to a corresponding wild-type reference (e.g., a wild-type MOD): 1 to 2 aa substitutions; 1 to 3 aa substitutions; 1 to 4 aa substitutions; 1 to 5 aa substitutions; 1 to 6 aa substitutions; 1 to 7 aa substitutions; 1 to 8 aa substitutions; 1 to 9 aa substitutions; 1 to 10 aa substitutions; 1 to 11 aa substitutions; 1 to 12 aa substitutions; 1 to 13 aa substitutions; 1 to 14 aa substitutions; 1 to 15 aa substitutions; 1 to 16 aa substitutions; 1 to 17 aa substitutions; 1 to 18 aa substitutions; 1 to 19 aa substitutions, or 1 to 20 aa substitutions.

As discussed above, variant MODs suitable for inclusion as domains (MOD polypeptides) in T-Cell-MMPs of the present disclosure (and/or their epitope conjugates) include those that exhibit reduced affinity for a Co-MOD, compared to the affinity of a corresponding wild-type MOD for the Co-MOD. Suitable variant MODs can be identified by, for example, mutagenesis, such as scanning mutagenesis (e.g., alanine, serine, or glycine scanning mutagenesis).

Exemplary pairs of MODs and Co-MODs include, but are not limited to entries (a) to (r) listed in the following table: Exemplary Pairs of MODs and Co-MODs

| | |
|---|---|
| a) 4-1BBL (MOD) and 4-1BB (Co-MOD); | k) CD40 (MOD) and CD40L (Co-MOD); |
| b) PD-Ll (MOD) and PD1 (Co-MOD); | l) CD83 (MOD) and CD83L (Co-MOD); |
| c) IL-2 (MOD) and IL-2 receptor (Co-MOD); | m) HVEM (CD270) (MOD) and CD160 (Co-MOD); |
| d) CD80 (MOD) and CD28 (Co-MOD); | n) JAG1 (CD339) (MOD) and Notch (Co-MOD); |
| e) CD86 (MOD) and CD28 (Co-MOD); | o) JAG1 (CD339) (MOD) and CD46 (Co-MOD); |
| f) OX40L (CD252) (MOD) and OX40 (CD134) (Co-MOD); | p) CD70 (MOD) and CD27 (Co-MOD); |
| g) Fas ligand (MOD) and Fas (Co-MOD); | q) CD80 (MOD) and CTLA4 (Co-MOD); and |
| h) ICOS-L (MOD) and ICOS (Co-MOD); | r) CD86 (MOD) and CTLA4 (Co-MOD) |
| i) ICAM (MOD) and LFA-1 (Co-MOD); | |
| j) CD30L (MOD) and CD30 (Co-MOD); | |

In some cases, a variant MOD present in a T-Cell-MMP of the present disclosure has a binding affinity for a Co-MOD that is from 100 nM to 100 µM. For example, in some cases, a variant MOD polypeptide present in a T-Cell-MMP of the present disclosure (or its epitope conjugate) has a binding affinity for a Co-MOD (e.g., a T-Cell-MMP or its epitope conjugate comprises a variant MOD that has a binding affinity for a Co-MOD) that is from about 100 nM to about 150 nM, from about 100 nM to about 500 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 500 nM to about 1 µM, from about 600 nM to about 700 nM, from about 700 nM to about 800 nM, from about 800 nM to about 900 nM, from about 900 nM to about 1 µM, from about 1 µM to about 5 µM, from about 1 µM to about 25 µM from about 5 µM to about 10 µM, from about 10 µM to about 15 µM, from about 15 µM to about 20 µM, from about 20 µM to about 25 µM, from about 25 µM to about 50 µM, from about 25 µM to about 100 µM, from about 50 µM to about 75 µM, or from about 75 µM to about 100 µM.

I.G.1 Wild-Type and Variant PD-L1 MODs

As one non-limiting example, in some cases, a variant MOD polypeptide present in a T-Cell-MMP of the present disclosure is a variant PD-L1 polypeptide. Wild-type PD-L1 binds to PD1.

A wild-type human PD-L1 polypeptide can comprise the following amino acid sequence:

```
                                          (SEQ ID NO: 13)
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPGNI LNVSIKICLT

LSPST
```

A wild-type human PD-L1 ectodomain can comprise the following amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:14).

A wild-type PD-1 polypeptide (NCBI Accession No. NP_005009.2, aas 21-288) can comprise the following amino acid sequence: PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL (SEQ ID NO:15).

In some cases, a variant PD-L1 polypeptide, which can be employed as a MOD polypeptide, exhibits reduced binding affinity to its Co-MOD PD-1 (e.g., a PD-1 polypeptide comprising the amino acid sequence set forth in SEQ ID NO:15) compared to the binding affinity of a PD-L1 polypeptide comprising the amino acid sequence set forth in SEQ ID NO:13 or SEQ ID NO:14. For example, in an embodiment, a variant PD-L1 polypeptide of the present disclosure binds PD-1 (e.g., a PD-1 polypeptide comprising the amino acid sequence set forth in SEQ ID NO:15) with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence set forth in SEQ ID NO:13 or SEQ ID NO:14.

In an embodiment, a variant PD-L1 polypeptide has a binding affinity to PD-1 that is from 1 nM to 1 μM. In some cases, a variant PD-L1 polypeptide of the present disclosure has a binding affinity to PD-1 that is from 100 nM to 100 μM. As another example, in some cases, a variant PD-L1 polypeptide has a binding affinity for PD1 (e.g., a PD1 polypeptide comprising the amino acid sequence set forth in SEQ ID NO:15) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant PD-L1 polypeptide has a single amino acid substitution compared to the PD-L1 amino acid sequence set forth in SEQ ID NO:1 or SEQ ID NO:2. In some cases, a variant PD-L1 polypeptide has from 2 to 10 amino acid substitutions compared to the PD-L1 amino acid sequence set forth in SEQ ID NO:13 or SEQ ID NO:14. In some cases, a variant PD-L1 polypeptide has 2, 3, 4, 5, 6, 7, 8, 9, or 10 amino acid substitutions compared to the PD-L1 amino acid sequence set forth in SEQ ID NO:13 or SEQ ID NO:14.

A suitable PD-L1 variant includes a polypeptide that comprises an amino acid sequence having at least 90%, at least 95%, at least 98%, at least 99%, or 100% amino acid sequence identity to the following amino acid sequence:

FT VTVPKXLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:14), where X is any amino acid other than Asp. In some cases, X is Ala. In some cases, X is Arg.

A suitable PD-L1 variant includes a polypeptide that comprises an amino acid sequence having at least 90%, at least 95%, at least 98%, at least 99%, or 100% amino acid sequence identity to the following amino acid sequence:

FT VTVPKDLYVV EYGSNMTIEC KFPVEKQLDL AALXVYWEME DKNIIQFVHG EEDLKVQHSS YRQRARLLKD QLSLGNAALQ ITDVKLQDAG

VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEI-FYCT FRRLDPEENH TAELVIPGNI LNVSIKI (SEQ ID NO:14), where X is any amino acid other than Ile. In some cases, X is Asp.

A suitable PD-L1 variant includes a polypeptide that comprises an amino acid sequence having at least 90%, at least 95%, at least 98%, at least 99%, or 100% amino acid sequence identity to the following amino acid sequence:
FT VTVPKDLYVV EYGSNMTIEC KFPVEKQLDL AALIVYWEME DKNIIQFVHG EXDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEI-FYCT FRRLDPEENH TAELVIPGNI LNVSIKI (SEQ ID NO:14), where X is any amino acid other than Glu. In some cases, X is Arg.

I.G.2 Wild-type and variant CD80 MODs

In some cases, a variant MOD polypeptide present in a T-Cell-MMP of the present disclosure is a variant CD80 polypeptide. Wild-type CD80 binds to CD28.

A wild-type amino acid sequence of the ectodomain of human CD80 can be as follows:

```
                                    (SEQ ID NO: 16)
VIHVTK EVKEVATLSC GHNVSVEELA QTRIYWQKEK

KMVLTMMSGD MNIWPEYKNR TIFDITNNLS IVILALRPSD

EGTYECVVLK YEKDAFKREH LAEVTLSVKA DFPTPSISDF

EIPTSNIRRI ICSTSGGFPE PHLSWLENGE ELNAINTTVS

QDPETELYAV SSKLDFNMTT NHSFMCLIKY GHLRVNQTFN

WNTTKQEHFP DN.
```

A wild-type CD28 amino acid sequence can be as follows:
MLRLLLALNL FPSIQVTGNK ILVKQSPMLV AYD-NAVNLSC KYSYNLFSRE FRASLHKGLD SAVEVCV-VYG NYSQQLQVYS KTGFNCDGKL GNESVTFYLQ NLYVNQTDIY FCKIEVMYPP PYLDNEKSNG TIIHVKGKHL CPSPLFPGPS KPFWVLVVVG GVLA-CYSLLV TVAFIIFWVR SKRSRLLHSD YMNMTPRRPG PTRKHYQPYA PPRDFAAYRS (SEQ ID NO:17). In some cases, where a T-Cell-MMP of the present disclosure comprises a variant CD80 polypeptide, a Co-MOD is a CD28 polypeptide comprising the amino acid sequence of SEQ ID NO:18.

A wild-type CD28 amino acid sequence can be as follows:
MLRLLLALNL FPSIQVTGNK ILVKQSPMLV AYD-NAVNLSW KHLCPSPLFP GPSKPFWVLV VVGGVLA-CYS LLVTVAFIIF WVRSKRSRLL HSDYMNMTPR RPGPTRKHYQ PYAPPRDFAA YRS (SEQ ID NO:17).

A wild-type CD28 amino acid sequence can be as follows:
MLRLLLALNL FPSIQVTGKH LCPSPLFPGP SKPFWVLVVV GGVLACYSLL VTVAFIIFWV RSKRSRLLHS DYMNMTPRRP GPTRKHYQPY APPRDFAAYR S (SEQ ID NO:19).

In some cases, a variant CD80 polypeptide exhibits reduced binding affinity to CD28, compared to the binding affinity of a CD80 polypeptide comprising the amino acid sequence set forth in SEQ ID NO:16 for CD28. For example, in some cases, a variant CD80 polypeptide binds CD28 with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less than the binding affinity of a CD80 polypeptide comprising the amino acid sequence set forth in SEQ ID NO:16 for CD28 (e.g., a CD28 polypeptide comprising the amino acid sequence set forth in one of SEQ ID NOs:17, 18, or 19).

In some cases, a variant CD80 polypeptide has a binding affinity to CD28 that is from 100 nM to 100 µM. As another example, in some cases, a variant CD80 polypeptide of the present disclosure has a binding affinity for CD28 (e.g., a CD28 polypeptide comprising the amino acid sequence set forth in SEQ ID NO:17, SEQ ID NO:18, or SEQ ID NO:19) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, from about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM.

In some cases, a variant CD80 polypeptide has a single amino acid substitution compared to the CD80 amino acid sequence set forth in SEQ ID NO:16. In some cases, a variant CD80 polypeptide has from 2 to 10 amino acid substitutions compared to the CD80 amino acid sequence set forth in SEQ ID NO:16. In some cases, a variant CD80 polypeptide has 2, 3, 4, 5, 6, 7, 8. 9, or 10 amino acid substitutions compared to the CD80 amino acid sequence set forth in SEQ ID NO:16.

Some suitable CD80 variants include a polypeptide that comprises an amino acid sequence having a sequence identity of at least 90% (less than 20 substitutions), at least 95% less than 10 substitutions), at least 97% (less than 6 substitutions), at least 98% (less than 4 substitutions), at least 99% (less than 2 substitutions), or at least 99.5% (one substitution) amino acid sequence identity to any one of the following amino acid sequences:
VIHVTK EVKEVATLSC GHX̲VSVEELA QTRIYWQKEK KMVLTMMSGD MNI̲WPEYKNR TIFDITNNLS IVILALRPSD EGTYECVVLK YEK-DAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO16), where X is any amino acid other than Asn. In some cases, X is Ala;
VIHVTK EVKEVATLSC GHNVSVEELA QTRIYWQKEK KMVLTMMSGD MNIWPEYKNR TIFDITX̲NLS IVILALRPSD EGTYECVVLK YEK-DAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Asn. In some cases, X is Ala;
VIHVTK EVKEVATLSC GHNVSVEELA QTRIYWQKEK KMVLTMMSGD MNIWPEYKNR TIFDITNNLS X̲VILALRPSD EGTYECVVLK YEK-DAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Ile. In some cases, X is Ala;

VIHVTK EVKEVATLSC GHNVSVEELA QTRIYWQKEK KMVLTMMSGD MNIWPEYKNR TIFDITNNLS IVILALRPSD EGTYECVVLX YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Lys. In some cases, X is Ala;

VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS XDPETELYAV SSKLDFNMTT NHSFMCLIKY GHLRVNQTFN WNTTKQEHFP DN (SEQ ID NO:16), where X is any amino acid other than Gln. In some cases, X is Ala;

VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QXPETELYAV SSKLDFNMTT NHSFMCLIKY GHLRVNQTFN WNTTKQEHFP DN (SEQ ID NO:16), where X is any amino acid other than Asp. In some cases, X is Ala;

VIHVTK EVKEVATLSC GHNVSVEEXA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Leu. In some cases, X is Ala;

VIHVTK EVKEVATLSC GHNVSVEELA QTRIXWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Tyr. In some cases, X is Ala;

VIHVTK EVKEVATLSC GHNVSVEELA QTRIYWXKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Gln. In some cases, X is Ala;

VIHVTK EVKEVATLSC GHNVSVEELA QTRIYWQKEK KXVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Met. In some cases, X is Ala;

VIHVTK EVKEVATLSC GHNVSVEELA QTRIYWQKEK KMXLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Val. In some cases, X is Ala;

VIHVTK EVKEVATLSC GHNVSVEELA QTRIYWQKEK KMVLTMMSGD MNXWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Ile. In some cases, X is Ala;

VIHVTK EVKEVATLSC GHNVSVEELA QTRIYWQKEK KMVLTMMSGD MNIWPEXKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Tyr. In some cases, X is Ala;

VIHVTK EVKEVATLSC GHNVSVEELA QTRIYWQKEK KMVLTMMSGD MNIWPEYKNR TIFXITNNLS IVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Asp. In some cases, X is Ala;

VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DXPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Phe. In some cases, X is Ala;

VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVX QDPETELYAV SSKLDFNMTT NHSFMCLIKY GHLRVNQTFN WNTTKQEHFP DN (SEQ ID NO:16), where X is any amino acid other than Ser. In some cases, X is Ala; and VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTXSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:16), where X is any amino acid other than Pro. In some cases, X is Ala.

I.G.3 Wild-Type and Variant CD86 MODs

In some cases, a variant MOD polypeptide present in a T-Cell-MMP of the present disclosure is a variant CD86 polypeptide. Wild-type CD86 binds to CD28.

The amino acid sequence of the full ectodomain of a wild-type human CD86 can be as follows:

```
                                           (SEQ ID NO: 20)
APLKIQAYFNETADLPCQFANSQNQSLSELVVFWQDQENLVLNE

VYLGKEKFDSVHSKYMNRTSFDSDSWTLRLHNLQIKDKGLYQCI

IHHKKPTGMIRIHQMNSELSVLANFSQPEIVPISNITENVYINL

TCSSIHGYPEPKKMSVLLRTKNSTIEYDGIMQKSQDNVTELYDV

SISLSVSFPDVTSNMTIFCILETDKTRLLSSPFSIELEDPQPPP

DHIP.
```

The amino acid sequence of the IgV domain of a wild-type human CD86 can be as follows:

```
                                           (SEQ ID NO: 21)
APLKIQAYFNETADLPCQFANSQNQSLSELVVFWQDQENLVLNE

VYLGKEKFDSVHSKYMNRTSFDSDSWTLRLHNLQIKDKGLYQCI

IHHKKPTGMIRIHQMNSELSVL.
```

In some cases, a variant CD86 polypeptide exhibits reduced binding affinity to CD28, compared to the binding affinity of a CD86 polypeptide comprising the amino acid sequence set forth in SEQ ID NO:20 or SEQ ID NO:21 for CD28. For example, in some cases, a variant CD86 polypeptide binds CD28 with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less than the binding affinity of a CD86 polypeptide comprising the amino acid sequence set forth in SEQ ID NO:20 or SEQ ID NO:21 for CD28 (e.g., a CD28 polypeptide comprising the amino acid sequence set forth in one of SEQ ID NOs:17, 18, or 19).

In some cases, a variant CD86 polypeptide has a binding affinity to CD28 that is from 100 nM to 100 µM. As another example, in some cases, a variant CD86 polypeptide of the present disclosure has a binding affinity for CD28 (e.g., a CD28 polypeptide comprising the amino acid sequence set forth in one of SEQ ID NOs:17, 18, or 19) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM.

In some cases, a variant CD86 polypeptide has a single amino acid substitution compared to the CD86 amino acid sequence set forth in SEQ ID NO:20. In some cases, a variant CD86 polypeptide has from 2 to 10 amino acid substitutions compared to the CD86 amino acid sequence set forth in SEQ ID NO:20. In some cases, a variant CD86 polypeptide has 2, 3, 4, 5, 6, 7, 8, 9, or 10 amino acid substitutions compared to the CD86 amino acid sequence set forth in SEQ ID NO:20.

In some cases, a variant CD86 polypeptide has a single amino acid substitution compared to the CD86 amino acid sequence set forth in SEQ ID NO:21. In some cases, a variant CD86 polypeptide has from 2 to 10 amino acid substitutions compared to the CD86 amino acid sequence set forth in SEQ ID NO:21. In some cases, a variant CD86 polypeptide has 2, 3, 4, 5, 6, 7, 8, 9, or 10 amino acid substitutions compared to the CD86 amino acid sequence set forth in SEQ ID NO:21.

Suitable CD86 variants include a polypeptide that comprises an amino acid sequence having at least 90%, at least 95%, at least 98%, at least 99%, or 100% amino acid sequence identity to any one of the following amino acid sequences:

APLKIQAYFNETADLPCQFANSQNQSL-SELVVFWQDQENLVLNEVYLGKEKFDSVHS KYMXRTSFDSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Asn. In some cases, X is Ala;

APLKIQAYFNETADLPCQFANSQNQSL-SELVVFWQDQENLVLNEVYLGKEKFDSVHS KYMNRTSFXSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Asp. In some cases, X is Ala;

APLKIQAYFNETADLPCQFANSQNQSL-SELVVFWQDQENLVLNEVYLGKEKFDSVHS KYMNRTSFDSDSXTLRLHNLQIKDKGLYQCI-IHHKKPTGMIRIHQMNSELSVLANFSQPEIVPISN ITENVYINLTCSSIHGYPEPKKMSVLLRTKN-STIEYDGIMQKSQDNVTELYDVSISLSVSFPDVTS NMTIFCILETDKTRLLSSPFSIELEDPQPPPDHIP (SEQ ID NO:20), where X is any amino acid other than Trp. In some cases, X is Ala;

APLKIQAYFNETADLPCQFANSQNQSL-SELVVFWQDQENLVLNEVYLGKEKFDSVHS KYMNRTSFDSDSWTLRLHNLQIKDKGLYQCI-IHXKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than His. In some cases, X is Ala;

```
                                           (SEQ ID NO: 20)
APLKIQAYFNETADLPCQFANSQNQSLSELVVFWQDQENLVLNE

VYLGKEKFDSVHSKYMXRTSFDSDSWTLRLHNLQIKDKGLYQCI

IHHKKPTGMIRIHQMNSELSVL,
``` where X is any amino acid other than Asn. In some cases, X is Ala;

APLKIQAYFNETADLPCQFANSQNQSLSELVVFWQDQENLVLNEVYLGKEKFDSVHSKYMNRTSFXSDSWTLRLHNLQIKDKGLYQCIIHHKKPTGMIRIHQMNSELSVL, (SEQ ID NO: 20)

where X is any amino acid other than Asp. In some cases, X is Ala;

APLKIQAYFNETADLPCQFANSQNQSLSELVVFWQDQENLVLNEVYLGKEKFDSVHSKYMNRTSFDSDSXTLRLHNLQIKDKGLYQCIIHHKKPTGMIRIHQMNSELSVL, (SEQ ID NO: 20)

where X is any amino acid other than Trp. In some cases, X is Ala;

APLKIQAYFNETADLPCQFANSQNQSLSELVVFWQDQENLVLNEVYLGKEKFDSVHSKYMNRTSFDSDSWTLRLHNLQIKDKGLYQCIIHXKKPTGMIRIHQMNSELSVL, (SEQ ID NO: 20)

where X is any amino acid other than His. In some cases, X is Ala;

APLKIQAYFNETADLPCQFANSQNQSL-SELVVFWQDQENLXLNEVYLGKEKFDSVHSKYMNRTSFDSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Val. In some cases, X is Ala;

APLKIQAYFNETADLPCQFANSQNQSLSELVVFWQDQENLXLNEVYLGKEKFDSVHSKYMNRTSFDSDSWTLRLHNLQIKDKGLYQCIIHHKKPTGMIRIHQMNSELSVL, (SEQ ID NO: 20)

where X is any amino acid other than Val. In some cases, X is Ala;

APLKIQAYFNETADLPCQFANSQNQSL-SELVVFWXDQENLVLNEVYLGKEKFDSVHSKYMNRTSFDSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Gln. In some cases, X is Ala;

APLKIQAYFNETADLPCQFANSQNQSLSELVVFWXDQENLVLNEVYLGKEKFDSVHSKYMNRTSFDSDSWTLRLHNLQIKDKGLYQCIIHHKKPTGMIRIHQMNSELSVL, (SEQ ID NO: 20)

where X is any amino acid other than Gln. In some cases, X is Ala;

APLKIQAYFNETADLPCQFANSQNQSL-SELVVXWQDQENLVLNEVYLGKEKFDSVHSKYMNRTSFDSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Phe. In some cases, X is Ala;

APLKIQAYFNETADLPCQFANSQNQSLSELVVXWQDQENLVLNEVYLGKEKFDSVHSKYMNRTSFDSDSWTLRLHNLQIKDKGLYQCIIHHKKPTGMIRIHQMNSELSVL, (SEQ ID NO: 20)

where X is any amino acid other than Phe. In some cases, X is Ala;

APLKIQAYFNETADLPCQFANSQNQSL-SELVVFWQDQENLVLNEVYLGKEKFDSVHSKYMNRTSFDSDSWTXRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Leu. In some cases, X is Ala;

APLKIQAYFNETADLPCQFANSQNQSLSELVVFWQDQENLVLNEVYLGKEKFDSVHSKYMNRTSFDSDSWTXRLHNLQIKDKGLYQCIIHHKKPTGMIRIHQMNSELSVL, (SEQ ID NO: 20)

where X is any amino acid other than Leu. In some cases, X is Ala;

APLKIQAYFNETADLPCQFANSQNQSL-SELVVFWQDQENLVLNEVYLGKEKFDSVHSKXMNRTSFDSDSWTLRLHNLQIKDKGLYQCI-IHHKKPTGMIRIHQMNSELSVLANFSQPEIVPIS NITENVYINLTCSSIHGYPEPKKMSVLLRTKN-STIEYDGIMQKSQDNVTELYDVSISLSVSFPDVT SNMTIFCILETDKTRLLSSPFSIELEDPQPPPDHIP (SEQ ID NO:20), where X is any amino acid other than Tyr. In some cases, X is Ala;

APLKIQAYFNETADLPCQFANSQNQSLSELVVFWQDQENLVLNEVYLGKEKFDSVHSKXMNRTSFDSDSWTLRLHNLQIKDKGLYQCIIHHKKPTGMIRIHQMNSELSVL, (SEQ ID NO: 20)

where X is any amino acid other than Tyr. In some cases, X is Ala;

APLKIQAYFNETADLPCQFANSQNQSL-SELVVFWQDQENLVLNEVYLGKEKFDSVHSKYMX₁RTSFDSDSWTLRLHNLQIKDKGLYQCIIHX₂KKPTGMIRIHQMNSELSVLANFSQPEIVPI SNITENVYINLTCSSIHGYPEPKKMSVLLRTKNSTIEYDGIMQKSQDNVTELYDVSISLSVSFPDV TSNMTIFCILETDKTRLLSSPFSIELEDPQPPPDHIP (SEQ ID NO:20), where X₁ is any amino acid other than Asn and the second X₂ is any amino acid other than His. In some cases, X₁ and X₂ are both Ala;

(SEQ ID NO: 20)
APLKIQAYFNETADLPCQFANSQNQSLSELVVFWQDQENLVLNEVYLGKE

KFDSVHSKYMX̲RTSFDSDSWTLRLHNLQIKDKGLYQCIIHX̲KKPTGMIRI

HQMNSELSVL, where X₁ is any amino acid other than Asn and X₂ is any amino acid other than His. In some cases, X₁ and X₂ are both Ala;
APLKIQAYFNETADLPCQFANSQNQSL-SELVVFWQDQENLVLNEVYLGKEKFDSVHS KYMNRTSFX̲₁SDSWTLRLHNLQIKDKGLY QCIIHX̲₂KKPTGMIRIHQMNSELSVLANFSQPEI VPI SNITENVYINLTCSSIHGYPEPKKMSVLLRT-KNSTIEYDGIMQKSQDNVTELYDVSIS-LSVSFPDV TSNMTIFCI-LETDKTRLLSSPFSIELEDPQPPPDHIP (SEQ ID NO:20), where X₁ is any amino acid other than Asp, and X₂ is any amino acid other than His. In some cases, X₁ is Ala and X₂ is Ala;
APLKIQAYFNETADLPCQFANSQNQSL-SELVVFWQDQENLVLNEVYLGKEKFDSVHS KYMNRTSFX̲₁SDSWTLRLHNLQIKDKGLYQ CIIHX̲₂KKPTGMIRIHQMNSELSVL (SEQ ID NO:20), where X₁ is any amino acid other than Asn and X₂ is any amino acid other than His. In some cases, X₁ and X₂ are both Ala;
APLKIQAYFNETADLPCQFANSQNQSL-SELVVFWQDQENLVLNEVYLGKEKFDSVHS KYMX̲₁RTSFX̲₂SDSWTLRLHNLQIKDKG LYQCIIHX̲₃KKPTGMIRIHQMNSELSVLAN FSQPEIVPI SNITENVYINLTCSSIHGY-PEPKKMSVLLRTKNSTIEYDGIMQKSQDNVTE-LYDVSISLSVSFPDV TSNMTIFCI-LETDKTRLLSSPFSIELEDPQPPPDHIP (SEQ ID NO:20), where X₁ is any amino acid other than Asn, X₂ is any amino acid other than Asp, and X₃ is any amino acid other than His. In some cases, X₁ is Ala, X₂ is Ala, and X₃ is Ala; and
APLKIQAYFNETADLPCQFANSQNQSL-SELVVFWQDQENLVLNEVYLGKEKFDSVHS KYMX̲₁RTSFX̲₂SDSWTLRLHNLQIKDKG LYQCIIHX̲₃KKPTGMIRIHQMNSELSVL (SEQ ID NO:21), where X₁ is any amino acid other than Asn, X₂ is any amino acid other than Asp, and X₃ is any amino acid other than His. In some cases, X₁ is Ala, X₂ is Ala, and X₃ is Ala.

I.G.4 Wild-Type and Variant 4-1BBL MODs

In some cases, a variant MOD polypeptide present in a T-Cell-MMP of the present disclosure is a variant 4-1BBL polypeptide. Wild-type 4-1BBL binds to 4-1BB (CD137).

A wild-type 4-1BBL amino acid sequence can be as follows: MEYASDASLD PEAPWPPAPR (SEQ ID NO: 22)
ARACRVLPWA LVAGLLLLLL LAAACAVFLA CPWAVSGARA

SPGSAASPRL REGPELSPDD PAGLLDLRQG MFAQLVAQNV

LLIDGPLSWY SDPGLAGVSL TGGLSYKEDT KELVVAKAGV

YYVFFQLELR RVVAGEGSGS VSLALHLQPL RSAAGAAALA

LTVDLPPASS EARNSAFGFQ GRLLHLSAGQ RLGVHLHTEA

RARHAWQLTQ GATVLGLFRV TPEIPAGLPS PRSE.

In some cases, a variant 4-1BBL polypeptide is a variant of the tumor necrosis factor (TNF) homology domain (THD) of human 4-1BBL.

A wild-type amino acid sequence of the THD of human 4-1BBL can be, e.g., one of SEQ ID NOs:23-25, as follows:

(SEQ ID NO: 23)
PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE;

(SEQ ID NO: 24)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE;
or (SEQ ID NO: 25)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPA.

A wild-type 4-1BB amino acid sequence can be as follows: MGNSCYNIVA TLLLVLNFER TRSLQDPCSN CPAGTFCDNN RNQICSPCPP NSFSSAGGQR TCDI-CRQCKG VFRTRKECSS TSNAECDCTP GFHCL-GAGCS MCEQDCKQGQ ELTKKGCKDC CFGTFNDQKR GICRPWTNCS LDGKSVLVNG TKER-DVVCGP SPADLSPGAS SVTPPAPARE PGHSPQIISF FLALTSTALL FLLFFLTLRF SVVKRGRKKL LYIFKQPFMR PVQTTQEEDG CSCRFPEEEE GGCEL (SEQ ID NO:26). In some cases, where a T-Cell-MMP of the present disclosure comprises a variant 4-1BBL polypeptide, a Co-MOD is a 4-1BB polypeptide comprising the amino acid sequence of SEQ ID NO:26.

In some cases, a variant 4-1BBL polypeptide exhibits reduced binding affinity to 4-1BB, compared to the binding affinity of a 4-1BBL polypeptide comprising the amino acid sequence set forth in one of SEQ ID NOs:22-25. For example, in some cases, a variant 4-1BBL polypeptide of the present disclosure binds 4-1BB with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less than the binding affinity of a 4-1BBL polypeptide comprising the amino acid sequence set forth in one of SEQ ID NOs:22-25 for a 4-1BB polypeptide (e.g., a 4-1BB polypeptide comprising the amino acid sequence set forth in SEQ ID NO:26), when assayed under the same conditions.

In some cases, a variant 4-1BBL polypeptide has a binding affinity to 4-1BB that is from 100 nM to 100 μM. As another example, in some cases, a variant 4-1BBL polypeptide has a binding affinity for 4-1BB (e.g., a 4-1BB polypeptide comprising the amino acid sequence set forth in SEQ ID NO:26) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant 4-1BBL polypeptide has a single amino acid substitution compared to the 4-1BBL amino acid sequence set forth in one of SEQ ID NOs:22-25. In some cases, a variant 4-1BBL polypeptide has from 2 to 10 amino acid substitutions compared to the 4-1BBL amino acid sequence set forth in one of SEQ ID NOs:22-25. In some cases, a variant 4-1BBL polypeptide has 2, 3, 4, 5, 6, 7, 8, 9, or 10 amino acid substitutions compared to the 4-1BBL amino acid sequence set forth in one of SEQ ID NOs:22-25.

Suitable 4-1BBL variants include a polypeptide that comprises an amino acid sequence having at least 90%, at least 95%, at least 98%, at least 99%, or 100% amino acid sequence identity to any one of the following amino acid sequences:

PAGLLDLRQG MFAQLVAQNV LLIDGPLSWY SDPGLAGVSL TGGLSYXEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Lys. In some cases, X is Ala;

PAGLLDLRQG MFAQLVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWXLTQ GATVLGLFRV TPEIPAGLPS PRSE (SEQ ID NO:23), where X is any amino acid other than Gln. In some cases, X is Ala;

PAGLLDLRQG XFAQLVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Met. In some cases, X is Ala;

PAGLLDLRQG MXAQLVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Phe. In some cases, X is Ala;

PAGLLDLRQG MFAXLVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gln. In some cases, X is Ala;

PAGLLDLRQG MFAQXVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLXAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAXNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gln. In some cases, X is Ala;

PAGLLDLRQG MFAQLVAQXV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Asn. In some cases, X is Ala;

PAGLLDLRQG MFAQLVAQNX LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAQNV XLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LXIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLXDGPLSWY SDPGLAGVSL TGGLSYKEDT KELVVAKAGV YYVFFQLELR RVVAGEGSGS VSLALHLQPL

RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ile. In some cases, X is Ala;

PAGLLDLRQG MFAQLVAQNV LLIXGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Asp. In some cases, X is Ala;

PAGLLDLRQG MFAQLVAQNV LLIDXPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGXLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Pro. In some cases, X is Ala;

PAGLLDLRQG MFAQLVAQNV LLIGGPXSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLXWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSXY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Trp. In some cases, X is Ala;

PAGLLDLRQG MFAQLVAQNV LLIGGPLSWX SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Tyr. In some cases, X is Ala;

PAGLLDLRQG MFAQLVAQNV LLIGGPLSWY XDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SXPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Asp. In some cases, X is Ala;

PAGLLDLRQG MFAQLVAQNV LLIGGPLSWY SDXGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Pro. In some cases, X is Ala;

PAGLLDLRQG MFAQLVAQNV LLIGGPLSWY SDPXLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGXAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAXVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGXSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAQNV LLIGGPLSWY SDPGLAGVXL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSX TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL XGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Thr. In some cases, X is Ala;

PAGLLDLRQG MFAQLVAQNV LLIGGPLSWY SDPGLAGVSL TXGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGXLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGGXSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLXYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSL TGGLSXKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Tyr. In some cases, X is Ala;

PAGLLDLRQG MFAQLVAQNV LLIGGPLSWY SDPGLAGVSL TGGLSYKXDT KELVVAKAGV YYVFFQLELR RVVAGEGSGS VSLALHLQPL RSAAGAAALA LTVDLPPASS

EARNSAFGFQ GRLLHLSAGQ RLGVHLHTEA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEXT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Asp. In some cases, X is Ala;

PAGLLDLRQG MFAQLVAQNV LLIGGPLSWY SDPGLAGVSL TGGLSYKEDX KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Thr. In some cases, X is Ala;

PAGLLDLRQG MFAQLVAQNV LLIGGPLSWY SDPGLAGVSL TGGLSYKEDT XELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Lys. In some cases, X is Ala;

PAGLLDLRQG MFAQLVAQNV LLIGGPLSWY SDPGLAGVSL TGGLSYKEDT KXLVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEDT KELVVAKAGV YYVXFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Phe. In some cases, X is Ala;

PAGLLDLRQG MFAQLVAQNV LLIGGPLSWY SDPGLAGVSL TGGLSYKEDT KELVVAKAGV YYVFXQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Phe. In some cases, X is Ala;

PAGLLDLRQG MFAQLVAQNV LLIGGPLSWY SDPGLAGVSL TGGLSYKEDT KELVVAKAGV YYVFFXLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gln. In some cases, X is Ala;

PAGLLDLRQG MFAQLVAQNV LLIGGPLSWY SDPGLAGVSL TGGLSYKEDT KELVVAKAGV YYVFFQXELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLXLR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEDT KELVVAKAGV YYVFFQLEXR RVVAGEGSGS VSLALHLQPL RSAAGAAALA LTVDLPPASS EARNSAFGFQ GRLLHLSAGQ RLGVHLHTEA RARHAWQLTQ

GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLELX RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR XVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR RXVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAQNV LLIGGPLSWY SDPGLAGVSL TGGLSYKEDT KELVVAKAGV YYVFFQLELR RVXAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAQNV LLIGGPLSWY SDPGLAGVSL TGGLSYKEDT KELVVAKAGV YYVFFQLELR RVVAXEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGGLSYKEDT KELVVAKAGV YYVFFQLELR RVVAGXGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEDT KELVVAKAGV YYVFFQLELR RVVAGEXSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGGLSYKEDT KELVVAKAGV YYVFFQLELR RVVAGEGXGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVXLPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Asp. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDXPPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLXPASS EARNSAFGFQ GRLLHLSAGQ RLGVHLHTEA RARHAWQLTQ GATVLGLFRV TPEIPAGLPS PRSE (SEQ ID NO:23), where X is any amino acid other than Pro. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPAXS EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASX EARNSAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS XARNSAFGFQ GRLLHLSAGQ RLGVHLHTEA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EAXNSAFGFQ GRLLHLSAGQ RLGVHLHTEA RARHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARXSAFGFQ GRLLHLSAGQ RLGVHLHTEA RARHAWQLTQ GATVLGLFRV TPEIPAGLPS PRSE (SEQ ID NO:23), where X is any amino acid other than Asn. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL

RSAAGAAALA LTVDLPPASS EARNXAFGFQ GRLLHLSAGQ RLGVHLHTEA RARHAWQLTQ GATVLGLFRV TPEIPAGLPS PRSE (SEQ ID NO:23), where X is any amino acid other than Ser. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAXGFQ GRLLHLSAGQ RLGVHLHTEA RARHAWQLTQ GATVLGLFRV TPEIPAGLPS PRSE (SEQ ID NO:23), where X is any amino acid other than Phe. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGX RLGVHLHTEA RARHAWQLTQ GATVLGLFRV TPEIPAGLPS PRSE (SEQ ID NO:23), where X is any amino acid other than Gln. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ XLGVHLHTEA RARHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RXGVHLHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLXVHLHTEA RARHAWQLTQ GATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGXHLHTEA RARHAWQLTQ GATVLGLFRV TPEIPAGLPS PRSE (SEQ ID NO:23), where X is any amino acid other than Val. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVXLHTEA RARHAWQLTQ GATVLGLFRV TPEIPAGLPS PRSE (SEQ ID NO:23), where X is any amino acid other than His. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHXHTEA RARHAWQLTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLXTEA RARHAWQLTQ GATVLGLFRV TPEIPAGLPS PRSE (SEQ ID NO:23), where X is any amino acid other than His. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHXEA RARHAWQLTQ GATVLGLFRV TPEIPAGLPS PRSE (SEQ ID NO:23), where X is any amino acid other than Thr. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTXA RARHAWQLTQ GATVLGLFRV TPEIPAGLPS PRSE (SEQ ID NO:23), where X is any amino acid other than Glu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA XARHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RAXHAWQLTQ GATVLGLFRV TPEIPAGLPS PRSE (SEQ ID NO:23), where X is any amino acid other than Arg. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARXAWQLTQ GATVLGLFRV TPEIPAGLPS PRSE (SEQ ID NO:23), where X is any amino acid other than His. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAXQLTQ GATVLGLFRV TPEIPAGLPS PRSE (SEQ ID NO:23), where X is any amino acid other than Trp. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQXTQ GATVLGLFRV TPEIPAGLPS PRSE (SEQ ID NO:23), where X is any amino acid other than Leu. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLXQ GATVLGLFRV TPEIPAGLPS PRSE (SEQ ID NO:23), where X is any amino acid other than Thr. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTX GATVLGLFRV TPEIPAGLPS PRSE (SEQ ID NO:23), where X is any amino acid other than Gln. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ XATVLGLFRV TPEIPAGLPS PRSE (SEQ ID NO:23), where X is any amino acid other than Gly. In some cases, X is Ala;

PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GAXVLGLFRV TPEIPAGLPS PRSE (SEQ ID NO:23), where X is any amino acid other than Thr. In some cases, X is Ala; and PAGLLDLRQG MFAQLVAQNV LLIGGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATXLGLFRV TPEIPAGLPS PRSE (SEQ ID NO:23), where X is any amino acid other than Val. In some cases, X is Ala.

I.G.5 IL-2 Variants

In some cases, a variant MOD polypeptide present in a T-Cell-MMP of the present disclosure is a variant IL-2 polypeptide. Wild-type IL-2 binds to IL-2 receptor (IL-2R), i.e., a heterotrimeric polypeptide comprising IL-2Rα, IL-2Rβ, and IL-2Rγ.

A wild-type IL-2 amino acid sequence can be as follows: APTSSSTKKT QLQLEHLLLD LQMILNGINN YKNPKLTRML TFKFYMPKKA TELKHLQCLEEELKPLEEVL NLAQSKNFHL RPRDLISNIN VIVLELKGSE TTFMCEYADE TATIVE-FLNRWITFCQSIIS TLT (SEQ ID NO:27).

Wild-type IL2 binds to an IL2 receptor (IL2R) on the surface of a cell. An IL2 receptor is in some cases a heterotrimeric polypeptide comprising an alpha chain (IL-2Rα; also referred to as CD25), a beta chain (IL-2Rβ; also referred to as CD122), and a gamma chain (IL-2Rγ; also referred to as CD132). Amino acid sequences of human IL-2Rα, IL2Rβ, and IL-2Rγ can be as follows.

Human IL-2Rα:
(SEQ ID NO: 28)
ELCDDDPPE IPHATFKAMA YKEGTMLNCE CKRGFRRIKS

GSLYMLCTGN SSHSSWDNQC QCTSSATRNT TKQVTPQPEE

QKERKTTEMQ SPMQPVDQAS LPGHCREPPP WENEATERIY

HFVVGQMVYY QCVQGYRALH RGPAESVCKM THGKTRWTQP

QLICTGEMET SQFPGEEKPQ ASPEGRPESE TSCLVTTTDF

QIQTEMAATM ETSIFTTEYQ VAVAGCVFLL ISVLLLSGLT

WQRRQRKSRR TI.

Human IL-2Rβ:
(SEQ ID NO: 29)
VNG TSQFTCFYNS RANISCVWSQ DGALQDTSCQ VHAWPDRRRW

NQTCELLPVS QASWACNLIL GAPDSQKLTT VDIVTLRVLC

REGVRWRVMA IQDFKPFENL RLMAPISLQV VHVETHRCNI

SWEISQASHY FERHLEFEAR TLSPGHTWEE APLLTLKQKQ

EWICLETLTP DTQYEFQVRV KPLQGEFTTW SPWSQPLAFR

TKPAALGKDT IPWLGHLLVG LSGAFGFIIL VYLLINCRNT

GPWLKKVLKC NTPDPSKFFS QLSSEHGGDV QKWLSSPFPS

SSFSPGGLAP EISPLEVLER DKVTQLLLQQ DKVPEPASLS

SNHSLTSCFT NQGYFFFHLP DALEIEACQV YFTYDPYSEE

DPDEGVAGAP TGSSPQPLQP LSGEDDAYCT FPSRDDLLLF

SPSLLGGPSP PSTAPGGSGA GEERMPPSLQ ERVPRDWDPQ

PLGPPTPGVP DLVDFQPPPE LVLREAGEEV PDAGPREGVS

FPWSRPPGQG EFRALNARLP LNTDAYLSLQ ELQGQDPTHL V.

Human IL-2Rγ:
(SEQ ID NO: 30)
LNTTILTP NGNEDTTADF FLTTMPTDSL SVSTLPLPEV

QCFVFNVEYM NCTWNSSSEP QPTNLTLHYW YKNSDNDKVQ

KCSHYLFSEE ITSGCQLQKK EIHLYQTFVV QLQDPREPRR

QATQMLKLQN LVIPWAPENL TLHKLSESQL ELNWNNRFLN

HCLEHLVQYR TDWDHSWTEQ SVDYRHKFSL PSVDGQKRYT

FRVRSRFNPL CGSAQHWSEW SHPIHWGSNT SKENPFLFAL

EAVVISVGSM GLIISLLCVY FWLERTMPRI PTLKNLEDLV

TEYHGNFSAW SGVSKGLAES LQPDYSERLC LVSEIPPKGG

ALGEGPGASP CNQHSPYWAP PCYTLKPET.

In some cases, where a T-Cell-MMP of the present disclosure comprises a variant IL-2 polypeptide, a Co-MOD is an IL-2R comprising polypeptides comprising the amino acid sequences of SEQ ID NO:28, 29, and 30.

In some cases, a variant IL-2 polypeptide exhibits reduced binding affinity to IL-2R, compared to the binding affinity of an IL-2 polypeptide comprising the amino acid sequence set forth in SEQ ID NO:27. For example, in some cases, a variant IL-2 polypeptide binds IL-2R with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less than the binding affinity of an IL-2 polypeptide comprising the amino acid sequence set forth in SEQ ID NO:27 for an IL-2R (e.g., an IL-2R comprising polypeptides comprising the amino acid sequence set forth in SEQ ID NOs:28-30), when assayed under the same conditions.

In some cases, a variant IL-2 polypeptide has a binding affinity to IL-2R that is from 100 nM to 100 μM. As another example, in some cases, a variant IL-2 polypeptide has a binding affinity for IL-2R (e.g., an IL-2R comprising polypeptides comprising the amino acid sequence set forth in SEQ ID NOs:28-30) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant IL-2 polypeptide has a single amino acid substitution compared to the IL-2 amino acid sequence set forth in SEQ ID NO:27. In some cases, a variant IL-2 polypeptide has from 2 to 10 amino acid substitutions compared to the IL-2 amino acid sequence set forth in SEQ ID NO:27. In some cases, a variant IL-2 polypeptide has 2, 3, 4, 5, 6, 7, 8, 9, or 10 amino acid substitutions compared to the IL-2 amino acid sequence set forth in SEQ ID NO:27.

Suitable IL-2 variant MOD polypeptides include a polypeptide that comprises an amino acid sequence having at least 90%, at least 95%, at least 98%, at least 99%, or 100% amino acid sequence identity to any one of the following amino acid sequences:

APTSSSTKKT QLQLEHLLLD LQMILNGINN YKNPKLTRML T<u>X</u>KFYMPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where X is any amino acid other than Phe. In some cases, X is Ala;

APTSSSTKKT QLQLEHLLL<u>X</u> LQMILNGINN YKNPKLTRML TFKFYMPK<u>K</u>A TELKHLQCLE EELKPLEEVL NLAQSKNFHL RPRDLISNIN VIVLELKGSE TTFMCEYADE TATIVEFLNR WITFCQSIIS TLT (SEQ ID NO:27), where X is any amino acid other than Asp. In some cases, X is Ala;

APTSSSTKKT QLQL<u>X</u>HLLLD LQMILNGINN YKNPKLTRML TFK<u>F</u>YMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:27), where X is any amino acid other than Glu. In some cases, X is Ala;

APTSSSTKKT QLQLE<u>X</u>LLLD LQMILNGINN YKNPKLTRML TFKF<u>Y</u>MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:27), where X is any amino acid other than His. In some cases, X is Ala;

APTSSSTKKT QLQLE<u>X</u>LLLD LQMILNGINN YKNPKLTRML TFKF<u>Y</u>MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:27), where X is any amino acid other than His. In some cases, X is Ala, Asn, Asp, Cys, Glu, Gln, Gly, Ile, Lys, Leu, Met, Phe, Pro, Ser, Thr, Tyr, Trp or Val;

APTSSSTKKT QLQLEHLLLD LQMILNGINN YKNPKLTRML TFKF<u>X</u>MPKKA TELKHLQCLE EELKPLEEVL NLA<u>Q</u>SKNFHL RPRDLISNIN VIVLELKGSE TTFMCEYADE TATIVEFLNR WITFCQSIIS TLT (SEQ ID NO:27), where X is any amino acid other than Tyr. In some cases, X is Ala;

APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFC<u>X</u>SIIS TLT (SEQ ID NO:27), where X is any amino acid other than Gln. In some cases, X is Ala;

APTSSSTKKT QLQLE<u>X</u>$_1$LLLD LQMILNGINN YKNPKLTRML T<u>X</u>$_2$KFYMPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where $X_1$ is any amino acid other than His, and where $X_2$ is any amino acid other than Phe. In some cases, $X_1$ is Ala. In some cases, $X_2$ is Ala. In some cases, $X_1$ is Ala; and $X_2$ is Ala;

APTSSSTKKT QLQLEHLLL<u>X</u>$_1$LQMILNGINN YKNPKLTRML T<u>X</u>$_2$KFYMPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where $X_1$ is any amino acid other than Asp; and where $X_2$ is any amino acid other than Phe. In some cases, $X_1$ is Ala. In some cases, $X_2$ is Ala. In some cases, $X_1$ is Ala; and $X_2$ is Ala;

APTSSSTKKT QLQL<u>X</u>$_1$HLLL<u>X</u>$_2$LQMILNGINN YKNPKLTRML T<u>X</u>$_3$KFYMPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where $X_1$ is any amino acid other than Glu; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLE<u>X</u>$_1$LLL<u>X</u>$_2$LQMILNGINN YKNPKLTRML T<u>X</u>$_3$KFYMPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where $X_1$ is any amino acid other than His; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLEHLLL<u>X</u>$_1$LQMILNGINN YKNPKLTRML T<u>X</u>$_2$KFYMPKKA TELKHLQCLE EELKPLEEVL <u>N</u>LAQSKNFHL RPRDLISNIN VIVLELKGSE TTFMCEYADE TATIVEFLNR WITFC<u>X</u>$_3$SIIS TLT (SEQ ID NO:27), where $X_1$ is any amino acid other than Asp; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLEHLLL<u>X</u>$_1$LQMILNGINN YKNPKLTRML T<u>X</u>$_2$KF<u>X</u>$_3$MPKKA TELKHLQCLE EELKPLEEVL <u>N</u>LAQSKNFHL RPRDLISNIN VIVLELKGSE TTFMCEYADE TATIVEFLNR WITFCQSIIS TLT (SEQ ID NO:27), where $X_1$ is any amino acid other than Asp; where $X_2$ is any amino acid other than Phe; and where $X_3$ is any amino acid other than Tyr. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLE<u>X</u>$_1$LLL<u>X</u>$_2$LQMILNGINN YKNPKLTRML T<u>X</u>$_3$KF<u>X</u>$_4$MPKKA TELKHLQCLE

EELKPLEEVL NLAQSKNFHL RPRDLISNIN VIVLELKGSE TTFMCEYADE TATIVEFLNR WITFCQSIIS TLT (SEQ ID NO:27), where X$_1$ is any amino acid other than His; where X$_2$ is any amino acid other than Asp; where X$_3$ is any amino acid other than Phe; and where X$_4$ is any amino acid other than Tyr. In some cases, X$_1$ is Ala. In some cases, X$_2$ is Ala. In some cases, X$_3$ is Ala. In some cases, X$_4$ is Ala. In some cases, X$_1$ is Ala; X$_2$ is Ala; X$_3$ is Ala; and X$_4$ is Ala;

APTSSSTKKT QLQLEHLLL$\overrightarrow{X_1}$ LQMILNGINN YKNPKLTRML T$X_2$KF$\overrightarrow{X_3}$MPKKA TELKHLQCLE EELKPLEEVL NLAQSKNFHL RPRDLISNIN VIVLELKGSE TTFMCEYADE TATIVEFLNR WITFC$\underline{X_4}$SIIS TLT (SEQ ID NO:27), where X$_1$ is any amino acid other than Asp; where X$_2$ is any amino acid other than Phe; where X$_3$ is any amino acid other than Tyr; and where X$_4$ is any amino acid other than Gln. In some cases, X$_1$ is Ala. In some cases, X$_2$ is Ala. In some cases, X$_3$ is Ala. In some cases, X$_4$ is Ala. In some cases, X$_1$ is Ala; X$_2$ is Ala; X$_3$ is Ala; and X$_4$ is Ala;

APTSSSTKKT QLQLE$\underline{X_1}$LLL$\underline{X_2}$ LQMILNGINN YKNPKLTRML T$\underline{X_3}$KF$\underline{X_4}$MPKKA TELKHLQCLE EELKPLEEVL NLAQSKNFHL RPRDLISNIN VIVLELKGSE TTFMCEYADE TATIVEFLNR WITFC$\underline{X_5}$SIIS TLT (SEQ ID NO:27), where X$_1$ is any amino acid other than His; where X$_2$ is any amino acid other than Asp; where X$_3$ is any amino acid other than Phe; where X$_4$ is any amino acid other than Tyr; and where X$_5$ is any amino acid other than Gln. In some cases, X$_1$ is Ala. In some cases, X$_2$ is Ala. In some cases, X$_3$ is Ala. In some cases, X$_4$ is Ala. In some cases, X$_5$ is Ala. In some cases, X$_1$ is Ala; X$_2$ is Ala; X$_3$ is Ala; X$_4$ is Ala; X$_5$ is Ala; and APTSSSTKKT QLQLE$\underline{X_1}$LLLD LQMILNGINN YKNPKLTRML T$\underline{X_2}$KFYMPKKA TELKHLQCLE EELKPLEEVL NLAQSKNFHL RPRDLISNIN VIVLELKGSE TTFMCEYADE TATIVEFLNR WITFC$\underline{X_3}$SIIS TLT (SEQ ID NO:27), where X$_1$ is any amino acid other than His; where X$_2$ is any amino acid other than Phe; and where X$_3$ is any amino acid other than Gln. In some cases, X$_1$ is Ala. In some cases, X$_2$ is Ala. In some cases, X$_3$ is Ala. In some cases, X$_1$ is Ala; X$_2$ is Ala; and X$_3$ is Ala.

In any of the wild-type or variant IL-2 sequences provided herein, the cysteine at position 125 may be substituted with an alanine (a C125A subsititution). In addition to any stability provided by the substitution, it may be employed where, for example, an epitope containing peptide or payload is to be conjugated to a cysteine residue elsewhere in a T-Cell-MMP first or second polypeptide, thereby avoiding competition from the C125 of the IL-2 MOD sequence.

I.H. Additional Polypeptides

A polypeptide chain of a T-Cell-MMP or its epitope conjugate can include one or more polypeptides in addition to those described above. Suitable additional polypeptides include epitope tags and affinity domains. The one or more additional polypeptide(s) can be included as part of a polypeptide translated by cell or cell free system at the N-terminus of a polypeptide chain of a multimeric polypeptide, at the C-terminus of a polypeptide chain of a multimeric polypeptide, or internally within a polypeptide chain of a multimeric polypeptide.

I.I. Epitope Tags

Suitable epitope tags include, but are not limited to, hemagglutinin (HA; e.g., YPYDVPDYA (SEQ ID NO:31)); FLAG (e.g., DYKDDDDK (SEQ ID NO32)); c-myc (e.g., EQKLISEEDL; SEQ ID NO:33)), and the like.

I.J. Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel SEPHAROSE®. Exemplary affinity domains include His5 (HHHHH) (SEQ ID NO34), HisX6 (HHHHHH) (SEQ ID NO:35), C-myc (EQKLISEEDL) (SEQ ID NO33), Flag (DYKDDDDK) (SEQ ID NO:32, StrepTag (WSHPQFEK) (SEQ ID NO:36), hemagglutinin, (e.g., HA Tag (YPYDVPDYA) (SEQ ID NO:31)), glutathione-S-transferase (GST), thioredoxin, cellulose binding domain, RYIRS (SEQ ID NO:37), Phe-His-His-Thr (SEQ ID NO:38), chitin binding domain, S-peptide, T7 peptide, SH2 domain, C-end RNA tag, WEAAAREACCRECCARA (SEQ ID NO:39), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

I.K. Payloads

A broad variety of payloads may be associated with T-Cell-MMPs and T-Cell-MMP-epitope conjugates, which may incorporate more than one type of payload in addition to epitopes conjugated (covalently) to the T-Cell-MMPs at a first or second chemical conjugation site. In addition, where the T-Cell-MMP molecules or their epitope conjugates multimerize, it may be possible to incorporate monomers labeled with different payloads into a multimer. Accordingly, it is possible to introduce one or more payloads selected from the group consisting of: therapeutic agents, chemotherapeutic agents, diagnostic agents, labels and the like. It will be apparent that some payloads may fall into more than one category (e.g., a radio label may be useful as a diagnostic and as a therapeutic for selectively irradiating specific tissue or cell type).

As noted above, T-Cell-MMP polypeptides (e.g., a scaffold or Fc polypeptide) can be modified with crosslinking reagents to conjugate payloads and/or epitopes to chemical conjugation sites attached to or in the first or second polypeptide of the T-Cell-MMPs (e.g., at a chemical conjugation site such as an engineered cysteine or lysine). Such crosslinking agents include succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate. Introducing payloads using an excess of such crosslinking agents can result in multiple molecules of payload being incorporated into the T-Cell-MMP. Some bifunctional linkers for introducing payloads into T-Cell-MMPs and their epitope conjugates include cleavable linkers and non-cleavable linkers. In some cases, the payload linker is a protease-cleavable linker. Suitable payload linkers include, e.g., peptides (e.g., from 2 to 10 amino acids in length; e.g., 2, 3, 4, 5, 6, 7, 8, 9, or 10 amino acids in length), alkyl chains, poly(ethylene glycol), disulfide groups, thioether groups, acid labile groups, photolabile groups, peptidase labile groups, and esterase labile groups. Non-limiting examples of suitable linkers are: N-succinimidyl-[(N-maleimidopropionamido)-tetraethyleneglycol]ester (NHS-PEG4-maleimide); N-succinimidyl 4-(2-pyridyldithio)butanoate (SPDB); disuccinimidyl suberate (DSS); disuccinimidyl glutarate (DGS); dimethyl adipimidate (DMA); N-succinimidyl 4-(2-pyridyldithio)2-sulfobutanoate (sulfo-SPDB); N-succinimidyl 4-(2-pyridyldithio) pentanoate (SPP); N-succinimidyl-4-(N-maleimidomethyl)-cyclohexane-1-carboxy-(6-amidocaproate) (LC-SMCC); κ-maleimidoundecanoic acid N-succinimidyl ester (KMUA); γ-maleimide butyric acid N-succinimidyl ester (GMBS); ε-maleimidocaproic acid N-hydroxysuccinimide ester (EMCS); m-maleimide benzoyl-N-hydroxysuccinimide ester (MBS); N-(α-maleimidoacetoxy)-succinimide ester (AMAS); succinimidyl-6-(β-maleimidopropionamide)hexanoate (SMPH); N-succinimidyl 4-(p-maleimidophenyl)butyrate (SMPB); N-(p-maleimidophenyl)isocyanate (PMPI); N-succinimidyl 4(2-pyridylthio)pentanoate (SPP); N-succinimidyl(4-iodoacetyl)aminobenzoate (SIAB); 6-maleimidocaproyl (MC); maleimidopropanoyl (MP); p-aminobenzyloxycarbonyl (PAB); N-succinimidyl 4-(maleimidomethyl)cyclohexanecarboxylate (SMCC); succinimidyl 3-(2-pyridyldithio)propionate (SPDP); PEG4-SPDP (PEGylated, long-chain SPDP crosslinker); $BS(PEG)_5$ (PEGylated bis(sulfosuccinimidyl) suberate); $BS(PEG)_9$ (PEGylated bis(sulfosuccinimidyl) suberate); maleimide-$PEG_6$-succinimidyl ester; maleimide-$PEG_8$-succinimidyl ester; maleimide-$PEG_{12}$-succinimidyl ester; PEG4-SPDP (PEGylated, long-chain SPDP crosslinker); $PEG_{12}$-SPDP (PEGylated, long-chain SPDP crosslinker); N-succinimidyl-4-(N-maleimidomethyl)-cyclohexane-1-carboxy-(6-amidocaproate), a "long chain" analog of SMCC (LC-SMCC); 3-maleimidopropanoic acid N-succinimidyl ester (BMPS); N-succinimidyl iodoacetate (SIA); N-succinimidyl bromoacetate (SBA); and N-succinimidyl 3-(bromoacetamido)propionate (SBAP).

Control of the stoichiometry of the reaction may result in some selective modification where engineered sites with chemistry orthogonal to all other groups in the molecule is not utilized. Reagents that display far more selectivity, such as the bis-thio linkers discussed above, tend to permit more precise control of the location and stoichiometry than reagents that react with single lysine, or cysteine residues.

Where a T-Cell-MMP of the present disclosure comprises a Fc polypeptide, the Fc polypeptide can comprise one or more covalently attached molecules of payload that are attached directly or indirectly through a linker. By way of example, where a T-Cell-MMP of the present disclosure comprises a Fc polypeptide, the polypeptide chain comprising the Fc polypeptide can be of the formula (A)-(L)-(C), where (A) is the polypeptide chain comprising the Fc polypeptide; where (L), if present, is a linker; and where (C) is a payload (e.g., a cytotoxic agent). (L), if present, links (A) to (C). In some cases, the polypeptide chain comprising the Fc polypeptide can comprise more than one molecule of payload (e.g., 2, 3, 4, 5, or more than 5 cytotoxic agent molecules).

In an embodiment, the payload is selected from the group consisting of: biologically active agents or drugs, diagnostic agents or labels, nucleotide or nucleoside analogs, nucleic acids or synthetic nucleic acids (e.g., antisense nucleic acids, small interfering RNA, double stranded (ds)DNA, single stranded (ss)DNA, ssRNA, dsRNA), toxins, liposomes (e.g., incorporating a chemotherapeutic such as 5-fluorodeoxyuridine), nanoparticles (e.g., gold or other metal bearing nucleic acids or other molecules, lipids, particle bearing nucleic acids or other molecules), and combinations thereof.

In an embodiment, the payload is selected from biologically active agents or drugs selected independently from the group consisting of: therapeutic agents (e.g., drugs or prodrugs), chemotherapeutic agents, cytotoxic agents, antibiotics, antivirals, cell cycle synchronizing agents, ligands for cell surface receptor(s), immunomodulatory agents (e g, immunosuppressants such as cyclosporine), pro-apoptotic agents, anti-angiogenic agents, cytokines, chemokines, growth factors, proteins or polypeptides, antibodies or antigen binding fragments thereof, enzymes, proenzymes, hormones and combinations thereof.

In an embodiment, the payload is selected from biologically active agents or drugs selected independently from therapeutic diagnostic agents or labels, selected independently from the group consisting of photodetectable labels (e.g., dyes, fluorescent labels, phosphorescent labels, luminescent labels), contrast agents (e.g., iodine or barium containing materials), radiolabels, imaging agents, paramagnetic labels/imaging agents (gadolinium containing magnetic resonance imaging labels), ultrasound labels and combinations thereof.

I.L. Therapeutic Agents and Chemotherapeutic Agents

A polypeptide chain of a T-Cell-MMP can comprise a payload, including, but not limited, to small molecule drug linked (e.g., covalently attached) to the first or second polypeptide chain at chemical conjugation sites. The linkage between a payload and a first or second polypeptide chain of a T-Cell-MMP or its epitope conjugate may be a direct or indirect linkage. Direct linkage can involve linkage directly to an amino acid side chain. Indirect linkage can be linkage via a linker. A drug (e.g., a payload such as a cancer chemotherapeutic agent) can be linked to a polypeptide chain (e.g., a Fc polypeptide) of a T-Cell-MMP of the present disclosure via a thioether bond, an amide bond, a carbamate bond, a disulfide bond, or an ether bond.

Suitable therapeutic agents include, e.g., rapamycin, retinoids, such as all-trans retinoic acid (ATRA); vitamin D3; vitamin D3 analogs; and the like. As noted above, in some cases, a drug is a cytotoxic agent. Cytotoxic agents are known in the art. A suitable cytotoxic agent can be any compound that results in the death of a cell, or induces cell death, or in some manner decreases cell viability, and includes, for example, maytansinoids and maytansinoid analogs, benzodiazepines, taxoids, CC-1065 and CC-1065 analogs, duocarmycins and duocarmycin analogs, enediynes, such as calicheamicins, dolastatins and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin.

For example, in some cases, the cytotoxic agent is a compound that inhibits microtubule formation in eukaryotic cells. Such agents include, e.g., maytansinoid, benzodiazepine, taxoid, CC-1065, duocarmycin, a duocarmycin analog, calicheamicin, dolastatin, a dolastatin analog, auristatin, tomaymycin, and leptomycin, or a pro-drug of any one of the foregoing. Maytansinoid compounds include, e.g., N(2')-deacetyl-N(2')-(3-mercapto-1-oxopropyl)-maytansine (DM1); N(2')-deacetyl-N(2')-(4-mercapto-1-oxopentyl)-maytansine (DM3); and N(2)-deacetyl-N2-(4-mercapto-4-methyl-1-oxopentyl)-maytansine (DM4). Benzodiazepines include, e.g., indolinobenzodiazepines and oxazolidinobenzodiazepines.

Cytotoxic agents include taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; maytansine or an analog or derivative thereof; an auristatin or a functional peptide analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; 6 mercaptopurine; 6 thioguanine; cytarabine; fludarabin; 5 fluorouracil; decarbazine; hydroxyurea; asparaginase; gemcitabine; cladribine; an alkylating agent; a platinum derivative; duocarmycin A; duocarmycin SA; rachelmycin (CC-1065) or an analog or derivative thereof; an antibiotic; pyrrolo[2,1-c][1,4]-benzodiazepines (PDB); diphtheria toxin; ricin toxin; cholera toxin; a Shiga-like toxin; LT toxin; C3 toxin; Shiga toxin; pertussis toxin; tetanus toxin; soybean Bowman-Birk protease inhibitor; *Pseudomonas* exotoxin; alorin; saporin; modeccin; gelanin; abrin A chain; modeccin A chain; alpha-sarcin; *Aleurites fordii* proteins; dianthin proteins; *Phytolacca americana* proteins; *Momordica charantia* inhibitor; curcin; crotin; *Sapaonaria officinalis* inhibitor; gelonin; mitogellin; restrictocin; phenomycin; enomycin toxins; ribonuclease (RNase); DNase I; Staphylococcal enterotoxin A; pokeweed antiviral protein; diphtherin toxin; and *Pseudomonas* endotoxin.

I.M. Diagnostic Agents and Labels

The first and/or second polypeptide chains of a T-Cell-MMP can comprise one or more molecules of payload of photodetectable labels (e.g., dyes, fluorescent labels, phosphorescent labels, luminescent labels), contrast agents (e.g., iodine or barium containing materials), radiolabels, imaging agents, spin labels, Forster Resonance Energy Transfer (FRET)-type labels, paramagnetic labels/imaging agents (e.g., gadolinium containing magnetic resonance imaging labels), ultrasound labels and combinations thereof.

In some embodiments, the conjugate moiety comprises a label that is or includes a radioisotope. Examples of radioisotopes or other labels include, but are not limited to, $^3$H, $^{11}$C, $^{14}$C, $^{15}$N, $^{35}$S, $^{18}$F, $^{32}$P, $^{33}$P, $^{64}$Cu, $^{68}$Ga, $^{89}$Zr, $^{90}$Y, $^{99}$Tc, $^{123}$I, $^{124}$I, $^{125}$I, $^{131}$I, $^{111}$In, $^{131}$In, $^{153}$Sm, $^{186}$Re, $^{188}$Re, $^{211}$At, $^{212}$Bi, and $^{153}$Pb.

II. Methods of Generating T-Cell-MMP Polypeptides

The present disclosure provides a method of obtaining T-Cell-MMPs and T-Cell-MMP-epitope conjugates, including those comprising one or more variant MODs that exhibit lower affinity for a Co-MOD compared to the affinity of the corresponding parental wild-type MOD for the Co-MOD, the method comprising:

A) generating a T-Cell-MMP by introducing nucleic acids encoding a first and a second polypeptide of the T-Cell-MMP in cells or cell free systems, wherein each member comprises:
   a) a first polypeptide comprising: i) a first MHC Class I polypeptide (e.g., a β2M polypeptide); and
   b) a second polypeptide comprising: i) a second MHC polypeptide (e.g., a MHC Class I heavy chain polypeptide); and ii) optionally an Ig Fc polypeptide or a non-Ig scaffold,
   wherein the first polypeptide comprises a first chemical conjugation site and/or the second polypeptides comprise a second chemical conjugation site, and at least one of the first polypeptide or second polypeptide comprises one or more independently selected MODs (e.g., 1, 2, 3 or more wild-type and/or variant MODs); and
B) contacting the first polypeptide and second polypeptide (if co-expressed in the same cell or cell-free system the polypeptides may come into contact as they are translated) to form a T-Cell-MMP;
   wherein when the T-Cell-MMP comprises one or more nascent (e.g., unactivated) chemical conjugation sites, the nascent chemical conjugation site may be optionally activated to produce a T-Cell-MMP with the first and/or second chemical conjugation site (e.g., reacting sulfatase motifs with a formyl glycine generating enzyme if the cells expressing the T-Cell-MMP do not express a formylglycine generating enzyme).

The method may be stopped at this point and the T-Cell-MMP obtained by purification; alternatively, where a T-Cell-MMP epitope conjugate is desired the method may be continued with the following step:

C) providing an epitope (e.g., an epitope peptide) suitable for conjugation with the first and/or second chemical conjugation site (e.g., a hydrazinyl or hydrazinyl indole modified peptide for reaction with a formyl glycine of a sulfatase motif) and contacting the epitope with the T-Cell-MMP (e.g., under suitable reaction conditions) to produce a T-Cell-MMP epitope conjugate.

Where it is desirable for a T-Cell-MMP to contain a payload (e.g., a small molecule drug, radio label, etc.), the payload may be reacted with the T-Cell-MMP in place of the epitope conjugate as described above. Where it is desirable for a T-Cell-MMP epitope conjugate to contain a payload, the payload may be reacted with the chemical conjugation site(s) either before or after the epitope is contacted and reacted with its chemical reaction site(s). The selectivity of the epitope and the payload for different conjugation sites (e.g., first and second chemical conjugation sites) may be controlled through the use of orthogonal chemistries and/or control of stoichiometry in the conjugation reactions. In embodiments, linkers (e.g., polypeptides or other bifunctional chemical linkers) may be used to attach the epitope and/or payloads to their conjugation sites.

The present disclosure provides a method of obtaining a T-Cell-MMP epitope conjugate comprising one or more variant MODs that exhibit lower affinity for a Co-MOD compared to the affinity of the corresponding parental wild-type MOD for the Co-MOD, the method comprising:

A) generating a library of T-Cell-MMP epitope conjugates comprising a plurality of members, wherein each member comprises: a) a first polypeptide comprising: i) an epitope; and ii) a first MHC polypeptide (e.g., a β2M polypeptide); and b) a second polypeptide comprising: i) a second MHC polypeptide (e.g., a MHC Class I heavy chain polypeptide); and ii) optionally an Ig Fc polypeptide or a non-Ig scaffold, wherein each member comprises a different variant MOD on the first polypeptide, the second polypeptide, or both the first and the second polypeptide;

B) determining the affinity of each member of the library for a Co-MOD; and

C) selecting a library member that exhibits reduced affinity for the Co-MOD.

In some cases, the affinity is determined by BLI using purified T-Cell-MMP library members and the Co-MOD. BLI methods are well known to those skilled in the art. A BLI assay is described above. See, e.g., Lad et al. (2015) *J. Biomol. Screen.* 20(4): 498-507; and Shah and Duncan (2014) *J. Vis. Exp.* 18:e51383.

The present disclosure provides a method of obtaining a T-Cell-MMP-epitope conjugate that exhibits selective binding to a T-cell, the method comprising:
  A) generating a library of T-Cell-MMP-epitope conjugates comprising a plurality of members, wherein each member comprises:
    a) a first polypeptide comprising: i) a first MHC polypeptide; and
    b) a second polypeptide comprising: i) a second MHC polypeptide; and ii) optionally an immunoglobulin (Ig) Fc polypeptide or a non-Ig scaffold,
    wherein each member comprises a different variant MOD on the first polypeptide, the second polypeptide, or both the first and the second polypeptide, wherein the variant MOD differs in amino acid sequence by from 1 aa to 10 aa from a parental wild-type MOD, wherein the T-Cell-MMP-epitope conjugate library members further comprise an epitope tag or a fluorescent label), and
    wherein one of the first or second polypeptides comprises an epitope covalently bound through a chemical conjugation site, either directly or indirectly through a linker, to the first and/or second polypeptide;
  B) contacting a T-Cell-MMP-epitope conjugate library member with a target T-cell expressing on its surface with: i) a Co-MOD that binds the parental wild-type MOD; and ii) a TCR that binds to the epitope;
  C) when the T-Cell-MMP epitope conjugate comprises an epitope tag, contacting the T-Cell-MMP epitope conjugate library member bound to the target T-cell with a fluorescently labeled binding agent that binds to the epitope tag (which is unnecessary with a fluorescently labeled T-Cell-MMP epitope conjugate), generating a library member/target T-cell/binding agent complex;
D) measuring the mean fluorescence intensity (MFI) of the T-Cell-MMP-epitope conjugate library member/target T-cell/binding agent complex using flow cytometry, wherein the MFI measured over a range of concentrations of the T-Cell-MMP-epitope conjugate library member provides a measure of the affinity and apparent avidity; and
E) selecting a T-Cell-MMP-epitope conjugate library member that selectively binds the target T-cell, compared to binding of the T-Cell-MMP-epitope conjugate library member to a control T-cell that comprises: i) the Co-MOD that binds the parental wild-type MOD; and ii) a TCR that binds to an epitope other than the epitope present in the T-Cell-MMP library member.

In some cases, a T-Cell-MMP library member that is identified as selectively binding to a target T-cell is isolated from the library. In some cases, parental wild-type MOD and Co-MOD pairs are selected from: IL-2 and IL-2 receptor; 4-1BBL and 4-1BB; PD-L1 and PD-1; FasL and Fas; TGFβ and TGFβ receptor; CD80 and CD28; CD86 and CD28; OX40L and OX40; ICOS-L and ICOS; ICAM and LFA-1; JAG1 and Notch; JAG1 and CD46; CD70 and CD27; CD80 and CTLA4; and CD86 and CTLA4.

The present disclosure provides a method of obtaining a T-Cell-MMP-epitope conjugate comprising one or more variant MODs that exhibit reduced affinity for a Co-MOD compared to the affinity of the corresponding parental wild-type MOD for the Co-MOD, the method comprising selecting, from a library of T-Cell-MMP-epitope conjugates comprising a plurality of members, a member that exhibits reduced affinity for the Co-MOD, wherein each of the plurality of members comprises: a) a first polypeptide comprising: i) an epitope covalently bound to a chemical conjugation site; and ii) a first MHC polypeptide; and b) a second polypeptide comprising: i) a second MHC polypeptide; and ii) optionally an Ig Fc polypeptide or a non-Ig scaffold, wherein the members of the library comprise a plurality of variant MODs present in the first polypeptide, the second polypeptide, or both the first and the second polypeptide. In some cases, the selecting step comprises determining the affinity, using BLI, of binding between T-Cell-MMP-epitope conjugate library members and the Co-MOD. In some cases, the T-Cell-MMP-epitope conjugate is as described above.

In some cases, the method of obtaining T-Cell-MMP-epitope conjugates comprising one or more variant MODs that exhibit reduced affinity for a Co-MOD compared to the affinity of the corresponding parental wild-type MODs for the Co-MOD further comprises: a) contacting the selected T-Cell-MMP-epitope conjugate library member with a target T-cell expressing on its surface: i) a Co-MOD that binds the parental wild-type MOD; and ii) a TCR that binds to the epitope, wherein the T-Cell-MMP-epitope conjugate library member comprises an epitope tag, such that the T-Cell-MMP-epitope conjugate library member binds to the target T-cell; b) contacting the selected T-Cell-MMP-epitope conjugate library member bound to the target T-cell with a fluorescently labeled binding agent that binds to the epitope tag, generating a selected T-Cell-MMP-epitope conjugate library member/target T-cell/binding agent complex; and c) measuring the MFI of the selected T-Cell-MMP-epitope conjugate library member/target T-cell/binding agent complex using flow cytometry, wherein the MFI measured over a range of concentrations of the selected T-Cell-MMP-epitope conjugate library member provides a measure of the affinity and apparent avidity. A selected T-Cell-MMP-epitope conjugate library member that selectively binds the target T-cell, compared to binding of the T-Cell-MMP-epitope conjugate library member to a control T-cell that comprises: i) the Co-MOD that binds the parental wild-type MOD; and ii) a TCR that binds to an epitope other than the epitope present in the T-Cell-MMP-epitope conjugate library member, is identified as selectively binding to the target T-cell. In some cases, the binding agent is an antibody specific for the epitope tag. In some cases, the variant MOD comprises from 1 to 20 amino acid substitutions (e.g., 1, 2, 3, 4, 5, 6, 7, 8, 9, 10, 11, 12, 13, 14, 15, 16, 17, 18, 19, or 20 amino acid substitutions) compared to the corresponding parental wild-type MOD. In some cases, the T-Cell-MMP-epitope conjugate comprises two variant MODs. In some cases, the two variant MODs comprise the same amino acid sequence. In some cases, the first polypeptide comprises one of the two variant MODs and the second polypeptide comprises the second of the two variant MODs. In some cases, the two variant MODs are on the same polypeptide chain of the T-Cell-MMP-epitope conjugate. In some cases, the two variant MODs are on the first polypeptide of the T-Cell-MMP-epitope conjugate. In some cases, the two variant MODs are on the second polypeptide of the T-Cell-MMP-epitope conjugate.

In some cases, the method of obtaining a T-Cell-MMP-epitope conjugate comprising one or more variant MODs that exhibit reduced affinity for a Co-MOD compared to the affinity of the corresponding parental wild-type MOD for the Co-MOD further comprises isolating the selected T-Cell-MMP-epitope conjugate library member from the library. In some cases, the method further comprises providing a nucleic acid comprising a nucleotide sequence encoding a T-Cell-MMP with at least one chemical conjugation site used to prepare the selected library member. In some cases, the nucleic acid is present in a recombinant expression vector. In some cases, the nucleotide sequence is operably linked to a transcriptional control element that is functional in a eukaryotic cell. In some cases, the method further comprises introducing the nucleic acid into a eukaryotic host cell, and culturing the cell in a liquid medium to synthesize the encoded T-Cell-MMP with at least one chemical conjugation site in the cell, isolating the synthesized T-Cell-MMP with at least one chemical conjugation site from the cell or from liquid culture medium, and conjugating it to at least one epitope to form the selected T-Cell-MMP-epitope conjugate. In some cases, the selected T-Cell-MMP with at least one chemical conjugation site comprises an Ig Fc polypeptide. In some cases, the method further comprises conjugating a drug to the Ig Fc polypeptide. In some cases, the drug is a cytotoxic agent that is selected from maytansinoid, benzodiazepine, taxoid, CC-1065, duocarmycin, a duocarmycin analog, calicheamicin, dolastatin, a dolastatin analog, auristatin, tomaymycin, and leptomycin, or a pro-drug of any one of the foregoing. In some cases, the drug is a retinoid. In some cases, the parental wild-type MOD and the Co-MODs are selected from: IL-2 and IL-2 receptor; 4-1BBL and 4-1BB; PD-L1 and PD-1; FasL and Fas; TGFβ and TGFβ receptor; CD70 and CD27; CD80 and CD28; CD86 and CD28; OX40L and OX40; FasL and Fas; ICOS-L and ICOS; ICAM and LFA-1; and JAG1 and Notch; JAG1 and CD46; CD80 and CTLA4; and CD86 and CTLA4.

The present disclosure provides a method of obtaining a T-Cell-MMP-epitope conjugate comprising one or more variant MODs that exhibit reduced affinity for a Co-MOD compared to the affinity of the corresponding parental wild-type MOD for the Co-MOD, the method comprising: A) providing a library of T-Cell-MMP-epitope conjugates comprising a plurality of members, wherein the plurality of member comprises: a) a first polypeptide comprising: i) an epitope covalently bound at a chemical conjugation site; and ii) a first MHC polypeptide; and b) a second polypeptide comprising: i) a second MHC polypeptide; and ii) optionally an Ig Fc polypeptide or a non-Ig scaffold, wherein the members of the library comprise a plurality of variant MODs present in the first polypeptide, the second polypeptide, or both the first and the second polypeptide; and B) selecting from the library a member that exhibits reduced affinity for the Co-MOD. In some cases, the selecting step comprises determining the affinity, using BLI, of binding between T-Cell-MMP-epitope conjugate library members and the Co-MOD. In some cases, the selecting step comprises determining the affinity, using BLI, of binding between T-Cell-MMP-epitope conjugate library members and the Co-MOD. In some cases, the T-Cell-MMP-epitope conjugate is as described above.

In some cases, the method further comprises: a) contacting the selected T-Cell-MMP-epitope conjugate library member with a target T-cell expressing on its surface: i) a Co-MOD that binds the parental wild-type MOD; and ii) a T-cell receptor that binds to the epitope, wherein the T-Cell-MMP-epitope conjugate library member comprises an epitope tag, such that the T-Cell-MMP-epitope conjugate library member binds to the target T-cell; b) contacting the selected T-Cell-MMP-epitope conjugate library member bound to the target T-cell with a fluorescently labeled binding agent that binds to the epitope tag, generating a selected T-Cell-MMP-epitope conjugate library member/target T-cell/binding agent complex; and c) measuring the MFI of the selected T-Cell-MMP-epitope conjugate library member/target T-cell/binding agent complex using flow cytometry, wherein the MFI measured over a range of concentrations of the selected T-Cell-MMP-epitope conjugate library member provides a measure of the affinity and apparent avidity. A selected T-Cell-MMP-epitope conjugate library member that selectively binds the target T-cell, compared to binding of the T-Cell-MMP-epitope conjugate library member to a control T-cell that comprises: i) the Co-MOD that binds the parental wild-type MOD; and ii) a T-cell receptor that binds to an epitope other than the epitope present in the T-Cell-MMP-epitope conjugate library member, is identified as selectively binding to the target T-cell. In some cases, the binding agent is an antibody specific for the epitope tag. In some cases, the variant MOD comprises from 1 to 20 amino acid substitutions (e.g., 1, 2, 3, 4, 5, 6, 7, 8, 9, 10, 11, 12, 13, 14, 15, 16, 17, 18, 19 or 20 amino acid substitutions) compared to the corresponding parental wild-type MOD. In some cases, the T-Cell-MMP-epitope conjugate comprises two variant MODs. In some cases, the two variant MODs comprise the same amino acid sequence. In some cases, the first polypeptide comprises one of the two variant MODs and the second polypeptide comprises the second of the two variant MODs. In some cases, the two variant MODs are on the same polypeptide chain of the T-Cell-MMP-epitope conjugate. In some cases, the two variant MODs are on the first polypeptide of the T-Cell-MMP-epitope conjugate. In some cases, the two variant MODs are on the second polypeptide of the T-Cell-MMP-epitope conjugate.

In some cases, the method further comprises isolating the selected T-Cell-MMP-epitope conjugate library member from the library. In some cases, the method further comprises providing a nucleic acid comprising a nucleotide sequence encoding a T-Cell-MMP with at least one chemical conjugation site used to prepare the selected library member. In some cases, the nucleic acid is present in a recombinant expression vector. In some cases, the nucleotide sequence is operably linked to a transcriptional control element that is functional in a eukaryotic cell. In some cases, the method further comprises introducing the nucleic acid into a eukaryotic host cell, and culturing the cell in a liquid medium to synthesize the encoded T-Cell-MMP with at least one chemical conjugation site in the cell, isolating the synthesized selected T-Cell-MMP with at least one chemical conjugation site from the cell or from liquid culture medium, and conjugating it to at least one epitope to form the selected T-Cell-MMP-epitope conjugate. In some cases, the selected T-Cell-MMP library member comprises an Ig Fc polypeptide. In some cases, the method further comprises conjugating a drug to the Ig Fc polypeptide. In some cases, the drug is a cytotoxic agent selected from maytansinoid, benzodiazepine, taxoid, CC-1065, duocarmycin, a duocarmycin analog, calicheamicin, dolastatin, a dolastatin analog, auristatin, tomaymycin, and leptomycin, or a pro-drug of any one of the foregoing. In some cases, the drug is a retinoid. In some cases, the parental wild-type MODs and the cognate MODs are selected from: IL-2 and IL-2 receptor; 4-1BBL and 4-1BB; PD-L1 and PD-1; FasL and Fas; TGFβ and TGFβ receptor; CD70 and CD27; CD80 and CD28; CD86 and CD28; OX40L and OX40; FasL and Fas; ICOS-L and ICOS; ICAM and LFA-1; and JAG1 and Notch; JAG1 and CD46; CD80 and CTLA4; and CD86 and CTLA4.

III. Nucleic Acids

The present disclosure provides a nucleic acid comprising a nucleotide sequence encoding a T-Cell-MMP of the present disclosure. The present disclosure provides a nucleic acid comprising a nucleotide sequence encoding a T-Cell-MMP of the present disclosure including chemical conjugation sites that are engineered into the polypeptides of the T-Cell-MMP.

The present disclosure provides nucleic acids comprising nucleotide sequences encoding the T-Cell-MMPs described herein. In some cases, the individual polypeptide chains of a T-Cell-MMP of the present disclosure are encoded in separate nucleic acids. In some cases, all polypeptide chains of a T-Cell-MMP of the present disclosure are encoded in a single nucleic acid. In some cases, a first nucleic acid comprises a nucleotide sequence encoding a first polypeptide of a T-Cell-MMP of the present disclosure; and a second nucleic acid comprises a nucleotide sequence encoding a second polypeptide of a T-Cell-MMP of the present disclosure. In some cases, a single nucleic acid comprises a nucleotide sequence encoding a first polypeptide of a T-Cell-MMP of the present disclosure and a second polypeptide of a T-Cell-MMP of the present disclosure.

III.A. Separate Nucleic Acids Encoding Individual Polypeptide Chains of a Multimeric Polypeptide The present disclosure provides nucleic acids comprising nucleotide sequences encoding a T-Cell-MMP. As noted above, in some cases, the individual polypeptide chains of a T-Cell-MMP are encoded in separate nucleic acids. In some cases, nucleotide sequences encoding the separate polypeptide chains of a T-Cell-MMP are operably linked to transcriptional control elements, e.g., promoters, such as promoters that are functional in a eukaryotic cell, where the promoter can be a constitutive promoter or an inducible promoter.

The present disclosure provides a first nucleic acid and a second nucleic acid, where the first nucleic acid comprises a nucleotide sequence encoding a first polypeptide of a T-Cell-MMP of the present disclosure, where the first polypeptide comprises, in order from N-terminus to C-terminus: a) a first MHC polypeptide; and b) a MOD (e.g., a reduced-affinity variant MOD polypeptide as described above); and where the second nucleic acid comprises a nucleotide sequence encoding a second polypeptide of a T-Cell-MMP, where the second polypeptide comprises, in order from N-terminus to C-terminus: a) a second MHC polypeptide; and b) an Ig Fc polypeptide. Suitable epitopes, MHC polypeptides, MODs, and Ig Fc polypeptides are described above. At least one of the first and second polypeptides comprises a chemical conjugation site (or a nascent site that can be converted to a chemical conjugation site). In some cases, the nucleotide sequences encoding the first and second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a T-Cell-MMP, where the first polypeptide comprises a first MHC polypeptide; and where the second nucleic acid comprises a nucleotide sequence encoding a second polypeptide of a T-Cell-MMP, where the second polypeptide comprises, in order from N-terminus to C-terminus: a) a MOD (e.g., a reduced-affinity variant MOD polypeptide as described above); b) a second MHC polypeptide; and c) an Ig Fc polypeptide. Suitable MHC polypeptides, MODs, and Ig Fc polypeptides are described above. At least one of the first and second polypeptides comprises a chemical conjugation site. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

III.B. Nucleic Acid Encoding Two or More Polypeptides Present in a T-Cell-MMP

The present disclosure provides a nucleic acid comprising nucleotide sequences encoding at least the first polypeptide and the second polypeptide of a T-Cell-MMP. In some cases, where a T-Cell-MMP of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a T-Cell-MMP include a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a T-Cell-MMP include an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a T-Cell-MMP include a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a T-Cell-MMP; in any of these embodiments, an IRES or a ribosome skipping signal can be used in place of the nucleotide sequence encoding the proteolytically cleavable linker.

In some cases provided for herein, a first nucleic acid (e.g., a recombinant expression vector, an mRNA, a viral RNA, etc.) comprises a nucleotide sequence encoding a first polypeptide chain of a T-Cell-MMP; and a second nucleic acid (e.g., a recombinant expression vector, an mRNA, a viral RNA, etc.) comprises a nucleotide sequence encoding a second polypeptide chain of a T-Cell-MMP. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus the elements: a) a first MHC polypeptide; b) a MOD (e.g., a reduced-affinity variant as described above); c) a proteolytically cleavable linker; d) a second MHC polypeptide; and e) an immunoglobulin (Ig) Fc polypeptide; wherein at least one of the elements comprises a chemical conjugation site that is not removed during cellular processing. The present disclosure provides a nucleic acid comprising a nucleotide sequence encoding a recombinant polypeptide, where the recombinant polypeptide comprises, in order from N-terminus to C-terminus the elements: a) a first leader peptide; b) a first MHC polypeptide; c) a MOD (e.g., a reduced-affinity variant as described above); d) a proteolytically cleavable linker; e) a second leader peptide; f) a second MHC polypeptide; and g) an Ig Fc polypeptide; wherein at least one of the elements comprises a chemical conjugation site that is not removed during cellular processing. The present disclosure provides a nucleic acid comprising a nucleotide sequence encoding a recombinant polypeptide, where the recombinant polypeptide comprises, in order from N-terminus to C-terminus, the elements: a) a first MHC polypeptide; b) a proteolytically cleavable linker; c) a MOD (e.g., a reduced-affinity variant as described above); d) a second MHC polypeptide; and e) an Ig Fc polypeptide; wherein at least one of the elements comprises a chemical conjugation site that is not removed during cellular processing. In some cases, the first leader peptide and the second leader peptide are β2M leader peptides. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and the second MHC polypeptide is a MHC Class I heavy chain polypeptide. In some cases, the β2-microglobulin polypeptide comprises an amino acid sequence having at least about 85% (e.g., at lease about 90%, 95%, 98%, 99%, or even 100%) amino acid sequence identity to a β2M amino acid sequence depicted in FIG. 4. In some cases, the MHC Class I heavy chain polypeptide is a HLA-A, HLA-B, HLA-C, HLA-E, HLA-F, HLA-G, HLA-K, or HLA-L heavy chain. In some cases, the MHC Class I heavy chain polypeptide comprises an amino acid sequence having at least 85% amino acid sequence identity to the amino acid sequence depicted in any one of FIGS. 3A-3D. In such an embodiment the MHC Class I heavy chain polypeptide may not comprise a transmembrane anchoring domain (e.g., the heavy chain polypeptide comprises a sequence in FIG. 3D).

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85% amino acid sequence identity to an amino acid sequence depicted in FIGS. 2A-2G.

Suitable immunomodulatory polypeptides (MODs) are described above.

In addition to any other proteolytically cleavable linkers, in some cases, the proteolytically cleavable linker comprises an amino acid sequence selected from the roup consisting of: a) LEVLFQGP (SEQ ID NO40); b) ENLYTQS (SEQ ID NO41); c) DDDDK (SEQ ID NO:42); d) LVPR (SEQ ID NO:43); and e) GSGATNFSLLKQAGDVEENPGP (SEQ ID NO:44).

In some cases, a linker comprising a first Cys residue attached to the first MHC polypeptide is provided, and the second MHC polypeptide comprises an amino acid substitution to provide a second (engineered) Cys residue, such that the first and second Cys residues provide for a disulfide linkage between the linker and the second MHC polypeptide. In some cases, the first MHC polypeptide comprises an amino acid substitution to provide a first engineered Cys residue, and the second MHC polypeptide comprises an amino acid substitution to provide a second engineered Cys residue, such that the first Cys residue and the second Cys residue provide for a disulfide linkage between the first MHC polypeptide and the second MHC polypeptide. As discussed above, where disulfide bridges are provided, it is possible to use either thiol reactive agents or bis-thiol linkers to incorporate payloads or epitopes.

III.C. Recombinant Expression Vectors

The present disclosure provides recombinant expression vectors comprising nucleic acids of the present disclosure. In some cases, the recombinant expression vector is a non-viral vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc., may be used in the expression vector (see, e.g., Bitter et al. (1987), Methods in Enzymology, 153:516-544).

In some embodiments, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art.

The expression vector may also contain a ribosome binding site for translation initiation and a transcription terminator. The expression vector may also include appropriate sequences for amplifying expression.

IV. Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2™), CHO cells (e.g., ATCC Nos. CRL-9618™, CCL-61™, CRL9096), 293 cells (e.g., ATCC No. CRL-1573™), Vero cells, NIH 3T3 cells (e.g., ATCC No. CRL-1658), Huh-7 cells, BHK cells (e.g., ATCC No. CCL-10™), PC12 cells (ATCC No. CRL-1721™), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC β2M and/or such that it does not synthesize endogenous MHC Class I heavy chains (MHC-H). In addition to the foregoing, host cells expressing formylglycine generating enzyme (FGE) activity are discussed above for use with T-Cell-MMPs comprising a sulfatase motif, and such cells may advantageously be modified such that they do not express at least one, if not both, of the endogenous MHC β2M and MHC-H proteins.

V. Compositions

The present disclosure provides compositions, including pharmaceutical compositions, comprising one or more T-Cell-MMPs and/or T-Cell-MMP-epitope conjugates. The present disclosure provides compositions, including pharmaceutical compositions, comprising a nucleic acid or a recombinant expression vector of the present disclosure.

V.A. Compositions Comprising T-Cell-MMPs

A composition of the present disclosure can comprise, in addition to a T-Cell-MMP of the present disclosure, one or more of: a salt, e.g., NaCl, $MgCl_2$, KCl, $MgSO_4$, etc.; a buffering agent, e.g., a Tris buffer, N-(2-Hydroxyethyl) piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications including, for example, "Remington: The Science and Practice of Pharmacy", $19^{th}$ Ed. (1995), or latest edition, Mack Publishing Co; A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a T-Cell-MMP of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include (e.g., be in the form of) aqueous solutions, powders, granules, tablets, pills, suppositories, capsules, suspensions, sprays, and the like. The composition may be formulated according to the various routes of administration described below.

Where a T-Cell-MMP of the present disclosure is administered as an injectable (e.g., subcutaneously, intraperitoneally, intramuscularly, and/or intravenously) directly into a tissue, a formulation can be provided as a ready-to-use dosage form, a non-aqueous form (e.g., a reconstitutable storage-stable powder) or an aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a T-Cell-MMP and/or T-Cell-MMP-epitope conjugate in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

The present disclosure provides compositions, including pharmaceutical compositions, comprising a T-Cell-MMP or its epitope conjugate. A composition can comprise: a) a T-Cell-MMP and/or a T-Cell-MMP-epitope conjugate; and b) an excipient, as described above for the T-Cell-MMPs and their epitope conjugates. In some cases, the excipient is a pharmaceutically acceptable excipient.

In some cases, a T-Cell-MMP and/or T-Cell-MMP-epitope conjugate is present in a liquid composition. Thus, the present disclosure provides compositions (e.g., liquid compositions, including pharmaceutical compositions) comprising a T-Cell-MMP and/or T-Cell-MMP-epitope conjugate of the present disclosure. In some cases, a composition of the present disclosure comprises: a) a T-Cell-MMP and/or T-Cell-MMP-epitope conjugate of the present disclosure; and b) saline (e.g., 0.9% or about 0.9% NaCl). In some cases, the composition is sterile. In some cases, the composition is suitable for administration to a human subject, e.g., where the composition is sterile and is free of detectable pyrogens and/or other toxins. Thus, the present disclosure provides a composition comprising: a) a T-Cell-MMP and/or T-Cell-MMP-epitope conjugate; and b) saline (e.g., 0.9% or about 0.9% NaCl), where the composition is sterile and is free of detectable pyrogens and/or other toxins.

VI. Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) one or more nucleic acids or one or more recombinant expression vectors comprising nucleotide sequences encoding a T-Cell-MMP; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (for example) N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethane-sulfonic acid (TES), N-tris(hydroxymethyl)methyl-glycine (Tricine), tris(hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some embodiments, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in one or more spherical bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers, surfactants and chelators. Suitable surfactants include, but are not limited to, fatty acids and/or esters or salts thereof, bile acids, and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

VII Methods of Modulating T-Cell Activity

The ' MODs on the T-Cell-MMP, and in some instances the payload the T-Cell-MMP and/or T-Cell-MMP-epitope conjugate may be carrying. T-Cell-MMPs lacking an epitope may be used to deliver payloads to classes of T-cells defined by the MOD and/or as a means of stimulating or inhibiting those classes of T-cells. In other cases, where the T-Cell-MMP has been conjugated to an epitope (i.e. it is a T-Cell-MMP-epitope conjugate), contacting the conjugate to a T-cell results in epitope-specific T-cell modulation. In some cases, the contacting occurs in vivo (e.g., in a mammal such as a human, rat, mouse, dog, cat, pig, horse, or primate). In some cases, the contacting occurs in vitro. In some cases, the contacting occurs ex vivo.

The present disclosure provides a method of selectively modulating the activity of an epitope-specific T-cell, the method comprising contacting the T-cell with a T-Cell-MMP-epitope conjugate of the present disclosure, where contacting the T-cell with a T-Cell-MMP-epitope conjugate of the present disclosure selectively modulates the activity of the epitope-specific T-cell. In some cases, the contacting occurs in vitro. In some cases, the contacting occurs in vivo. In some cases, the contacting occurs ex vivo.

In some cases, e.g., where the target T-cell is a CD8$^+$ T-cell, the T-Cell-MMP-epitope conjugate comprises Class I MHC polypeptides (e.g., β2-microglobulin and Class I MHC heavy chain).

Where a T-Cell-MMP-epitope conjugate of the present disclosure includes a MOD that is an activating polypeptide, contacting the T-cell with the T-Cell-MMP-epitope conjugate activates the epitope-specific T-cell. In some instances, the epitope-specific T-cell is a T-cell that is specific for an epitope present on a cancer cell, and contacting the epitope-specific T-cell with the T-Cell-MMP-epitope conjugate increases cytotoxic activity of the T-cell toward the cancer cell. In some instances, the epitope-specific T-cell is a T-cell that is specific for an epitope present on a cancer cell, and contacting the epitope-specific T-cell with the T-Cell-MMP-epitope conjugate increases the number of the epitope-specific T-cells.

In some instances, the epitope-specific T-cell is a T-cell that is specific for an epitope present on a virus-infected cell, and contacting the epitope-specific T-cell with the T-Cell-MMP-epitope conjugate increases cytotoxic activity of the T-cell toward the virus-infected cell. In some instances, the epitope-specific T-cell is a T-cell that is specific for an epitope present on a virus-infected cell, and contacting the epitope-specific T-cell with the T-Cell-MMP-epitope conjugate increases the number of the epitope-specific T-cells.

Where a T-Cell-MMP-epitope conjugate of the present disclosure includes a MOD that is an inhibiting polypeptide, contacting the T-cell with the multimer inhibits the epitope-specific T-cell. In some instances, the epitope-specific T-cell is a self-reactive T-cell that is specific for an epitope present in a self-antigen, and the contacting reduces the number of the self-reactive T-cells.

VIII Methods of Selectively Delivering a Costimulatory Polypeptide (MOD)

The present disclosure provides a method of delivering a MOD or a reduced-affinity variant of a naturally occurring MOD (such as an variant disclosed herein) to a selected T-cell or a selected T-cell population, e.g., in a manner such that a TCR specific for a given epitope is targeted. The present disclosure provides a method of delivering a MOD or a reduced-affinity variant of a naturally occurring MOD disclosed herein, selectively to a target T-cell bearing a TCR specific for the epitope present in a T-Cell-MMP-epitope conjugate of the present disclosure. The method comprises contacting a population of T-cells with a T-Cell-MMP-epitope conjugate of the present disclosure. The population of T-cells can be a mixed population that comprises: i) the target T-cell; and ii) non-target T-cells that are not specific for the epitope (e.g., T-cells that are specific for an epitope(s) other than the epitope to which the epitope-specific T-cell binds). The epitope-specific T-cell is specific for the epitope-presenting peptide present in the T-Cell-MMP epitope conjugate and binds to the peptide HLA complex or peptide MHC complex provided by the T-Cell-MMP epitope conjugate. Accordingly, contacting the population of T-cells with the T-Cell-MMP epitope conjugate delivers the costimulatory polypeptide (e.g., a wild-type MOD or a reduced-affinity variant of the wild-type MOD, as described herein) selectively to the T-cell(s) that are specific for the epitope present in the T-Cell-MMP epitope conjugate.

Thus, the present disclosure provides a method of delivering a MOD (such as IL-2), or a reduced-affinity variant of a naturally occurring MOD (such as an IL-2 variant) disclosed herein, or a combination of both, selectively to a target T-cell, the method comprising contacting a mixed population of T-cells with a T-Cell-MMP-epitope conjugate of the present disclosure. The mixed population of T-cells comprises the target T-cell and non-target T-cells. The target T-cell is specific for the epitope present within the T-Cell-MMP-epitope conjugate. Contacting the mixed population of T-cells with a T-Cell-MMP-epitope conjugate of the present disclosure delivers the MOD(s) present within the T-Cell-MMP-epitope conjugate to the target T-cell.

For example, a T-Cell-MMP epitope conjugate of the present disclosure is contacted with a population of T-cells comprising: i) a target T-cell(s) that is specific for the epitope present in the T-Cell-MMP-epitope conjugate; and ii) a non-target T-cell(s), e.g., a T-cell(s) that is specific for a second epitope(s) that is not the epitope present in the T-Cell-MMP-epitope conjugate. Contacting the population results in selective delivery of the MOD(s) (e.g., naturally-occurring MOD (e.g., naturally occurring IL-2) or reduced-affinity variant of a naturally occurring MOD (e.g., an IL-2 variant disclosed herein)), which is present in the T-Cell-MMP-epitope conjugate, to the target T-cell. Thus, e.g., less than 50%, less than 40%, less than 30%, less than 25%, less than 20%, less than 15%, less than 10%, less than 5%, or less than 4%, 3%, 2% or 1%, of the non-target T-cells bind the T-Cell-MMP epitope conjugate and, as a result, the costimulatory polypeptide (e.g., IL-2 or IL-2 variant) is not delivered to the non-target T-cells. As another example, contacting the population results in selective delivery of the costimulatory polypeptide(s) (e.g., naturally-occurring costimulatory polypeptide (e.g., naturally occurring 4-1BBL) or reduced-affinity variant of a naturally occurring costimulatory polypeptide (e.g., a 4-1BBL variant disclosed herein)), which is present in the T-Cell-MMP epitope conjugate, to the target T-cell. Thus, e.g., less than 50%, less than 40%, less than 30%, less than 25%, less than 20%, less than 15%, less than 10%, less than 5%, or less than 4%, 3%, 2% or 1%, of the non-target T-cells bind the T-Cell-MMP epitope conjugate and, as a result, the costimulatory polypeptide (e.g., 4-1BBL or 4-1BBL variant) is not delivered to the non-target T-cells.

In some cases, the population of T-cells is in vitro. In some cases, the population of T-cells is in vitro, and a biological response (e.g., T-cell activation and/or expansion and/or phenotypic differentiation) of the target T-cell population to the T-Cell-MMP-epitope conjugate of the present disclosure is elicited in the context of an in vitro culture. For example, a mixed population of T-cells can be obtained from an individual, and can be contacted with a T-Cell-MMP-epitope conjugate in vitro. Such contacting can comprise single or multiple exposures of the population of T-cells to a defined dose(s) and/or exposure schedule(s). In some cases, said contacting results in selectively binding/activating and/or expanding target T-cells within the population of T-cells, and results in generation of a population of activated and/or expanded target T-cells. As an example, a mixed population of T-cells can be peripheral blood mononuclear cells (PBMC). For example, PBMC from a patient can be obtained by standard blood drawing and PBMC enrichment techniques before being exposed to 0.1-1000 nM of a multimeric polypeptide of the present disclosure under standard lymphocyte culture conditions. At time points before, during, and after exposure of the mixed T-cell population at a defined dose and schedule, the abundance of target T-cells in the in vitro culture can be monitored by specific peptide-MHC multimers and/or phenotypic markers and/or functional activity (e.g., cytokine ELISpot assays). In some cases, upon achieving an optimal abundance and/or phenotype of antigen specific cells in vitro, all or a portion of the population of activated and/or expanded target T-cells is administered to the individual (the individual from whom the mixed population of T-cells was obtained).

In some cases, the population of T-cells is in vitro. For example, a mixed population of T-cells is obtained from an individual, and is contacted with a T-Cell-MMP-epitope conjugate of the present disclosure in vitro. Such contacting, which can comprise single or multiple exposures of the T-cells to a defined dose(s) and/or exposure schedule(s) in the context of in vitro cell culture, can be used to determine whether the mixed population of T-cells includes T-cells that are specific for the epitope presented by the T-Cell-MMP-epitope conjugate. The presence of T-cells that are specific for the epitope of the T-Cell-MMP-epitope conjugate can be determined by assaying a sample comprising a mixed population of T-cells, which population of T-cells comprises T-cells that are not specific for the epitope (non-target T-cells) and may comprise T-cells that are specific for the epitope (target T-cells). Known assays can be used to detect activation and/or proliferation of the target T-cells, thereby providing an ex vivo assay that can determine whether a particular T-Cell-MMP-epitope conjugate possesses an epitope that binds to T-cells present in the individual and thus whether the T-Cell-MMP-epitope conjugate has potential use as a therapeutic composition for that individual. Suitable known assays for detection of activation and/or proliferation of target T-cells include, e.g., flow cytometric characterization of T-cell phenotype and/or antigen specificity and/or proliferation. Such an assay to detect the presence of epitope-specific T-cells, e.g., a companion diagnostic, can further include additional assays (e.g., effector cytokine ELISpot assays) and/or appropriate controls (e.g., antigen-specific and antigen-nonspecific multimeric peptide-HLA staining reagents) to determine whether the T-Cell-MMP-epitope conjugate is selectively binding/activating and/or expanding the target T-cell. Thus, for example, the present disclosure provides a method of detecting, in a mixed population of T-cells obtained from an individual, the presence of a target T-cell that binds an epitope of interest, the method comprising: a) contacting in vitro the mixed population of T-cells with a T-Cell-MMP-epitope conjugate of the present disclosure, wherein the T-Cell-MMP-epitope conjugate comprises the epitope of interest; and b) detecting activation and/or proliferation of T-cells in response to said contacting, wherein activated and/or proliferated T-cells indicate the presence of the target T-cell. Alternatively, and/or in addition, if activation and/or expansion (proliferation) of the desired T-cell population is obtained using the T-Cell-MMP-epitope conjugate, then all or a portion of the population of T-cells comprising the activated/expanded T-cells can be administered back to the individual as a therapy.

In some instances, the population of T-cells is in vivo in an individual. In such instances, a method of the present disclosure for selectively delivering a MOD (e.g., IL-2 or a reduced-affinity IL-2; 4-1BBL or a reduced affinity 4-1BBL; PD-L1 or a reduced affinity PD-L1; CD80 or a reduced affinity CD80; or CD86 or a reduced affinity CD86) to an epitope-specific T-cell comprises administering the T-Cell-MMP-epitope conjugate to the individual.

The epitope-specific T-cell to which a MOD (e.g., IL-2 or a reduced-affinity IL-2; 4-1BBL or a reduced affinity 4-1BBL; PD-L1 or a reduced affinity PD-L1; CD80 or a reduced affinity CD80; or CD86 or a reduced affinity CD86) is being selectively delivered is also referred to herein as a "target T-cell." In some cases, the target T-cell is a regulatory T-cell (Treg). In some cases, the Treg inhibits or suppresses activity of an autoreactive T-cell.

In some cases, the target T-cell is a cytotoxic T-cell. For example, the target T-cell can be a cytotoxic T-cell specific for a cancer epitope (e.g., an epitope presented by a cancer cell).

XI. Treatment Methods

The present disclosure provides a method of selectively modulating the activity of an epitope-specific T-cell in an individual (e.g., treat an individual), the method comprising administering to the individual an amount of a T-Cell-MMP or T-Cell-MMP-epitope conjugate of the present disclosure, or one or more nucleic acids encoding a T-Cell-MMP, which after conjugation to an epitope is effective to selectively modulate the activity of an epitope-specific T-cell in an individual. Also provided is a T-Cell-MMP epitope conjugate of the present disclosure for use in a method of treatment of the human or animal body. In some cases, a treatment method of the present disclosure comprises administering to an individual in need thereof one or more recombinant expression vectors comprising nucleotide sequences encoding a T-Cell-MMP of the present disclosure. In some cases, a treatment method of the present disclosure comprises administering to an individual in need thereof one or more mRNA molecules comprising nucleotide sequences encoding a T-Cell-MMP of the present disclosure. In some cases, a treatment method of the present disclosure comprises administering to an individual in need thereof a T-Cell-MMP-epitope conjugate of the present disclosure. Conditions that can be treated include, infections, cancer, and autoimmune disorders, examples of some of which are described below.

In some cases, a T-cell-MMP-epitope conjugate of the present disclosure, when administered to an individual in need thereof, induces both an epitope-specific T-cell response and an epitope non-specific T-cell response. In other words, in some cases, a T-cell-MMP-epitope conjugate of the present disclosure, when administered to an individual in need thereof, induces an epitope-specific T-cell response by modulating the activity of a first T-cell that displays both: i) a TCR specific for the epitope present in the T-Cell-MMP; and ii) a Co-MOD that binds to the MOD present in the T-Cell-MMP-epitope conjugate; and induces an epitope non-specific T-cell response by modulating the activity of a second T-cell that displays: i) a TCR specific for an epitope other than the epitope present in the T-Cell-MMP; and ii) a Co-MOD that binds to the MOD present in the T-Cell-MMP. The ratio of the epitope-specific T-cell response to the epitope-non-specific T-cell response is at least 2:1, at least 5:1, at least 10:1, at least 15:1, at least 20:1, at least 25:1, at least 50:1, or at least 100:1. The ratio of the epitope-specific T-cell response to the epitope-non-specific T-cell response is from about 2:1 to about 5:1, from about 5:1 to about 10:1, from about 10:1 to about 15:1, from about 15:1 to about 20:1, from about 20:1 to about 25:1, from about 25:1 to about 50:1, from about 50:1 to about 100:1, or more than 100:1. "Modulating the activity" of a T-cell can include one or more of: i) activating a cytotoxic (e.g., $CD8^+$) T-cell; ii) inducing cytotoxic activity of a cytotoxic (e.g., $CD8^+$) T-cell; iii) inducing production and release of a cytotoxin (e.g., a perforin; a granzyme; a granulysin) by a cytotoxic (e.g., $CD8^+$) T-cell; iv) inhibiting activity of an autoreactive T-cell; and the like.

In embodiments, such as where a patient is generally immunosuppressed, one or more T-Cell-MMPs bearing independently selected MODs (e.g., wild-type) or variant MODs with reduced affinity for their Co-MODs may be administered to a patient to simulate their overall immune status/responsiveness (e.g., as measured by their ability to react to a vaccine antigen or infection). In other embodiments, such as where a patient is generally immunosuppressed, one or more T-Cell-MMPs bearing independently selected MODs (e.g., wild-type) or variant MODs with reduced affinity for their Co-MODs may be administered in combination with a T-Cell-MMP-epitope conjugate to a patient to simulate the patient's immune response.

In embodiments, one or more T-Cell-MMPs bearing independently selected MODs (e.g., wild-type), or variant MODs with reduced affinity for their Co-MODs, may be administered to a patient in conjunction with a vaccine to a pathogen (e.g., protein or nucleic acid vaccine) in order to simulate/enhance the development of immunity against the pathogen. In another embodiment, one or more T-Cell-MMP-epitope conjugates bearing an epitope to a pathogen are administered to a patient in conjunction with a vaccine to a pathogen (e.g., protein or nucleic acid vaccine) to simulate the development of immunity against the pathogen. In such a case, the T-Cell-MMP-epitope conjugate may comprise independently selected MODs (e.g., wild-type), or variant MODs with reduced affinity for their Co-MODs. Where a T-Cell-MMP is administered in conjunction with a vaccine (e.g., protein or nucleic acid), it may be co-administered in combination with the vaccine or in a separate formulation administered at the same or a different time from the vaccine administration.

The combination of the reduced affinity of the MOD for its Co-MOD, and the affinity of the epitope for a TCR, provides for enhanced selectivity of a T-Cell-MMP-epitope conjugate of the present disclosure. Thus, for example, a T-Cell-MMP-epitope conjugate of the present disclosure binds with higher avidity to a first T-cell that displays both: i) a TCR specific for the epitope present in the T-Cell-MMP-epitope conjugate; and ii) a Co-MOD that binds to the MOD present in the T-Cell-MMP-epitope conjugate, compared to the avidity to which it binds to a second T-cell that displays: i) a TCR specific for an epitope other than the epitope present in the T-Cell-MMP epitope conjugate; and ii) a Co-MOD that binds to the MOD present in the T-Cell-MMP epitope conjugate.

The present disclosure provides a method of selectively modulating the activity of an epitope-specific T-cell in an individual, the method comprising administering to the individual an effective amount of a T-Cell-MMP or a T-Cell-MMP-epitope conjugate of the present disclosure, where the T-Cell-MMP or its epitope conjugate selectively modulates the activity of the epitope-specific T-cell in the individual. Selectively modulating the activity of an epitope-specific T-cell can treat a disease or disorder in the individual. Thus, the present disclosure provides a treatment method comprising administering to an individual in need thereof an effective amount of a T-Cell-MMP or its epitope conjugate.

In some cases, the MOD is an activating polypeptide, and the T-Cell-MMP-epitope conjugate activates the epitope-specific T-cell. In some cases, the epitope is a cancer-associated epitope, and the T-Cell-MMP-epitope conjugate increases the activity of a T-cell specific for the cancer-associated epitope.

The present disclosure provides a method of treating cancer in an individual, the method comprising administering to the individual an effective amount of a T-Cell-MMP-epitope conjugate of the present disclosure where the T-Cell-MMP-epitope conjugate comprises a T-cell epitope that is a cancer epitope, and where the T-Cell-MMP-epitope conjugate comprises a stimulatory MOD. In some cases, an "effective amount" of a T-Cell-MMP-epitope conjugate is an amount that, when administered in one or more doses to an individual in need thereof, reduces the number of cancer cells in the individual. For example, in some cases, an "effective amount" of a T-Cell-MMP or T-Cell-MMP-epitope conjugate of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, at least 95%, or to undetectable levels compared to the number of cancer cells in the individual before administration of the T-Cell-MMP or T-Cell-MMP-epitope conjugate, or in the absence of administration with the T-Cell-MMP-epitope conjugate. In another case, an "effective amount" of a T-Cell-MMP-epitope conjugate of the present disclosure is an amount that, when administered in one or more doses to an individual in need thereof, reduces volume of at least one solid tumor in the individual by at least 10%, at least 15%, at least 20%, at least 25%, at least 30%, at least 40%, at least 50%, at least 60%, at least 70%, at least 80%, at least 90%, at least 95%, or to undetectable levels compared to the volume of that tumor at the time of administering the first dose of the T-Cell-MMP or T-Cell-MMP-epitope conjugate.

In some cases, an "effective amount" of a T-Cell-MMP or T-Cell-MMP-epitope conjugate of the present disclosure is an amount that, when administered in one or more doses to an individual in need thereof (an individual having a tumor), reduces either the number of cancer cells, or the volume of at least one tumor, in the individual to undetectable levels. In some cases, an "effective amount" of a T-Cell-MMP or T-Cell-MMP-epitope conjugate of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, at least 95%, or to an undetectable level compared to the total tumor mass in the individual before administration of the T-Cell-MMP or T-Cell-MMP-epitope conjugate, or in the absence of administration of the T-Cell-MMP or T-Cell-MMP-epitope conjugate. In another embodiment, the "effective amount" of a T-Cell-MMP or T-Cell-MMP-epitope conjugate of the present disclosure is an amount that, when administered in one or more doses to an individual in need thereof (an individual having a tumor), reduces the tumor volume of at least one tumor in the individual. For example, in some cases, an "effective amount" of a multimeric polypeptide of the present disclosure is an amount that, when administered in one or more doses to an individual in need thereof (an individual having a tumor), reduces the tumor volume by at least 10%, at least 15%, at least 20%, at least 25%, at least 30%, at least 40%, at least 50%, at least 60%, at least 70%, at least 80%, at least 90%, at least 95%, or to undetectable levels (volume) compared to the tumor volume in the individual before administration of the T-Cell-MMP or T-Cell-MMP-epitope conjugate, or in the absence of administration of the T-Cell-MMP or T-Cell-MMP-epitope conjugate. In such an embodiment the mass may be calculated based on tumor density and volume.

In some cases, an "effective amount" of a T-Cell-MMP or T-Cell-MMP-epitope conjugate of the present disclosure is an amount that, when administered in one or more doses to an individual in need thereof, increases survival time of the individual. For example, in some cases, an "effective amount" of a T-Cell-MMP or T-Cell-MMP-epitope conjugate of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the T-Cell-MMP or T-Cell-MMP-epitope conjugate.

In some cases, an "effective amount" of a T-Cell-MMP or a T-Cell-MMP-epitope conjugate of the present disclosure is an amount that, when administered in one or more doses to individuals in a population of individuals in need thereof, increases average survival time of the population. For example, in some cases, an "effective amount" of a T-Cell-MMP or T-Cell-MMP-epitope conjugate of the present disclosure is an amount that, when administered in one or more doses to individuals in a population of individual in need thereof, increases survival time of the population of individuals receiving the T-Cell-MMP or T-Cell-MMP-epitope conjugate by at least 1 month, at least 2 months, at least 3 months, from 3 months to 6 months, from 6 months to 1 year, from 1 year to 2 years, from 2 years to 5 years, from 5 years to 10 years, or more than 10 years, compared to the survival time of the individuals not receiving the T-Cell-MMP or T-Cell-MMP-epitope conjugate; wherein the population is an age, gender, weight, and disease state (disease and degree of progression) matched population. In some instances, the epitope-specific T-cell is a T-cell that is specific for an epitope present on a virus-infected cell, and contacting the epitope-specific T-cell with the T-Cell-MMP-epitope conjugate increases cytotoxic activity of the T-cell toward the virus-infected cell. In some instances, the epitope-specific T-cell is a T-cell that is specific for an epitope present on a virus-infected cell, and contacting the epitope-specific T-cell with the T-Cell-MMP-epitope conjugate increases the number of the epitope-specific T-cells. Accordingly, the present disclosure provides a method of treating a virus infection in an individual, the method comprising administering to the individual an effective amount of a T-Cell-MMP-epitope conjugate of the present disclosure, where the T-Cell-MMP-epitope conjugate comprises a T-cell epitope that is a viral epitope, and where the T-Cell-MMP-epitope conjugate comprises a stimulatory MOD. In some cases, an "effective amount" of a T-Cell-MMP-epitope conjugate is an amount that, when administered in one or more doses to an individual in need thereof, reduces the number of virus-infected cells in the individual. For example, in some cases, an "effective amount" of a T-Cell-MMP-epitope conjugate of the present disclosure is an amount that, when administered in one or more doses to an individual in need thereof, reduces the number of virus-infected cells in the individual by at least 10%, at least 15%, at least 20%, at least 25%, at least 30%, at least 40%, at least 50%, at least 60%, at least 70%, at least 80%, at least 90%, or at least 95%, compared to the number of virus-infected cells in the individual before administration of the T-Cell-MMP-epitope conjugate, or in the absence of administration with the T-Cell-MMP-epitope conjugate. In some cases, an "effective amount" of a T-Cell-MMP-epitope conjugate of the present disclosure is an amount that, when administered in one or more doses to an individual in need thereof, reduces the number of virus-infected cells in the individual to undetectable levels.

The present disclosure also provides a method of treating an infection in an individual, the method comprising administering to the individual an effective amount of a T-Cell-MMP and/or T-Cell-MMP-epitope conjugate of the present disclosure, where the T-Cell-MMP-epitope conjugate comprises a T-cell epitope that is a pathogen-associated epitope, and where the T-Cell-MMP and/or T-Cell-MMP-epitope conjugate comprises a stimulatory MOD. In some cases, an "effective amount" of a T-Cell-MMP is an amount that, when administered in one or more doses to an individual in need thereof, reduces the number of pathogens in the individual. For example, in some cases, an "effective amount" of a T-Cell-MMP and/or T-Cell-MMP-epitope conjugate of the present disclosure is an amount that, when administered in one or more doses to an individual in need thereof, reduces the number of pathogens in the individual by at least 10%, at least 15%, at least 20%, at least 25%, at least 30%, at least 40%, at least 50%, at least 60%, at least 70%, at least 80%, at least 90%, or at least 95%, compared to the number of pathogens in the individual before administration of the T-Cell-MMP and/or T-Cell-MMP-epitope conjugate, or in the absence of administration with the T-Cell-MMP and/or T-Cell-MMP-epitope conjugate. In some cases, an "effective amount" of a T-Cell-MMP and/or T-Cell-MMP-epitope conjugate of the present disclosure is an amount that, when administered in one or more doses to an individual in need thereof, reduces the number of pathogens in the individual to undetectable levels. Pathogens include viruses, bacteria, protozoans, and the like.

In some cases, the MOD is an inhibitory polypeptide, and the T-Cell-MMP-epitope conjugate inhibits activity of the epitope-specific T-cell. In some cases, the epitope is a self-epitope, and the T-Cell-MMP-epitope conjugate selectively inhibits the activity of a T-cell specific for the self-epitope.

The present disclosure provides a method of treating an autoimmune disorder in an individual, the method comprising administering to the individual an effective amount of a T-Cell-MMP (or one or more nucleic acids comprising nucleotide sequences encoding the T-Cell-MMP) and/or T-Cell-MMP-epitope conjugate comprising a self-epitope, where the T-Cell-MMP and/or T-Cell-MMP-epitope conjugate comprises an inhibitory MOD. In such cases, an "effective amount" of a T-Cell-MMP and/or T-Cell-MMP-epitope conjugate is an amount that, when administered in one or more doses to an individual in need thereof, reduces the number of self-reactive T-cells by at least 10%, at least 15%, at least 20%, at least 25%, at least 30%, at least 40%, at least 50%, at least 60%, at least 70%, at least 80%, at least 90%, or at least 95%, compared to the number of self-reactive T-cells in the individual before administration of the T-Cell-MMP and/or T-Cell-MMP-epitope conjugate, or in the absence of administration of the T-Cell-MMP and/or T-Cell-MMP-epitope conjugate. In some cases, an "effective amount" of such a T-Cell-MMP and/or T-Cell-MMP-epitope conjugate is an amount that, when administered in one or more doses to an individual in need thereof, reduces production of Th2 cytokines (e.g., by at least 10%, at least 15%, at least 20%, at least 25%, at least 30%, at least 40%, at least 50%, at least 60%, at least 70%, at least 80%, at least 90%, or at least 95%) in the individual. In some cases, an "effective amount" of such a T-Cell-MMP and/or T-Cell-MMP-epitope conjugate is an amount that, when administered in one or more doses to an individual in need thereof, ameliorates one or more symptoms associated with an autoimmune disease in the individual.

As noted above, in some cases, in carrying out a subject treatment method, a T-Cell-MMP and/or T-Cell-MMP-epitope conjugate of the present disclosure is administered to an individual in need thereof, as the polypeptide per se. In other instances, in carrying out a subject treatment method, one or more nucleic acids comprising nucleotide sequences encoding a T-Cell-MMP of the present disclosure is/are administered to an individual in need thereof. Thus, in other instances, one or more nucleic acids of the present disclosure, e.g., one or more recombinant expression vectors of the present disclosure, is/are administered to an individual in need thereof.

X. Formulations

Suitable formulations are described above, where suitable formulations include a pharmaceutically acceptable excipient. In some cases, a suitable formulation comprises: a) a T-Cell-MMP and/or T-Cell-MMP-epitope conjugate of the present disclosure; and b) a pharmaceutically acceptable excipient. In some cases, a suitable formulation comprises: a) a nucleic acid comprising a nucleotide sequence encoding a T-Cell-MMP of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a T-Cell-MMP of the present disclosure; b) a second nucleic acid comprising a nucleotide sequence encoding the second polypeptide of a T-Cell-MMP of the present disclosure; and c) a pharmaceutically acceptable excipient. In some cases, a suitable formulation comprises: a) a recombinant expression vector comprising a nucleotide sequence encoding a T-Cell-MMP of the present disclosure; and b) a pharmaceutically acceptable excipient. In some cases, a suitable formulation comprises: a) a first recombinant expression vector comprising a nucleotide sequence encoding the first polypeptide of a T-Cell-MMP of the present disclosure; b) a second recombinant expression vector comprising a nucleotide sequence encoding the second polypeptide of a T-Cell-MMP of the present disclosure; and c) a pharmaceutically acceptable excipient.

Suitable pharmaceutically acceptable excipients are described above.

X.A. Dosages

A suitable dosage can be determined by an attending physician, or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, route of administration, general health, and other drugs being administered concurrently. A T-Cell-MMP and/or T-Cell-MMP-epitope conjugate of the present disclosure may be administered in amounts between 1 ng/kg body weight and 20 mg/kg body weight per dose, e.g., between 0.1 mg/kg body weight to 10 mg/kg body weight, e.g., between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute. A T-Cell-MMP and/or T-Cell-MMP-epitope conjugate of the present disclosure can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a T-Cell-MMP and/or T-Cell-MMP-epitope conjugate of the present disclosure is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a T-Cell-MMP and/or T-Cell-MMP-epitope conjugate of the present disclosure is administered in maintenance doses, ranging from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight.

Those of skill will readily appreciate that dose levels can vary as a function of the specific T-Cell-MMP, the severity of the symptoms and the susceptibility of the subject to side effects. Preferred dosages for a given compound are readily determinable by those of skill in the art by a variety of means.

In some embodiments, multiple doses of a T-Cell-MMP and/or T-Cell-MMP-epitope conjugate of the present disclosure, a nucleic acid of the present disclosure, or a recombinant expression vector of the present disclosure are administered. The frequency of administration of a T-Cell-MMP and/or T-Cell-MMP-epitope conjugate of the present disclosure, a nucleic acid of the present disclosure, or a recombinant expression vector of the present disclosure can vary depending on any of a variety of factors, e.g., severity of the symptoms, etc. For example, in some embodiments, a T-Cell-MMP and/or T-Cell-MMP-epitope conjugate of the present disclosure, a nucleic acid of the present disclosure, or a recombinant expression vector of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a T-Cell-MMP and/or T-Cell-MMP-epitope conjugate of the present disclosure, a nucleic acid of the present disclosure, or a recombinant expression vector of the present disclosure, e.g., the period of time over which a T-Cell-MMP and/or T-Cell-MMP-epitope conjugate of the present disclosure, a nucleic acid of the present disclosure, or a recombinant expression vector of the present disclosure is administered can vary, depending on any of a variety of factors, e.g., patient response, etc. For example, a T-Cell-MMP and/or T-Cell-MMP-epitope conjugate of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

X.B. Routes of Administration

An active agent (a T-Cell-MMP and/or T-Cell-MMP-epitope conjugate of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intralymphatic, intratracheal, intracranial, subcutaneous, intradermal, topical, intravenous, intraarterial, rectal, nasal, oral, and other enteral and parenteral routes of administration. Routes of administration may be combined, if desired, or adjusted depending upon the T-Cell-MMP and/or T-Cell-MMP-epitope conjugate and/or the desired effect. A T-Cell-MMP and/or T-Cell-MMP-epitope conjugate of the present disclosure, or a nucleic acid or recombinant expression vector of the present disclosure, can be administered in a single dose or in multiple doses.

In some embodiments, a T-Cell-MMP and/or T-Cell-MMP-epitope conjugate of the present disclosure, a nucleic acid of the present disclosure, or a recombinant expression vector of the present disclosure is administered intravenously. In some embodiments, a T-Cell-MMP and/or T-Cell-MMP-epitope conjugate of the present disclosure, a nucleic acid of the present disclosure, or a recombinant expression vector of the present disclosure is administered intramuscularly. In some embodiments, a T-Cell-MMP and/or T-Cell-MMP-epitope conjugate of the present disclosure, a nucleic acid of the present disclosure, or a recombinant expression vector of the present disclosure is administered intralymphatically. In some embodiments, a T-Cell-MMP and/or T-Cell-MMP-epitope conjugate, a nucleic acid of the present disclosure, or a recombinant expression vector of the present disclosure is administered locally. In some embodiments, a T-Cell-MMP and/or T-Cell-MMP-epitope conjugate of the present disclosure, a nucleic acid of the present disclosure, or a recombinant expression vector of the present disclosure is administered intratumorally. In some embodiments, a T-Cell-MMP and/or T-Cell-MMP-epitope conjugate of the present disclosure, a nucleic acid of the present disclosure, or a recombinant expression vector of the present disclosure is administered peritumorally. In some embodiments, a T-Cell-MMP and/or T-Cell-MMP-epitope conjugate of the present disclosure, a nucleic acid of the present disclosure, or a recombinant expression vector of the present disclosure is administered intracranially. In some embodiments, a T-Cell-MMP and/or T-Cell-MMP-epitope conjugate of the present disclosure, a nucleic acid of the present disclosure, or a recombinant expression vector of the present disclosure is administered subcutaneously.

In some embodiments, a T-Cell-MMP and/or T-Cell-MMP-epitope conjugate of the present disclosure is administered intravenously. In some embodiments, a T-Cell-MMP and/or T-Cell-MMP-epitope conjugate of the present disclosure is administered intramuscularly. In some embodiments, a T-Cell-MMP and/or T-Cell-MMP-epitope conjugate of the present disclosure is administered locally. In some embodiments, a T-Cell-MMP and/or T-Cell-MMP-epitope conjugate of the present disclosure is administered intratumorally. In some embodiments, a T-Cell-MMP and/or T-Cell-MMP-epitope conjugate of the present disclosure is administered peritumorally. In some embodiments, a T-Cell-MMP and/or T-Cell-MMP-epitope conjugate of the present disclosure is administered intracranially. In some embodiments, a T-Cell-MMP and/or T-Cell-MMP-epitope conjugate is administered subcutaneously. In some embodiments, a T-Cell-MMP and/or T-Cell-MMP-epitope conjugate is administered intralymphatically. In some embodiments, a T-Cell-MMP and/or T-Cell-MMP-epitope conjugate is administered intralymphatically.

A T-Cell-MMP and/or T-Cell-MMP-epitope conjugate of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, intralymphatic, peritumoral, and intravenous routes, i.e., any route of administration other than through the alimentary canal. Parenteral administration can be carried out to effect systemic or local delivery of a T-Cell-MMP and/or T-Cell-MMP-epitope conjugate of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

X.C. Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for an autoimmune disease but who failed to respond to the treatment.

In certain instances, e.g., where a T-cell modulatory multimeric polypeptide of the present disclosure comprises an HBV epitope, an individual suitable for treatment is an individual who has been infected with HBV. In some cases, the individual has an acute HBV infection. In some cases, the individual has an acute HBV infection, and does not have liver cancer. In some cases, the individual is an inactive carrier of HBV. In some cases, the individual is an inactive carrier of HBV, and does not have liver cancer. In some cases, the individual has chronic active HBV. In some cases, the individual has chronic active HBV, and does not have liver cancer. In some cases, the individual has liver cancer due to an HBV infection.

In certain instances, e.g., where a T-cell modulatory multimeric polypeptide of the present disclosure comprises an HBV epitope, an individual suitable for treatment is an individual who has been infected with HBV, where the individual is Asian, e.g., where the individual has a HLA-A11, HLA-A24, or HLA-A33 allele. In some cases, the individual has an acute HBV infection. In some cases, the individual has an acute HBV infection, and does not have liver cancer, where the individual is Asian, e.g., where the individual has a HLA-A11, HLA-A24, or HLA-A33 allele. In some cases, the individual is an inactive carrier of HBV, where the individual is Asian, e.g., where the individual has a HLA-A11, HLA-A24, or HLA-A33 allele. In some cases, the individual is an inactive carrier of HBV, and does not have liver cancer, where the individual is Asian, e.g., where the individual has a HLA-A11, HLA-A24, or HLA-A33 allele. In some cases, the individual has chronic active HBV, where the individual is Asian, e.g., where the individual has a HLA-A11, HLA-A24, or HLA-A33 allele. In some cases, the individual has chronic active HBV, and does not have liver cancer, where the individual is Asian, e.g., where the individual has a HLA-A11, HLA-A24, or HLA-A33 allele. In some cases, the individual has liver cancer due to an HBV infection, where the individual is Asian, e.g., where the individual has a HLA-A11, HLA-A24, or HLA-A33 allele.

XI. Certain Embodiments

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, and/or process step or steps, to the objective, spirit and scope of the present invention. All such modifications are intended to be within the scope of the claims appended hereto.

1. A T-Cell-MMP (T-Cell-MMP) comprising:
    a) a first polypeptide comprising,
        i) a first major histocompatibility complex (MHC) polypeptide having an N-terminus and a C-terminus;
    b) a second polypeptide comprising, in order from N-terminus to C-terminus,
        i) a second MHC polypeptide; and
        ii) optionally an immunoglobulin (Ig) Fc polypeptide or a non-Ig polypeptide scaffold;
    c) one or more first polypeptide chemical conjugation sites attached to (e.g., at the N- or C-terminus) or within the first polypeptide, and/or one or more second polypeptide chemical conjugation sites attached to (e.g., at the N- or C-terminus) or within the second polypeptide; and
    d) one or more immunomodulatory polypeptides (MODs), wherein at least one of the one or more MODs is
        A) at the C-terminus of the first polypeptide,
        B) at the N-terminus of the second polypeptide,
        C) at the C-terminus of the second polypeptide, or
        D) at the C-terminus of the first polypeptide and at the N-terminus of the second polypeptide;
    wherein each of the one or more MODs is an independently selected wild-type or variant MOD.

2. The T-Cell-MMP of embodiment 1, wherein the first polypeptide comprises:
    a first MHC polypeptide without a linker on its N-terminus and C-terminus,
    a first MHC polypeptide bearing a linker on its N-terminus, a first MHC polypeptide bearing a linker on its C-terminus, or a first MHC polypeptide bearing a linker on its N-terminus and C-terminus.

3. The T-Cell-MMP of any one of embodiments 1 to 2, wherein at least one of the one or more first polypeptide chemical conjugation sites is:
   a) attached to (e.g., at the N- or C-terminus), or within, the sequence of the first MHC polypeptide, where the first MHC polypeptide is without a linker on its N- and C-terminus;
   b) attached to (e.g., at the N- or C-terminus), or within, the sequence of the first MHC polypeptide where the first MHC polypeptide comprises a linker on its N- and C-terminus;
   c) attached to (e.g., at the N- or C-terminus) or within, the sequence of the linker on the N-terminus of the first MHC polypeptide; and/or
   d) attached to (e.g., at the N- or C-terminus) or within, the sequence of the linker on the C-terminus of the first MHC polypeptide.

4. The T-Cell-MMP of any one of embodiments 1 to 3, wherein the first and second MHC polypeptides are Class I MHC polypeptides, and the first MHC polypeptide comprises:
   a beta-2-microglobulin ("β2M") polypeptide having an N-terminus and a C-terminus without a linker on its N- and C-terminus,
   a β2M polypeptide bearing a linker on its N-terminus,
   a β2M polypeptide bearing a linker on its C-terminus, or
   a β2M polypeptide bearing a linker on its N-terminus and C-terminus.

5. The T-Cell-MMP of embodiment 4, wherein in at least one of the one or more first polypeptide chemical conjugation sites is:
   a) attached to (e.g., at the N- or C-terminus) or within the sequence of the β2M polypeptide without a linker on its N- or C-terminus;
   b) attached to (e.g., at the N- or C-terminus) or within the sequence of the β2M polypeptide where the β2M polypeptide comprises a linker on its N- and C-terminus;
   c) attached to (e.g., at the N- or C-terminus) or within the sequence of the linker on the N-terminus of the β2M polypeptide; and/or
   d) attached to (e.g., at the N- or C-terminus) or within, the sequence of the linker on the C-terminus of the β2M polypeptide.

6. The T-Cell-MMP of any one of embodiments 1 to 5, wherein the second polypeptide comprises:
   a second MHC polypeptide (comprising e.g., a MHC Class I heavy chain ("MHC-H") polypeptide) without a linker on its N-terminus and C-terminus,
   a second MHC polypeptide bearing a linker on its N-terminus,
   a second MHC polypeptide bearing a linker on its C-terminus, or
   a second MHC polypeptide bearing a linker on its N-terminus and C-terminus.

7. The T-Cell-MMP of embodiment 6, wherein the second polypeptide further comprises an immunoglobulin (Ig) Fc polypeptide or a non-Ig polypeptide scaffold.

8. The T-Cell-MMP of embodiment 7, wherein the second polypeptide comprises, in order from N-terminus to C-terminus:

a second MHC polypeptide bearing a linker on its C-terminus followed by an immunoglobulin (Ig) Fc polypeptide or a non-Ig polypeptide scaffold; or a second MHC polypeptide bearing a linker on its N-terminus and/or C-terminus followed by an immunoglobulin (Ig) Fc polypeptide or a non-Ig polypeptide scaffold.

9. The T-Cell-MMP of any one of embodiments 1 to 8, wherein at least one of the one or more second polypeptide chemical conjugation sites is:
   a) attached to (e.g., at the N- or C-terminus) or within the sequence of the second MHC polypeptide, wherein the second MHC polypeptide is without a linker on its N- and C-terminus;
   b) attached to (e.g., at the N- or C-terminus) or within, the sequence of the second MHC polypeptide where the second MHC polypeptide comprises a linker on its N- and/or C-terminus;
   c) attached to (e.g., at the N- or C-terminus) or within, the sequence of the linker on the N-terminus of the second MHC polypeptide;
   d) attached to (e.g., at the N- or C-terminus) or within, the sequence of the linker on the C-terminus of the second MHC polypeptide and/or
   e) attached to (e.g., at the N- or C-terminus) or within the sequence of an immunoglobulin (Ig) Fc polypeptide or a non-Ig polypeptide scaffold when the second MHC polypeptide is followed by an immunoglobulin (Ig) Fc polypeptide or a non-Ig polypeptide scaffold.

10. The T-Cell-MMP of any one of embodiments 1 to 9, wherein the second MHC polypeptide comprises: a MHC Class I heavy chain ("MHC-H") polypeptide having an N-terminus and a C-terminus without a linker on its N- and C-terminus, a MHC-H polypeptide bearing a linker on its N-terminus, a MHC-H polypeptide bearing a linker on its C-terminus, or a MHC-H polypeptide bearing a linker on its N-terminus and C-terminus.

11. The T-Cell-MMP of any one of embodiments 4-10, wherein in at least one of the one or more first polypeptide chemical conjugation sites is:
   a) attached to (e.g., at the N- or C-terminus), or within, the sequence of the β2M polypeptide without a linker on its N- or C-terminus;
   b) attached to (e.g., at the N- or C-terminus) or within, the sequence of the β2M polypeptide where the β2M polypeptide comprises a linker on its N- and C-terminus;
   c) attached to (e.g., at the N- or C-terminus) or within, the sequence of the linker on the N-terminus of the β2M polypeptide; and/or
   d) attached to (e.g., at the N- or C-terminus) or within, the sequence of the linker on the C-terminus of the β2M polypeptide.

12. The T-Cell-MMP of any one of embodiments 4-10, wherein in at least one of the one or more first polypeptide chemical conjugation sites replaces and/or is inserted between any of the amino terminal 15 amino acids of a mature β2M polypeptide sequence lacking its signal sequence (e.g., a β2M polypeptide sequence shown in FIG. 4).

13. The T-Cell-MMP of any one of embodiments 1 to 12, wherein the second polypeptide comprises an Ig Fc polypeptide.

14. The T-Cell-MMP of embodiment 13, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.
15. The T-Cell-MMP of embodiment 14, wherein the Ig Fc polypeptide comprises an amino acid sequence having at least 85% amino acid sequence identity (e.g., at least 90%, 95%, 98% or 99% identity, or even 100% identity) to an amino acid sequence depicted in one of FIG. 2A-2D, or a portion of a sequence (at least about 50, 75, 100, 125 or 150 amino acids in length) in one of FIG. 2A-2D corresponding to the IgFc polypeptide.
16. The T-Cell-MMP of embodiment 15, wherein the IgFc polypeptide is an IgG1 Fc polypeptide.
17. The T-Cell-MMP of embodiment 16, wherein the IgG1 Fc polypeptide comprises one or more amino acid substitutions selected from N297A, L234A, L235A, L234F, L235E, and P331S.
18. The T-Cell-MMP of embodiment 17, wherein the IgG1 Fc polypeptide comprises L234A and L235A substitutions.
19. The T-Cell-MMP of any one of embodiments 1 to 18, wherein T-Cell-MMP comprises one or more independently selected wild-type and/or variant MOD polypeptides; wherein at least one of the one or more variant MOD polypeptides exhibits a reduced affinity to a Co-MOD (its Co-MOD) compared to the affinity of a corresponding wild-type MOD for the Co-MOD (e.g., the ratio of the binding affinity of a control T-Cell-MMP-epitope conjugate (where the control comprises a wild-type MOD) to a Co-MOD to ii) the binding affinity of a T-Cell-MMP-epitope conjugate of the present disclosure comprising a variant of the wild-type MOD to the Co-MOD, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1).
20. The T-Cell-MMP of embodiment 19, wherein the variant MOD polypeptides comprises from 1 to 10 amino acid substitutions, insertions, or deleteions relative to a corresponding wild-type immunomodulatory polypeptide: or comprises an amino acid sequence having at least 85% amino acid sequence identity (e.g., at least 90%, 95%, 98% or 99% identity, or even 100% identity) to an amino acid sequence of the corresponding wild-type MOD, or a portion of the sequence of a wild-type MOD (e.g., at least about 50, 75, 100, 125 or 150 contiguous amino acids of the wild-type MOD in length).
21. The T-Cell-MMP of any one of embodiments 1 to 20, wherein the wild-type immunomodulatory polypeptide is selected independently from the group consisting of IL-2, 4-1BBL, PD-L1, CD70, CD80, CD86, ICOS-L, OX-40L, FasL, JAG1, TGFβ, ICAM, and PD-L2.
22. The T-Cell-MMP of any one of embodiments 1 to 21, wherein the first MHC polypeptide is a β2Microglobulin β2M polypeptide; and wherein the second MHC polypeptide is a MHC Class I heavy chain polypeptide.
23. The T-Cell-MMP of any one of embodiments 4 to 22, wherein the β2M polypeptide comprises an amino acid sequence having at least 85% amino acid sequence identity (e.g., at least 90%, 95%, 98% or 99% identity, or even 100% identity) to one of the amino acid sequences set forth in FIG. 4, or a portion of a mature sequence β2M polypeptide in FIG. 4 (e.g., at least about 60, 70, 80, or 90 amino acids in length).
24. The T-Cell-MMP of any one of embodiments 4 to 23, wherein the β2M polypeptide comprises, consists essentially of, or consists of a sequence of at least 20, 30, 40, 50, 60, 70, 80, 90 or 99 contiguous amino acids having identity with at least a portion of one of the amino acid sequence set forth in FIG. 4 (e.g., a sequence having 20-99, 20-40, 30-50, 40-60, 40-90, 50-70, 60 to 80, 60-99, 70-90, or 79-99 contiguous amino acids with identity to a sequence of mature β2M polypeptide lacking its signal sequence set forth in FIG. 4).
25. The T-Cell-MMP of any one of embodiments 10 to 24, wherein the MHC Class I heavy chain polypeptide is a HLA-A, a HLA-B, or a HLA-C heavy chain (e.g., a HLA-A HLA-B, or HLA-C from FIG. 3, including HLA-A11, HLA-A24 and HLA-A33).
26. The T-Cell-MMP of embodiment 25, wherein the MHC Class I heavy chain polypeptide sequence comprises an amino acid sequence having at least 85% amino acid sequence identity (e.g., at least 90%, 95%, 98% or 99% identity, or even 100% identity) to the amino acid sequences set forth in one of FIGS. 3A-3D, or a portion of a sequence in one of FIGS. 3A-3D corresponding to the MHC Class I heavy chain polypeptide (e.g., a sequence having 20-100, 20-40, 30-50, 40-60, 40-90, 50-70, 60-80, 60-90, 70-90, 80-100, 100-150, 150-200, 200-250, or more than 250 contiguous amino acids with identity to a sequence of set forth in one of FIGS. 3A-3D), and optionally subject to the proviso that the MHC Class I heavy chain polypeptide does not comprise a functional transmembrane anchoring domain.
27. The T-Cell-MMP of embodiment 26, wherein the MHC Class I heavy chain polypeptide comprises a sequence of at least 20, 30, 40, 50, 80, 100, 150, 200, or 250 contiguous amino acids having identity with a portion of at least one of the amino acid sequence set forth in FIGS. 3A-3D, with the proviso that the MHC Class I heavy chain polypeptide does not comprise a functional transmembrane domain.
28. The T-Cell-MMP of any one of embodiments 10 to 27, wherein the MHC Class I heavy chain polypeptide sequence comprises a disulfide bond between a cysteine the carboxyl end portion of the α1 helix and a cysteine in the amino end portion of the α2-1 helix, and/or a cysteine or a cysteine substitution at any one or more (two, three, four, etc.) of amino acid residues 2, 7, 84, 5, 59, 116, 139, 167, 168, 170, or 171.
29. The T-Cell-MMP of embodiment 28, wherein the carboxyl end portion of the α1 helix is from about amino acid position 79 to about amino acid position 89 and the amino end portion of the α2-1 helix is from about amino acid position 134 to amino acid position 144 of the MHC Class I heavy chain, wherein the amino acid positions are determined based on the sequence of the heavy chains without their leader sequence (see, e.g., FIG. 3D).
30. The T-Cell-MMP of any one of embodiments 28 to 29, wherein the disulfide bond is between a cysteine located at positions 83, 84, or 85 and a cysteine located at position 138, 139 or 140 (e.g., from position 83 to position 138, 139 or 140, from position 84 to position 138, 139 or 140, or from position 85 to position 138, 139 or 140).

31. The T-Cell-MMP of any one of embodiments 28 to 30, wherein the disulfide bond is between a cysteine located at positions 84 and a cysteine located at position 139.
32. The T-Cell-MMP of embodiment 28, wherein the MHC Class I heavy chain sequence may have insertions, deletions and/or substitutions of 1 to 5 amino acids preceding or following the cysteines forming the disulfide bond between the carboxyl end portion of the α1 helix and the amino end portion of the α2-1 helix.
33. The T-Cell-MMP of embodiment 32, wherein when substitutions and/or insertions are present, the amino acids may be selected from any naturally occurring amino acid, or any naturally occurring amino acid except glycine and proline.
34. The T-Cell-MMP of any one of embodiments 25 to 33, wherein the MHC Class I heavy chain polypeptide amino acid sequence at positions 1 to 79 has at least 85% amino acid sequence identity (e.g., at least 90%, 95%, 98% or 99% identity, or even 100% identity) to the corresponding portion of at least one sequence set forth in FIG. 3D (e.g., the sequence has 1, 2, 3, 4, 5, 6, 7, 8, 9 or 10 amino acid insertions, deletions, or substitutions relative to sequence in FIG. 3D).
35. The T-Cell-MMP of any one of embodiments 25 to 34, wherein the MHC Class I heavy chain polypeptide amino acid sequence from position 89 to 134 (inclusive of those positions) has at least 85% amino acid sequence identity (e.g., at least 90%, 95%, 98% or 99% identity, or even 100% identity) to the corresponding portion of at least one sequence set forth in FIG. 3D (e.g., the sequence has 1, 2, 3, 4, 5 or 6 amino acid insertions, deletions, or substitutions relative to sequence in FIG. 3D).
36. The T-Cell-MMP of any one of embodiments 25 to 35, wherein the MHC Class I heavy chain polypeptide amino acid sequence from position 144 to 230 (inclusive of those positions) has at least 85% amino acid sequence identity (e.g., at least 90%, 95%, 98% or 99% identity, or even 100% identity) to the corresponding portion of at least one sequence set forth in FIG. 3D (e.g., the sequence has 1, 2, 3, 4, 5, 6, 7, 8, 9, 10, 11, 12 or 13 amino acid insertions, deletions, or substitutions relative to sequence in FIG. 3D).
37. The T-Cell-MMP of any one of embodiments 25 to 36, wherein the MHC Class I heavy chain polypeptide amino acid sequence from positions 242 to 274 (inclusive of those positions) has at least 85% amino acid sequence identity (e.g., at least 90%, 95%, 98% or 99% identity, or even 100% identity) to the corresponding portion of at least one sequence set forth in FIG. 3D (e.g., the sequence has 1, 2, 3, or 4 amino acid insertions, deletions, or substitutions relative to sequence in FIG. 3D).
38. The T-Cell-MMP of any one of embodiments 1 to 37, wherein the first polypeptide and the second polypeptide are non-covalently associated.
39. The T-Cell-MMP of any one of embodiments 1 to 37, wherein the first polypeptide and the second polypeptide are covalently linked to one another.
40. The T-Cell-MMP of embodiment 39, wherein the covalent linkage is via a disulfide bond.
41. The T-Cell-MMP of any one of embodiments 1 to 40 comprising two or more, three or more, or four or more independently selected MOD.
42. The T-Cell-MMP of embodiment 41, comprises a peptide linker between any two or more, three or more, or four or more of the two or more (e.g., two, three or four) wild-type or variant MODs.
43. The T-Cell-MMP of any one of embodiments 1 to 42, wherein the first polypeptide comprises a peptide linker between the first MHC polypeptide and at least one wild-type or variant MOD.
44. The T-Cell-MMP of any one of embodiments 1 to 42, wherein the second polypeptide comprises a peptide linker between the second MHC polypeptide and at least one wild-type or variant MOD.
45. The T-Cell-MMP of any one embodiments 2 to 44, wherein the linker has a length of from 5 amino acids to 30 amino acids (e.g., 5-10, 10-20, or 20-30 amino acids).
46. The T-Cell-MMP of embodiment 45, wherein the linker is a peptide of the formula (AAAGG)n or (GGGGS)n, where n is from 1 to 8 (e.g., 1, 2, 3, 4, 5, 6, 7, or 8, or in a range selected from 1 to 4, 3 to 6, or 4 to 8).
47. The T-Cell-MMP of any one of embodiments 1 to 46, wherein the first and second chemical conjugation sites are independently selected from:
    a) peptide sequences that act as an enzymatic modification sequence (e.g., a sulfatase motif);
    b) non-natural amino acids and/or selenocysteines;
    c) engineered amino acid chemical conjugation sites;
    d) carbohydrate or oligosaccharide moieties; and/or
    e) IgG nucleotide binding sites.
48. The T-Cell-MMP of any one of embodiments 1 to 47 wherein at least one of the one or more first and second chemical conjugation sites comprises an enzymatic modification sequence.
49. The T-Cell-MMP of embodiment 48, wherein at least one of the one or more first or second chemical conjugation site is a sulfatase motif.
50. The T-Cell-MMP of embodiment 49, wherein the sulfatase motif comprises the sequence X1Z1X2Z2X3Z3, X1(C/S) X2(P/A)X3Z3, X1CX2PX3Z3 or CX2PX3R; wherein
    Z1 is cysteine or serine;
    Z2 is either a proline or alanine residue;
    Z3 is a basic amino acid (arginine, lysine, or histidine, usually lysine), or an aliphatic amino acid (alanine, glycine, leucine, valine, isoleucine, or proline, usually A, G, L, V, or I);
    X1 is present or absent and, when present, can be any amino acid, though usually an aliphatic amino acid, a sulfur-containing amino acid, or a polar, uncharged amino acid (i.e., other than an aromatic amino acid or a charged amino acid), usually L, M, V, S or T, more usually L, M, S or V, with the proviso that, when the sulfatase motif is at the N-terminus of the target polypeptide, X1 is present; and
    X2 and X3 independently can be any amino acid, though usually an aliphatic amino acid, a polar, uncharged amino acid, or a sulfur containing amino acid (i.e., other than an aromatic amino acid or a charged amino acid), usually S, T, A, V, G or C, more usually S, T, A, V or G.
51. The T-Cell-MMP of embodiment 50, comprising one or more fGly amino acid residue in the amino acid sequence of first polypeptide or the second polypeptide.
52. T-Cell-MMP of any one of embodiments 1 to 51, wherein at least one of the one or more first or second chemical conjugation site is a Sortase A enzyme site comprising the amino acid sequence LP(X5)TG, LP(X5)TG, LP(X5)TA, LP(X5)TGG, LP(X5)TAA, LPETGG, or LPETAA positioned at the C-terminus of the first and/or second polypeptide and wherein X5 is any amino acid.
53. T-Cell-MMP of any one of embodiments 1 to 52, wherein at least one of the one or more first or second chemical conjugation site is a Sortase A enzyme site comprising at least one oligoglycine (e.g., $(G)_{2, 3, 4, or 5}$) at the amino terminus of the first and/or second polypeptides, and/or at least one oligo alanine (e.g., $(A)_{2, 3, 4, or 5}$) at the amino terminus of the first and/or second polypeptides.
54. T-Cell-MMP of any one of embodiments 1 to 53, wherein at least one of the one or more first or second chemical conjugation site is a transglutaminase site.
55. The T-Cell-MMP of embodiment 54, wherein at least one of the one or more transglutaminase site is selected from the group consisting of: LQG, LLQGG, LLQG, LSLSQG, GGGLLQGG, GLLQG, LLQ, GSPLAQSHGG, GLLQGGG, GLLQGG, GLLQ, LLQLLQGA, LLQGA, LLQYQGA, LLQGSG, LLQYQG, LLQLLQG, SLLQG, LLQLQ, LLQLLQ, LLQGR, LLQGPP, LLQGPA, GGLLQGPP, GGLLQGA, LLQGPGK, LLQGPG, LLQGP, LLQP, LLQPGK, LLQAPGK, LLQGAPG, LLQGAP, and LLQLQG.
56. The T-Cell-MMP of any one of embodiments 1 to 55, wherein at least one of the one or more first and second chemical conjugation sites comprises a selenocysteine or an amino acid sequence containing one or more independently selected non-natural amino acids.
57. The T-Cell-MMP of embodiment 56, wherein at least one of the one or more non-natural amino acid is selected from the group consisting of para-acetylphenylalanine, para-azido phenylalanine and propynyl-tyrosine.
58. The T-Cell-MMP of any one of embodiments 1 to 57, wherein at least one of the one or more first and second chemical conjugation sites comprises an engineered amino acid site.
59. The T-Cell-MMP of any one of embodiments 1 to 57, wherein at least one of the one or more first and second chemical conjugation sites comprises one or more sulfhydryl or amine groups (e.g., a cysteine substitution at any one or more (two, three, four, etc.) of amino acid residues 2, 7, 84, 5, 59, 116, 139, 167, 168, 170, or 171).
60. The T-Cell-MMP of embodiment 59, wherein at least one of the one or more sulfhydryl or amine groups results from the presence of a lysine or cysteine in the first and or second polypeptide.
61. The T-Cell-MMP of any one of embodiments 1 to 60, wherein at least one of the one or more first and second chemical conjugation sites comprises an independently selected carbohydrate, monosaccharide, disaccharide and/or oligosaccharide.
62. The T-Cell-MMP of any one of embodiments 1 to 61, wherein at least one of the one or more first and second chemical conjugation sites comprises one or more IgG nucleotide antibody binding sites.
63. The T-Cell-MMP of any one of embodiments 1 to 62, further comprising an epitope (e.g., epitope polypeptide); wherein the epitope is conjugated (covalently attached) to the first polypeptide or the second polypeptide directly, or indirectly via a spacer or linker, at first polypeptide chemical conjugation site, or at a second polypeptide chemical conjugation site, to form a T-Cell-MMP-epitope conjugate.
64. The T-Cell-MMP-epitope conjugate of embodiment 63, wherein at least one of the one or more MODs is a variant MOD.
65. The T-Cell-MMP-epitope conjugate of any one of embodiments 63 to 64, wherein the epitope is indirectly covalently bound by a linker or spacer to the first or second peptide chemical conjugation site.
66. The T-Cell-MMP-epitope conjugate of any one of embodiments 63 to 65, wherein the epitope is conjugated through a linker, selected from a peptide, or non-peptide polymer.
67. The T-Cell-MMP-epitope conjugate of embodiment 66, wherein the linker is a peptide having a length of from 10 amino acids to 30 amino acids (e.g., 10-20 or 20-30 amino acids), including, but not limited to glycine polymers (G)n, glycine-serine polymers (including, for example, (GS)n, (GSGGS)n, (GGGS)n, GGSG), (GGSGG), (GSGSG), (GSGGG)n, (GGGSG)n, (GSSSG)n, and (GGGGS)n), glycine-alanine polymers such as (AAAGG)n, alanine-serine polymers, and cysteine containing linkers such as GCGGS(G4S)n GCGASGGGGSGGGGS, GCGGSGGGGSGGGGSGGGGS, or GCGGSGGGGSGGGGS, where n is an integer of at least one, (e.g., 1, 2, 3, 4, 5, 6, 7, 8, 9, or 10).
68. The T-Cell-MMP-epitope conjugate of 67, wherein the linker is a peptide of the formula (AAAGG)n or (GGGGS)n, where n is from 1 to 8 (e.g., 1, 2, 3, 4, 5, 6, 7, or 8, or in a range selected from 1 to 4, 3 to 6, or 4 to 8).
69. The T-Cell-MMP-epitope conjugate of any one of embodiments 63 to 68, wherein:
   (a) the T-Cell-MMP-epitope conjugate binds to a first T-cell with an affinity that is at least 25% higher (1.25 times higher) than the affinity with which the T-Cell-MMP binds a second T-cell,
      wherein the first T-cell expresses on its surface a Co-MOD and a TCR that binds the epitope with an affinity of at least $10^{-7}$ M (e.g., 10 or $10^{-9}$ M), and
      wherein the second T-cell expresses on its surface the Co-MOD but does not express on its surface a TCR that binds the epitope with an affinity of at least $10^{-7}$ M (e.g., an affinity less than $10^{-7}$ M, such as $10^{-6}$ or $10^{-5}$ M); or
   (b) wherein the T-Cell-MMP-epitope conjugate binds to a first T-cell with an affinity that is at least 10% (e.g., at least 15%, at least 20%, at least 25%, at least 30%, at least 40%, at least 50%, at least 60%, at least 70%, at least 80%, at least 90%), or at least 2-fold (e.g., at least 2.5-fold, at least 5-fold, at least 10-fold, at least 15-fold, at least 20-fold, at least 25-fold, at least 50-fold, at least 100-fold, or more than 100-fold) higher than the affinity to which it binds the second T-cell,
      wherein the first T-cell that displays both i) a TCR specific for the epitope present in the T-Cell-MMP-epitope conjugate, and ii) a Co-MOD that binds to the MOD present in the T-Cell-MMP-epitope conjugate, and
      wherein the second T-cell that displays: i) a TCR specific for an epitope other than the epitope present in the T-Cell-MMP-epitope conjugate; and ii) a Co-MOD that binds to the MOD present in the T-Cell-MMP-epitope conjugate.
70. The T-Cell-MMP-epitope conjugate of any one of embodiments 63 to 68, comprising one or more variant MODs, wherein the one or more MODs exhibit reduced affinity to its Co-MOD compared to the affinity of a corresponding wild-type MOD for the Co-MOD when measured by bio-layer interferometry, (e.g., the ratio of the binding affinity of a control T-Cell-MMP-epitope conjugate (where the control comprises a wild-type MOD) to a Co-MOD to ii) the binding affinity of a T-Cell-MMP-epitope conjugate of the present disclosure comprising a variant of the wild-type MOD to the Co-MOD, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5 \times 10^2$:1, at least $10^3$:1, at least $5 \times 10^3$:1, at least $10^4$:1, at least $10^5$:1, or at least $10^6$:1).

71. The T-Cell-MMP-epitope conjugate of any one of embodiments 63 to 70, wherein the epitope is a cancer epitope, a viral epitope, or an autoepitope.

72. The T-Cell-MMP-epitope conjugate of any one of embodiments 63 to 70, wherein the epitope is a viral epitope selected from an HPV CMV or HBV epitope.

73. The T-Cell-MMP-epitope conjugate of any one of embodiments 63 to 72, wherein the epitope is a peptide fragment of 4 amino acids (aa), 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, or 20 aa in length.

74. The T-Cell-MMP-epitope conjugate of any one of embodiments 63 to 72, wherein the epitope is conjugated at a sortase, sulfatase, or transglutaminase site.

75. The T-Cell-MMP-epitope conjugate of any one of embodiments 63 to 72, wherein the epitope is conjugated through a non-natural amino acid or selenocysteine.

76. The T-Cell-MMP-epitope conjugate of any one of embodiments 63 to 72, wherein the epitope is conjugated through an engineered amino acid.

77. The T-Cell-MMP-epitope conjugate of any one of embodiments 63 to 76, further comprising one or more independently selected payloads covalently bound to one or more first and/or second chemical conjugation sites either directly or indirectly through a spacer or linker, wherein the spacer or linker is optionally cleavable (e.g., in an endosome of a mammalian cell).

78. The T-Cell-MMP-epitope conjugate of embodiment 77, wherein the payload comprises one or more independently selected biologically active agents or drugs, diagnostic agent or labels, nucleotide or nucleoside analogs, a nucleic acids or synthetic nucleic acids, or toxin, a liposome (e.g., incorporating a drugs such as such as 5-fluorodeoxyuridine), a nanoparticle, or a combination thereof.

79. The T-Cell-MMP-epitope conjugate of embodiment 77, comprising a payload selected from one or more biologically active agents or drug selected independently from the group consisting of: therapeutic agents (e.g., drug or prodrug), chemotherapeutic agents, cytotoxic agents, antibiotics, antivirals, cell cycle synchronizing agents, ligands for cell surface receptor(s), immunomodulatory agents (e.g., immunosuppressants such as cyclosporine), pro-apoptotic agents, anti-angiogenic agents, cytokines, chemokines, growth factors, proteins or polypeptides, antibodies or an antigen binding fragment thereof, enzymes, proenzymes, hormones or combinations thereof.

80. The T-Cell-MMP-epitope conjugate of embodiment 77, comprising a payload selected from one or diagnostic agent or labels, selected independently from the group consisting of a photodetectable labels (e.g., dyes, fluorescent labels, phosphorescent labels, luminescent labels) and radiolabels, an imaging agents, a contrast agents, a paramagnetic labels, ultrasound labels and combinations thereof.

81. The T-Cell-MMP-epitope conjugate of embodiment 77, comprising a payload selected from one or more nucleotides or nucleosides, nucleoside analogs, nucleic acids, or synthetic nucleic acids selected from the group consisting of single or double stranded DNA, single or double stranded RNA, DNA/RNA hybrids, ribozymes, siRNA, antisense RNA, cDNA, spherical nucleic acids, and plasmids.

82. The T-Cell-MMP-epitope conjugate of embodiment 77, comprising a payload selected from one or more liposomes and/or nanoparticles selected independently from the groups consisting of micelles, metal nanoparticles (e.g., gold nanoparticles), and non-metal nanoparticles any or all of which may be conjugated to nucleic acids and or proteins.

83. The T-Cell-MMP-epitope conjugate of embodiment 77, wherein the payload is conjugated via linker have from 1 to 20, (e.g., 1-2, 2-4, 5-10 or 10-20) independently selected alpha, beta, delta, gamma amino acids, or a combination thereof; or wherein the linker is a peptide of the formula poly-glycine poly-alanine, a random poly glycine/alanine copolymer, or poly (GGGGS)n where n is 1, 2, 3, 4, 5, 6, 7, or 8.

84. The T-Cell-MMP-epitope conjugate of embodiment 77, wherein the payload is attached to a chemical conjugations site by a spacer, wherein the spacer comprises two or more carbon atoms joined by a single or double bond, a disulfide bond, a carbon-oxygen bond, a carbon nitrogen bond or a combination thereof.

85. The T-Cell-MMP-epitope conjugate of embodiment 77, wherein the payload is attached to a chemical conjugations site by a spacer, wherein the spacer results from the action of a homofunctional (e.g., homobifunctional) crosslinker or a heterofunctional (e.g., heterobifunctional) crosslinker.

86. The T-Cell-MMP-epitope conjugate of any one of embodiments 77-85, wherein the payload is bound by a linker and can be removed from the T-Cell-MMP by cleavage of the linker or spacer within a human T-cell endosome, or by reduction with excess of thiol reducing agent (e.g., dithiothreitol, DTT).

87. A composition comprising the T-Cell-MMP-epitope conjugate of any one of embodiments 63-85.

88. A composition comprising:
   a) the T-Cell-MMP-epitope conjugate of any one of embodiments 63 to 87; and
   b) a pharmaceutically acceptable excipient.

89. A method of modulating an immune response in an individual, the method comprising: administering to the individual an effective amount of the T-Cell-MMP-epitope conjugate of any one of embodiments 63 to 87.

90. A method of delivering an immunomodulatory polypeptide (MOD) to a target T-cell (e.g., a regulatory T-Cell or cytotoxic T-cell) in a epitope-selective or epitope-selective/specific manner in vitro, or to an individual in vivo, comprising:
   contacting a T-Cell-MMP-epitope conjugate of any one of embodiments 63 to 86 with the T-Cell in vitro, or administering the T-Cell-MMP-epitope conjugate of any one of embodiments 63 to 86 or a composition comprising the T-Cell-MMP-epitope conjugate of any one of embodiments 87 to 88 to the individual;

wherein the target T-cells are specific for the epitope present in the T-Cell-MMP-epitope conjugate.
91. The method of embodiment 90, wherein the MOD is a wild-type or variant MOD selected from an IL-2, 4-1BBL, PD-L1, CD70, CD80, CD86, ICOS-L, OX-40L, FasL, ICAM, or PD-L2 polypeptide.
92. The method of any one of embodiments 89 to 91, wherein the individual is a human.
93. The method of any one of embodiments 89 to 92, wherein said modulating comprises increasing a cytotoxic T-cell response to a cancer cell.
94. The method of any one of embodiments 89 to 93, wherein said modulating comprises reducing a T-cell response to an autoantigen.
95. The method of any one of embodiments 89 to 94, wherein said administering is rectal, nasal, oral, and other enteral and/or parenteral routes of administration.
96. The method of any one of embodiments 89 to 95, wherein said administering is intratumoral, peritumoral, intramuscular, intratracheal, intracranial, subcutaneous, intralymphatic, intradermal, topical, intravenous, and/or intraarterial.
97. One or more nucleic acids comprising nucleotide sequences encoding the first and the second polypeptide of the T-Cell-MMP of any one of embodiments 1 to 62.
98. The one or more nucleic acids of embodiment 97, wherein the first polypeptide is encoded by a first nucleotide sequence, the second polypeptide is encoded by a second nucleotide sequence, and wherein the first and the second nucleotide sequences are present in a single nucleic acid (e.g., a plasmid).
99. The one or more nucleic acids of any one of embodiments 97 to 98, wherein the first nucleotide sequence and the second nucleotide sequence are operably linked to a transcriptional control element.
100. The one or more nucleic acids of embodiment 97, wherein the first polypeptide is encoded by a first nucleotide sequence present in a first nucleic acid (e.g., a first plasmid), and the second polypeptide is encoded by a second nucleotide sequence present in a second nucleic acid (e.g., a second plasmid).
101. The one or more nucleic acids of any one of embodiments 98 or 100, wherein the first nucleotide sequence is operably linked to a first transcriptional control element and the second nucleotide sequence is operably linked to a second transcriptional control element.
102. A composition comprising: the one or more nucleic acids of any one of embodiments 97-101.
103. A method of making a T-Cell-MMP of any one of embodiments 1 to 62, the method comprising:
  a) providing a nucleic acid encoding the first MHC polypeptide, a nucleic acid encoding the second MHC polypeptide, and nucleic acid(s) encoding one or more independently selected MODS, and optionally nucleic acids encoding any one or more of an immunoglobulin (Ig) Fc polypeptide, a non-Ig polypeptide scaffold, and/or one or more independently selected linkers;
  b) conducting steps i and ii in any order, those steps comprising:
    i) modifying at least one of the provided nucleic acids to include (engineer into the coding sequence) one or more chemical conjugation sites into one of the provided nucleic acid, other than the nucleic acid(s) encoding the one or more independently selected MODs; and
    ii) incorporating the provided nucleic acids into first nucleic acid encoding the first polypeptide and a second nucleic acid encoding the second polypeptide;
  c) expressing the polypeptides encoded by the first and second nucleic acids to obtain a T-Cell-MMP to obtain the first polypeptide and the second polypeptide.
104. The method of embodiment 103, wherein the one or more chemical conjugation site are selected independently from peptide sequences that act as an enzymatic modification sequence, non-natural amino acids and/or selenocysteines, engineered amino acid chemical conjugation sites; IgG nucleotide binding sites.
105. The method of embodiment 104, wherein modifying at least one of the provided nucleic acids comprises modifying one or more of provided nucleic acids, other than the nucleic acid(s) encoding MOD(s), to encode as polypeptide sequence including a naturally occurring amino acid at a location where it is not present the peptide sequence of wild-type first MHC polypeptide, the second MHC polypeptide, the MODs, or in any optional immunoglobulin (Ig) Fc polypeptide, non-Ig polypeptide scaffold, or linker.
106. The method of any of embodiments 103 to 105, further comprising:
  a) providing an epitope peptide bearing a reactive group, or an epitope peptide conjugated to an optional linker bearing a reactive group;
  b) contacting the epitope peptide, or an epitope peptide conjugated to an optional linker, with a T-Cell-MMP of any one of embodiments 103 to 105, under conditions where a covalent bond is formed between the reactive group and a chemical conjugation site; thereby producing a T-Cell-MMP-epitope conjugate.
107. The method of embodiment 106, wherein covalent bond is selectively formed between the reactive group and a chemical conjugation site in the first MHC polypeptide or a linker attached to the first MHC polypeptide.
108. The method of embodiment 107, wherein the first MHC polypeptide comprises a beta-2-microglobulin (β2M) polypeptide that has an optional peptide linker attached to its N-terminus.
109. The method of 108, wherein the β2M polypeptide is at the N-terminus of the first polypeptide.
110. The method of any one of embodiments 103 to 109, further comprising contacting a payload bearing a reactive group with a T-Cell-MMP or a T-Cell-MMP-epitope conjugate to form a payload conjugate of the T-Cell-MMP or a T-Cell-MMP-epitope conjugate.
111. The T-Cell-MMP-epitope conjugate of any of embodiments 63 to 86, wherein the chemical conjugation site to which the epitope was covalently bound to create the T-Cell-MMP-epitope is not located in an amino acid sequence having 100% amino acid identity to:
  the Fc polypeptide sequence in FIGS. 2A-2G;
  the MHC Class I heavy chain polypeptides sequences in FIGS. 3A-3D; or
  the β-2 microglobulin polypeptide sequences in FIG. 4.
112. The T-Cell-MMP-epitope conjugate of any of embodiments 63 to 86, wherein the chemical conjugation site to which the epitope was covalently bound to create the T-Cell-MMP-epitope is not located in a 10, 20, 30, 40, or 50 amino acid long sequence having 100% amino acid identity to any portion of any one of:
the Fc polypeptide sequence in FIGS. 2A-2G;
the MHC Class I heavy chain polypeptides sequences in FIGS. 3A-3D; or
the β-2 microglobulin polypeptide sequences in FIG. 4.

113. The T-Cell-MMP-epitope conjugate of any of embodiments 63-86, wherein the chemical conjugation site to which the epitope was covalently bound to create the T-Cell-MMP-epitope is not an amino acid appearing in a 5, 6, 7, 8, 9, 10, 20, 30, 40, 50, 60, or 70 amino acid long sequence having 100% amino acid identity to any portion of any one of:
the Fc polypeptides in FIGS. 2A-2G;
the MHC Class I heavy chain polypeptides in FIGS. 3A-3D; or
the β-2 microglobulin polypeptide sequences in FIG. 4.

114. The T-Cell-MMP-epitope conjugate of any of embodiments 63-86, wherein the chemical conjugation site to which the epitope was covalently bound to create the T-Cell-MMP-epitope conjugate is not a lysine, cysteine, serine, threonine, arginine, aspartic acid, glutamic acid, asparagine, or glutamine located in an 10, 20, 30, 40, 50, 60, or 70 amino acid long sequence having 100% amino acid identity to any portion of any one of:
the Fc polypeptide sequence in FIGS. 2A-2G;
the MHC Class I heavy chain polypeptides sequences in FIGS. 3A-3D; or
the β-2 microglobulin polypeptide sequences in FIG. 4.

115. A polypeptide comprising,
a mature β2M polypeptide sequence (lacking its signal sequence) having an N-terminus and a C-terminus;
an optional linker; and
one or more chemical conjugation sites within the sequence of the mature β2M polypeptide or attached to the mature β2M polypeptide via an optional linker.

116. The polypeptide of embodiment 115, wherein the mature β2M polypeptide has a sequence with at least 85%, (e.g., at least 90%, 95%, 98% or 99% identity, or even 100%) amino acid sequence identity to the sequence of a mature β2M provided in FIG. 4; wherein identity between the β2M polypeptide and the corresponding sequences in FIG. 4 is determined without consideration of the added sulfatase motif and any optional linker sequences present.

117. The polypeptide of any of embodiments 115 to 116, wherein the β2M polypeptide sequence comprises, consists essentially of, or consists of a sequence of at least 20, 30, 40, 50, 60, 70, 80, 90 or 99 contiguous amino acids having identity with at least a portion of one of the amino acid sequence set forth in FIG. 4 (e.g., a sequence having 20-99, 20-40, 30-50, 40-60, 40-90, 50-70, 60 to 80, 60-99, 70-90, or 79-99 contiguous amino acids with identity to a sequence of mature β2M lacking its signal sequence set forth in FIG. 4).

118. The polypeptide of any one of embodiments 115 to 117, wherein the β2M polypeptide sequence comprises a cysteine at one, two or more of amino acid positions 10, 11, 12, 13, or 14 of the mature β2M polypeptide sequence.

119. The polypeptide of embodiment 118, wherein the first 12 amino acids of the β2M polypeptide sequence are IQRTPKIQVYSC.

120. The polypeptide of any of embodiments 115 to 119, wherein the sulfatase motif comprises the sequence X1Z1X2Z2X3Z3, X1(C/S) X2(P/A)X3Z3, X1CX2PX3Z3 or CX2PX3R; wherein
Z1 is cysteine or serine;
Z2 is either a proline or alanine residue;
Z3 is a basic amino acid (arginine, lysine, or histidine, usually lysine), or an aliphatic amino acid (alanine, glycine, leucine, valine, isoleucine, or proline, usually A, G, L, V, or I);
X1 is present or absent and, when present, can be any amino acid, though usually an aliphatic amino acid, a sulfur-containing amino acid, or a polar, uncharged amino acid (i.e., other than an aromatic amino acid or a charged amino acid), usually L, M, V, S or T, more usually L, M, S or V, with the proviso that, when the sulfatase motif is at the N-terminus of the target polypeptide, X1 is present; and
X2 and X3 independently can be any amino acid, though usually an aliphatic amino acid, a polar, uncharged amino acid, or a sulfur containing amino acid (i.e., other than an aromatic amino acid or a charged amino acid), usually S, T, A, V, G or C, more usually S, T, A, V or G.

121. The polypeptide of any of embodiments 115 to 120, wherein the sulfatase motif is linked directly, or indirectly via a linker, to the N-terminus of the β2M polypeptide sequence.

122. The polypeptide of any of embodiments 115 to 121, further comprising a signal sequence, or a signal sequence and a linker, wherein the signal sequence is the a amino terminal most element of the polypeptide.

123. The polypeptide of any one of embodiments 115 to 122, wherein the any one or more linkers comprises, consists essentially of, or consists of an independently selected polypeptide.

124. The polypeptide of embodiment 123, where any one or more of the linkers is selected independently from a peptides of formula (AAAGG)n or (GGGGS)n, where n is from 1 to 8 (e.g., 1, 2, 3, 4, 5, 6, 7, or 8, or in a range selected from 1 to 4, 3 to 6, or 4 to 8).

125. The polypeptide of embodiment 123, wherein the poly peptide has the sequence:

MSRSVALAVLALLSLSGLEALCTPSRGGGGSIQRTPKIQVYSCHPAENGK

SNFLNCYVSGFHPSDIEVDLLKNGERIEKVEHSDLSFSKDWSFYLLYYTE

FTPTEKDEYACRVNHVTLSQPKIVKWDRDM or the sequence

MSRSVALAVLALLSLSGLEAGGGGSLCTPSRGGGGSIQRTPKIQVYSCHP

AENGKSNFLNCYVSGFHPSDIEVDLLKNGERIEKVEHSDLSFSKDWSFYL

LYYTEFTPTEKDEYACRVNHVTLSQPKIVKWDRDM.

126. The polypeptide of any of embodiments 115 to 125, wherein a serine or cysteine of the sulfatase motif has been converted to an fGly (formylglycine) residue.

127. The polypeptide of embodiment 126, further comprising an epitope covalently bound to the polypeptide through a chemical reaction with the fGly residue (e.g., the reaction of a thiosemicarbazide, aminooxy, hydrazide, or hydrazino modified epitope polypeptide with the aldehyde of the fGly).

128. The polypeptide of embodiment 127, wherein the epitope comprises a hydrazinyl indole group for reaction with the aldehyde of the fGly residue.

129. The polypeptide of embodiment 127 or 128, wherein the epitope is a polypeptide epitope.
130. A composition comprising a polypeptide of any one of embodiments 115 to 129.
131. A composition comprising a polypeptide of any one of embodiments 127 to 129 and a pharmaceutically acceptable carrier.
132. A polypeptide comprising, in order from N-terminus to C-terminus,
    a mature MHC Class 1 heavy chain polypeptide sequence (lacking its signal sequence);
    an optional linker; and
    an immunoglobulin (Ig) Fc polypeptide or a non-Ig polypeptide scaffold.
133. The polypeptide of embodiment 132, wherein the MHC Class I heavy chain polypeptide has a sequence with at least 85%, (e.g., at least 90%, 95%, 98% or 99% identity, or even 100%) amino acid sequence identity to the sequence provided in FIG. 3D; wherein identity between the MHC Class I heavy chain polypeptide and the corresponding sequences in FIG. 3D is determined without consideration of the (Ig) Fc polypeptide and any optional linker present.
134. The polypeptide of any of embodiments 132 to 133, wherein the MHC Class I heavy chain polypeptide comprises, consists essentially of, or consists of a sequence of at least 20, 30, 40, 50, 60, 70, 80, 90 or 100 contiguous amino acids having identity with at least a portion of one of the amino acid sequence set forth in FIG. 3D (e.g., a sequence having 20-100, 20-40, 30-50, 40-60, 40-90, 50-70, 60-80, 60-90, 70-90, or 80-100 contiguous amino acids with identity to a sequence of MHC Class I heavy chain polypeptide set forth in FIG. 3D).
135. The polypeptide of embodiment 134, wherein the MHC Class I heavy chain polypeptide comprises one, two or three sequences selected from the group consisting of:
    i) a sequence from about amino acid position 79 to about amino acid position 89;
    ii) a sequence from about amino acid position 134 to about amino acid position 144; and
    iii) a sequence from about amino acid position 231 to about amino acid position 241 of the MHC Class I heavy chain sequences set forth in FIG. 3D.
136. The polypeptide of embodiment 135, wherein the MHC Class I heavy chain polypeptide comprises:
    i) the sequence from about amino acid position 79 to about amino acid position 89; and
    ii) the sequence from about amino acid position 134 to about amino acid position 144;
wherein one positions 83, 84, or 85 have been substituted with cysteine that forms an intrachain disulfide bond with a cysteine substituted at one of positions 138, 139, or 140.
137. The polypeptide of any of embodiments 135 to 136, wherein the polypeptide comprises a MHC Class I heavy chain polypeptide sequence from about amino acid position 231 to about amino acid position 241 of the MHC Class I heavy chain sequences set forth in FIG. 3D wherein one of positions 235, 236 or 237 have been substituted by a cysteine.
138. The polypeptide of any one of embodiments 132 to 137, wherein any one or more of the linkers is selected independently from peptides of formula (AAAGG)n or (GGGGS)n, where n is from 1 to 8 (e.g., 1, 2, 3, 4, 5, 6, 7, or 8, or in a range selected from 1 to 4, 3 to 6, or 4 to 8).
139. The polypeptide of embodiment 137, wherein the polypeptide has the sequence:

MYRMQLLSCIALSLALVTNSAPTSSSTKKTQLQLEALLLDLQMILNGINN

YKNPKLTRMLTAKFYMPKKATELKHLQCLEEELKPLEEVLNLAQSKNFHL

RPRDLISNINVIVLELKGSETTFMCEYADETATIVEFLNRWITFCQSIIS

TLTGGGGSGGGGSGGGGSGGGGSAPTSSSTKKTQLQLEALLLDLQMILNG

INNYKNPKLTRMLTAKFYMPKKATELKHLQCLEEELKPLEEVLNLAQSKN

FHLRPRDLISNINVIVLELKGSETTFMCEYADETATIVEFLNRWITFCQS

IISTLTGGGGSGGGGSGGGGSGGGGSGS*HSMRYFFTSVSRPGRGEPRHAV*

*GYVDDTQFVRFDSDAASQRMEPRAPWIEQEGPEYWDGETRKVKAHSQTHR*

*VDLGTLRGCYNQSEAGSHTVQRMYGCDVGSDWRFLRGYHQYAYDGKDYIA*

*LKEDLRSWTAADMCAQTTKHKWEAAHVAEQLRAYLEGTCVEWLRRYLENG*

*KETLQRTDAPKTHMTHHAVSDHEATLRCWALSFYPAEITLTWQRDGEDQT*

*QDTELVETRPCGDGTFQKWAAVVVPSGQEQRYTCHVQHEGLPKPLTLRWE*

AAAGGDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK.

140. A composition comprising a polypeptide of any one of embodiments 132 to 139.
141. A composition comprising a polypeptide of any one of embodiments 132 to 139 and a pharmaceutically acceptable carrier.
142. A method of preparing a T-Cell-MMP-epitope conjugate comprising:
    a) incorporating a nucleotide sequence encoding chemical conjugation site into a nucleic acid sequence encoding a first polypeptide and/or a second polypeptide of a T-Cell-MMP, to introduce a first polypeptide chemical conjugation site and/or a second polypeptide chemical conjugation site;
    b) introducing the nucleic acid into a cell to express the T-Cell-MMP and obtain a T-Cell-MMP having a first and/or second polypeptide chemical conjugation site, and optionally purifying the T-Cell-MMP (partially or completely);
    c) where the chemical conjugation site(s) require enzymatic activation or chemical conversion, activating or converting the chemical conjugation site(s) (e.g., with an enzyme); and
    d) contacting the T-Cell-MMP having a first and/or second polypeptide chemical conjugation site with an epitope (or an epitope with an attached linker) capable of undergoing a reaction with the first or second polypeptide chemical conjugation site under reaction conditions suitable to cause formation of a covalent bond (e.g., in the presence of an enzyme or catalyst) between the first or second polypeptide chemical conjugation site and the epitope (or the linker attached to the epitope) to produce the T-Cell-MMP-epitope conjugate.

143. The method of embodiment 142, wherein the chemical conjugation site is a sulfatase motif (e.g., a sulfatase motif of Formula (I) or (II) such as X1CX2PX3Z3; CX1PX2Z3).

144. The method of embodiment 143, wherein the cell:
  i) expresses a FGE and converts the serine or cysteine of the sulfatase motif to a FGly, or
  ii) does not express a FGE that converts a serine or cysteine of the sulfatase motif to a FGly, and the method further includes contacting the T-Cell-MMP having a first and/or second polypeptide chemical conjugation site with a FGE that converts the serine or cysteine of the sulfatase motif to a FGly; and
  iii) contacting the FGly-containing polypeptides with an epitope that has been functionalized with a group that forms a covalent bond between the aldehyde of the FGly and the epitope,
thereby forming T-Cell-MMP-epitope conjugate.

XII. Examples

Example 1. Preparation of a T-Cell-MMP with a Formyl Glycine (fGly) Chemical Conjugation Site This prophetic example provides for the preparation of a T-Cell-MMP having a first polypeptide containing a fGly chemical conjugation site and a second polypeptide. the first and second polypeptides taken together form a T-Cell-MMP into which an epitope can be conjugated.

The polypeptides are prepared by assembling the coding sequences of the first and second polypeptides in expression cassettes that include constitutive or inducible promoter elements for driving the expression of mRNA molecules encoding the first and second polypeptides along with polyadenylation and stop codons. The expression cassettes are assembled into separate vectors (plasmid, viral etc.), or a single vector, for transient expression from a suitable cell line (e.g., CHO, HEK, Vero, COS, yeast etc.). Alternatively, the assembled cassettes are stably integrated into such cells for constitutive or induced expression of the first and second polypeptides.

The linkers, shown in the first and second polypeptides of the T-Cell-MMP polypeptides described below are optional. When present the linkers are an amino acid sequence (e.g., from 1 to 50 amino acids such as AAAGG (SEQ ID NO:75) or (GGGGS)$_n$ where n is 1, 2, 3, 4, 5, 6, 7, 8, 9, or 10, (SEQ ID NO:76). Where more than one linker sequence is shown the linker sequence selected for each location may be the same or different from the linker sequence selected other any other site where a linker appears.

1A. First Polypeptides

The first polypeptide of this example comprises from the N-terminus to the C-terminus a) a leader sequence, b) sulfatase motif to introduce an fGly chemical coupling site, c) an optional linker, and d) a β2M polypeptide. Following the action of a FGE first peptides have a cysteine in the motif converted to a formylglycine (fGly) residue. Accordingly, mRNAs encode the first polypeptides having the overall sequences (shown prior to leader sequence removal and FGE action to create the fGly residue):

```
MSRSVALAVLALLSLSGLEA-linker-X1Z1X2Z2X3Z3IQRTP (remainder of a β2M e.g., from FIG. 4);

MSRSVALAVLALLSLSGLEA-linker-X1Z1X2Z2X3Z3-linker-

IQRTP(remainder of a β2M e.g., from FIG. 4);
```

```
MSRSVALAVLALLSLSGLEA-linker-X1Z1X2Z2X3RTP (remainder of a β2M e.g., from FIG. 4);

MSRSVALAVLALLSLSGLEA-linker-X1CX2PX3IQRTP (remainder of a β2M e.g., from FIG. 4);

MSRSVALAVLALLSLSGLEA-linker-X1CX2PX3Z3-linker-

IQRTP(remainder of a β2M e.g., from FIG. 4);
or

MSRSVALAVLALLSLSGLEA-linker-X1CX2PX3RTP(K/Q)

IQVYS . . . (remainder of a β2M e.g., from FIG. 4).
```

Within the above-mentioned first peptide, the sequence MSRSVALAVLALLSLSGLEA (SEQ ID NO:167) serves as the signal sequence and is removed during cellular processing during maturation of the polypeptide. The residues of the sulfatase motif, (X1, Z1, X2, Z2, X3, and Z3), are described in Section I.A above. A map of such a first polypeptide is shown in FIG. 9 part A, where the sulfatase motif (LCTPSR) is shown within the G$_4$S (GGGGS) SEQ ID NO:76 linker to emphasize that linkers may be placed before and/or after the motif. The map also indicates the location of a potential amino acid substitution at position 12 in the β2M polypeptide changing an arginine to a cysteine (R12C). Below the map appears an exemplary peptide sequence for a first polypeptide including the leader sequence. The β2M polypeptide is shown in bold with italics and the sulfatase sequence (LCTPSR) is shown in bold.

1B. Second Polypeptides

The second polypeptide of this example comprises from N-terminus to C-terminus a) a leader sequence, b) a MOD polypeptide(s), c) an optional linker, d) a MHC Class 1 heavy chain polypeptide, e) an optional linker, and f) an immunoglobulin Fc region.

The mRNAs encode the second polypeptide polypeptides having the overall structure: signal sequence-linker-IL2 polypeptide-linker-IL2 polypeptide-MHC Class 1 heavy chain poly peptide-linker-immunoglobulin heavy chain Fc polypeptide where the signal sequence is a human IL2 signal sequences. A map of such a second polypeptide is shown in FIG. 9, part B, where polypeptide contains the signal sequence MYRMQLLSCIALSLALVTNS (SEQ ID NO:168), a repeat of the human IL2 MOD (shown in bold) separated by a linker with four G$_4$S (GGGGS) repeats (SEQ ID NO:76). The polypeptide also contains a huma HLA-A polypeptide (shown in bold and italics) and a human IgG1 Fc polypeptide. Indicated below the map are the locations of a potential amino acid substitutions including the location of the Y84C, A139C, and the A236C cysteine substitutions. The Y84C and A139C substitutions permit a stabilizing disulfide bond to form between the region near the carboxyl end of the HLA α1 helix and the region around the amino terminus of the HLA α2-1 helix. The cysteine resulting from the A236C substitution can form an interchain disulfide bond with a cysteine at, for example position 12, of the β2M polypeptide in the first polypeptide. Below the map appears an exemplary peptide sequence for a second polypeptide including the leader sequence.

1C. Expression and Maturation of the First Second Polypeptides

As indicated above, first and second polypeptides are prepared by transient or stable expression in a suitable cell line (e.g., a eukaryotic or mammalian cell line). Processing in the cell removes the signal sequence and forms a fGly residue when the cells employed for polypeptide expression also express an FGE that is capable converting a cysteine or serine of the sulfatase motif to a formylglycine (fGly) residue.

T-Cell-MMPs can be processed by cells as a complex that includes the first and second polypeptide and a bound (non-covalently associated) epitope or null polypeptide. The introduction of the disulfide bond in the HLA heavy chain polypeptide between the region at the carboxyl end of the α1 helix and the region at the amino terminus of the α2-1 helix permits expression in the absence of an epitope polypeptide associated with the first and second polypeptides. In addition, as the T-Cell-MMP complexes do not contain a membrane anchor region, the complex is released from the expressing cell in soluble form.

Cell culture media containing the expressed T-Cell-MMP is collected after suitable levels of the expressed T-Cell-MMP have been attained. Where the cells used for expression did not have FGE activity the T-Cell-MMPs are treated with an FGE capable of forming the fGly residue at the sulfatase motif. Isolation and concentration of the T-Cell-MMP form the media is conducted using, for example, chromatographic methods to produce a purified T-Cell-MMP having a fGly chemical conjugation site at or near the amino terminus of the first polypeptide of the complex. The resulting T-Cell-MMP has the general structure shown in FIG. 5, part B, where the MHC-1 in the first polypeptide is the β2M polypeptide, the second polypeptide "MOD" is the pair of IL2 polypeptides, the MHC-2 is a HLA-A polypeptide, and Fc is a IGg1 heavy chain constant region. The disulfide bond between the first and second polypeptides results from the cysteines arising from the β2M polypeptide R12C and HLA-A A236C substitutions.

Example 2. Preparation of a T-Cell-MMP-Epitope Conjugate

Epitope polypeptides are conjugated to the fGly polypeptides prepared in Example 1 by forming on the epitope peptide a group capable of reacting with the fGly aldehyde in the T-Cell-MMP. While thiosemicarbazide, aminooxy, hydrazide, or hydrazino aldehyde reactive groups can be utilized, this example is illustrated by the use of a hydrazinyl group attached to an indole, where the epitope peptide (R in FIG. 8) is covalently bound, directly or indirectly, to the nitrogen of the indole ring. As shown in FIG. 8, depending on the specific structure of the hydrazinyl indole, contacting the epitope peptide (R) with the fGly containing polypeptide of the T-Cell-MMP (circled polypeptide) results in the T-Cell-MMP and epitope become covalent linked through the formation of a tricyclic group, thereby forming the T-Cell-MMP-epitope conjugates. The conjugate has the generalized structure of embodiment B in FIG. 6, where the tricyclic group covalently linking the epitope and the β2M polypeptide is not shown.

Example 3. T-Cell-MMPs Conjugated to HBV Epitopes

Non-limiting examples of T-Cell-MMP constructs that can be made to produce T-Cell-MMP complexes included those depicted in FIGS. 10A-10D and FIGS. 11A-11E. Although exemplified by specific complexes, any combination of a peptide from FIG. 10 and a peptide from FIG. 11 can be used to form a T-Cell-MMP that can be conjugated to an epitope peptide to form a T-Cell-MMP complex. Each of the peptides shown in IG. 10 contains amino acids making up a human IL-2 sequence; a HLA-A heavy chain sequence, and an IgG scaffold. The HLA-A sequence is stabilized by the incorporation of cysteines at amino acids 89 and 139, as described above, to form a stabilizing intrachain disulfide bond, and a cysteine at amino acid 236, which can form an interchain disulfide with the β2M containing polypeptide described next. In each in instance the polypeptide shown in FIG. 11 contains a β2M sequence with a cysteine substitution at position 12 for interchain disulfide formation and a sulfatase motif (SEQ ID NO:45) flanked by optional linkers: $(linker)_{0-4}$-X1Z1X2Z2X3Z3-$(linker)_{0-4}$. The sulfatase motif amino acids may be selected as described above (e.g., as in Examples 1 and 2) to include sulfatase amino acid sequences such as LCTPSR. The linkers on the amino and carboxyl side of the sulfatase motif are selected independently, and when present, may be any desired amino acid sequence such as 1-4 repeats of GGGGS (SEQ ID NO:76). Expression in, for example, mammalian cells results in the formation of the T-Cell-MMP complex comprising the HLA-A heavy chain and the peptide comprising the sulfatase and β2M sequences. An epitope peptide, such as an HBV epitope peptide selected from: LIMPARFYPK (SEQ ID NO:91); AIMPARFYPK (SEQ ID NO:92); YVNVNMGLK (SEQ ID NO:93); FLPSDFFPSV (SEQ ID NO:84); STLPETTVV (SEQ ID NO:90); or other HBV epitopes listed in the Table of HBV Epitopes can be conjugated to the first and second peptide complex by formation of a formyl glycine in the sulfatase motif followed by conjugating that formyl group to an appropriately modified peptide (e.g., a peptide bearing a thiosemicarbazide, aminooxy, hydrazide, or hydrazino group such as a hydrazinyl indole at or near its carboxyl terminus).

In one non-limiting example of a T-Cell-MMP the complex comprises the MHC heavy chain containing the amino acid sequence designated 1775' in FIG. 10A; and the second polypeptide is the polypeptide designated 1783' in FIG. 11A. That polypeptide will in some cases not include the signal peptide (MYRMQLLSCIALSLALVTNS (SEQ ID NO:168)), and the polypeptide containing the β2M sequence will in some cases not include the leader peptide (MSRSVA-LAVLALLSLSGLEA (SEQ ID NO:167)). In some cases, the epitope peptide is other than the LIMPARFYPK (SEQ ID NO:91) peptide depicted in FIG. 11A.

In a second non-limiting example of a T-Cell-MMP the complex comprises the MHC heavy chain containing the amino acid sequence designated 1777' in FIG. 10B; and the second polypeptide is the polypeptide designated 1783' in FIG. 11A. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the LIMPARFYPK (SEQ ID NO:91) peptide depicted in FIG. 11A.

In a third non-limiting example of a T-Cell-MMP the complex comprises the MHC heavy chain containing the amino acid sequence designated 1779' in FIG. 10C; and the second polypeptide is the polypeptide designated 1783' in FIG. 11A. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA SEQ ID NO:167)). In some cases, the epitope peptide is other than the LIMPARFYPK (SEQ ID NO:91) peptide depicted in FIG. 11A.

In a fourth non-limiting example of a T-Cell-MMP the complex comprises the MHC heavy chain containing the amino acid sequence designated 1781' in FIG. 10D; and the second polypeptide is the polypeptide designated 1783' in FIG. 11A. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the LIM-PARFYPK (SEQ ID NO:91) peptide depicted in FIG. 11A.

In a fifth non-limiting example of a T-Cell-MMP the complex comprises the MHC heavy chain containing the amino acid sequence designated 1775' in FIG. 10A; and the second polypeptide is the polypeptide designated 1784' in FIG. 11B. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the AIM-PARFYPK (SEQ ID NO:92) peptide depicted in FIG. 11B.

In a sixth non-limiting example of a T-Cell-MMP the complex comprises the MHC heavy chain containing the amino acid sequence designated 1777' in FIG. 10B; and the second polypeptide is the polypeptide designated 1784' in FIG. 11B. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the AIM-PARFYPK (SEQ ID NO:92) peptide depicted in FIG. 11B.

In a seventh non-limiting example of a T-Cell-MMP the complex comprises the MHC heavy chain containing the amino acid sequence designated 1779' in FIG. 10C; and the second polypeptide is the polypeptide designated 1784' in FIG. 11B. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the AIM-PARFYPK (SEQ ID NO:92) peptide depicted in FIG. 11B.

In an eighth non-limiting example of a T-Cell-MMP the complex comprises the MHC heavy chain containing the amino acid sequence designated 1781' in FIG. 10D; and the second polypeptide is the polypeptide designated 1784' in FIG. 11B. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the AIM-PARFYPK (SEQ ID NO:92) peptide depicted in FIG. 11B.

In a ninth non-limiting example of a T-Cell-MMP the complex comprises the MHC heavy chain containing the amino acid sequence designated 1775' in FIG. 10A; and the second polypeptide is the polypeptide designated 1785' in FIG. 11C. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the YVNVNMGLK (SEQ ID NO:93) peptide depicted in FIG. 11C.

In a tenth non-limiting example of a T-Cell-MMP the complex comprises the MHC heavy chain containing the amino acid sequence designated 1777' in FIG. 10B; and the second polypeptide is the polypeptide designated 1785' in FIG. 11C. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the YVNVNMGLK (SEQ ID NO:93) peptide depicted in FIG. 11C.

In an eleventh non-limiting example of a T-Cell-MMP the complex comprises the MHC heavy chain containing the amino acid sequence designated 1779' in FIG. 10C; and the second polypeptide is the polypeptide designated 1785' in FIG. 11C. That polypeptide will in some cases not include the signal peptide (MYRMQLLSCIALSLALVTNS (SEQ ID NO:168)); and the polypeptide containing the β2M sequence will in some cases not include the leader peptide (MSRSVALAVLALLSLSGLEA (SEQ ID NO:167)). In some cases, the epitope peptide is other than the YVNVNMGLK (SEQ ID NO:93) peptide depicted in FIG. 11C.

In a twelfth non-limiting example of a T-Cell-MMP the complex comprises the MHC heavy chain containing the amino acid sequence designated 1781' in FIG. 10D; and the second polypeptide is the polypeptide designated 1785' in FIG. 11C. That polypeptide will in some cases not include the signal peptide (MYRMQLLSCIALSLALVTNS (SEQ ID NO:168)), and the polypeptide containing the β2M sequence will in some cases not include the leader peptide (MSRSVALAVLALLSLSGLEA (SEQ ID NO:167)). In some cases, the epitope peptide is other than the YVNVNMGLK (SEQ ID NO:93) peptide depicted in FIG. 11C.

Example 4. T-Cell-MMPs Conjugated to CMV Epitopes

A first polypeptide comprising, in order, a signal peptide (MSRSVALAVLALLSLSGLEA (SEQ ID NO:167)), a sulfatase motif (SEq ID NO:45) flanked by optional linkers, and a β2M sequence (see SEQ ID NO:151 and FIG. 4):

MSRSVALAVLALLSLSGLEA(linker)$_{0-4}$X1Z1X2Z2X3Z3

(linker)$_{0-4}$IQRTPKIQVYS<u>C</u>HPAENGKSNFLNCYVSGFHPSDIEVDL

LKNGERIEKVEHSDLSFSKDWSFYLLYYTEFTPTEKDEYACRVNHVTLSQ

PKIVKWDRDM may be expressed with a second polypeptide containing a signal sequence (MYRMQLLSCIALSLALVTNS (SEQ ID NO:168)) followed by human IL-2 MODs, a HLA-A11 (HLA A*1101) sequence with Y84C, A139C and A236C amino acid substitutions:

(SEQ ID NO: 169)
MYRMQLLSCIALSLALVTNSAPTSSSTKKTQLQLEALLLDLQMILNGINN

YKNPKLTRMLTAKFYMPKKATELKHLQCLEEELKPLEEVLNLAQSKNFHL

RPRDLISNINVIVLELKGSETTFMCEYADETATIVEFLNRWITFCQSIIS

TLTGGGGSGGGGSGGGGSGGGGSAPTSSSTKKTQLQLEALLLDLQMILNG

-continued

INNYKNPKLTRMLTAKFYMPKKATELKHLQCLEEELKPLEEVLNLAQSKN

FHLRPRDLISNINVIVLELKGSETTFMCEYADETATIVEFLNRWITFCQS

IISTLTGGGGSGGGGSGGGGSGGGGSGSHSMRYFYTSVSRPGRGEPRFIA

VGYVDDTQFVRFDSDAASQRMEPRAPWIEQEGPEYWDQETRNVKAQSQTD

RVDLGTLRGCYNQSEDGSHTIQIMYGCDVGPDGRFLRGYRQDAYDGKDYI

ALNEDLRSWTCADMCAQITKRKWEAAHAAEQQRAYLEGTCVEWLRRYLEN

GKETLQRTDPPKTHMTHHPISDHEATLRCWALGFYPAEITLTWQRDGEDQ

TQDTELVETRPCGDGTFQKWAAVVVPSGEEQRYTCHVQHEGLPKPLTLRW

EAAAGGDKTHTCPPCPAPEAAGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQQGNVFSCSVMHEALHNHYTQKSLSLSPGK.

Other MHC Class 1 heavy chain constructs such as those in FIG. 10 may be coexpressed as an alternative to the HLA-A containing construct shown above. The linkers and sulfatase motifs are as described above in, for example, Examples 1 and 2.

Coexpression results in the production of a T-Cell-MMP complex with a sulfatase motif that may be conjugated to a polypeptide. Where the sulfatase motif is, for example LCTPSR (L(fGly)TPSR after conversion to the aldehyde) and the epitope for conjugation is from CMV (e.g., NLVPMVATV (SEQ ID NO:170)) the first polypeptide, after conversion to contain an FGly residue and conjugation to the c-terminus of the epitope peptide may appear as:

NLVPMVATV(linker)$_{0-4}$L(fGly)TPSR(linker)$_{0-4}$IQRTPKIQ

VYSCHPAENGKSNFLNCYVSGFHPSDIEVDLLKNGERIEKVEHSDLSFSK

DWSFYLLYYTEFTPTEKDEYACRVNHVTLSQPKIVKWDRDM (β2M seq see SEQ ID NO: 151 and FIG. 4).

The signal peptide has been removed by cellular processing and the linkage between cysteine 12 and the HLA-A*1101 containing construct is not shown.

What is claimed is:

1. A T-cell modulatory multimeric polypeptide (T-Cell-MMP) comprising:
   a) a first polypeptide comprising,
      i) a first major histocompatibility complex (MHC) polypeptide having an N-terminus and a C-terminus, wherein the first MHC polypeptide comprises a beta-2-microglobulin (β2M) polypeptide;
   b) a second polypeptide having an N-terminus and a C-terminus comprising, in order from N-terminus to C-terminus,
      (i) a second MHC polypeptide, wherein the second MHC polypeptide comprises a class I MHC heavy chain polypeptide comprising a binding pocket;
      (ii) optionally a peptide linker; and
      (iii) optionally an immunoglobulin (Ig) Fc polypeptide or a non-Ig polypeptide scaffold;
   c) (i) a first polypeptide chemical conjugation site that is part of a linker attached to the first polypeptide or is within the first polypeptide, or
      (ii) a second polypeptide chemical conjugation site that is part of a linker attached to the second polypeptide or is within the second polypeptide;
      wherein the first and second polypeptide chemical conjugation sites are sites at which a molecule comprising an epitope peptide may be covalently bound, either directly or indirectly through a linker, to the first or second polypeptide and positioned in the binding pocket of the T-Cell MMP for presentation to a cell bearing a T-cell receptor specific for the epitope presented by the epitope peptide; and
   d) one or more immunomodulatory polypeptides (MODs), wherein at least one of the one or more MODs is
      i) at the C-terminus of the first polypeptide,
      ii) at the N-terminus of the second polypeptide,
      iii) at the C-terminus of the second polypeptide, or
      iv) at the C-terminus of the first polypeptide and at the N-terminus of the second polypeptide;
   wherein each of the one or more MODs is an independently selected wild-type or variant MOD.

2. The T-Cell-MMP of claim 1, wherein the second polypeptide comprises an immunoglobulin (Ig) Fc polypeptide or a non-Ig polypeptide scaffold.

3. The T-Cell-MMP of claim 1, wherein the T-Cell-MMP comprises one or more independently selected variant MOD polypeptides; wherein at least one of the one or more variant MOD polypeptides exhibits a reduced affinity to its Co-MOD compared to the affinity of a corresponding wild-type MOD for the Co-MOD; and wherein the ratio of i) the binding affinity of a control T-Cell-MMP-epitope conjugate to a Co-MOD to ii) the binding affinity of a T-Cell-MMP-epitope conjugate comprising a variant of the wild-type MOD to the Co-MOD, when measured by bio-layer interferometry ("BLI"), is at least 1.5:1 or in a range of from 1.5:1 to $10^6$:1.

4. The T-Cell-MMP of claim 1, wherein the wild-type MOD polypeptides are selected independently from the group consisting of IL-2, 4-1BBL, PD-L1, CD70, CD80, CD86, ICOS-L, OX-40L, FasL, JAG1, TGFβ, ICAM, and PD-L2, and the variant MOD polypeptides are variants thereof.

5. The T-Cell-MMP of claim 1, wherein the first or second chemical conjugation site is independently selected from:
   peptide sequences that act as an enzymatic modification sequence;

non-natural amino acids and/or selenocysteines;
engineered amino acid chemical conjugation sites;
carbohydrate or oligosaccharide moieties; and/or
IgG nucleotide binding sites.

6. The T-Cell-MMP of claim 5, wherein the first or second chemical conjugation site comprises an engineered amino acid chemical conjugation site.

7. The T-Cell-MMP of claim 6, wherein the engineered amino acid chemical conjugation site comprises a cysteine.

8. The T-Cell-MMP of claim 7, wherein: the cysteine of the chemical conjugation site is present in the β2M polypeptide sequence, and said β2M polypeptide sequence has at least 90% amino acid sequence identity to amino acids 21-119 of any one of SEQ ID NOs: 151-155; and said class I MHC heavy chain polypeptide has at least 90% sequence identity to at least 250 contiguous amino acids of an MHC heavy chain sequence set forth in any one of SEQ ID NOs: 134-150.

* * * * *